US010070632B2

(12) United States Patent
Purcell et al.

(10) Patent No.: US 10,070,632 B2
(45) Date of Patent: Sep. 11, 2018

(54) RODENTS HAVING A HUMANIZED TMPRSS GENE

(71) Applicant: REGENERON PHARMACEUTICALS, INC., Tarrytown, NY (US)

(72) Inventors: Lisa Purcell, Garnerville, NY (US); Alexander O. Mujica, Elmsford, NY (US); Yajun Tang, White Plains, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 15/442,857

(22) Filed: Feb. 27, 2017

(65) Prior Publication Data

US 2017/0245482 A1 Aug. 31, 2017

Related U.S. Application Data

(60) Provisional application No. 62/301,023, filed on Feb. 29, 2016.

(51) Int. Cl.

| | |
|---|---|
| ***A01K 67/027*** | (2006.01) |
| ***C12N 5/0735*** | (2010.01) |
| ***C12N 9/64*** | (2006.01) |

(52) U.S. Cl.

CPC ........ *A01K 67/0278* (2013.01); *C12N 5/0606* (2013.01); *C12N 9/6424* (2013.01); *A01K 2207/15* (2013.01); *A01K 2217/072* (2013.01); *A01K 2227/10* (2013.01); *A01K 2227/105* (2013.01); *A01K 2267/0337* (2013.01)

(58) Field of Classification Search

CPC ............ A01K 67/0278; A01K 2207/15; A01K 2217/072; A01K 2227/105; A01K 2267/0337; C12N 5/0606; C12N 9/6424

See application file for complete search history.

(56) References Cited

U.S. PATENT DOCUMENTS

| | | | | |
|---|---|---|---|---|
| 6,586,251 B2 | 7/2003 | Economides et al. | | |
| 7,294,754 B2 | 11/2007 | Poueymirou et al. | | |
| 7,576,259 B2 | 8/2009 | Poueymirou et al. | | |
| 7,659,442 B2 | 2/2010 | Poueymirou et al. | | |
| 2004/0132156 A1* | 7/2004 | Parry | C07K 16/30 | 435/226 |
| 2005/0003416 A1* | 1/2005 | Wu | C12N 9/6424 | 435/6.16 |
| 2005/0022256 A1* | 1/2005 | Laferla | A01K 67/0275 | 800/11 |
| 2005/0026255 A1* | 2/2005 | Morser | C12Q 1/37 | 435/69.1 |
| 2006/0101531 A1* | 5/2006 | Vasioukhin | A01K 67/0275 | 800/10 |
| 2008/0078000 A1 | 3/2008 | Poueymirou et al. | | |
| 2013/0273070 A1* | 10/2013 | Purcell Ngambo | A61K 39/3955 | 424/158.1 |
| 2014/0235933 A1 | 8/2014 | Lee et al. | | |
| 2014/0310828 A1 | 10/2014 | Lee et al. | | |
| 2015/0106961 A1 | 4/2015 | Rojas et al. | | |
| 2015/0143558 A1 | 5/2015 | McWhirter et al. | | |
| 2015/0143559 A1 | 5/2015 | McWhirter et al. | | |

FOREIGN PATENT DOCUMENTS

| | | |
|---|---|---|
| WO | 2011/044050 A2 | 4/2011 |
| WO | 2012/112544 A2 | 8/2012 |
| WO | 2013/063556 A1 | 5/2013 |
| WO | 2013/158516 A1 | 10/2013 |
| WO | 2013/192030 A1 | 12/2013 |
| WO | 2014/039782 A2 | 3/2014 |
| WO | 2015/042557 A1 | 3/2015 |
| WO | 2015/196051 A1 | 12/2015 |
| WO | 2016/089692 A1 | 6/2016 |
| WO | 2016/094481 A1 | 6/2016 |
| WO | 2015/171861 A1 | 11/2016 |

OTHER PUBLICATIONS

Bottcher-Friebertshauser et al, J. Virol. 84(11):5605-5614, 2010.*

Kuhn, Studies on the host response to influenza A virus infections in mouse knock-out mutants, University of Veterinary Medicine, Hannover, 2015.*

Sun, http://www.dtic.mil/docs/citations/ADA525092; 2009.*

Macchiarini et al, J. Exp. Med. 202(10):1307-1311, 2005.*

Bodewes et al, Expert Reviews Vaccines 9(1): 59-72, 2010.*

Bertram S. et al., "Novel Insights into Proteolytic Cleavage of Influenza Virus Hemagglutinin", Rev. Med. Viral. 20:298-310 (2010).

Böttcher-Friebertshäuser E. et al., "Cleavage of Influenza Virus Hemagglutinin by Airway Proteases TMPRSS2 and HAT Differs in Subcellular Localization and Susceptibility to Protease Inhibitors", Journal of Virology 84 (11):5605-5614 (Jun. 2010).

Devoy A. et al., "Genomically Humanized Mice: Technologies and Promises", Nature Reviews Genetics 13(1):14-20 (Jan. 2012).

Kühn N., "Studies on the Host Response to Influenza A Virus Infections in Mouse Knock-Out Mutants", Thesis—University of Veterinary Medicine Hannover pp. 1-74 (2015).

MacDonald L.E. et al., "Precise and In Situ Genetic Humanization of 6 Mb of Mouse Immunoglobulin Genes", PNAS 111(14):5147-5152 (Apr. 8, 2014).

Murphy A.J. et al., "Mice With Megabase Humanization of Their Immunoglobulin Genes Generate Antibodies as Efficiently as Normal Mice", PNAS 111(14):5153-5158 (Apr. 8, 2014).

(Continued)

*Primary Examiner* — Kevin Kai Hill

(74) *Attorney, Agent, or Firm* — Scully, Scott, Murphy & Presser, P.C.; Brian A. Cocca

(57) ABSTRACT

Genetically modified rodents such as mice and rats, and methods and compositions for making and using the same, are provided. The rodents comprise a humanization of at least one endogenous rodent Tmprss gene, such as an endogenous rodent Tmprss2, Tmprss4, or Tmprss11d gene.

23 Claims, 16 Drawing Sheets

Specification includes a Sequence Listing.

(56) References Cited

OTHER PUBLICATIONS

Radigan K.A. et al., "Modeling Human Influenza Infection in the Laboratory", Infection and Drug Resistance 3:311-320 (2015).
Rajagowthamee R. et al., "Animal Models for Influenza Virus Pathogenesis, Transmission, and Immunology", Journal of Immunological Methods 410:60-79 (2014).
Sun Y., "Characterization of the TMPRSS2 Protease as a Modulator of Prostate Cancer Metastasis", Defense Technical Information Center, pp. 1-12 (Mar. 2009).
International Search Report and Written Opinion dated Jun. 19, 2017 received in International Application No. PCT/US2017/019574.
Anderson P., "Post-Transcriptional Control of Cytokine Production", Nature Immunology 9(4):353-359 (Apr. 2008).
Bahgat M.M. et al., "Inhibition of Lung Serine Proteases in Mice: A Potentially New Approach to Control Influenza Infection", Virology Journal 8:27 (15 pagers) (2011).
Bertram S. et al., "TMPRSS2 and TMPRSS4 Facilitate Trypsin-Independent Spread of Influenza Virus in Caco-2 Cells", Journal of Virology 84(19):10016-10025 (Oct. 2010).
Böttcher-Friebertshäuser E. et al., "Inhibition of Influenza Virus Infection in Human Airway Cell Cultures by an Antisense Peptide-Conjugated Morpholino Oligomer Targeting the Hemagglutinin-Activating Protease TMPRSS2", Journal of Virology 85(4):1554-1562 (Feb. 2011).
Böttcher E. et al., "MDCK Cells that Express Proteases TMPRSS2 and HAT Provide a Cell System to Propagate Influenza Viruses in the Absence of Trypsin and to Study Cleavage of HA and its Inhibition", Vaccine 27:6324-6329 (2009).
Böttcher E. et al., "Proteolytic Activation of Influenza Viruses by Serine Proteases TMPRSS2 and HAT from Human Airway Epithelium", Journal of Virology 80(19):9896-9898 (Oct. 2006).
Bugge T.H. et al., "Type II Transmembrane Serine Proteases", The Journal of Biological Chemistry 284 (35):23177-23181 and Supplementary Tables (Aug. 28, 2009).
Guipponi M. et al., "The Transmembrane Serine Protease (TMPRSS3) Mutated in Deafness DFNB8/10 Activates the Epithelial Sodium Channel (ENaC) In Vitro", Human Molecular Genetics 11(23):2829-2836 (2002).
Hooper J.D. et al., "Type II Transmembrance Serine Proteases", The Journal of Biological Chemistry 276 (2):857-860 (Jan. 12, 2001).
Rongvaux A. et al., "Human Thrombopoietin Knockin Mice Efficiently Support Human Hematopoiesis In Vivo", PNAS 108(6):2378-2383 (Feb. 8, 2011).
Szabo R. et al., "Type II Transmembrane Serine Proteases in Development and Disease", The International Journal of Biochemistry & Cell Biology 40:1297-1316 (2008).
Tong C. et al., "Generating Gene Knockout Rats by Homologous Recombination in Embryonic Stem Cells", Nature Protocols 6(6):827-844 (Jun. 2011).
Tong C. et al., "Production of p53 Gene Knockout Rats by Homologous Recombination in Embryonic Stem Cells", Nature 467:211-215 (Sep. 2010).
Valenzuela D.M. et al., "High-Throughput Engineering of the Mouse Genome Coupled With High-Resolution Expression Analysis", Nature Biotechnology 21(6):652-659 (Jun. 2003).
Vuagniaux G. et al., "Synergistic Activation of ENaC by Three Membrane-Bound Channel-Activating Serine Proteases (mCAP1, mCAP2, and mCAP3) and Serum- and Glucocorticoid-Regulated Kinase (Sgk1) in Xenopus Oocytes", J. Gen. Physiol. 120:191-201 (Aug. 2002).
Willinger T. et al., "Human IL-3/GM-CSF Knock-in Mice Support Human Alveolar Macrophage Development and Human Immune Responses in the Lung", PNAS 108(6):2390-2395 (Feb. 8, 2011).
Willinger T. et al., Improving Human Hemato-Lymphoid-System Mice by Cytokine Knock-in Gene Replacement, Trends in Immunology 32(7):321-327 (Jul. 2011).
GenBank NCBI Reference Sequence No. NM_005656.3 (5 pages) (Apr. 30, 2017).
GenBank NCBI Reference Sequence No. NM_015775.2 (5 pages) (Apr. 25, 2017).
GenBank NCBI Reference Sequence No. NM_145403.2 (4 pages) (Sep. 4, 2016).
GenBank NCBI Reference Sequence No. NM_001173551.1 (5 pages) (Apr. 17, 2017).
GenBank NCBI Reference Sequence No. NM_004262.2 (4 pages) (Sep. 9, 2016).
GenBank NCBI Reference Sequence No. NM_145561.2 (3 pages) (Feb. 15, 2015).
NCBI Reference Sequence No. NG_047085.1 (13 pages) (Sep. 13, 2017).
NCBI CCDS report for TMPRSS11D, https://www.ncbi.nlm.nih.gov/CCDS/CcdsBrowse.cgi?REQUEST=CCDS&DATA=CCDS3518, (2 pages) downloaded Dec. 7, 2017.
ENSG00000153802, http://www.ensembl.org/Homo_sapiens/Gene/Summary?g=ENSG00000153802; r=4:67820876-67884032 (2 pages), downloaded Dec. 7, 2017.
GenBank No. CH471057.1 (4 pages) (Mar. 23, 2015).
NCBI Reference Sequence No. NP_004253.1 (3 pages) (Mar. 15, 2015).
NCBI Reference Sequence No. NG_011858.2 (13 pages) (May 4, 2014).

* cited by examiner

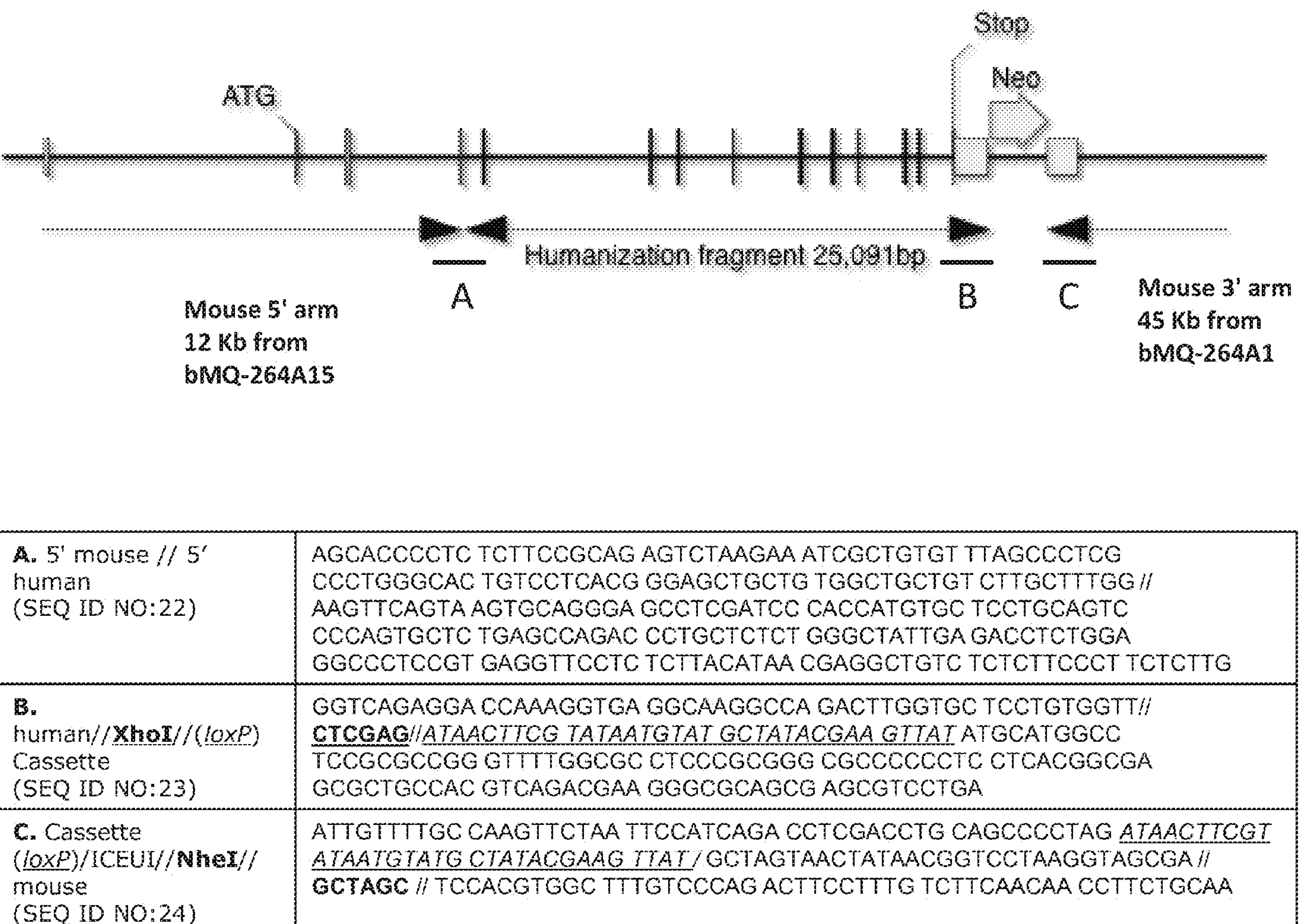

| | |
|---|---|
| **A.** 5' mouse // 5' human (SEQ ID NO:22) | AGCACCCCTC TCTTCCGCAG AGTCTAAGAA ATCGCTGTGT TTAGCCCTCG CCCTGGGCAC TGTCCTCACG GGAGCTGCTG TGGCTGCTGT CTTGCTTTGG // AAGTTCAGTA AGTGCAGGGA GCCTCGATCC CACCATGTGC TCCTGCAGTC CCCAGTGCTC TGAGCCAGAC CCTGCTCTCT GGGCTATTGA GACCTCTGGA GGCCCTCCGT GAGGTTCCTC TCTTACATAA CGAGGCTGTC TCTCTTCCCT TCTCTTG |
| **B.** human//**XhoI**//(*loxP*) Cassette (SEQ ID NO:23) | GGTCAGAGGA CCAAAGGTGA GGCAAGGCCA GACTTGGTGC TCCTGTGGTT// **CTCGAG**//*ATAACTTCG TATAATGTAT GCTATACGAA GTTAT* ATGCATGGCC TCCGCGCCGG GTTTTGGCGC CTCCCGCGGG CGCCCCCCTC CTCACGGCGA GCGCTGCCAC GTCAGACGAA GGGCGCAGCG AGCGTCCTGA |
| **C.** Cassette (*loxP*)/ICEUI//**NheI**// mouse (SEQ ID NO:24) | ATTGTTTTGC CAAGTTCTAA TTCCATCAGA CCTCGACCTG CAGCCCCTAG *ATAACTTCGT ATAATGTATG CTATACGAAG TTAT* / GCTAGTAACTATAACGGTCCTAAGGTAGCGA // **GCTAGC** // TCCACGTGGC TTTGTCCCAG ACTTCCTTTG TCTTCAACAA CCTTCTGCAA |

Figure 1B

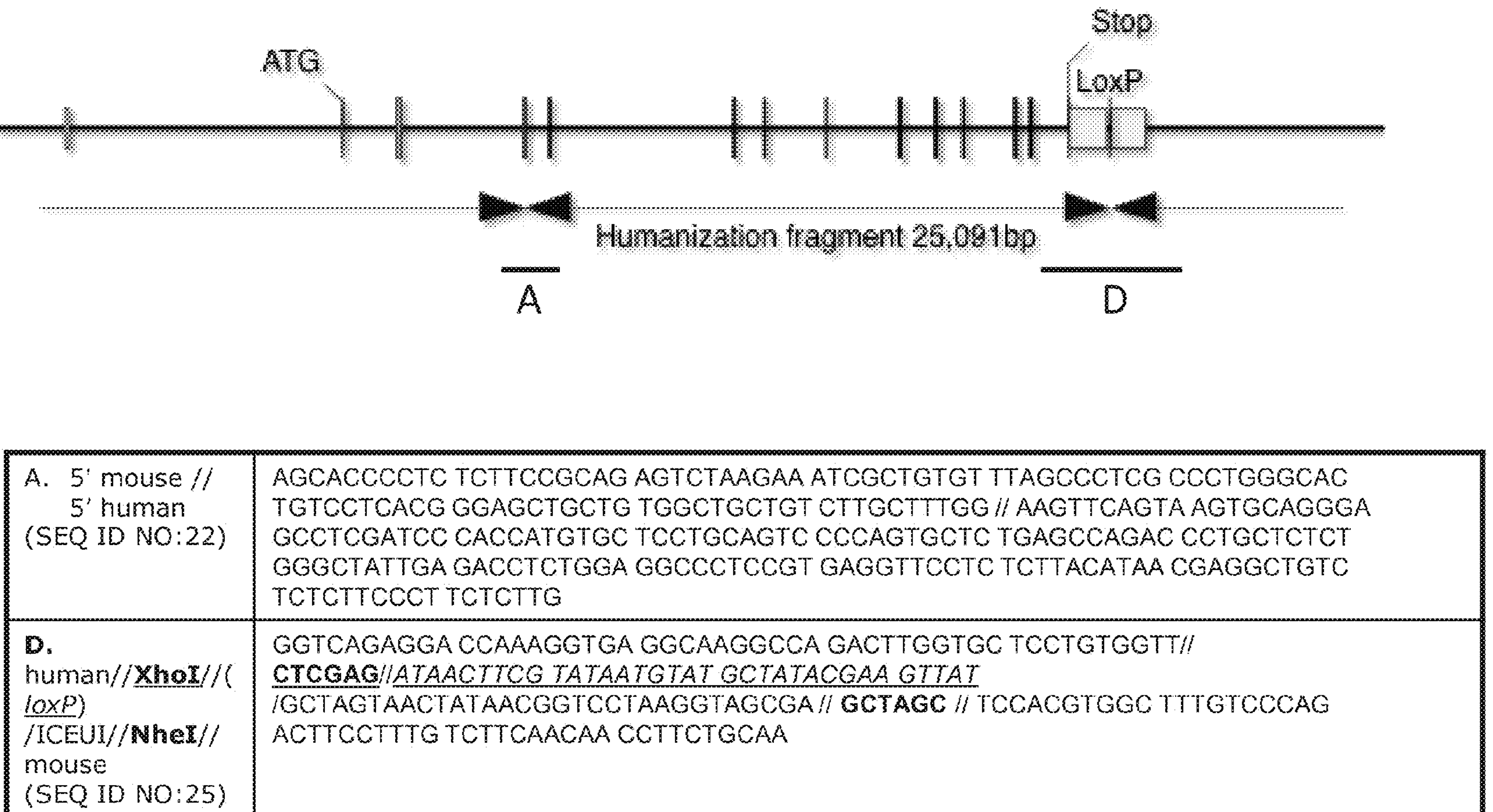

| | |
|---|---|
| A. 5′ mouse // 5′ human (SEQ ID NO:22) | AGCACCCCTC TCTTCCGCAG AGTCTAAGAA ATCGCTGTGT TTAGCCCTCG CCCTGGGCAC TGTCCTCACG GGAGCTGCTG TGGCTGCTGT CTTGCTTTGG // AAGTTCAGTA AGTGCAGGGA GCCTCGATCC CACCATGTGC TCCTGCAGTC CCCAGTGCTC TGAGCCAGAC CCTGCTCTCT GGGCTATTGA GACCTCTGGA GGCCCTCCGT GAGGTTCCTC TCTTACATAA CGAGGCTGTC TCTCTTCCCT TCTCTTG |
| **D.** human//**<u>XhoI</u>**//(*<u>loxP</u>*) /ICEUI//**NheI**// mouse (SEQ ID NO:25) | GGTCAGAGGA CCAAAGGTGA GGCAAGGCCA GACTTGGTGC TCCTGTGGTT// **<u>CTCGAG</u>**//*<u>ATAACTTCG TATAATGTAT GCTATACGAA GTTAT</u>* /GCTAGTAACTATAACGGTCCTAAGGTAGCGA // **GCTAGC** // TCCACGTGGC TTTGTCCCAG ACTTCCTTTG TCTTCAACAA CCTTCTGCAA |

Figure 1C

Tmprss2 protein alignment

```
                           10        20        30        40        50        60
hTMPRSS2          MALNSGSPPAIGPYYENHGYQPENPYPAQPTVVPTVYEVHPAQYYPSPVPQYAPRVLTQA
mTmprss2          MALNSGSPPGIGPCYENHGYQSEHICPPRPPVAPNGYNLYPAQYYPSPVPQYAPRITTQA
7010 mutant pro   MALNSGSPPGIGPCYENHGYQSEHICPPRPPVAPNGYNLYPAQYYPSPVPQYAPRITTQA
                  ********* *** ******* *.  * .* * *. *  . **************. ***

                           70        80        90       100       110       120
hTMPRSS2          SNPVVCTQPKSPSGTVCTSKTKKALCITLTLGTFLVGAALAAGLLWKFMGSKCSNSGIEC
mTmprss2          STSVIHTHPKS-SGALCTSKSKKSLCLALALGTVLTGAAVAAVLLWRFWDSNCSTSEMEC
7010 mutant pro   STSVIHTHPKS-SGALCTSKSKKSLCLALALGTVLTGAAVAAVLLWKFMGSKCSNSGIEC
                  *. *. *.*** **..****.**.**..*.*** * ***.** ***.*   * **.*  .**

                          130       140       150       160       170       180
hTMPRSS2          DSSGTCINPSNWCDGVSHCPGGEDENRCVRLYGPNFILQVYSSQRKSWHPVCQDDWNENY
mTmprss2          GSSGTCISSSLWCDGVAHCPNGEDENRCVRLYGQSFILQVYSSQRKAWYPVCQDDWSESY
7010 mutant pro   DSSGTCINPSNWCDGVSHCPGGEDENRCVRLYGPNFILQVYSSQRKSWHPVCQDDWNENY
                   ******  * *****.***.***********   ***********.* ******* * *

                          190       200       210       220       230       240
hTMPRSS2          GRAACRDMGYKNNFYSSQGIVDDSGSTSFMKLNTSAGNVDIYKKLYHSDACSSKAVVSLR
mTmprss2          GRAACKDMGYKNNFYSSQGIPDQSGATSFMKLNVSSGNVDLYKKLYHSDSCSSRMVVSLR
7010 mutant pro   GRAACRDMGYKNNFYSSQGIVDDSGSTSFMKLNTSAGNVDIYKKLYHSDACSSKAVVSLR
                  *****.************** * **.******* *.****.********.***. *****

                          250       260       270       280       290       300
hTMPRSS2          CIACGVNLNSSRQSRIVGGESALPGAWPWQVSLHVQNVHVCGGSIITPEWIVTAAHCVEK
mTmprss2          CIECGVRS-VKRQSRIVGGLNASPGDWPWQVSLHVQGVHVCGGSIITPEWIVTAAHCVEE
7010 mutant pro   CIACGVNLNSSRQSRIVGGESALPGAWPWQVSLHVQNVHVCGGSIITPEWIVTAAHCVEK
                  ** ***     ******** * ** *********.*********************
```

Figure 1D

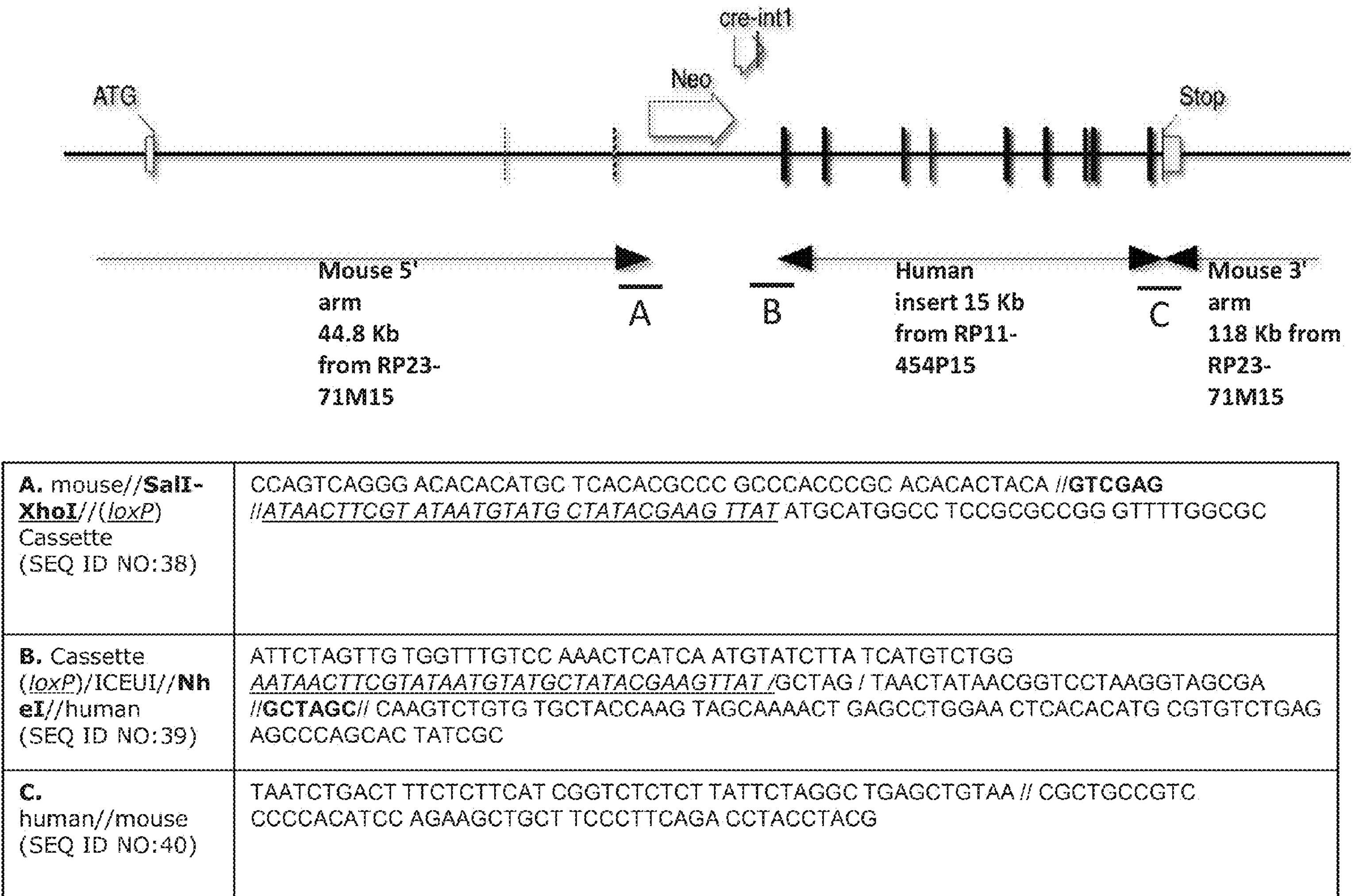

| | |
|---|---|
| **A.** mouse//**SalI-XhoI**//(*loxP*) Cassette (SEQ ID NO:38) | CCAGTCAGGG ACACACATGC TCACACGCCC GCCCACCCGC ACACACTACA //**GTCGAG** //*ATAACTTCGT ATAATGTATG CTATACGAAG TTAT* ATGCATGGCC TCCGCGCCGG GTTTTGGCGC |
| **B.** Cassette (*loxP*)/ICEUI//**NheI**//human (SEQ ID NO:39) | ATTCTAGTTG TGGTTTGTCC AAACTCATCA ATGTATCTTA TCATGTCTGG *AATAACTTCGTATAATGTATGCTATACGAAGTTAT* /GCTAG / TAACTATAACGGTCCTAAGGTAGCGA //**GCTAGC**// CAAGTCTGTG TGCTACCAAG TAGCAAAACT GAGCCTGGAA CTCACACATG CGTGTCTGAG AGCCCAGCAC TATCGC |
| **C.** human//mouse (SEQ ID NO:40) | TAATCTGACT TTCTCTTCAT CGGTCTCTCT TATTCTAGGC TGAGCTGTAA // CGCTGCCGTC CCCCACATCC AGAAGCTGCT TCCCTTCAGA CCTACCTACG |

Figure 2B

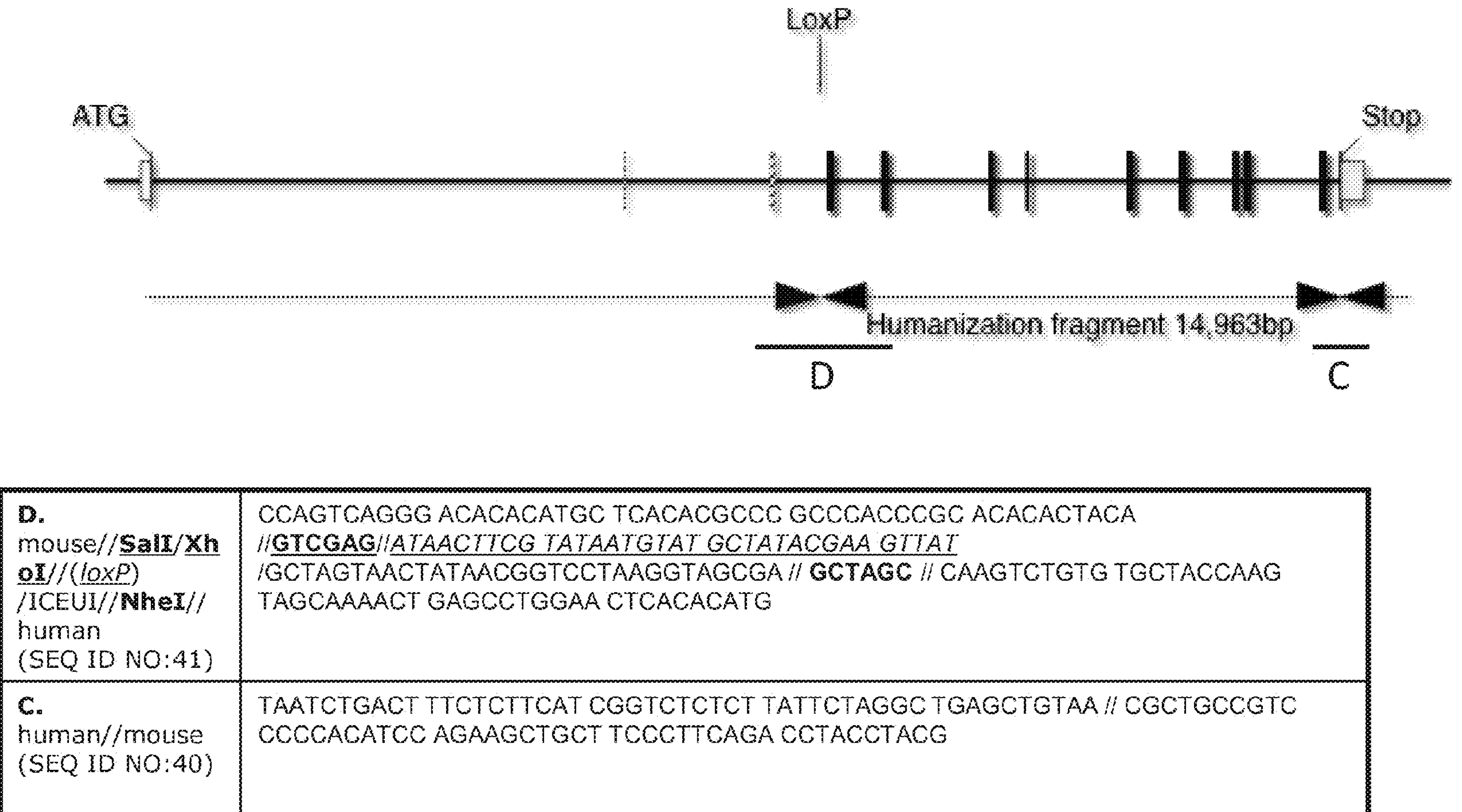

| | |
|---|---|
| **D.** mouse//**SalI/XhoI**//(*loxP*) /ICEUI//**NheI**// human (SEQ ID NO:41) | CCAGTCAGGG ACACACATGC TCACACGCCC GCCCACCCGC ACACACTACA //**GTCGAG**//*ATAACTTCG TATAATGTAT GCTATACGAA GTTAT* /GCTAGTAACTATAACGGTCCTAAGGTAGCGA // **GCTAGC** // CAAGTCTGTG TGCTACCAAG TAGCAAAACT GAGCCTGGAA CTCACACATG |
| **C.** human//mouse (SEQ ID NO:40) | TAATCTGACT TTCTCTTCAT CGGTCTCTCT TATTCTAGGC TGAGCTGTAA // CGCTGCCGTC CCCCACATCC AGAAGCTGCT TCCCTTCAGA CCTACCTACG |

Figure 2C

Tmprss4 protein alignment

```
                           10        20        30        40        50        60
hTMPRSS4          MLQDPDSDQPLNSLDVKPLRKPRIPMETFRKVGIPIIIALLSLASIIIVVVLIKVILDKY
mTmprss4            MESDSGQPLNNRDIVPFRKPRRPQETFKKVGIPIIAVLLSLIALVIVALLIKVILDKY
7224 mutant pro     MESDSGQPLNNRDIVPFRKPRRPQETFKKVGIPIIAVLLSLIALVIVALLIKVILDKY

                           70        80        90       100       110       120
hTMPRSS4          YFLCGQPLHFIPRKQLCDGELDCPLGEDEEHCVKSFPEGPAVAVRLSKDRSTLQVLDSAT
mTmprss4          YFICGSPLTFIQRGQLCDGHLDCASGEDEEHCVKDFPEKPGVAVRLSKDRSTLQVLDAAT
7224 mutant pro   YFLCGQPLHFIPRKQLCDGELDCPLGEDEEHCVKSFPEGPAVAVRLSKDRSTLQVLDSAT

                          130       140       150       160       170       180
hTMPRSS4          GNWFSACFDNFTEALAETACRQMGYSSKPTFRAVEIGPDQDLDVVEITENSQELRMRNSS
mTmprss4          GTWASVCFDNFTEALAKTACRQMGYDSQPAFRAVEIRPDQNLPVAQVTGNSQELQVQNGS
7224 mutant pro   GNWFSACFDNFTEALAETACRQMGYSSKPTFRAVEIGPDQDLDVVEITENSQELRMRNSS

                          190       200       210       220       230       240
hTMPRSS4          GPCLSGSLVSLHCLACGKSLKTPRVVGGEEASVDSWPWQVSIQYDKQHVCGGSILDPHWV
mTmprss4          RSCLSGSLVSLRCLDCGKSLKTPRVVGGVEAPVDSWPWQVSIQYNKQHVCGGSILDPHWI
7224 mutant pro   GPCLSGSLVSLHCLACGKSLKTPRVVGVEEASVDSWPWQVSIQYDKQHVCGGSILDPHWV

                          250       260       270       280       290       300
hTMPRSS4          LTAAHCFRKHTDVFNWKVRAGSDKLGSFPSLAVAKIIIIEFNPMYPKDNDIALMKLQFPL
mTmprss4          LTAAHCFRKYLDVSSWKVRAGSNILGNSPSLPVAKIFIAEPNPLYPKEKDIALVKLQMPL
7224 mutant pro   LTAAHCFRKHTDVFNWKVRAGSDKLGSFPSLAVAKIIIIEFNPMYPKDNDIALMKLQFPL
```

Figure 2D

Tmprss4 protein alignment

```
                  310       320       330       340       350       360
hTMPRSS4          TFSGTVRPICLPFFDEELTPATPLWIIGWGFTKQNGGKMSDILLQASVQVIDSTRCNADD
mTmprss4          TFSGSVRPICLPFSDEVLVPATPVWVIGWGFTEENGGKMSDMLLQASVQVIDSTRCNAED
7224 mutant pro   TFSGTVRPICLPFFDEELTPATPLWIIGWGFTKQNGGKMSDILLQASVQVIDSTRCNADD
                  ****.******** ** * ****.*.****** .*******.****************.*

                  370       380       390       400       410       420
hTMPRSS4          AYQGEVTEKMMCAGIPEGGVDTCQGDSGGPLMYQSDQWHVVGIVSWGYGCGGPSTPGVYT
mTmprss4          AYEGEVTAEMLCAGTPQGGKDTCQGDSGGPLMYHSDKWQVVGIVSWGHGCGGPSTPGVYT
7224 mutant pro   AYQGEVTEKMMCAGIPEGGVDTCQGDSGGPLMYQSDQWHVVGIVSWGYGCGGPSTPGVYT
                  **.****  *.*** *.** *************.**.*.******** ************

                  430
hTMPRSS4          KVSAYLNWIYNVWKAEL
mTmprss4          KVTAYLNWIYNVRKSEM
7224 mutant pro   KVSAYLNWIYNVWKAEL
                  **.********* *.*.
```

solid line: TM
solid box: LDLRa
dotted box: SRCR domain
dotted line: peptidase S1

Figure 2D (Continued)

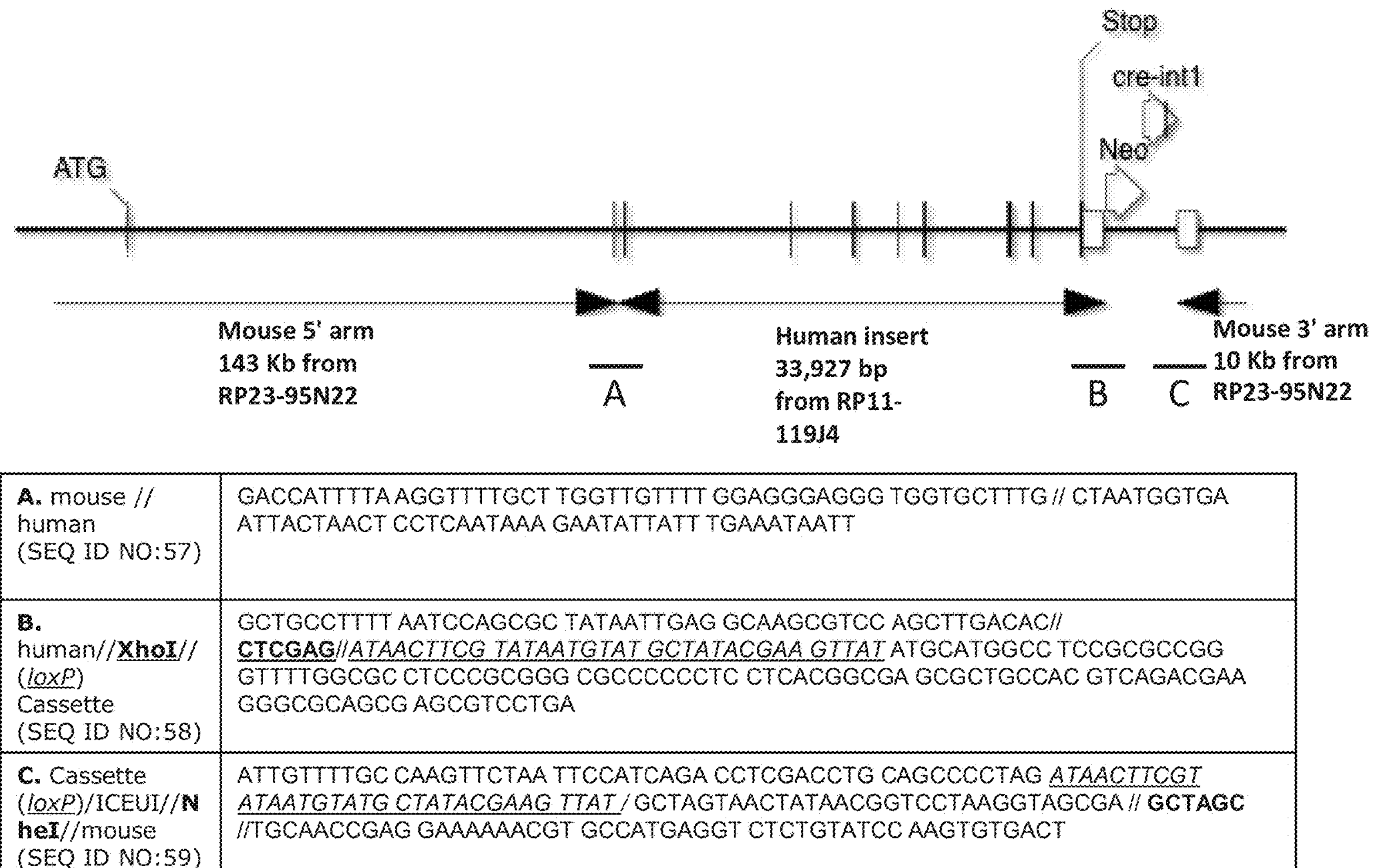

| | |
|---|---|
| **A.** mouse // human (SEQ ID NO:57) | GACCATTTTA AGGTTTTGCT TGGTTGTTTT GGAGGGAGGG TGGTGCTTTG // CTAATGGTGA ATTACTAACT CCTCAATAAA GAATATTATT TGAAATAATT |
| **B.** human//**XhoI**//(*loxP*) Cassette (SEQ ID NO:58) | GCTGCCTTTT AATCCAGCGC TATAATTGAG GCAAGCGTCC AGCTTGACAC// **CTCGAG**//*ATAACTTCG TATAATGTAT GCTATACGAA GTTAT* ATGCATGGCC TCCGCGCCGG GTTTTGGCGC CTCCCGCGGG CGCCCCCCTC CTCACGGCGA GCGCTGCCAC GTCAGACGAA GGGCGCAGCG AGCGTCCTGA |
| **C.** Cassette (*loxP*)/ICEUI//**NheI**//mouse (SEQ ID NO:59) | ATTGTTTTGC CAAGTTCTAA TTCCATCAGA CCTCGACCTG CAGCCCCTAG *ATAACTTCGT ATAATGTATG CTATACGAAG TTAT* / GCTAGTAACTATAACGGTCCTAAGGTAGCGA // **GCTAGC** //TGCAACCGAG GAAAAAACGT GCCATGAGGT CTCTGTATCC AAGTGTGACT |

Figure 3B

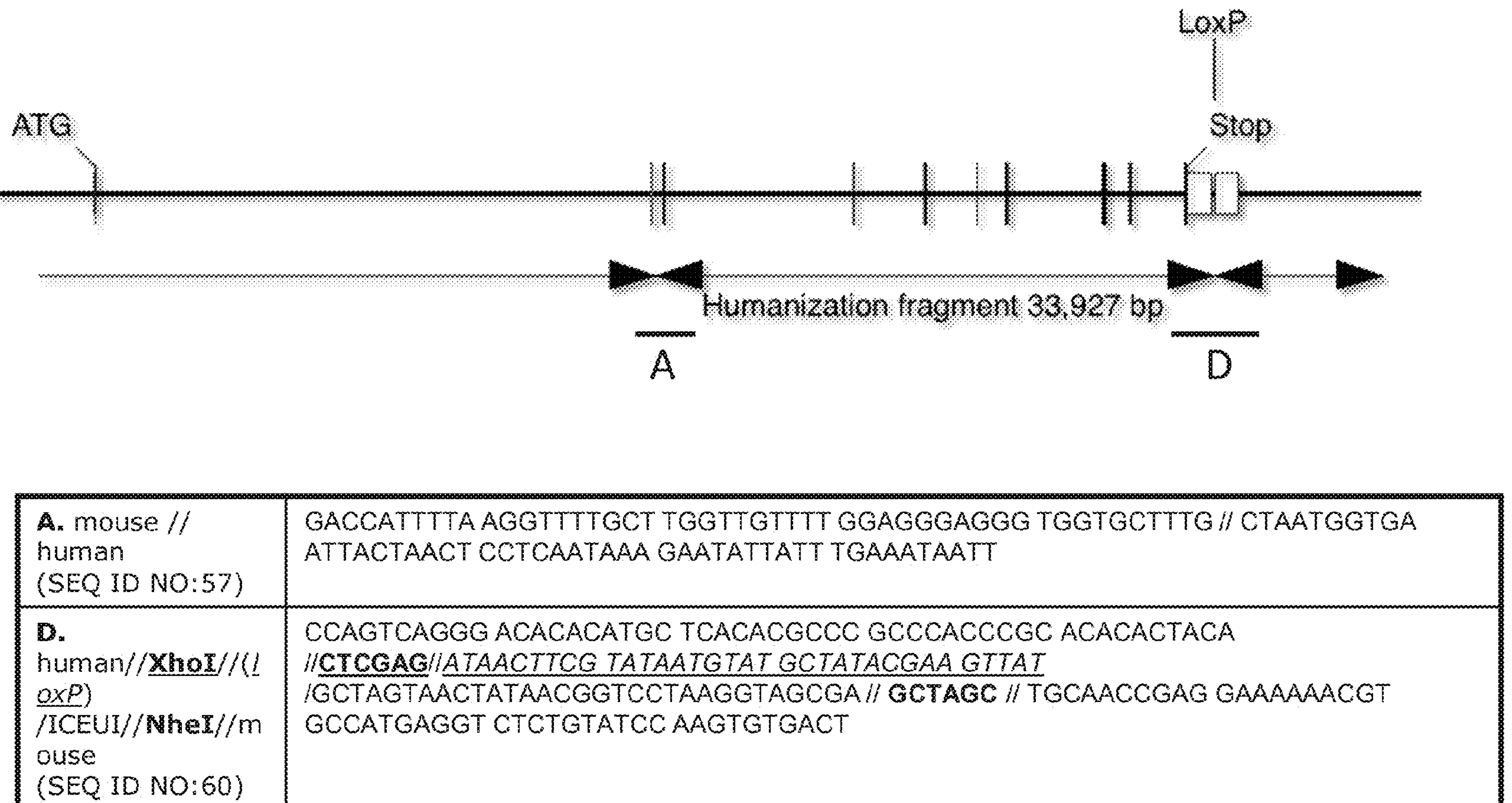

| | |
|---|---|
| **A.** mouse // human (SEQ ID NO:57) | GACCATTTTA AGGTTTTGCT TGGTTGTTTT GGAGGGAGGG TGGTGCTTTG // CTAATGGTGA ATTACTAACT CCTCAATAAA GAATATTATT TGAAATAATT |
| **D.** human//**XhoI**//(*loxP*) /ICEUI//**NheI**//mouse (SEQ ID NO:60) | CCAGTCAGGG ACACACATGC TCACACGCCC GCCCACCCGC ACACACTACA //**CTCGAG**//*ATAACTTCG TATAATGTAT GCTATACGAA GTTAT* /GCTAGTAACTATAACGGTCCTAAGGTAGCGA // **GCTAGC** // TGCAACCGAG GAAAAAACGT GCCATGAGGT CTCTGTATCC AAGTGTGACT |

Figure 3C

Tmprss11d protein alignment

```
                            10        20        30        40        50        60
hTMPRSS11D        MYRPARVTSTSRFLNPYVVCFIVVAGVVILAVTIALLVYFLAFDQKSYFYRSSFQLLNVE
mTmprss11d        MYRPRPMLSPSRFFTPFAVAFVVIITVGLLAMMAGLLIHFLAFDKKAYFYHSSFQILNVE
7226 mutant pro   MYRPRPMLSPSRFFTPFAVAFVVIITVGLLAMMAGLLIHFLAFDQKSYFYRSSFQLLNVE
                  ****   . * ***  .*. *.*.*.  *  .**.    **. *****.*.***.****.****

                            70        80        90       100       110       120
hTMPRSS11D        YNSQLNSPATQEYRTLSGRIESLITKTFKESNLRNQFIRAHVAKLRQDGSGVRADVVMKF
mTmprss11d        YTEALNSPATHEYRTLSERIEAMITDEFRGSSLKSEFIRTHVVKLRKEGTGVVADVVMKF
7226 mutant pro   YNSQLNSPATQEYRTLSGRIESLITKTFKESNLRNQFIRAHVAKLRQDGSGVRADVVMKF
                  *.  ******.****** ***..**  *. * *. .***.** ***..*.** *******

                           130       140       150       160       170       180
hTMPRSS11D        QFTRNNNGASMKSRIESVLRQMLNNSGNLEINPSTEITSLTDQAAANWLINECGAGPDLI
mTmprss11d        RSSKRNNRKVMKTRIQSVLRR-LSSSGNLEIAPSNEITSLTDQDTENVLTQECGARPDLI
7226 mutant pro   QFTRNNNGASMKSRIESVLRQMLNNSGNLEINPSTEITSLTDQAAANWLINECGAGPDLI
                  . ..  **   **.**.****. *  ****** **.******** .  * *  .**** ****

                           190       200       210       220       230       240
hTMPRSS11D        TLSEQRILGGTEAEEGSWPWQVSLRLNNAHHCGGSLINNMWILTAAHCFRSNSNPRDWIA
mTmprss11d        TLSEERIIGGMQAEPGDWPWQVSLQLNNVHHCGGALISNMWVLTAAHCFKSYPNPQYWTA
7226 mutant pro   TLSEQRILGGTEAEEGSWPWQVSLRLNNAHHCGGSLINNMWILTAAHCFRSNSNPRDWIA
                  ****.**.**  .** * *******.*** *****.** ***.*******.*   **. * *

                           250       260       270       280       290       300
hTMPRSS11D        TSGISTTFPKLRMRVRNILIHNNYKSATHENDIALVRLENSVTFTKDIHSVCLPAATQNI
mTmprss11d        TFGVSTMSPRLRVRVRAILAHDGYSSVTRDNDIAVVQLDRSVAFSRNIHRVCLPAATQNI
7226 mutant pro   TSGISTTFPKLRMRVRNILIHNNYKSATHENDIALVRLENSVTFTKDIHSVCLPAATQNI
                  * *.**  *.**.*** ** *  .* * *..****.*.*. **.*..  ** *********
```

Figure 3D

Tmprss11d protein alignment

```
                             310       320       330       340       350       360
hTMPRSS11D        PPGSTAYVTGWGAQEYAGHTVPELRQGQVRIISNDVCNAPHSYNGAILSGMLCAGVPQGG
mTmprss11d        IPGSVAYVTGWGSLTYGGNAVTNLRQGEVRIISSEECNTPAGYSGSVLPGMLCAGMRSGA
7226 mutant pro   PPGSTAYVTGWGAQEYAGHTVPELRQGQVRIISNDVCNAPHSYNGAILSGMLCAGVPQGG
                   *** *******.  *  * ..*  ****.*****  .  **.*  * *..* ******.  *

                             370       380       390       400       410
hTMPRSS11D        VDACQGDSGGPLVQEDSRRLWFIVGIVSWGDQCGLPDKPGVYTRVTAYLDWIRQQTGI
mTmprss11d        VDACQGDSGGPLVQEDSRRLWFVVGIVSWGYQCGLPNKPGVYTRVTAYRNWIRQQTGI
7226 mutant pro   VDACQGDSGGPLVQEDSRRLWFIVGIVSWGDQCGLPDKPGVYTRVTAYLDWIRQQTGI
                  **********************.******* ***** ***********  ********
```

solid line: TM
solid box: SEA domain
dotted line: peptidase S1

Figure 3D (Continued)

RODENTS HAVING A HUMANIZED TMPRSS GENE

CROSS REFERENCE TO RELATED APPLICATION

This application claims the benefit of priority from U.S. Provisional Application No. 62/301,023, filed Feb. 29, 2016, the entire contents of which are incorporated herein by reference.

INCORPORATION BY REFERENCE OF SEQUENCE LISTING

The Sequence Listing in the ASCII text file, named as 33093_10234US01_SequenceListing.txt of 275 KB, created on Feb. 13, 2017, and submitted to the United States Patent and Trademark Office via EFS-Web, is incorporated herein by reference.

BACKGROUND

Type II transmembrane serine proteases are a family of proteases characterized by an N-terminal transmembrane domain (Bugge et al., *J. Biol. Chem.* 284 (35): 23177-23181, 2009; Hooper et al., *J. Biol. Chem.* 272(2): 857-860, 2001). All members of this family are expressed as single-chain zymogens and are proteolytically activated by cleavage within a highly conserved R/(IV)VGG motif. One member of the family, transmembrane protease, serine type 4 (TMPRSS4), has been shown to activate the epithelial sodium channel (ENaC) regulating the sodium and water flux across epithelia (Guipponi et al. 2002 *Hum. Mol. Genet.* 11:2829; Vuagniaux et al. 2002 *J. Gen. Physiol.* 120:191). The proteolytical activators of TMPRSS4 are unknown; however, data available to date suggests that the protein is autoactivated. When activated, the catalytic domain of TMPRSS4 remains bound to the N-terminus of the protein via a disulphide linkage. TMPRSS4, TMPRSS2 and TMPRSS11D (or Human Airway Trypsin-like protease; "HAT") have been shown in vitro to cleave influenza A hemagglutinin (HA), which is the first essential step in the viral life cycle. This cleavage is essential for activity of HA, as the protein is synthesized as a precursor protein (HA0) and requires cleavage into HA1 and HA2 for activity. RNAi knock-down of TMPRSS4 in Caco-2 cells resulted in reduced spread of the virus. In addition, TMPRSS4 was shown to be strongly upregulated in the lungs of mice infected with influenza (Böttcher et al. 2006 *J. Virol.* 80:9896; Böttcher et al. 2009 Vaccine 27: 6324; Böttcher-Friebershäusser et al. 2010 *J. Virol.* 84: 5604; Bertam et al. 2010 *J. Virol.* 84:10016; Bertam et al. 2010 *J. Virol.* 84:10016; Böttcher-Friebershäusser et al. 2011 *J. Virol.* 85: 1554; Bahgat et al. 2011 *Virol. J.* 8:27).

Development of an in vivo system, e.g., a rodent model of infection, is needed in order to identify and test compounds including antibodies that specifically target human type II transmembrane serine proteases for the treatment and prevention of viral infection and other diseases.

SUMMARY

The present invention encompasses the recognition that it is desirable to engineer rodent animals to provide in vivo systems for identifying and developing new therapeutics. For example, the present invention encompasses the recognition that rodents having a humanized Tmprss gene are desirable for use in identifying and developing therapeutics for the treatment and prevention of viral infections.

In one aspect, the invention provides a rodent whose genome contains a humanized Tmprss gene that includes a nucleotide sequence of an endogenous rodent Tmprss gene and a nucleotide sequence of a cognate human TMPRSS gene, wherein the humanized Tmprss gene is under control of a 5' regulatory sequence(s), such as the promoter and/or enhancer(s), of the endogenous rodent Tmprss gene.

In some embodiments, the humanized Tmprss gene in rodents disclosed herein encodes a humanized Tmprss protein that contains an ectodomain substantially identical (e.g., at least 85%, 90%, 95%, 98%, 99% or 100% identical in sequence) to the ectodomain of a human TMPRSS protein. In some embodiments, the humanized Tmprss protein contains a cytoplasmic and transmembrane portion that is substantially identical (e.g., at least 85%, 90%, 95%, 98%, 99% or 100% identical in sequence) to the cytoplasmic and transmembrane portion of an endogenous rodent Tmprss protein.

In some embodiments, a rodent disclosed herein contains a humanized Tmprss gene that includes a nucleotide sequence of an endogenous rodent Tmprss gene and a nucleotide sequence of a cognate human TMPRSS gene, wherein the nucleotide sequence of the cognate human TMPRSS gene encodes a polypeptide substantially identical (e.g., at least 85%, 90%, 95%, 98%, 99% or 100% identical in sequence) to the ectodomain of the human TMPRSS protein encoded by the cognate human TMPRSS gene. In some embodiments, a rodent disclosed herein contains a humanized Tmprss gene that includes a nucleotide sequence of an endogenous rodent Tmprss gene and a nucleotide sequence of a cognate human TMPRSS gene, wherein the nucleotide sequence of the endogenous rodent Tmprss gene encodes a polypeptide substantially identical (e.g., at least 85%, 90%, 95%, 98%, 99% or 100% identical in sequence) to the cytoplasmic and transmembrane portion of the endogenous rodent Tmprss protein encoded by the endogenous rodent Tmprss gene.

In some embodiments, a rodent disclosed herein contains a humanized Tmprss gene located at an endogenous rodent Tmprss locus that results from a replacement of a contiguous genomic sequence of an endogenous rodent Tmprss gene with a contiguous genomic sequence of a cognate human TMPRSS gene. In specific embodiments, the contiguous genomic sequence of a cognate human TMPRSS gene being inserted includes exon sequences encoding an ectodomain substantially identical with the ectodomain of the human TMPRSS protein encoded by human TMPRSS gene. In some embodiments, the contiguous genomic sequence of a cognate human TMPRSS gene also includes the 3' UTR of the cognate human TMPRSS gene.

In some embodiments, a rodent disclosed herein is heterozygous for a humanized Tmprss gene at an endogenous rodent Tmprss locus. In other embodiments, a rodent is homozygous for a humanized Tmprss gene at an endogenous rodent Tmprss locus.

In further embodiments, a rodent contains two or more humanized Tmprss genes at different endogenous rodent Tmprss loci with each endogenous rodent Tmprss locus being humanized with a respective cognate human TMPRSS gene; for example, two or more of humanized Tmprss2, humanized Tmprss4, and humanized Tmprss11d genes.

In some embodiments, a rodent disclosed herein contains a humanized Tmprss2 gene that includes a nucleotide sequence of an endogenous rodent Tmprss2 gene and a nucleotide sequence of a human TMPRSS2 gene, wherein the humanized Tmprss2 gene is under control of the promoter of the endogenous rodent Tmprss2 gene.

In some embodiments, the humanized Tmprss2 gene encodes a humanized Tmprss2 protein that contains an ectodomain substantially identical (e.g., at least 85%, 90%, 95%, 98%, 99% or 100% identical in sequence) with the ectodomain of the human TMPRSS2 protein encoded by the human TMPRSS2 gene used in humanization. The human TMPRSS2 protein contains, in some embodiments, an amino acid sequence at least 85% identical (e.g., at least 90%/a, 95%, 98%, 99% or 100% identical) with the amino acid sequence as set forth in SEQ ID NO: 4. In some embodiments, a humanized Tmprss2 protein contains an ectodomain substantially identical (e.g., at least 85%, 90%, 95%, 98%, 99% or 100% identical) with the amino acid sequence composed of residues W106 to G492 or the C-terminal 387 amino acids of a human TMPRSS2 protein as set forth in, e.g., SEQ ID NO: 4. In some embodiments, the humanized Tmprss2 gene encodes a humanized Tmprss2 protein that further contains a cytoplasmic and transmembrane portion that is substantially identical (e.g., at least 85%, 90%, 95%, 98%, 99% or 100% identical) with the cytoplasmic and transmembrane portion of the rodent Tmprss2 protein encoded by the endogenous rodent Tmprss2 gene being humanized. An exemplary endogenous rodent Tmprss2 protein is set forth in SEQ ID NO: 2.

In some embodiments, a rodent contains a humanized Tmprss2 gene that includes a nucleotide sequence of an endogenous rodent Tmprss2 gene and a nucleotide sequence of a human TMPRSS2 gene, wherein the nucleotide sequence of the human TMPRSS2 gene encodes an ectodomain substantially identical (e.g., at least 85%, 90%, 95%, 98%, 99% or 100% identical in sequence) with the ectodomain of the human TMPRSS2 protein encoded by the human TMPRSS2 gene. In specific embodiments, the nucleotide sequence of a human TMPRSS2 gene is a contiguous genomic sequence of a human TMPRSS2 gene containing coding exon 4 through the stop codon in coding exon 13 of the human TMPRSS2 gene. In particular embodiments, the contiguous genomic sequence of a human TMPRSS2 gene further contains the 3' UTR of the human TMPRSS2 gene. In some embodiments, the nucleotide sequence of an endogenous rodent Tmprss2 gene included in a humanized Tmprss2 gene encodes a cytoplasmic and transmembrane portion that is substantially identical (e.g., at least 85%, 90%/a, 95%, 98%, 99% or 100% identical) with the cytoplasmic and transmembrane portion of the endogenous rodent Tmprss2 protein encoded by the endogenous rodent Tmprss2 gene.

In particular embodiments, a humanized Tmprss2 gene contains coding exons 1-2 of an endogenous rodent Tmprss2 gene, and coding exon 4 through coding exon 13 of a human TMPRSS2 gene, wherein the humanized Tmprss2 gene encodes a humanized Tmprss2 protein that contains a cytoplasmic and transmembrane portion that is substantially identical with the cytoplasmic and transmembrane portion of the rodent Tmprss2 protein encoded by the endogenous rodent Tmprss2 gene, and an ectodomain that is substantially identical with the ectodomain of the human TMPRSS2 protein encoded by the human TMPRSS2 gene. The humanized Tmprss2 gene contains an exon 3 that in some embodiments is coding exon 3 of a human TMPRSS2 gene, and in other embodiments is coding exon 3 of an endogenous rodent Tmprss2 gene. In some embodiments, the humanized Tmprss2 gene contains an exon 3 that includes a 5' portion of coding exon 3 of an endogenous rodent Tmprss2 gene and a 3' portion of coding exon 3 of a human TMPRSS2 gene.

In some embodiments, a rodent disclosed herein contains a humanized Tmprss4 gene that includes a nucleotide sequence of an endogenous rodent Tmprss4 gene and a nucleotide sequence of a human TMPRSS4 gene, wherein the humanized Tmprss4 gene is under control of the promoter of the endogenous rodent Tmprss4 gene.

In some embodiments, the humanized Tmprss4 gene encodes a humanized Tmprss4 protein that contains an ectodomain substantially identical (e.g., at least 85%, 90%, 95%, 98%, 99% or 100% identical in sequence) with the ectodomain of the human TMPRSS4 protein encoded by the human TMPRSS4 gene used in humanization. The human TMPRSS4 protein contains, in some embodiments, an amino acid sequence at least 85% identical (e.g., at least 90%, 95%, 98%, 99% or 100% identical) with the amino acid sequence as set forth in SEQ ID NO: 11. In some embodiments, a humanized Tmprss4 protein contains an ectodomain substantially identical (e.g., at least 85%, 90%, 95%, 98%, 99% or 100% identical) with the amino acid sequence composed of residues K54 to LA37 or the C-terminal 384 amino acids of a human TMPRSS4 protein as set forth in, e.g., SEQ ID NO: 11. In some embodiments, the humanized Tmprss4 gene encodes a humanized Tmprss4 protein that further contains a cytoplasmic and transmembrane portion that is substantially identical (e.g., at least 85%, 90%, 95%, 98%, 990/0 or 100% identical) with the cytoplasmic and transmembrane portion of the rodent Tmprss4 protein encoded by the endogenous rodent Tmprss4 gene being humanized. An exemplary endogenous rodent Tmprss4 protein is set forth in SEQ ID NO: 9.

In some embodiments, a rodent contains a humanized Tmprss4 gene that includes a nucleotide sequence of an endogenous rodent Tmprss4 gene and a nucleotide sequence of a human TMPRSS4 gene, wherein the nucleotide sequence of a human TMPRSS4 gene encodes an ectodomain substantially identical with the ectodomain of the human TMPRSS4 protein encoded by the human TMPRSS4 gene. In specific embodiments, the nucleotide sequence of a human TMPRSS4 gene is a contiguous genomic sequence containing coding exon 4 through the stop codon in coding exon 13 of a human TMPRSS4 gene. In some embodiments, the nucleotide sequence of an endogenous rodent Tmprss4 gene included in a humanized Tmprss4 gene encodes a cytoplasmic and transmembrane portion that is substantially identical with the cytoplasmic and transmembrane portion of the rodent Tmprss4 protein encoded by the endogenous rodent Tmprss4 gene.

In particular embodiments, a humanized Tmprss4 gene contains coding exon 1 through coding exon 3 of an endogenous rodent Tmprss4 gene, and coding exon 4 through the stop codon in coding exon 13 of a human TMPRSS4 gene.

In some embodiments, a rodent disclosed herein contains a humanized Tmprss11d gene that includes a nucleotide sequence of an endogenous rodent Tmprss11d gene and a nucleotide sequence of a human TMPRSS11D gene, wherein the humanized Tmprss11d gene is under control of the promoter of the endogenous rodent Tmprss11d gene.

In some embodiments, the humanized Tmprss11d gene encodes a humanized Tmprss11d protein that contains an ectodomain substantially identical (e.g., at least 85%, 90% 0, 95%, 98%, 99% or 100% identical in sequence) with the ectodomain of the human TMPRSS11D protein encoded by the human TMPRSS11D gene used in humanization. The human TMPRSS11D protein contains, in some embodiments, an amino acid sequence at least 85% identical (e.g., at least 90%, 95%, 98%, 99% or 100% identical) with the amino acid sequence as set forth in SEQ ID NO: 18. In some embodiments, a humanized Tmprss11d protein contains an ectodomain substantially identical (e.g., at least 85%, 90%, 95%, 98%, 99% or 100% identical) with the amino acid sequence composed of residues A42-I418 or the C-terminal 377 amino acids of a human TMPRSS11D protein as set forth in, e.g., SEQ ID NO: 18. In some embodiments, the humanized Tmprss11d gene encodes a humanized Tmprss11d protein that further contains a cytoplasmic and transmembrane portion that is substantially identical (e.g., at least 85%, 90%, 95%, 98%, 99% or 100% identical) with the cytoplasmic and transmembrane portion of the endogenous rodent Tmprss11d protein encoded by the endogenous rodent Tmprss11d gene being humanized. An exemplary endogenous rodent Tmprss11d protein is set forth in SEQ ID NO: 16.

In some embodiments, a rodent contains a humanized Tmprss11d gene that includes a nucleotide sequence of an endogenous rodent Tmprss11d gene and a nucleotide sequence of a human TMPRSS11D gene, wherein the nucleotide sequence of the human TMPRSS11D gene encodes an ectodomain substantially identical with the ectodomain of the human TMPRSS11D protein encoded by the human TMPRSS11D gene. In specific embodiments, the nucleotide sequence of a human TMPRSS11d gene is a contiguous genomic sequence containing coding exon 3 through the stop codon in coding exon 10 of a human TMPRSS11D gene. In particular embodiments, the contiguous genomic sequence of a human TMPRSS11D gene further contains the 3' UTR of the human TMPRSS11D gene. In some embodiments, the nucleotide sequence of an endogenous rodent Tmprss11d gene included in a humanized Tmprss11d gene encodes a cytoplasmic and transmembrane portion that is substantially identical with the cytoplasmic and transmembrane portion of the rodent Tmprss11d protein encoded by the endogenous rodent Tmprss11d gene.

In particular embodiments, a humanized Tmprss11d gene contains coding exons 1-2 of an endogenous rodent Tmprss11d gene, and coding exon 3 through coding exon 13 of a human TMPRSS11D gene.

In another aspect, the invention provides an isolated rodent cell or tissue whose genome contains a humanized Tmprss gene as described herein. In specific embodiments, the humanized Tmprss gene is selected from the group consisting of a humanized Tmprss2 gene, a humanized Tmprss4 gene, and a humanized Tmprss11d gene.

In still another aspect, the invention provides a rodent embryonic stem cell whose genome contains a humanized Tmprss gene as described herein. In specific embodiments, the humanized Tmprss gene is selected from the group consisting of a humanized Tmprss2 gene, a humanized Tmprss4 gene, and a humanized Tmprss11d gene.

In another aspect, a rodent embryo generated from the rodent embryonic stem cell disclosed herein is also provided.

In one aspect, the invention provides a nucleic acid vector suitable for use in humanizing an endogenous Tmprss gene in a rodent. In some embodiments, the nucleic acid vector includes a human Tmprss nucleic acid sequence (e.g., a human genomic DNA encoding the ectodomain of a human TMPRSS protein), flanked by a 5' homology arm and a 3' homology arm. The 5' and 3' homology arms are nucleic acid sequences that are placed at 5' and 3', respectively, to the human Tmprss nucleic acid sequence and are homologous to genomic DNA sequences at an endogenous Tmprss locus in a rodent that flank a rodent genomic DNA encoding the ectodomain of a cognate rodent Tmprss protein. Thus, the 5' and 3' homology arms are capable of mediating homologous recombination and replacement of the rodent genomic DNA encoding the ectodomain of the cognate rodent Tmprss protein with the human Tmprss nucleic acid sequence to form a humanized Tmprss gene as described herein.

In a further aspect, the invention is directed to a method of providing a rodent whose genome contains a humanized Tmprss gene. The method includes modifying the genome of a rodent to replace a genomic sequence of an endogenous rodent Tmprss gene with a genomic sequence of a cognate human TMPRSS gene to form a humanized Tmprss gene.

In some embodiments, the invention provides a method of making a rodent (such as a mouse or a rat) having a humanized Tmprss gene, the method including the steps of (a) inserting a genomic fragment into an endogenous rodent Tmprss locus in a rodent embryonic stem cell, wherein the genomic fragment contains a nucleotide sequence of a cognate human TMPRSS gene, thereby forming a humanized Tmprss gene (such as those described herein); (b) obtaining a rodent embryonic stem cell comprising the humanized Tmprss gene of (a); and (c) creating a rodent using the rodent embryonic stem cell of (b).

In some embodiments, the humanized Tmprss gene is selected from the group consisting of a humanized Tmprss2 gene, a humanized Tmprss4 gene, and a humanized Tmprss11d gene. In various embodiments, the humanized Tmprss gene encodes a humanized Tmprss protein that contains an ectodomain substantially identical (e.g., at least 90%, 95%, 98%, 99% or 100% identical in sequence) to the ectodomain of the human TMPRSS protein encoded by the human TMPRSS gene used for humanization. In specific embodiments, the humanized Tmprss protein contains the ectodomain of a human TMPRSS protein selected from the group consisting of a human TMPRSS2 protein, a human TMPRSS4 protein, and a human TMPRSS11D protein. In specific embodiments, the humanized Tmprss protein further contains a cytoplasmic and transmembrane portion that is substantially identical with the cytoplasmic and transmembrane portion of the rodent Tmprss protein encoded by the endogenous rodent Tmprss gene being humanized.

In another aspect, the invention provides a method of using a rodent disclosed herein to assess the therapeutic efficacy of a compound (e.g., candidate inhibitors that specifically target a human TMPRSS protein) in treating influenza virus infection. The method can include the steps of providing a rodent described herein, administering an influenza virus and a candidate compound to the rodent; and monitoring the presence and severity of influenza virus infection in the rodent to determine the therapeutic efficacy of the drug candidate.

In some embodiments, the influenza virus is administered to the rodent before the compound. In other embodiments, the influenza virus is administered to the rodent after the compound.

In some embodiments, the candidate compound is an antibody or antigen-binding fragment thereof specific for a human TMPRSS protein. In specific embodiments, the candidate compound is an antibody or antigen-binding fragment thereof specific for a human TMPRSS protein selected from the group consisting of a human TMPRSS2 protein, a human TMPRSS4 protein, and a human TMPRSS11D protein.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The Drawings included herein, which are composed of the following Figures, are for illustration purposes only and not for limitation.

FIGS. 1A-1D. Exemplary strategy for humanization of mouse Tmprss2.

FIG. 1A shows a diagram, not to scale, of the genomic organization of mouse Tmprss2 and human TMPRSS2 genes. Exons are represented by thin bars placed across the genomic sequences, with the first coding exon for both genes indicated by the start codon "ATG" above the exon, and the last coding exon indicated by the "Stop" codon above the exon. A mouse genomic fragment of about 25,291 bp to be deleted and a human genomic fragment of about 25,091 bp to be inserted are indicated. Locations of probes used in an assay described in Example 1 are indicated. TM: transmembrane domain; SRCR: scavenger receptor cysteine-rich like domain; LDLRa: low density lipoprotein receptor class A.

FIG. 1B illustrates, not to scale, an exemplary modified BAC vector for humanization of an endogenous mouse Tmprss2 gene, along with the junction sequences (SEQ ID NOS: 22, 23 and 24).

FIG. 1C illustrates, not to scale, a humanized Tmprss2 allele after the neomycin cassette has been deleted, along with the junction sequences (SEQ ID NOS: 22 and 25).

FIG. 1D sets forth a sequence alignment of a human TMPRSS2 protein (SEQ ID NO: 4), a mouse Tmprss2 protein (SEQ ID NO: 2), and a humanized Tmprss2 protein ("7010 mutant pro") (SEQ ID NO: 7).

FIGS. 2A-2D. Exemplary strategy for humanization of mouse Tmprss4.

FIG. 2A shows a diagram, not to scale, of the genomic organization of mouse Tmprss4 and human TMPRSS4 genes. Exons are represented by thin bars placed across the genomic sequences, with the first exon (also the first coding exon) for both genes indicated by the start codon "ATG" above the exon, and the last coding exon indicated by the "Stop" codon above the exon. The mouse genomic fragment of about 11,074 bp to be deleted and the human genomic fragment of about 14,963 bp to be inserted are indicated. Locations of probes used in an assay described in Example 2 are indicated. TM: transmembrane domain; SRCR: scavenger receptor cysteine-rich like domain; LDLRa: low density lipoprotein receptor class A.

FIG. 2B illustrates, not to scale, an exemplary modified BAC vector for humanization of an endogenous mouse Tmprss4 gene, along with the junction sequences (SEQ ID NOS: 38, 39 and 40).

FIG. 2C illustrates, not to scale, a humanized Tmprss4 allele after the neomycin cassette has been deleted, along with the junction sequences (SEQ ID NOS: 41 and 40).

FIG. 2D sets forth a sequence alignment of a human TMPRSS4 protein (SEQ ID NO: 11), a mouse Tmprss4 protein (SEQ ID NO: 9), and a humanized Tmprss4 protein ("7224 mutant pro") (SEQ ID NO: 14).

FIGS. 3A-3D. Exemplary strategy for humanization of mouse Tmprss11d.

FIG. 3A shows a diagram, not to scale, of the genomic organization of mouse Tmprss11d and human TMPRSS11D genes. Exons are represented by thin bars placed across the genomic sequences, with the first exon (also the first codon exon) for both genes indicated by the start codon "ATG" above the exon, and the last coding exon indicated by the "Stop" codon above the exon. A mouse genomic fragment of about 35,667 bp to be deleted and a human genomic fragment of about 33,927 bp to be inserted are indicated. Locations of probes used in an assay described in Example 3 are indicated. TM: transmembrane domain; SEA: domain found in sea urchin sperm protein, enterokinase and agrin.

FIG. 3B illustrates, not to scale, an exemplary modified BAC vector for humanization of an endogenous mouse Tmprss11d gene, along with the junction sequences (SEQ ID NOS: 57, 58 and 59).

FIG. 3C illustrates, not to scale, a humanized Tmprss11 allele after the neomycin cassette has been deleted, along with the junction sequences (SEQ ID NOS: 57 and 60).

FIG. 3D sets forth a sequence alignment of a human TMPRSS11D protein (SEQ ID NO: 18), a mouse Tmprss11d protein (SEQ ID NO: 16), and a humanized Tmprss11d protein ("7226 mutant pro") (SEQ ID NO: 21).

DETAILED DESCRIPTION OF CERTAIN EMBODIMENTS

Figure 1A:
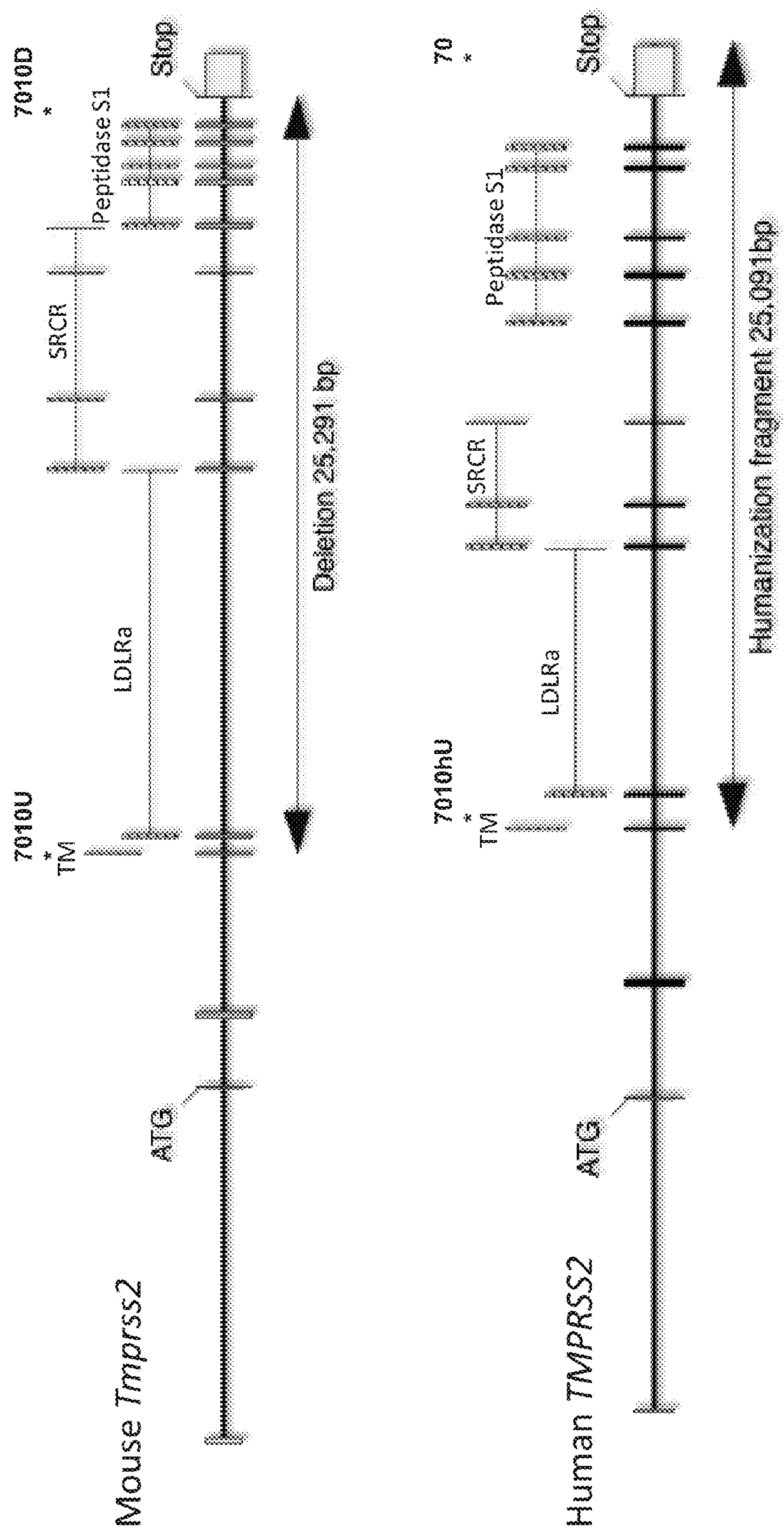

The present invention relates to genetically modified rodents (e.g., mice and rats) having a humanized gene encoding a type II transmembrane serine protease (or "Tmprss", for transmembrane protease/serine). The genetically modified rodents are suitable for use in screening for candidate compounds that specifically target a human TMPRSS molecule for the treatment and prevention of diseases such as influenza virus infection. Accordingly, the present invention provides genetically modified rodents having a humanized Tmprss gene, cells and tissues isolated from the genetically modified rodents, methods and compositions for making the genetically modified rodents, and use of the genetically modified rodents for screening and testing therapeutic compounds. The various embodiments of the present invention are further described below.

Type II Transmembrane Serine Proteases ("Tmprss")

Type II transmembrane serine proteases, also referred to herein as "Tmprss" for non-human molecules or "TMPRSS" for human molecules ("transmembrane protease/serine"), are a family of proteins characterized by an N-terminal transmembrane domain and a C-terminal extracellular serine protease domain. At least 18 members have been identified in the family, which are grouped into four subfamilies (Bugge et al. (2009), supra). All members share several common structural features that define the family, including (i) a short N-terminal cytoplasmic domain, (ii) a transmembrane domain, and (iii) an ectodomain that contains a protease domain and a stem region that links the transmembrane domain with the protease domain. The stem region contains a combination of modular structural domains of six different types: a SEA (sea urchin sperm protein/enteropeptidase/agrin) domain, a group A scavenger receptor domain, a LDLA (low-density lipoprotein receptor class A) domain, a CUB (Cls/Clr urchin embryonic growth factor, bone morphogenetic protein-1) domain, a MAM (meprin/A5 antigen/receptor protein phosphatase mu) domain, and a frizzled domain. See review by Bugge et al. (2009), supra. For example, TMPRSS2 and TMPRSS4, both of which belong to the hepsin/TMPRSS subfamily, have a group A scavenger receptor domain, preceded by a single LDLA domain in the stem region. TMPRSS11D, also known as "HAT" for human airway trypsin-like protease that belongs to the HAT/DESC subfamily, has a single SEA domain. See FIG. 1 of Bugge et al. (2009), supra.

Type II transmembrane serine proteases are produced initially as inactive proenzymes that require activation by cleavage following a basic amino acid residue in a consensus activation motif preceding the protease domain. Some of the activated proteases remain membrane bound as a result of a disulfide bond between the prodomain and the protease domain. The extracellular domains are considered to be critical for cellular localization, activation, inhibition, and/or substrate specificity of these proteases (Bugge et al. (2009), supra; Szabo et al., *Int. J. Biochem. Cell Biol.* 40: 1297-1316 (2008)).

Various biochemical and pathophysiological information has been documented for members of the type II transmembrane serine proteases. TMPRSS2, TMPRSS4 and TMPRSS11D have been shown in vitro to cleave influenza A hemagglutinin (HA), which is the first essential step in the viral life cycle. Genetically modified rodent animals having a humanized Tmprss gene disclosed herein provide useful in vivo systems that allow for a thorough understanding of the biological functions of the TMPRSS molecules, as well as for screening therapeutic compounds that specifically target human TMPRSS molecules.

Exemplary Tmprss sequences, including mouse, human and humanized Tmprss nucleic acid and protein sequences, are provided in this application and are summarized in the following table. Primer and probe sequences used in the assays described in the examples section, and insertion junction sequences of exemplary humanized Tmprss alleles, are also included in the table.

Summary Description of Sequences

| SEQ ID NO | Description | Features |
|---|---|---|
| 1 | *Mus musculus* Tmprss2, mRNA, NM_015775.2 | Length: 3175 bp CDS: 231-1703 Exons: 1-177; 178-245 (second exon, and first coding exon); 246-465; 466-552; 553-672; 673-799; 800-910; 911-954; 955-1123; 1124-1299; 1300-1395; 1396-1538; 1539-1691; 1692-3161. |
| 2 | *Mus musculus* Tmprss2, protein | Length: 490 aa |
| 3 | *Homo sapiens* TMPRSS2, transcript variant 2, mRNA, NM_005656.3 | Length: 3212 bp CDS: 135-1613 Exons: 1-78; 79-149 (second exon, and first coding exon); 150-372; 373-459; 460-579; 580-706; 707-817; 818-861; 862-1033; 1034-1209; 1210-1305; 1306-1448; 1449-1601; 1602-3204, |
| 4 | *Homo sapiens* TMPRSS2, transcript variant 2, protein | Length: 492 aa Ectodomain: begins at W106. |

-continued

Summary Description of Sequences

| SEQ ID NO | Description | Features |
|---|---|---|
| 5 | Humanization Tmprss2 genomic fragment | Length: 27,947 bp 1-84: mouse sequence 85-25175: human sequence (total 25091 bp) 25176-27866: XhoI-LoxP-Cassette-loxP-ICeUI-NheI (total 2691 bp) 27867-27947: mouse sequence |
| 6 | Humanization Tmprss2 genomic fragment with cassette deleted | Length: 25,333 bp 1-84: mouse sequence 85-25175: human sequence (total 25091 bp) 25176-25252: XhoI-loxP-ICeUI-NheI (77 bp) 25253-25333: mouse sequence |
| 7 | Humanized Tmprss2 protein | Length: 491 aa |
| 8 | *Mus musculus* Tmprss4, mRNA, NM_145403.2 | Length: 2267 bp CDS: 289-1596 Exons: 1-291 (first exon and first coding exon); 292-325; 326-439; 440-592; 593-722; 723-824; 825-865; 866-1025; 1026-1192; 1193-1291; 1292-1434; 1435-1584; 1585-2267. |
| 9 | *Mus musculus* Tmprss4, protein | Length: 435 aa |
| 10 | *Homo sapiens* TMPRSS4, transcript variant 4, mRNA, NM_001173551.1 | Length: 3543 bp CDS: 292-1599 Exons: 1-294 (first exon and first coding exon); 295-328; 329-442; 443-595; 596-725; 726-827; 828-868; 869-1028; 1029-1195; 1196-1294; 1295-1437; 1438-1587; 1588-3529. |
| 11 | *Homo sapiens* TMPRSS4, transcript variant 4, protein | Length: 437 aa Ectodomain: begins at K54. |
| 12 | Humanization Tmprss4 genomic fragment containing cassette | Length: 20,078 bp 1-18: mouse sequence 19-5014: SalI/XhoI-LoxP-hUbi-EM7-Neo-Pm-Cre-loxP-ICeuI-NheI (total 4996 bp) 5015-19977: HUMAN sequence (total 14963 bp) 19978-20078: mouse sequence |
| 13 | Humanization Tmprss4 genomic fragment with cassette deleted | Length: 15159 bp 1-18: mouse sequence 19-95: SalI/XhoI-LoxP-ICeuI-NheI (total 77 bp) 96-15058: HUMAN sequence (total 14963 bp) 15059-15159: mouse sequence |
| 14 | Humanized Tmprss4 Protein | Length: 435 aa |
| 15 | *Mus musculus* Tmprss11d, mRNA, NM_145561.2 | Length: 2046 bp CDS: 36-1289 Exons: 1-43 (first exon and first coding exon), 44-165, 166-284; 285-352; 353-507; 508-546; 547-724; 725-984; 985-1127; 1128-2046. |
| 16 | *Mus musculus* Tmprss11d, protein | Length: 417 aa |
| 17 | *Homo sapiens* TMPRSS11D, mRNA, NM_004262.2 | Length: 2800 bp CDS: 66-1322 Exons: 1-73 (first exon and first coding exon); 74-195; 196-314; 315-382; 383-540; 541-579; 580-757; 758-1017; 1018-1160; 1161-2783. |
| 18 | *Homo sapiens* TMPRSS11D, protein | Length: 418 aa Ectodomain begins at A42. |

-continued

| Summary Description of Sequences | | |
|---|---|---|
| SEQ ID NO | Description | Features |
| 19 | Humanization Tmprss11d genomic fragment containing cassette | Length: 38,992 1-19: mouse sequence 20-33,946: HUMAN sequence (total 33,927 bp) 33,947-38,942: XhoI-LoxP-hUbi-EM7-Neo-Pm-Cre-loxP-ICeuI-NheI (total 4,996 bp) 38,943-38,992: mouse sequence |
| 20 | Humanization Tmprss11d genomic fragment with cassette deleted | Length: 34,073 bp 1-19: mouse sequence 20-33,946: HUMAN sequence (total 33,927 bp) 33,947-34,023: XhoI-LoxP-ICeuI-NheI (77 bp) 34,024-34,073: mouse sequence |
| 21 | Humanized Tmprss11d Protein | 418 aa |
| 22 | 5' mouse/5' human junction sequence for Tmprss2 humanization | 5' mouse//5' human |
| 23 | 3' human/cassette junction sequence for Tmprss2 humanization | Human//XhoI//loxP Cassette |
| 24 | Cassette/3' mouse junction sequence for Tmprss2 humanization | Cassette (loxP)/ICEUI//NheI//mouse |
| 25 | 3' human/loxP/3' mouse junction for Tmprss2 humanization | 3' human//XhoI//(loxP)/ICEUI// NheI//3' mouse |
| 26-37 | Primers and probes for loss of allele and gain of allele assays for Tmprss2 humanization | Table 1 |
| 38 | 5' mouse/Cassette junction sequence for Tmprss4 humanization | 5' mouse//SalI-XhoI//(loxP) Cassette |
| 39 | Cassette/5' human junction sequence for Tmprss4 humanization | Cassette (loxP)/ICEUI//NheI//5' human |
| 40 | 3' human/3' mouse junction sequence for Tmprss4 humanization | 3' human/3' mouse |
| 41 | 5' mouse/loxP/5' human junction for Tmprss4 humanization | 5' mouse//SalI/XhoI//(loxP)/ICEUI// NheI//5' human |
| 42-56 | Primers and probes for loss of allele and gain of allele assays for Tmprss4 humanization | Table 2 |
| 57 | 5' mouse/5' human junction sequence for Tmprss11d humanization | 5' mouse//5' human |
| 58 | 3' human/cassette junction sequence for Tmprss11d humanization | 3' human//XhoI//(loxP) Cassette |
| 59 | Cassette/3' mouse junction sequence for Tmprss11d humanization | Cassette (loxP)/ICEUI//NheI//3' mouse |
| 60 | 3' human/loxP/3' mouse junction for Tmprss11d humanization | 3' human//XhoI//(loxP)/ICEUI// NheI//3' mouse |
| 61-72 | Primers and probes for loss of allele and gain of allele assays for Tmprss11d humanization | Table 3 |

Humanized Tmprss Rodent Animals

In one aspect, the present invention provides rodent animals that contain in the germline a humanized Tmprss gene encoding a humanized Tmprss protein.

The term "humanized", when used in the context of nucleic acids or proteins, refers to nucleic acids or proteins whose structures (i.e., nucleotide or amino acid sequences) include portions that correspond substantially or identically with structures of a particular gene or protein found in nature in a rodent animal, and also include portions that differ from that found in the relevant rodent gene or protein and instead correspond more closely or identically with structures found in a corresponding human gene or protein. A rodent containing a humanized gene or expressing a humanized protein is a "humanized" rodent.

In some embodiments, a rodent of the present invention is selected from a mouse, a rat, and a hamster. In some embodiments, a rodent of the present invention is selected from the superfamily Muroidea. In some embodiments, a genetically modified rodent of the present invention is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, *Malagasy* rats and mice), Platacanthomyidae (e.g., spiny dormice), and Spalacidae (e.g., mole rates, bamboo rats, and zokors). In some certain embodiments, a genetically modified rodent of the present invention is selected from a true mouse or rat (family Muridae), a gerbil, a spiny mouse, and a crested rat. In some certain embodiments, a genetically modified mouse of the present invention is from a member of the family Muridae.

In some embodiments, the rodent disclosed herein contains a humanized Tmprss gene in the genome that includes a nucleotide sequence of an endogenous rodent Tmprss gene and a nucleotide sequence of a human TMPRSS gene, wherein the nucleotide sequence of the endogenous rodent Tmprss gene and the nucleotide sequence of the human TMPRSS gene are operably linked to each other such that the humanized Tmprss gene encodes a Tmprss protein and is under control of a 5' regulatory element(s), such as the promoter and/or enhancer(s), of the endogenous rodent Tmprss gene.

The present invention is particularly directed to like-for-like humanization; in other words, a nucleotide sequence of an endogenous rodent Tmprss gene is operably linked to a nucleotide sequence of a cognate human TMPRSS gene to form a humanized gene. For example, in some embodiments, a nucleotide sequence of an endogenous rodent Tmprss2 gene is operably linked to a nucleotide sequence of a human TMPRSS2 gene to form a humanized Tmprss2 gene. In other embodiments, a nucleotide sequence of an endogenous rodent Tmprss4 gene is operably linked to a nucleotide sequence of a human TMPRSS4 gene to form a humanized Tmprss4 gene. In still other embodiments, a nucleotide sequence of an endogenous rodent Tmprss11d gene is operably linked to a nucleotide sequence of a human TMPRSS11D gene to form a humanized Tmprss11d gene.

In some embodiments, a genetically modified rodent of this invention contains a humanized Tmprss gene in its genome, wherein the humanized Tmprss gene encodes a humanized Tmprss protein that contains an ectodomain that is substantially identical with the ectodomain of a human TMPRSS protein. The term "ectodomain" refers to the portion of a transmembrane protein that extends outside of the cell membrane, i.e., the extracellular portion of a transmembrane protein. The ectodomain of a TMPRSS molecule includes a protease domain and a stem region that links the transmembrane domain with the protease domain. By an ectodomain or polypeptide that is "substantially identical with the ectodomain of a human TMPRSS protein", it is meant in some embodiments, a polypeptide that is at least 85%, 90%, 95%, 95%, 99% or 100% identical in sequence with the ectodomain of a human TMPRSS protein; in some embodiments, a polypeptide that differs from the ectodomain of a human TMPRSS protein by not more than 10, 9, 8, 7, 6, 5, 4, 3, 2 or 1 amino acid(s); in some embodiments, a polypeptide that differs from the ectodomain of a human TMPRSS protein only at the N- or C-terminus of the ectodomain, e.g., by lacking amino acids or having additional amino acids at the at the N- or C-terminus of the ectodomain; and in some embodiments, a polypeptide that is substantially the ectodomain of a human TMPRSS protein. By "substantially the ectodomain" of a human TMPRSS protein, it is meant a polypeptide that is identical with the ectodomain, or differs from the ectodomain by lacking 1-5 (i.e., 1, 2, 3, 4 or 5) amino acids or having additional 1-5 amino acids at the N- or C-terminus.

In some embodiments, the humanized Tmprss gene encodes a humanized Tmprss protein that further contains a cytoplasmic and transmembrane portion that is substantially identical with the cytoplasmic and transmembrane portion of an endogenous rodent Tmprss protein. By a cytoplasmic and transmembrane portion or polypeptide that is "substantially identical with the cytoplasmic and transmembrane portion of an endogenous rodent Tmprss protein", it is meant in some embodiments, a polypeptide that is at least 85%, 90%, 95%, 95%, 99% or 100% identical in sequence with the cytoplasmic and transmembrane portion of an endogenous rodent Tmprss protein; in some embodiments, a polypeptide that differs from the cytoplasmic and transmembrane portion of an endogenous rodent Tmprss protein by not more than 10, 9, 8, 7, 6, 5, 4, 3, 2 or 1 amino acid(s); in some embodiments, a polypeptide that differs from the cytoplasmic and transmembrane portion of an endogenous rodent Tmprss protein only at the C-terminus, e.g., by lacking amino acids or having additional amino acids at the at the C-terminus of the transmembrane domain; and in some embodiments, a polypeptide composed of the cytoplasmic domain and substantially the transmembrane domain of an endogenous rodent Tmprss protein. By "substantially the transmembrane domain" of an endogenous rodent Tmprss protein, it is meant a polypeptide that is identical with the transmembrane domain, or differs from the transmembrane domain by lacking 1-5 amino acids or having additional 1-5 amino acids at the C-terminus.

In some embodiments, the humanized Tmprss gene in the genome of a genetically modified rodent includes a nucleotide sequence of an endogenous rodent Tmprss gene and a nucleotide sequence of a cognate human TMPRSS gene, wherein the nucleotide sequence of the cognate human TMPRSS gene encodes a polypeptide substantially identical to the ectodomain of the human TMPRSS protein encoded by the human TMPRSS gene. In certain embodiments, the nucleotide sequence of a cognate human TMPRSS gene in a humanized Tmprss gene encodes the ectodomain of the human TMPRSS protein encoded by the human TMPRSS gene.

In some embodiments, the humanized Tmprss gene in the genome of a genetically modified rodent includes a nucleotide sequence of an endogenous rodent Tmprss gene and a nucleotide sequence of a cognate human TMPRSS gene, wherein the nucleotide sequence of an endogenous rodent Tmprss gene encodes a polypeptide substantially identical to the cytoplasmic and transmembrane portion of the endogenous rodent Tmprss protein encoded by the rodent Tmprss gene. In specific embodiments, the nucleotide sequence of an endogenous rodent Tmprss gene present in a humanized Tmprss gene encodes the cytoplasmic and transmembrane domains of the endogenous rodent Tmprss protein encoded by the endogenous rodent Tmprss gene.

In some embodiments, a humanized Tmprss gene results from a replacement of a nucleotide sequence of an endogenous rodent Tmprss gene at an endogenous rodent Tmprss locus with a nucleotide sequence of a cognate human TMPRSS gene.

In some embodiments, a contiguous genomic sequence of a rodent Tmprss gene at an endogenous rodent Tmprss locus has been replaced with a contiguous genomic sequence of a cognate human TMPRSS gene to form a humanized Tmprss gene.

In specific embodiments, a contiguous genomic sequence of a human TMPRSS gene inserted into an endogenous rodent Tmprss gene includes exons, in full or in part, of a human TMPRSS gene, that encode an ectodomain that is substantially identical with the ectodomain of the human TMPRSS protein encoded by the human TMPRSS gene.

In certain embodiments, the genomic sequence of an endogenous rodent Tmprss gene that remains at an endogenous rodent Tmprss locus after the humanization replacement and is operably linked to the inserted contiguous human TMPRSS genomic sequence encodes a cytoplasmic and transmembrane portion that is substantially identical with the cytoplasmic and transmembrane portion of the endogenous rodent Tmprss protein encoded by the endogenous rodent Tmprss gene.

In circumstances where an endogenous Tmprss protein and a human TMPRSS protein share common amino acids near the junction between the transmembrane domain and the ectodomain, it may not be necessary to insert a human TMPRSS genomic sequence that encodes precisely the ectodomain of the human TMPRSS protein. It is possible to insert a slightly longer or shorter genomic sequence of a human TMPRSS gene, which encodes substantially the ectodomain of the human TMPRSS protein, in operable linkage to a genomic sequence of an endogenous rodent Tmprss gene that encodes the cytoplasmic domain and substantially the transmembrane domain of the endogenous rodent Tmprss protein, such that the humanized Tmprss protein encoded by the resulting humanized Tmprss gene includes an ectodomain that is identical with the ectodomain of the human TMPRSS protein and a transmembrane domain that is identical with the transmembrane domain of the endogenous rodent Tmprss protein.

In some embodiments, the nucleotide sequence of a human TMPRSS gene included in a humanized Tmprss gene also includes the 3' untranslated region ("UTR") of the human TMPRSS gene. In certain embodiments, in addition to the 3' UTR of a human TMPRSS gene, a humanized Tmprss gene also includes an additional human genomic sequence from the human TMPRSS gene locus, following the human TMPRSS3' UTR. The additional human genomic sequence can consist of at least 10-200 bp, e.g., 50 bp, 75 bp, 100 bp, 125 bp, 150 bp, 175 bp, 200 bp, or more, found in the human TMPRSS gene locus immediately downstream of the 3' UTR of the human TMPRSS gene. In other embodiments, the nucleotide sequence of a human TMPRSS gene present in a humanized Tmprss gene does not include a human 3' UTR; instead, the 3' UTR of an endogenous rodent Tmprss gene is included and follows immediately the stop codon of the humanized Tmprss gene. For example, a humanized Tmprss gene can include a nucleotide sequence of an endogenous rodent Tmprss gene containing exon sequences encoding the cytoplasmic and transmembrane domains of the endogenous rodent Tmprss protein, followed by a nucleotide sequence of a human TMPRSS gene containing exon sequences encoding the ectodomain through the stop codon of the human TMPRSS protein, with the 3' UTR of the endogenous rodent Tmprss gene following immediately after the stop codon.

In some embodiments, a humanized Tmprss gene results in an expression of the encoded humanized Tmprss protein in a rodent. In some embodiments, a humanized Tmprss protein is expressed in a pattern comparable with, or substantially the same as, a counterpart rodent Tmprss protein in a control rodent (e.g., a rodent without the humanized Tmprss gene). In some embodiments, a humanized Tmprss protein is expressed at a level comparable with, or substantially the same as, a counterpart rodent Tmprss protein in a control rodent (e.g., a rodent without the humanized Tmprss gene). In certain embodiments, a humanized Tmprss protein is expressed and detected at the cell surface. In certain embodiments, a humanized Tmprss protein or a soluble form (e.g., a shed ectodomain form) is expressed and detected in serum of a rodent, e.g., at a level comparable with, or substantially the same as, a counterpart rodent Tmprss protein or a soluble form thereof in a control rodent. In the context of comparing a humanized gene or protein in a humanized rodent with an endogenous rodent gene or protein in a control rodent, the term "comparable" means that the molecules or levels being compared may not be identical to one another but are sufficiently similar to permit comparison there between so that conclusions may reasonably be drawn based on differences or similarities observed; and the term "substantially the same" in referring to expression levels means that the levels being compared are not different from one another by more than 20%, 19%, 18%, 17%, 16%, 15%, 14%, 13%, 12%, 11%, 10%, 9%, 8%, 7%, 6%, 5%, 4%, 3%, 2%, or 1%.

In some embodiments, the present invention further provides an isolated cell or tissue from a rodent animal as described herein. In some embodiments, a cell is selected from a dendritic cell, lymphocyte (e.g., a B or T cell), macrophage and a monocyte. In some embodiments, a tissue is selected from adipose, bladder, brain, breast, bone marrow, eye, heart, intestine, kidney, liver, lung, lymph node, muscle, pancreas, plasma, serum, skin, spleen, stomach, thymus, testis, ovum, and a combination thereof.

In some embodiments, the present invention provides a rodent embryonic stem cell whose genome contains a humanized Tmprss gene as described herein. In some embodiments, a rodent embryonic stem cell is a mouse embryonic stem cell. In other embodiments, a rodent embryonic stem cell is a rat embryonic stem cell. A rodent embryonic stem cell containing a humanized Tmprss gene in its genome can be used to make a humanized rodent animal, as further described herein below.

In some embodiments, a rodent provided herein is heterozygous for a humanized Tmprss gene in its genome. In other embodiments, a rodent provided herein is homozygous for a humanized Tmprss gene in its genome.

In certain embodiments, a rodent includes multiple, i.e., two or more, humanized Tmprss genes in its genome. In other words, two or more different endogenous Tmprss loci in a rodent have been humanized using nucleotide sequences of cognate human TMPRSS genes. For example, a rodent has been humanized at two or more of the gene loci selected from: Tmprss2, Tmprss4, and Tmprss11d.

Exemplary humanized Tmprss2 rodents (such as mice), humanized Tmprss4 rodents (such as mice), and humanized Tmprss11d rodents (such as mice) are further described below.

Humanized Tmprss2 Rodents

In some embodiments, this invention provides a rodent whose genome contains a humanized Tmprss2 gene that includes a nucleotide sequence of an endogenous rodent Tmprss2 gene and a nucleotide sequence of a human TMPRSS2 gene, and that is under control of a 5' regulatory element(s), such as the promoter and/or enhancer(s), of the endogenous rodent Tmprss2 gene. Examples of rodents include mice and rats.

In some embodiments, a humanized Tmprss2 gene encodes a humanized Tmprss2 protein that contains an ectodomain that is substantially identical with the ectodomain of a human TMPRSS2 protein.

In specific embodiments, the human TMPRSS2 protein has an amino acid sequence having at least 85%, 90%, 95%, 98%, 99% or 100% identity with the amino acid sequence as set forth in SEQ ID NO: 4.

In some embodiments, a humanized Tmprss2 protein contains the C-terminal 387 amino acids of a human TMPRSS2 protein, for example, amino acids 106 to 492 of a human TMPRSS2 protein. In some embodiments, a humanized Tmprss2 protein contains an ectodomain that is substantially identical with the amino acid sequence composed of W106 to G492 of SEQ ID NO: 4. In specific embodiments, a humanized Tmprss2 protein contains an ectodomain having at least 85%, 90%, 95%, 98%, 99% or 100% identity with the amino acid sequence composed of W106 to G492 of SEQ ID NO: 4; an ectodomain that differs from the amino acid sequence composed of W106 to G492 of SEQ ID NO: 4 by not more than 10, 9, 8, 7, 6, 5, 4, 3, 2 or 1 amino acid(s); or an ectodomain that differs from the amino acid sequence composed of W106 to G492 of SEQ ID NO: 4 only at the N- or C-terminus of the ectodomain, e.g., lacking 1-5 amino acids or having additional 1-5 amino acids at the at the N- or C-terminus.

In some embodiments, a humanized Tmprss2 protein further contains a cytoplasmic and transmembrane portion that is substantially identical with the cytoplasmic and transmembrane portion of an endogenous rodent Tmprss2 protein. In some embodiments, a humanized Tmprss2 protein further includes the transmembrane domain and the cytoplasmic domain of an endogenous rodent Tmprss2 protein.

In specific embodiments, a humanized Tmprss2 protein contains the transmembrane domain and the cytoplasmic domain of an endogenous rodent Tmprss2 protein, and the ectodomain of a human TMPRSS2 protein. In particular embodiments, a humanized Tmprss2 gene encodes a humanized Tmprss2 protein having the amino acid sequence as set forth in SEQ ID NO: 7.

In some embodiments, a humanized Tmprss2 gene results from a replacement of a nucleotide sequence of an endogenous rodent Tmprss2 gene at an endogenous rodent Tmprss2 locus with a nucleotide sequence of a human TMPRSS2 gene.

In some embodiments, a contiguous genomic sequence of an endogenous rodent Tmprss2 gene at an endogenous rodent Tmprss2 locus has been replaced with a contiguous genomic sequence of a human TMPRSS2 gene to form a humanized Tmprss2 gene.

In specific embodiments, the contiguous genomic sequence of a human TMPRSS2 gene inserted into an endogenous rodent Tmprss2 gene includes exon sequences, i.e., exons in full or in part, of a human TMPRSS2 gene, that encode an ectodomain that is substantially identical to the ectodomain of the human TMPRSS2 protein encoded by the human TMPRSS2 gene. In circumstances where an endogenous Tmprss2 protein and a human TMPRSS2 protein share common amino acids near the junction of the transmembrane domain and the ectodomain, it may not be necessary to insert a human TMPRSS2 genomic sequence that encodes precisely the ectodomain of the human TMPRSS2 protein, and it is possible to use a slightly longer or shorter human TMPRSS2 genomic sequence that encodes substantially the ectodomain of a human TMPRSS2 protein in order to make a humanized Tmprss2 protein having an ectodomain that is identical with the ectodomain of the human TMPRSS2 protein.

In specific embodiments, a contiguous genomic sequence of a human TMPRSS2 gene being inserted into an endogenous rodent Tmprss2 gene contains at least coding exon 4 through the stop codon in coding exon 13 of the human TMPRSS2 gene.

In certain embodiments, a contiguous genomic sequence of a human TMPRSS2 gene being inserted into an endogenous rodent Tmprss2 gene contains intron 3 and coding exon 4 through the stop codon in coding exon 13 of the human TMPRSS2 gene. In particular embodiments, a contiguous genomic sequence of a human TMPRSS2 gene being inserted into an endogenous rodent Tmprss 2 gene contains a 3' portion of coding exon 3, intron 3, and coding exon 4 through the stop codon in coding exon 13 of the human TMPRSS2 gene. In specific embodiments, the 3' portion of coding exon 3 of a human TMPRSS2 gene included in the humanization is about 5-10 base pair in length, i.e., about 5, 6, 7, 8, 9 or 10 base pair of the 3' end of coding exon 3.

In some embodiments, a contiguous genomic sequence of a human TMPRSS2 gene being inserted into an endogenous rodent Tmprss2 gene also contains the 3' UTR of the human TMPRSS2 gene. In specific embodiments, the entire coding exon 13 of a human TMPRSS2 gene is included in the contiguous human TMPRSS2 genomic sequence for humanization, which includes the 3' UTR of the human TMPRSS2 gene. In particular embodiments, a contiguous genomic sequence of a human TMPRSS2 gene includes an additional human genomic sequence downstream of the 3' UTR of the human TMPRSS2 gene. The additional human genomic sequence can be a sequence of at least 10-200 bp, or at least 10, 20, 30, 40, 50, 75, 100, 125, 150, 175, or 200 bp, that is found immediately downstream of the 3' UTR of the human TMPRSS2 gene at a human TMPRSS2 locus.

In some embodiments, the nucleotide sequence of an endogenous rodent Tmprss2 gene remaining at a humanized Tmprss2 locus encodes a polypeptide that is substantially identical with the cytoplasmic and transmembrane portion of the endogenous rodent Tmprss2 protein. In circumstances where an endogenous Tmprss2 protein and a human TMPRSS2 protein share common amino acids near the junction of the transmembrane domain and the ectodomain, it may not be necessary to maintain the endogenous rodent Tmprss2 genomic sequence that encodes precisely the transmembrane domain of the endogenous rodent Tmprss2 protein, and it is possible to maintain a slightly longer or shorter rodent Tmprss2 genomic sequence that encodes substantially the transmembrane domain of the endogenous rodent Tmprss2 protein in the humanization replacement in order to encode a humanized Tmprss2 protein having a transmembrane domain that is identical with the transmembrane of the endogenous rodent Tmprss2 protein. In some embodiments, the nucleotide sequence of an endogenous rodent Tmprss2 gene remaining at a humanized Tmprss2 locus includes exons 1-2 and a 5' portion of coding exon 3 of an endogenous rodent Tmprss2 gene, wherein the 5' portion of coding exon 3 is a substantial portion of codon exon 3, e.g., the entire coding exon 3 except 5-10 base pairs at the 3' end of coding exon 3.

In specific embodiments, a humanized Tmprss2 gene contains coding exons 1-2 and a 5' portion of coding exon 3 of an endogenous rodent Tmprss2 gene, and a 3' portion of coding exon 3 and coding exon 4 through coding exon 13 of a human TMPRSS2 gene, wherein the humanized Tmprss2 gene encodes a humanized Tmprss2 protein that contains a cytoplasmic and transmembrane portion that is substantially identical with the cytoplasmic and transmembrane portion of the rodent Tmprss2 protein, and an ectodomain that is substantially identical with the ectodomain of the human TMPRSS2 protein. In certain embodiments, the humanized Tmprss2 gene encodes a humanized Tmprss2 protein that contains the cytoplasmic domain and the transmembrane domain of the rodent Tmprss2 protein encoded by an endogenous rodent Tmprss2 gene, and the ectodomain of the human TMPRSS2 protein encoded by a human TMPRSS2 gene. In particular embodiments, a humanized Tmprss2 gene encodes a humanized Tmprss2 protein having the amino acid sequence as set forth in SEQ ID NO: 7.

In some embodiments, the exons and introns of a human TMPRSS2 gene and a rodent Tmprss2 gene used in the humanization are those found in SEQ ID NOS: 1, 3 and 5-6.

In some embodiments, a humanized Tmprss2 gene results in an expression of the encoded humanized Tmprss2 protein in a rodent. In some embodiments, a humanized Tmprss2 protein is expressed in a pattern comparable with, or substantially the same as, a counterpart rodent Tmprss2 protein in a control rodent (e.g., a rodent without the humanized Tmprss2 gene). In some embodiments, a humanized Tmprss2 protein is expressed at a level comparable with, or substantially the same as, a counterpart rodent Tmprss2 protein in a control rodent (e.g., a rodent without the humanized Tmprss2 gene). In certain embodiments, a humanized Tmprss2 protein is expressed and detected at the cell surface. In certain embodiments, a humanized Tmprss2 protein or a soluble form (e.g., a shed ectodomain form) is expressed and detected in serum of a rodent, e.g., at a level comparable with, or substantially the same as, a counterpart rodent Tmprss2 protein or a soluble form thereof in a control rodent.

Humanized Tmprss4 Rodents

In some embodiments, this invention provides a rodent whose genome contains a humanized Tmprss4 gene that includes a nucleotide sequence of an endogenous rodent Tmprss4 gene and a nucleotide sequence of a human TMPRSS4 gene, and that is under control of a 5' regulatory element(s), such as the promoter and/or an enhancer(s), of the endogenous rodent Tmprss4 gene. Examples of rodents include mice and rats.

In some embodiments, a humanized Tmprss4 gene encodes a humanized Tmprss4 protein that contains an ectodomain that is substantially identical with the ectodomain of a human TMPRSS4 protein. In specific embodiments, the human TMPRSS4 protein has an amino acid sequence having at least 85%, 90%, 95%, 98%, 99% or 100% identity with the amino acid sequence as set forth in SEQ ID NO: 11.

In some embodiments, a humanized Tmprss4 protein contains the C-terminal 384 amino acids of a human TMPRSS4 protein, for example, amino acids 54 to 437 of a human TMPRSS4 protein. In some embodiments, a humanized Tmprss4 protein contains an ectodomain that is substantially identical with the amino acid sequence composed of K54 to L437 of SEQ ID NO: 11. In specific embodiments, a humanized Tmprss4 protein contains an ectodomain having at least 85%, 90%, 95%, 98%, 99% or 100% identity with the amino acid sequence composed of K54 to LA37 of SEQ ID NO: 11; an ectodomain that differs from the amino acid sequence composed of K54 to L437 of SEQ ID NO: 11 by not more than 10, 9, 8, 7, 6, 5, 4, 3, 2 or 1 amino acid(s); or an ectodomain that differs from the amino acid sequence composed of K54 to L437 of SEQ ID NO: 11 only at the N- or C-terminus of the ectodomain, e.g., lacking 1-5 amino acids or having additional 1-5 amino acids at the N- or C-terminus.

In some embodiments, a humanized Tmprss4 protein further contains a cytoplasmic and transmembrane portion that is substantially identical with the cytoplasmic and transmembrane portion of an endogenous rodent Tmprss4 protein. In some embodiments, a humanized Tmprss4 protein further includes the transmembrane domain and the cytoplasmic domain of an endogenous rodent Tmprss4 protein.

In specific embodiments, a humanized Tmprss4 protein contains the transmembrane domain and the cytoplasmic domain of an endogenous rodent Tmprss4 protein, and the ectodomain of a human TMPRSS4 protein. In particular embodiments, a humanized Tmprss4 gene encodes a humanized Tmprss4 protein having the amino acid sequence as set forth in SEQ ID NO: 14.

In some embodiments, a humanized Tmprss4 gene results from a replacement of a nucleotide sequence of an endogenous rodent Tmprss4 gene at an endogenous rodent Tmprss4 locus with a nucleotide sequence of a human TMPRSS4 gene.

In some embodiments, a contiguous genomic sequence of an endogenous rodent Tmprss4 gene at an endogenous rodent Tmprss4 locus has been replaced with a contiguous genomic sequence of a human TMPRSS4 gene to form a humanized Tmprss4 gene.

In specific embodiments, the contiguous genomic sequence of a human TMPRSS4 gene inserted into an endogenous rodent Tmprss4 gene includes exon sequences, i.e., exons in full or in part, of a human TMPRSS4 gene that encode an ectodomain that is substantially identical with the ectodomain of the human TMPRSS4 protein encoded by the human TMPRSS4 gene. In circumstances where an endogenous Tmprss4 protein and a human TMPRSS4 protein share common amino acids near the junction of the transmembrane domain and the ectodomain, it may not be necessary to insert a human TMPRSS4 genomic sequence that encodes precisely the ectodomain of the human TMPRSS4 protein, and it is possible to use a slightly longer or shorter human TMPRSS4 genomic sequence that encodes substantially the ectodomain of a human TMPRSS4 protein in order to make a humanized Tmprss4 protein having an ectodomain that is identical with the ectodomain of the human TMPRSS4 protein.

In specific embodiments, a contiguous genomic sequence of a human TMPRSS4 gene being inserted into an endogenous rodent Tmprss4 gene contains at least coding exon 4 through the stop codon in coding exon 13 of the human TMPRSS4 gene.

In certain embodiments, a contiguous genomic sequence of a human TMPRSS4 gene being inserted into an endogenous rodent Tmprss4 gene includes a 3' portion of intron 3, and coding exon 4 through the stop codon in coding exon 13 of a human TMPRSS4 gene. In specific embodiments, the 3' portion of intron 3 of a human TMPRSS4 gene included in the humanization is about 140-160 base pair in length, i.e., about 140, 145, 150, 155, 160 base pair of the 3' end of intron 3.

In some embodiments, a contiguous genomic sequence of a human TMPRSS4 gene being inserted into an endogenous rodent Tmprss4 gene contains the 3' UTR of the human TMPRSS4 gene. In specific embodiments, a contiguous genomic sequence of a human TMPRSS4 gene being inserted into an endogenous rodent Tmprss4 gene does not contain the 3' UTR of the human TMPRSS4 gene, and the 3' UTR of the endogenous rodent Tmprss4 gene follows immediately after the stop codon in the humanized Tmprss4 gene.

In some embodiments, the nucleotide sequence of an endogenous rodent Tmprss4 gene remaining at a humanized Tmprss4 locus encodes a polypeptide that is substantially identical with the cytoplasmic and transmembrane portion of the endogenous rodent Tmprss4 protein. In circumstances where an endogenous Tmprss4 protein and a human TMPRSS4 protein share common amino acids near the junction of the transmembrane domain and the ectodomain, it may not be necessary to maintain the endogenous rodent Tmprss4 genomic sequence that encodes precisely the transmembrane domain of the endogenous rodent Tmprss4 protein, and it is possible to maintain a slightly longer or shorter rodent Tmprss4 genomic sequence that encodes substantially the transmembrane domain of the endogenous rodent Tmprss4 protein in the humanization replacement in order to encode a humanized Tmprss4 protein having a transmembrane domain that is identical with the transmembrane of the endogenous rodent Tmprss4 protein.

In specific embodiments, a humanized Tmprss4 gene contains coding exons 1-3 of an endogenous rodent Tmprss4 gene, and coding exon 4 through the stop codon of coding exon 13 of a human TMPRSS4 gene. In particular embodiments, a humanized Tmprss4 gene contains coding exons 1-3 and a 5' portion of intron 3 of an endogenous rodent Tmprss4 gene, and a 3' portion of intron 3 and coding exon 4 through the stop codon of coding exon 13 of a human TMPRSS4 gene. In certain embodiments, the humanized Tmprss4 gene encodes a humanized Tmprss4 protein that contains the cytoplasmic domain and the transmembrane domain of the rodent Tmprss4 protein encoded by an endogenous rodent Tmprss4 gene, and the ectodomain of the human TMPRSS4 protein encoded by a human TMPRSS4 gene. In particular embodiments, a humanized Tmprss4 gene encodes a humanized Tmprss4 protein having the amino acid sequence as set forth in SEQ ID NO: 14.

In some embodiments, the exons and introns of a human TMPRSS4 gene and a rodent Tmprss4 gene used in the humanization are those found in SEQ ID NOS: 8, 10 and 12-13.

In some embodiments, a humanized Tmprss4 gene results in an expression of the encoded humanized Tmprss4 protein in a rodent. In some embodiments, a humanized Tmprss4 protein is expressed in a pattern comparable with, or substantially the same as, a counterpart rodent Tmprss4 protein in a control rodent (e.g., a rodent without the humanized Tmprss4 gene encoding the humanized Tmprss4 protein). In some embodiments, a humanized Tmprss4 protein is expressed at a level comparable with, or substantially the same as, a counterpart rodent Tmprss4 protein in a control rodent (e.g., a rodent without the humanized Tmprss4 gene encoding the humanized Tmprss4 protein). In certain embodiments, a humanized Tmprss4 protein is expressed and detected at the cell surface. In certain embodiments, a humanized Tmprss4 protein or a soluble form (e.g., a shed ectodomain form) is expressed and detected in serum of a rodent, e.g., at a level comparable with, or substantially the same as, a counterpart rodent Tmprss4 protein or a soluble form thereof in a control rodent.

Humanized Tmprss11d Rodents

In some embodiments, this invention provides a rodent whose genome contains a humanized Tmprss11d gene that includes a nucleotide sequence of an endogenous rodent Tmprss11d gene and a nucleotide sequence of a human TMPRSS11D gene, and that is under control of a 5' regulatory element(s), such as the promoter and/or enhancer(s) of the endogenous rodent Tmprss11d gene. Examples of rodents include mice and rats.

In some embodiments, a humanized Tmprss11d gene encodes a humanized Tmprss11d protein that contains an ectodomain that is substantially identical with the ectodomain of a human TMPRSS11D protein.

In specific embodiments, the human TMPRSS11D protein has an amino acid sequence having at least 85%, 90%, 95%, 98%, 99% or 100% identity with the amino acid sequence as set forth in SEQ ID NO: 18.

In some embodiments, a humanized Tmprss11d protein contains the C-terminal 377 amino acids of a human TMPRSS11D protein, for example, amino acids 42 to 418 of a human TMPRSS11D protein. In some embodiments, a humanized Tmprss11d protein contains an ectodomain that is substantially identical with the amino acid sequence composed of A42 to 1418 of SEQ ID NO: 18. In specific embodiments, a humanized Tmprss11d protein contains an ectodomain having at least 85%, 90%, 95%, 98%, 99% or 100% identity with the amino acid sequence composed of A42 to 1418 of SEQ ID NO: 18; an ectodomain that differs from the amino acid sequence composed of A42 to 1418 of SEQ ID NO: 18 by not more than 10, 9, 8, 7, 6, 5, 4, 3, 2 or 1 amino acid(s); or an ectodomain that differs from the amino acid sequence composed of A42 to 1418 of SEQ ID NO: 18 only at the N- or C-terminus, e.g., by lacking 1-5 amino acids or having additional 1-5 amino acids at the N- or C-terminus.

In some embodiments, a humanized Tmprss11d protein further contains a cytoplasmic and transmembrane portion that is substantially identical with the cytoplasmic and transmembrane portion of an endogenous rodent Tmprss11d protein. In some embodiments, a humanized Tmprss11d protein includes the transmembrane domain and the cytoplasmic domain of an endogenous rodent Tmprss11d protein.

In specific embodiments, a humanized Tmprss11d protein contains the transmembrane domain and the cytoplasmic domain of an endogenous rodent Tmprss11d protein, and the ectodomain of a human TMPRSS11D protein. In particular embodiments, a humanized Tmprss11d gene encodes a humanized Tmprss11d protein having the amino acid sequence as set forth in SEQ ID NO: 21.

In some embodiments, a humanized Tmprss11d gene results from a replacement of a nucleotide sequence of an endogenous rodent Tmprss11d gene at an endogenous rodent Tmprss11d locus with a nucleotide sequence of a human TMPRSS11D gene.

In some embodiments, a contiguous genomic sequence of an endogenous rodent Tmprss11d gene at an endogenous rodent Tmprss11d locus has been replaced with a contiguous genomic sequence of a human TMPRSS11D gene to form a humanized Tmprss11d gene. In specific embodiments, the contiguous genomic sequence of a human TMPRSS11D gene inserted into an endogenous rodent Tmprss11d gene includes exon sequences, i.e., exons in full or in part, of a human TMPRSS11D gene that encode an ectodomain that is substantially identical with the ectodomain of the human TMPRSS11D protein encoded by the human TMPRSS11D gene. In circumstances where an endogenous Tmprss11d protein and a human TMPRSS11D protein share common amino acids near the junction of the transmembrane domain and the ectodomain, it may not be necessary to insert a human TMPRSS11D genomic sequence that encodes precisely the ectodomain of the human TMPRSS11D protein, and it is possible to use a slightly longer or shorter human TMPRSS11D genomic sequence that encodes substantially the ectodomain of a human TMPRSS11D protein in order to make a humanized Tmprss11d protein having an ectodomain that is identical with the ectodomain of the human TMPRSS11D protein.

In specific embodiments, a contiguous genomic sequence of a human TMPRSS11D gene being inserted into an endogenous rodent Tmprss11d gene contains at least coding exon 3 through the stop codon in coding exon 10 of a human TMPRSS11D gene.

In certain embodiments, a contiguous genomic sequence of a human TMPRSS11D gene being inserted into an endogenous rodent Tmprss11d gene contains at least a 3' portion of intron 2 and coding exon 3 through the stop codon in coding exon 10 of the human TMPRSS11D gene. In specific embodiments, the 3' portion of intron 2 of a human TMPRSS2 gene included in the humanization is about 444 base pairs in length.

In some embodiments, a contiguous genomic sequence of a human TMPRSS11D gene being inserted into an endogenous rodent Tmprss11d gene contains the 3' UTR of the human TMPRSS11D gene. In specific embodiments, the entire coding exon 10 of a human TMPRSS11D gene is included in the contiguous human TMPRSS11D genomic sequence for humanization, which includes the 3' UTR of a human TMPRSS11D gene. In particular embodiments, a contiguous genomic sequence of a human TMPRSS11D gene includes an additional human genomic sequence downstream of the 3' UTR of the human TMPRSS11D gene. The additional human genomic sequence can be a sequence of 10-200 bp, 50-200 bp, or about 150, 160, 170, 180 bp, that is found immediately downstream of the 3' UTR of the human TMPRSS11D gene at a human TMPRSS11D locus.

In some embodiments, the nucleotide sequence of an endogenous rodent Tmprss11d gene remaining at a humanized Tmprss11d locus encodes a polypeptide that is substantially identical with the cytoplasmic and transmembrane portion of the endogenous rodent Tmprss11d protein encoded by the endogenous rodent Tmprss11d gene. In circumstances where an endogenous Tmprss11d protein and a human TMPRSS11D protein share common amino acids near the junction of the transmembrane domain and the ectodomain, it may not be necessary to maintain the endogenous rodent Tmprss11d genomic sequence that encodes precisely the transmembrane domain of the endogenous rodent Tmprss11d protein, and it is possible to maintain a slightly longer or shorter rodent Tmprss11d genomic sequence that encodes substantially the transmembrane domain of the endogenous rodent Tmprss11d protein in the humanization replacement in order to encode a humanized Tmprss11d protein having a transmembrane domain that is identical with the transmembrane of the endogenous rodent Tmprss11d protein.

In specific embodiments, a humanized Tmprss11d gene contains coding exons 1-2 of an endogenous rodent Tmprss11d gene, and coding exon 3 through coding exon 10 of a human TMPRSS11D gene. In certain embodiments, the humanized Tmprss11d gene encodes a humanized Tmprss11d protein that contains the cytoplasmic domain and the transmembrane domain of the rodent Tmprss 11d protein encoded by an endogenous rodent Tmprss11d gene, and the ectodomain of the human TMPRSS11D protein encoded by a human TMPRSS11D gene. In particular embodiments, a humanized Tmprss11d gene encodes a humanized Tmprss11d protein having the amino acid sequence as set forth in SEQ ID NO: 21.

In some embodiments, the exons and introns of a human TMPRSS11D gene and a rodent Tmprss11d gene used in the humanization are those found in SEQ ID NOS: 15, 17 and 19-20.

In some embodiments, a humanized Tmprss11D gene results in an expression of the encoded humanized Tmprss11d protein in a rodent. In some embodiments, a humanized Tmprss11d protein is expressed in a pattern comparable with, or substantially the same as, a counterpart rodent Tmprss11d protein in a control rodent (e.g., a rodent without the humanized Tmprss11d gene encoding the humanized Tmprss11d protein). In some embodiments, a humanized Tmprss11d protein is expressed at a level comparable with, or substantially the same as, a counterpart rodent Tmprss11d protein in a control rodent (e.g., a rodent without the humanized Tmprss11d gene encoding the humanized Tmprss11d protein). In certain embodiments, a humanized Tmprss11d protein is expressed and detected at the cell surface. In certain embodiments, a humanized Tmprss11d protein or a soluble form (e.g., a shed ectodomain form) is expressed and detected in serum of a rodent, e.g., at a level comparable with, or substantially the same as, a counterpart rodent Tmprss11d protein or a soluble form thereof in a control rodent.

Methods of Making Humanized Tmprss Rodent Animals

Further aspects of this disclosure are directed to methods for making a humanized Tmprss rodent described above, as well as nucleic acid vectors and non-human embryonic stem cells suitable for use in making a humanized Tmprss rodent.

The rodents provided herein can be made using methods known in the art. In exemplary embodiments, a bacterial artificial chromosome (BAC) clone carrying a rodent Tmprss gene can be modified using bacterial homologous recombination and VELOCIGENE® technology (see, e.g., U.S. Pat. No. 6,586,251 and Valenzuela et al. (2003), High-throughput engineering of the mouse genome coupled with high-resolution expression analysis, *Nature Biotech.* 21(6): 652-659). As a result, a rodent Tmprss nucleotide sequence has been deleted from the original BAC clone, and a human Tmprss nucleotide sequence has been inserted, resulting in a modified BAC clone carrying a humanized Tmprss gene, flanked with 5' and 3' rodent homology arms. The modified BAC clone, once linearized, can be introduced into rodent embryonic stem (ES) by, e.g., electroporation. Both mouse ES cells and rat ES cells have been described in the art. See, e.g., U.S. Pat. No. 7,576,259, U.S. Pat. No. 7,659,442, U.S. Pat. No. 7,294,754, and US 2008-0078000 A1 (all of which are incorporated herein by reference) describe mouse ES cells and the VELOCIMOUSE® method for making a genetically modified mouse; US 2014/0235933 A1, US 2014/0310828 A1, Tong et al. (2010) *Nature* 467:211-215, and Tong et al. (2011) *Nat Protoc.* 6(6): doi: 10.1038/nprot.2011.338 (all of which are incorporated herein by reference) describe rat ES cells and methods for making a genetically modified rat.

ES cells having a humanized Tmprss gene integrated in the genome can be selected. In some embodiments, ES cells having a humanized Tmprss integrated into an endogenous rodent Tmprss locus can be selected based on loss of rodent allele and/or gain of human allele assays. Selected ES cells are then used as donor ES cells for injection into a pre-morula stage embryo (e.g., 8-cell stage embryo) by using the VELOCIMOUSE® method (see, e.g., U.S. Pat. No. 7,576,259, U.S. Pat. No. 7,659,442, U.S. Pat. No. 7,294,754, and US 2008-0078000 A1), or methods described in US 2014/0235933 A1 and US 2014/0310828 A1. The embryo comprising the donor ES cells is incubated until blastocyst stage and then implanted into a surrogate mother to produce an F0 rodent fully derived from the donor ES cells. Rodent pups bearing the humanized Tmprss gene can be identified by genotyping of DNA isolated from tail snips using loss of rodent allele and/or gain of human allele assays.

Rodents heterozygous for a humanized Tmprss gene can be crossed to generated homozygous rodents. Rodents containing one humanized Tmprss gene can be crossed with rodents containing another humanized Tmprss gene to make rodents containing multiple humanized Tmprss genes. For example, rodents containing a humanized Tmprss2 gene can be crossed with rodents containing a humanized Tmprss4 gene to make rodents containing a humanized Tmprss2 gene and a humanized Tmprss4 gene.

Methods Employing Rodents Having Humanized Tmprss Genes

Rodents disclosed herein provide a useful in vivo system and source of biological materials (e.g., cells) expressing humanized Tmprss proteins for identifying and testing compounds that specifically target human TMPRSS proteins.

In one aspect, a rodent disclosed herein is used to determine the ability of a candidate compound, such as an inhibitor of a human TMPRSS protein, to treat and/or prevent influenza virus infection.

In some embodiments, a rodent containing a humanized Tmprss gene and expressing a humanized Tmprss protein disclosed herein is administered with a candidate compound prior to experimental influenza virus infection. The prophylactic efficacy of the compound can be evaluated by determining whether the rodent exhibits fewer and/or less severe symptoms of influenza virus infection, and/or improved viability, as compared to control rodent(s).

In other embodiments, a rodent containing a humanized Tmprss gene and expressing a humanized Tmprss protein comprising the ectodomain of a human TMPRSS protein is administered with a candidate inhibitor of that human TMPRSS protein after experimental influenza virus infection. The treatment efficacy of the candidate inhibitor can be evaluated by determining whether the rodent exhibits fewer and/or less severe symptoms of influenza virus infection, and/or improved viability, as compared to control rodent(s).

Suitable control rodents include, e.g., rodents containing a humanized Tmprss gene without being subjected to the experimental infection; and rodents containing a humanized Tmprss gene subjected to the experimental infection without any compound; and rodents containing a humanized Tmprss gene subjected to the experimental infection and a compound known to be therapeutically effective.

Compounds that can be evaluated in the methods of this invention include candidate TMPRSS inhibitors, for example, a small molecule protease inhibitor, a nucleic acid-based inhibitor (e.g., siRNA, ribozyme, antisense construct, etc.), antigen-binding protein (e.g., antibody or antigen-binding fragment thereof), or a blocking peptide/peptide inhibitor. A TM PRSS inhibitor may function by inhibiting or reducing the ability of a TMPRSS protein to proteolytically cleave hemagglutinin precursor protein (HA0) into the HA1 and HA2 subunits.

In some embodiments, a candidate inhibitor is an antibody or antigen-binding fragment thereof. Both monoclonal and polyclonal antibodies are suitable for purposes of this invention. In specific embodiments, the antibody specifically binds to a TMPRSS protein and inhibits the protease activity of that TMPRSS protein and does not substantially inhibit the protease activity of another TMPRSS protein. For example, an anti-TMPRSS2 antibody inhibitor specifically binds to a TMPRSS2 protein and inhibits the protease activity of the TMPRSS2 protein, and has no effect on the proteolytic activity of TMPRSS4 or TMPRSS11D, or reduces the proteolytic activity of TMPRSS4 or TMPRSS11D by no more than 25% (e.g., by 20%, 15%, 10%, 5%, or less) relative to a non-inhibitory control molecule tested under identical or substantially identical experimental conditions.

In some embodiments, the inhibitor is an anti-TMPRSS2 antibody or antigen-binding fragment thereof. In some embodiments, the inhibitor is an anti-TMPRSS4 antibody or antigen-binding fragment thereof. In other embodiments, the inhibitor is an anti-TMPRSS11D antibody or antigen-binding fragment thereof.

Experimental influenza virus infection can be induced and monitored following known protocols. See, e.g., US 2013/0273070 A1. For example, rodent animals can be administered intranasally with influenza virus. The infected animals can be evaluated to determine the symptoms and severity of the infection. For example, the animals can be analyzed for (1) weight change and survival, (2) cellular changes via flow cytometry, (3) immunochemistry, PAS and H&E staining of whole lungs, and (4) cytokine levels in serum. Control animals known to be susceptible to the virus exhibit a significant increase in the frequency of dendritic cells, the levels influenza-positive alveolar macrophages, neutrophils or epithelial cells in the lungs, and the levels of IFNγ, as compared to uninfected animals.

EXAMPLES

The following examples are provided so as to describe to those of ordinary skill in the art how to make and use methods and compositions of the invention, and are not intended to limit the scope of what the inventors regard as their invention. Unless indicated otherwise, temperature is indicated in Celsius, and pressure is at or near atmospheric.

Example 1. Humanization of an Endogenous Tmprss2 Gene

This example illustrates exemplary methods of humanizing an endogenous gene encoding Tmprss2 in a rodent (e.g., a mouse). The methods described in this example can be employed to humanize an endogenous Tmprss2 gene of a rodent using any human sequence, or combination of human sequences (or sequence fragments) as desired.

A targeting vector for humanization of an endogenous Tmprss2 gene was constructed using bacterial artificial chromosome (BAC) clones and VELOCIGENE® technology (see, e.g., U.S. Pat. No. 6,586,251 and Valenzuela et al. (2003) High-throughput engineering of the mouse genome coupled with high-resolution expression analysis, *Nature Biotech.* 21(6):652-659; incorporated herein by reference).

Figure 1D:
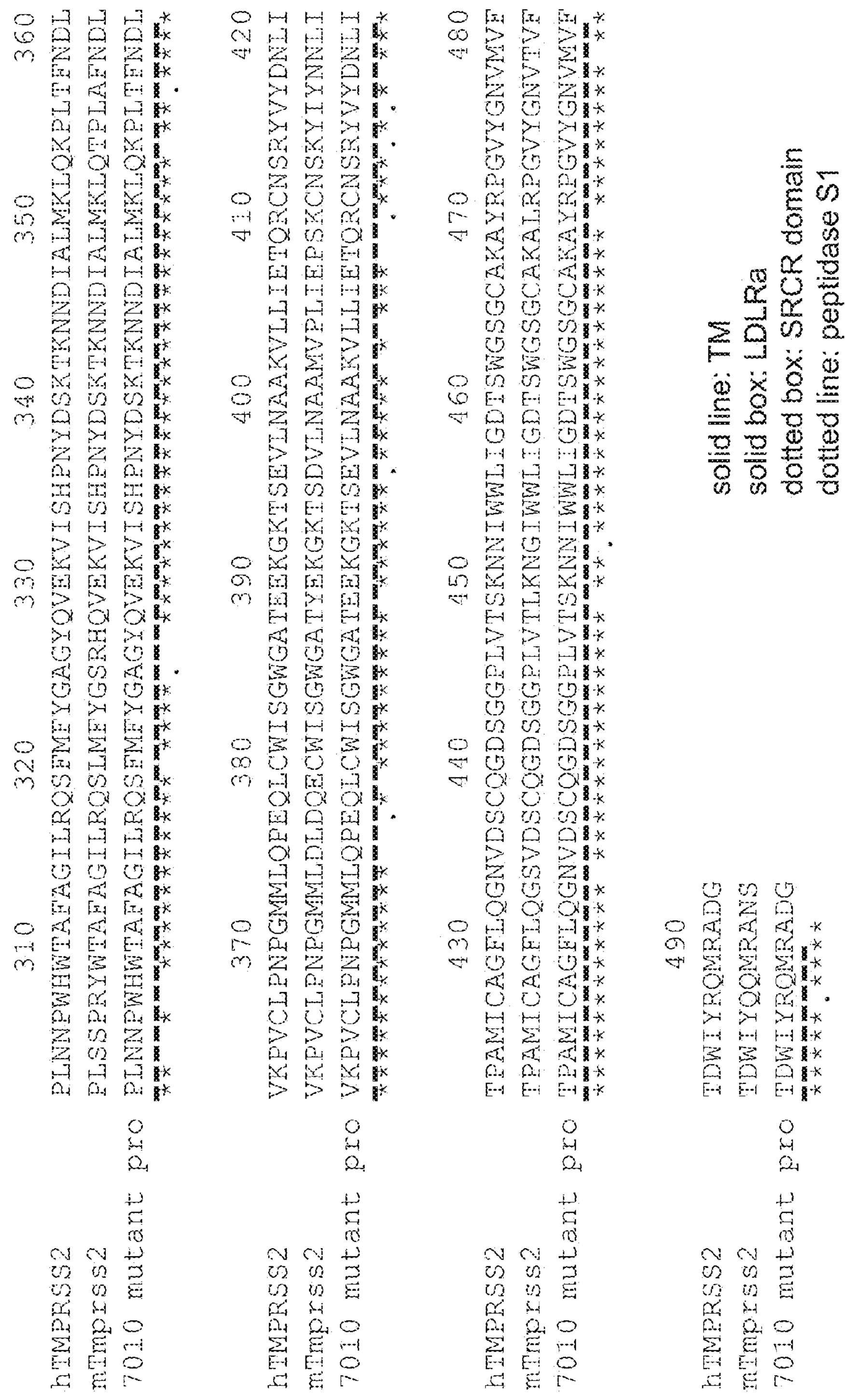

Briefly, mouse bacterial artificial chromosome (BAC) clone bMQ-264A15 containing a mouse Tmprss2 gene was used and modified as follows. A DNA fragment was generated to include a 5' mouse homology nucleotide sequence, a human TMPRSS2 genomic DNA of about 25,091 bp (containing the last 7 bp of coding exon 3, intron 3, and coding exon 4 through coding exon 13 (including the 3' UTR which is part of coding exon 13), of a human TMPRSS2 gene), a self-deleting neomycin cassette of about 2,691 bp, and a 3' mouse homology sequence. This DNA fragment was used to modify BAC clone bMQ-264A15 through homologous recombination in bacterial cells. As a result, an ectodomain-encoding mouse Tmprss2 genomic fragment (of about 25,291 bp) in the BAC clone was replaced with the human TMPRSS2 genomic fragment of about 25,091 bp, followed by a self-deleting neomycin cassette of about 2691 bp. Specifically, the mouse Tmprss2 genomic fragment that was replaced included the last 7 bp of coding exon 3, intron 3, and coding exon 4 through the stop codon in coding exon 13 of the mouse Tmprss2 gene (FIGS. 1A-1B). The human TMPRSS2 genomic fragment that was inserted included the last 7 bp of coding exon 3, intron 3, and coding exon 4 through coding exon 13 of a human TMPRSS2 gene (including the 3' UTR of human TMPRSS2), and a human 3' genomic sequence of 131 bp downstream of the 3' UTR of human TMPRSS2 (FIGS. 1A-1B). The resulting modified BAC clone included, from 5' to 3', (i) a 5' mouse homology arm containing about 12 kb of mouse genomic DNA including a mouse Tmprss2 5' UTR, mouse Tmprss2 exon 1 (non-coding), coding exons 1-3 (except the last 7 bp of coding exon 3); (ii) a human TMPRSS2 genomic fragment of about 25,091 bp including the last 7 bp of human coding exon 3, intron 3, human coding exons 4 through 13 (including the 3' UTR of human TMPRSS2), and a human 3' genomic sequence; (iii) a self-deleting neomycin cassette of about 2691 bp, followed by (iv) a 3' mouse homology arm of 45 kb containing the mouse Tmprss2 3'UTR and the remaining mouse genomic DNA in the original BAC clone. See FIGS. 1A-1B. The junction sequences are also set forth at the bottom of FIG. 1B. The part of the modified BAC clone containing the human TMPRSS2 genomic fragment and the neomycin cassette, as well as the upstream and downstream insertion junctions, is set forth in SEQ ID NO: 5. The amino acid sequence of the protein encoded by the humanized Tmprss2 gene is set forth in SEQ ID NO: 7. An alignment of this humanized Tmprss2 protein ("7010 mutant protein"), a mouse Tmprss2 protein (SEQ ID NO: 2), and a human TMPRSS2 protein (SEQ ID NO: 4), is provided in FIG. 1D.

The modified BAC clone containing the humanized Tmprss2 gene, as described above, was used to electroporate mouse embryonic stem (ES) cells to create modified ES cells comprising a humanized Tmprss2 gene. Positively targeted ES cells containing a humanized Tmprss2 gene were identified by an assay (Valenzuela et al., supra) that detected the presence of the human TMPRSS2 sequences (e.g., coding exons 4-13 of human TMPRSS2) and confirmed the loss and/or retention of mouse Tmprss2 sequences (e.g., loss of coding exons 4-13 of mouse Tmprss2). Table 1 sets forth the primers and probes that were used to confirm humanization of an endogenous Tmprss2 gene as described above (FIGS. 1A-1B). Once a correctly targeted ES cell clone has been selected, the neomycin selection cassette can be excised by introducing a Cre recombinase, e.g., via electroporation. Alternatively, the neomycin selection cassette can be removed by crossing the progeny generated from the ES clone with a deletor rodent strain that expresses a Cre recombinase. The humanized Tmprss2 locus after the deletion of the cassette is depicted in FIG. 1C, with the junction sequences shown at the bottom of FIG. 1C.

Selected ES cell clones (with or without the cassette) were used to implant female mice using the VELOCIMOUSE® method (see, e.g., U.S. Pat. No. 7,294,754 and Poueymirou et al., F0 generation mice that are essentially fully derived from the donor gene-targeted ES cells allowing immediate phenotypic analyses, 2007, *Nature Biotech.* 25(1):91-99) to generate a litter of pups containing a humanized Tmprss2 allele in the genome. Mice bearing a humanized Tmprss2 allele can be again confirmed and identified by genotyping of DNA isolated from tail snips using a modification of allele assay (Valenzuela et al., supra) that detects the presence of the human TMPRSS2 gene sequences. Pups are genotyped and cohorts of animals heterozygous for the humanized Tmprss2 locus are selected for characterization. Animals homozygous for the humanized Tmprss2 locus are made by crossing heterozygous animals.

A targeting vector for humanization of an endogenous Tmprss4 gene was constructed using bacterial artificial chromosome (BAC) clones and VELOCIGENE® technology (see, e.g., U.S. Pat. No. 6,586,251 and Valenzuela et al. (2003), supra).

Figure 2A:
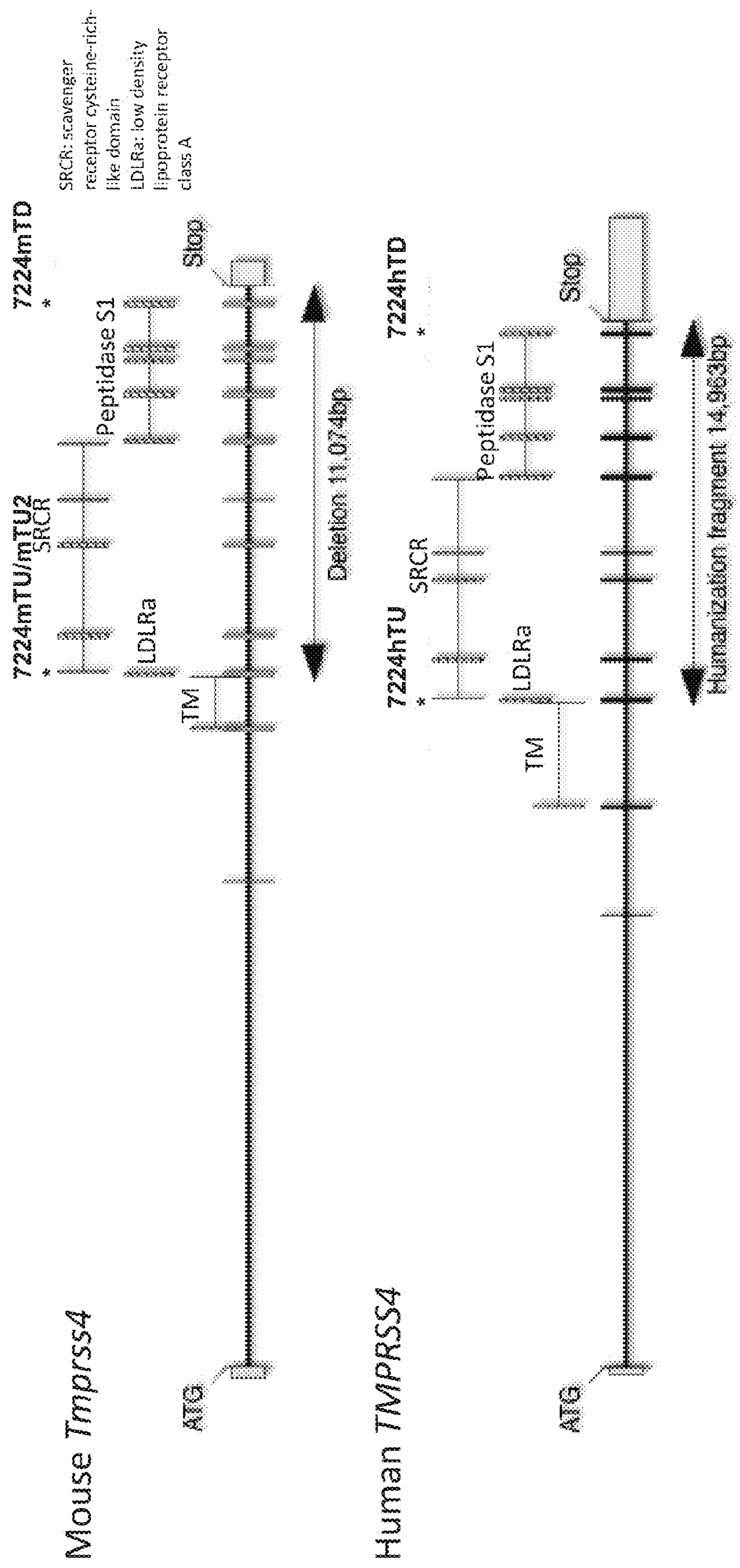

Briefly, mouse bacterial artificial chromosome (BAC) clone RP23-71M15 containing a mouse Tmprss4 gene was used and modified as follows. A DNA fragment was generated to include a 5' mouse homology nucleotide sequence, a self-deleting neomycin cassette of about 4,996 bp, a human genomic DNA of about 14,963 bp (containing coding exon 4 through the stop codon in coding exon 13 of a human TMPRSS4 gene), and a 3' mouse homology sequence. This DNA fragment was used to modify BAC clone RP23-71M15 through homologous recombination in bacterial cells. As a result, an ectodomain-encoding mouse genomic fragment (of about 11,074 bp) in the BAC clone was replaced with a self-deleting neomycin cassette of about 4,996 bp, followed by the human genomic DNA of about 14,963 bp. Specifically, the mouse genomic fragment that was deleted and replaced included the 3' 130 bp of mouse intron 3, coding exon 4 through the stop codon in coding exon 13 of the mouse Tmprss4 gene (FIGS. 2A-2B). The human genomic fragment that was inserted included a 3' portion of human TMPRSS4 intron 3 of about 150 bp, and human TMPRSS4 coding exon 4 through the stop codon in coding exon 13 (FIGS. 2A-2B). The resulting modified BAC clone included, from 5' to 3', a 5' mouse homology arm containing about 44.8 kb of mouse genomic DNA (including a mouse Tmprss4 5' UTR, mouse Tmprss4 coding exons 1 through 3, mouse Tmprss4 intron 3 in part (without the 3' 130 bp), a self-deleting neomycin cassette of about 4996 bp, a 3' portion of human TMPRSS4 intron 3 of about 150 bp, human TMPRSS4 coding exons 4 through the stop codon in coding exon 13, followed directly by the mouse Tmprss4 3' UTR and the remaining mouse genomic DNA in the original BAC clone (a 3' mouse homology arm of about 118 kb in total). See FIGS. 2A-2B. The junction sequences are also set forth at the bottom of FIG. 2B. The part of the modified BAC clone containing the neomycin cassette and the human TMPRSS4 genomic fragment, as well as the upstream and downstream insertion junctions, is set forth in SEQ ID NO: 12. The amino acid sequence of the protein encoded by the humanized Tmprss4 gene is set forth in SEQ ID NO: 14. An alignment of this humanized Tmprss4 protein ("7224 mutant pro"), a mouse Tmprss4 protein (SEQ ID NO: 9), and a human TMPRSS4 protein (SEQ ID NO: 11), is provided in FIG. 2D.

TABLE 1

| Name | Primer | Sequence (5'-3') | SEQ ID NO |
|---|---|---|---|
| 7010U | Forward | GCCGTGACTGTGACCTTCTC | (SEQ ID NO: 26) |
| | Probe (BHQ) | TGGAGGAGCCACCTGATGCCTC | (SEQ ID NO: 27) |
| | Reverse | GCCTTGCCCTCAATGGAAAC | (SEQ ID NO: 28) |
| 7010D | Forward | GGTTGCACAGCAAGGAAGAAG | (SEQ ID NO: 29) |
| | Probe (BHQ) | CCAGGAGTTCCTGTGAGCCTACCC | (SEQ ID NO: 30) |
| | Reverse | TGGAATGGAAGGAGCTGGAG | (SEQ ID NO: 31) |
| 7010hU | Forward | GTCCCACCTCCTGCAACTG | (SEQ ID NO: 32) |
| | Probe (BHQ) | TGAGCCTTCCCATCAGCCTGGG | (SEQ ID NO: 33) |
| | Reverse | CCACAATGGCACATGGGTCTG | (SEQ ID NO: 34) |
| 7010hTD | Forward | GGTGCTTGCTCCCCAAGA | (SEQ ID NO: 35) |
| | Probe (BHQ) | CCTAAAAGGTGTTGTAATGG | (SEQ ID NO: 36) |
| | Reverse | GGCAATAAAGAAGGAAGACGTTTT | (SEQ ID NO: 37) |

Example 2. Humanization of an Endogenous Tmprss4 Gene

This example illustrates exemplary methods of humanizing an endogenous gene encoding Tmprss4 in a rodent (e.g., a mouse). The methods described in this example can be employed to humanize an endogenous Tmprss4 gene of a rodent using any human sequence, or combination of human sequences (or sequence fragments) as desired.

The modified BAC clone containing the humanized Tmprss4 gene, as described above, was used to electroporate mouse embryonic stem (ES) cells to create modified ES cells comprising a humanized Tmprss4 gene. Positively targeted ES cells containing a humanized Tmprss4 gene were identified by an assay (Valenzuela et al., supra) that detected the presence of the human TMPRSS4 sequences (e.g., coding exons 4-13 of human TMPRSS4) and confirmed the loss and/or retention of mouse Tmprss4 sequences (e.g., loss of coding exons 4-13 of mouse Tmprss4). Table 2 sets forth the primers and probes that were used to confirm humanization of an endogenous Tmprss4 gene as described above (FIGS. 2A-2B). Once a correctly targeted ES cell clone has been selected, the neomycin selection cassette can be excised by introducing a Cre recombinase, e.g., via electroporation. Alternatively, the neomycin selection cassette can be removed by crossing the progeny generated from the ES clone with a deletor rodent strain that expresses a Cre recombinase. The humanized Tmprss4 locus after the deletion of the cassette is depicted in FIG. 2C, with the junction sequences shown at the bottom of FIG. 2C.

Selected ES cell clones (with or without the cassette) were used to implant female mice using the VELOCIMOUSE® method (see, e.g., U.S. Pat. No. 7,294,754 and Poueymirou et al. (2007), supra) to generate a litter of pups containing a humanized Tmprss4 allele in the genome. Mice bearing a humanized Tmprss4 allele were again confirmed and identified by genotyping of DNA isolated from tail snips using a modification of allele assay (Valenzuela et al., supra) that detected the presence of the human TMPRSS4 gene sequences. Pups were genotyped and cohorts of animals heterozygous for the humanized Tmprss4 locus were selected for characterization. Animals homozygous for the humanized Tmprss4 locus were made by crossing heterozygous animals.

TABLE 2

| Name | Primer | Sequence (5'-3') | SEQ ID NO |
|---|---|---|---|
| 7224mTU | Forward | GAGCAGGGCCATGACACAT | (SEQ ID NO: 42) |
| | Probe (BHQ) | ACCATTAGATCCCAGCACTGGACA | (SEQ ID NO: 43) |
| | Reverse | AAACCCTTCCCGAGAGAGAA | (SEQ ID NO: 44) |
| 7224mTU2 | Forward | GAGGAACACTGTGTCAAGGACTT | (SEQ ID NO: 45) |
| | Probe (BHQ) | CCTGAAAAGCCCGGAGTGGCAG | (SEQ ID NO: 46) |
| | Reverse | GGGCAGAGACCACATCTGA | (SEQ ID NO: 47) |
| 7224mTD | Forward | GGAAGCCCTCTCTCGATACTTG | (SEQ ID NO: 48) |
| | Probe (BHQ) | TTCTACCCTGAGGGCATGCAGC | (SEQ ID NO: 49) |
| | Reverse | TGGGATGTAGAAGGTTGTCAGA | (SEQ ID NO: 50) |
| 7224hTU | Forward | CTGAGCCTGGAACTCACACATG | (SEQ ID NO: 51) |
| | Probe (BHQ) | TCTGAGAGCCCAGCACTATCGCC | (SEQ JD NO: 52) |
| | Reverse | GCTGAGGGTCAGGCTTGAG | (SEQ ID NO: 53) |
| 7224hTD | Forward | TCTGCAGGGTAGGGAGAGAAG | (SEQ ID NO: 54) |
| | Probe (BHQ) | TGTTTCAGAAAAGGAAGACTCACGTTA CA | (SEQ ID NO: 55) |
| | Reverse | GAGACCGATGAAGAGAAAGTCAGA | (SEQ ID NO: 56) |

Example 3. Humanization of an Endogenous Tmprss11d Gene

This example illustrates exemplary methods of humanizing an endogenous gene encoding Tmprss11d in a rodent (e.g., a mouse). The methods described in this example can be employed to humanize an endogenous Tmprss11d gene of a rodent using any human sequence, or combination of human sequences (or sequence fragments) as desired.

A targeting vector for humanization of an endogenous Tmprss11d gene was constructed using bacterial artificial chromosome (BAC) clones and VELOCIGENE® technology (see, e.g., U.S. Pat. No. 6,586,251 and Valenzuela et al. (2003), supra).

Figure 3A:
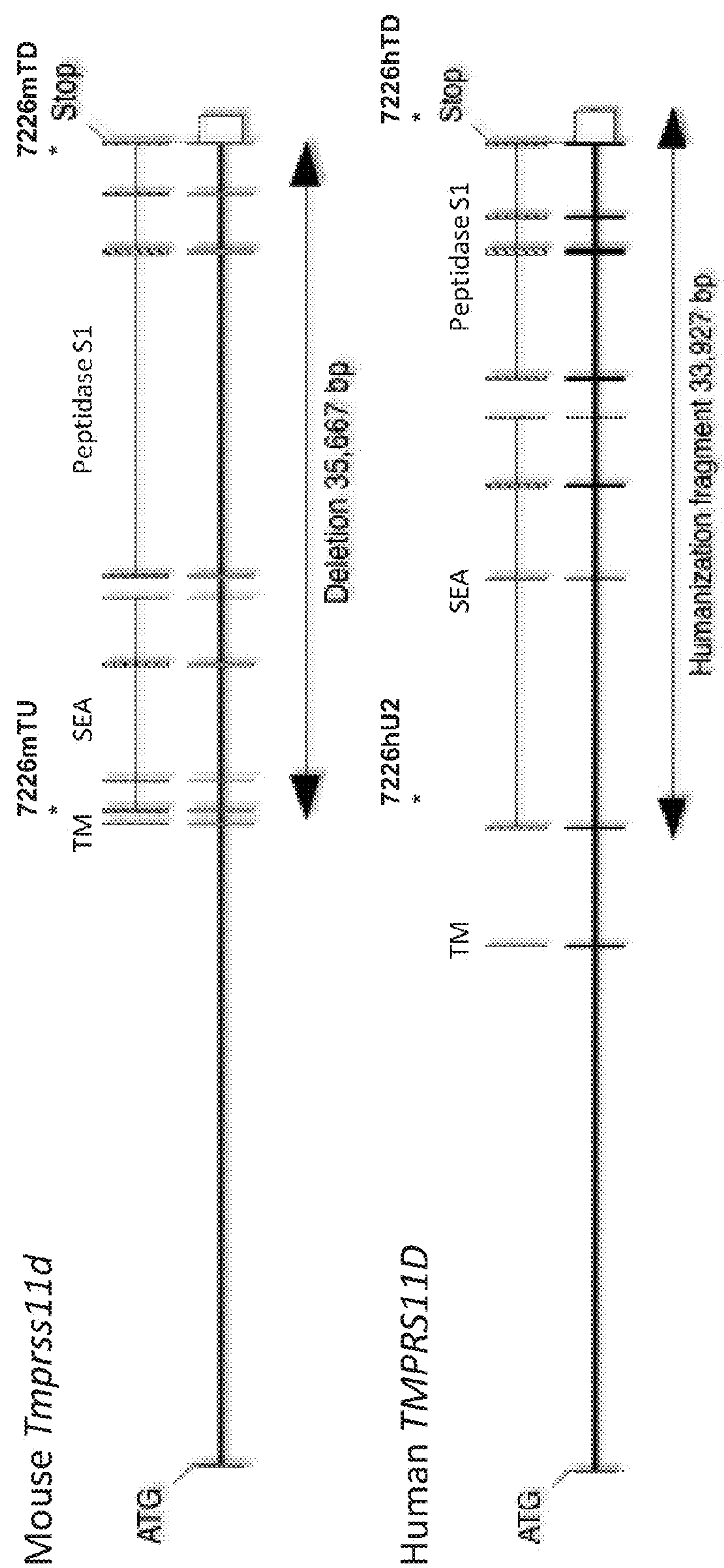

Briefly, mouse bacterial artificial chromosome (BAC) clone RP23-95N22 containing a mouse Tmprss11d gene was used and modified as follows. A DNA fragment was generated to include a 5' mouse homology nucleotide sequence, a human TMPRSS11D genomic DNA of about 33,927 bp (containing 444 bp at the 3' end of intron 2, and coding exon 3 through coding exon 10 (including the 3' UTR which is part of coding exon 10), of a human TMPRSS11D gene), a self-deleting neomycin cassette of about 4,996 bp, and a 3' mouse homology sequence. This DNA fragment was used to modify BAC clone RP23-95N22 through homologous recombination in bacterial cells. As a result, an ectodomain-encoding mouse Tmprss11d genomic fragment (of about 35,667 bp) in the BAC clone was replaced with the human TMPRSS11D genomic fragment of about 33,927 bp, followed by a self-deleting neomycin cassette of about 4,996 bp. Specifically, the mouse Tmprss11d genomic fragment that was replaced included a 3' portion of intron 2, and coding exon 3 through the stop codon in coding exon 10 of the mouse Tmprss11d gene (FIGS. 3A-3B). The human TMPRSS11D genomic fragment that was inserted included 444 bp at the 3' end of intron 2, and coding exon 3 through coding exon 10 of a human TMPRSS11D gene (including the 3' UTR of human TMPRSS11D), and a human 3' genomic sequence of about 172 bp downstream of the 3' UTR of human TMPRSS11D (FIGS. 3A-3B). The resulting modified BAC clone included, from 5' to 3', (i) a 5' mouse homology arm containing about 143 kb of mouse genomic DNA including a mouse Tmprss11d 5' UTR, mouse Tmprss11d coding exons 1-2 and a 5' portion of intron 2; (ii) a human TMPRSS11D genomic fragment including a 3' portion of intron 2 and coding exons 3 through 10 (including the 3' UTR) of human TMPRSS11D, and a human 3' genomic sequence; (iii) a self-deleting neomycin cassette of about 4,996 bp, followed by (iv) a 3' mouse homology arm of 10 kb containing the mouse Tmprss11d 3'UTR and the remaining mouse genomic DNA in the original BAC clone. See FIGS. 3A-3B. The junction sequences are also set forth at the bottom of FIG. 3B. The part of the modified BAC clone containing the human TMPRSS11D genomic fragment and the neomycin cassette, as well as the upstream and downstream insertion junctions, is set forth in SEQ ID NO: 19. The amino acid sequence of the protein encoded by the humanized Tmprss11d gene is set forth in SEQ ID NO: 21. An alignment of this humanized Tmprss11d protein ("7226 mutant pro"), a mouse Tmprss11d protein (SEQ ID NO: 16), and a human TMPRSS11D protein (SEQ ID NO: 18), is provided in FIG. 3D.

The modified BAC clone containing the humanized Tmprss11d gene, as described above, is used to electroporate mouse embryonic stem (ES) cells to create modified ES cells comprising a humanized Tmprss11d gene. Positively targeted ES cells containing a humanized Tmprss11d gene are identified by an assay (Valenzuela et al., supra) that detects the presence of the human TMPRSS11D sequences (e.g., coding exons 3-10 of human TMPRSS11D) and confirms the loss and/or retention of mouse Tmprss11d sequences (e.g., loss of coding exons 3-10 of mouse Tmprss11d). Table 3 sets forth the primers and probes that were used to confirm humanization of an endogenous Tmprss11d gene as described above (FIGS. 3A-3B). Once a correctly targeted ES cell clone has been selected, the neomycin selection cassette can be excised by introducing a Cre recombinase, e.g., via electroporation. Alternatively, the neomycin selection cassette can be removed by crossing the progeny generated from the ES clone with a deletor rodent strain that expresses a Cre recombinase. The humanized Tmprss11d locus after the deletion of the cassette is depicted in FIG. 3C, with the junction sequences shown at the bottom of FIG. 3C.

Selected ES cell clones (with or without the cassette) are used to implant female mice using the VELOCIMOUSE® method (see, e.g., U.S. Pat. No. 7,294,754 and Poueymirou et al. (2007), supra) to generate a litter of pups containing a humanized Tmprss11d allele in the genome. Mice bearing a humanized Tmprss11d allele are again confirmed and identified by genotyping of DNA isolated from tail snips using a modification of allele assay (Valenzuela et al., supra) that detects the presence of the human TMPRSS11D gene sequences. Pups are genotyped and cohorts of animals heterozygous for the humanized Tmprss11d locus are selected for characterization. Animals homozygous for the humanized Tmprss11d locus are made by crossing heterozygous animals.

TABLE 3

| Name | Primer | Sequence (5'-3') | SEQ ID NO |
|---|---|---|---|
| 7226mTU | Forward | TCCTCTCCAGACAAGAAAGCT | (SEQ ID NO: 61) |
| | Probe (BHQ) | TCATAGCAGCTTTCAAATCCTAAACGTTGA | (SEQ ID NO: 62) |
| | Reverse | TCGTGTGTAGCATGGTGAGTT | (SEQ ID NO: 63) |
| 7226mTD | Forward | CATGCGATCACAGGAGGAGATC | (SEQ ID NO: 64) |
| | Probe (BHQ) | AATTGGGCCCGAAGCCAGATGC | (SEQ ID NO: 65) |
| | Reverse | CGGAAGGGTTCTGTGACTTC | (SEQ ID NO: 66) |
| 7226hTU | Forward | GTCTCCCACTTCTGACATAATGAAC | (SEQ ID NO: 67) |
| | Probe (BHQ) | CCCAGTGTTAACCCTACATCTGGTTCC | (SEQ ID NO: 68) |
| | Reverse | TGGGAAGAGACTGTTGGACA | (SEQ ID NO: 69) |
| 7226hTD | Forward | ATGAGCTCCTAGTACAGCTAAAGTT | (SEQ ID NO: 70) |
| | Probe (MGB) | ATGCATGATCATCTATGCGTCAGAGC | (SEQ ID NO: 71) |
| | Reverse | TGCCCAGATGCAGGGAGTTAG | (SEQ ID NO: 72) |

Example 4. Evaluation of Group 1 and Group 2 Influenza A Viruses in MAID7225 HumIn Vs. Wild-Type Tmprss4 Mice To validate the use of humanized Tmprss rodents as an animal model of infection, experiments were conducted to evaluate the survival of MAID7225 HumIn TMPRSS4 mice versus wild-type (WT) littermates in an influenza A group 1 and group 2 model of severe influenza infection.

MAID7225 HumIn TMPRSS4 mice are homozygous for a humanized Tmprss4 gene in its genome and were generated as described in Example 2. The viral strains used in these studies included the historical A/Puerto Rico/08/1934 (H1N1) influenza A virus group 1 isolate and an in-house mouse-adapted A/Aichi/02/1968 (HA, NA) X-31 (H3N2) influenza A virus group 2 isolate. All experiments were performed in 6-8 week-old male and female MAID7225 HumIn TMPRSS4 mice or WT littermates. Mice were challenged with 1150 plaque-forming units (PFUs) of A/Puerto Rico/08/1934 (H1N1) or 10,000 PFUs of A/Aichi/02/1968-X31 (H3N2). In these survival models, mice were challenged intranasally (IN) on day 0 post-infection (p.i.). Mice were weighed and observed daily up to day 14 p.i. and were sacrificed when they lost 20% of their starting weight. Results are reported as percent survival (Table 4).

TABLE 4

| Group ID | Number of mice per group | Percent survival (no. of surviving mice/total no. of mice in the group) |
|---|---|---|
| Uninfected control (2 HumIn, 2 WT mice) | 4 | 100 (4/4) |
| WT TMPRSS4; H1_PR34 infected | 10 | 20 (2/10) |
| HumIn TMPRSS4; H1_PR34 infected | 8 | 25 (2/8) |
| WT TMPRSS4; H3_X31 infected | 9 | 11.1 (1/9) |
| HumIn TMPRSS4; H3_X31 infected | 8 | 25 (2/8) |

Figure 4:
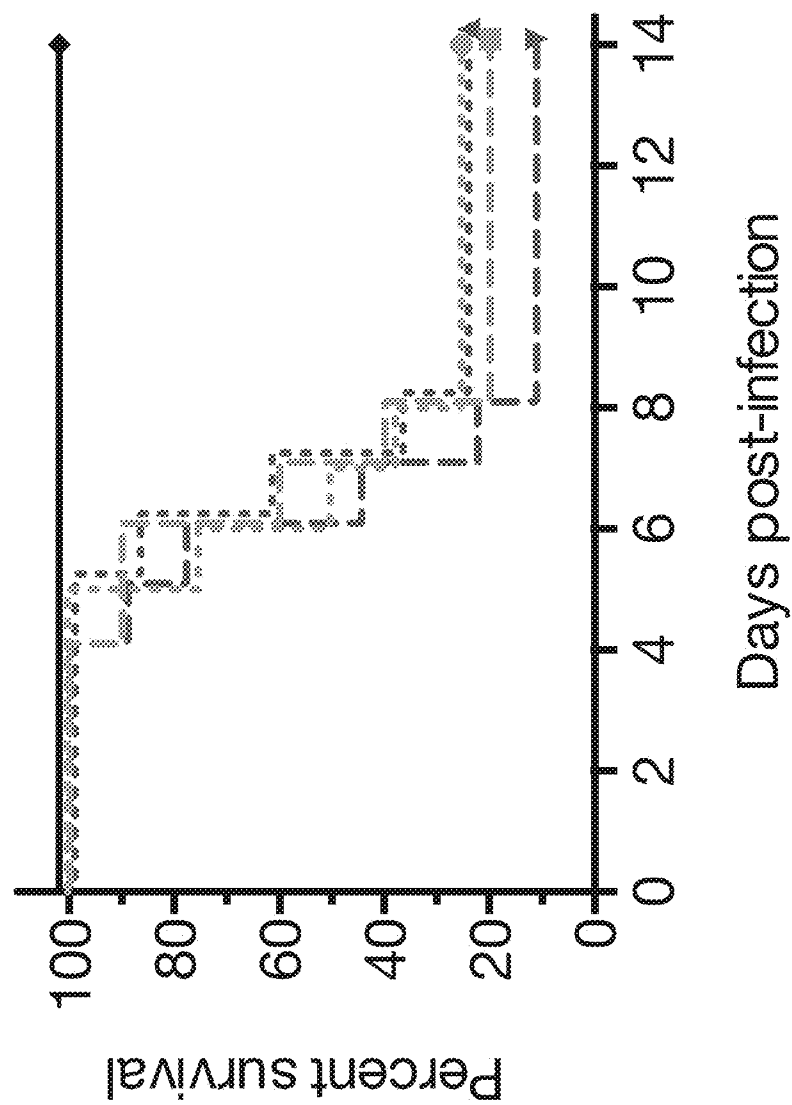
FIG. 4 depicts the results of an experiment showing that MAID7225 HumInTMPRSS4 mice do not differ in their susceptibility to challenge with high doses of severe influenza A H1N1 or severe, mouse-adapted H3N2. MAID7225 HumIn TMRPSS4 mice challenged with A/Puerto Rico/08/1934 (H1N1) (light gray circles, dotted line) showed similar survival rates compared to wild-type mice (light gray squares, dotted line). Likewise, MAID7225 HumIn TMRPSS4 mice challenged with A/Aichi/02/1968-X31 (H3N2) (dark gray triangles, dotted line) showed similar survival rates compared to wild-type mice (light gray inverse triangles, dashed line). Mice were infected IN on day 0 with either 1150 PFUs of A/Puerto Rico/08/1934 (H1N1) or 10,000 PFUs of A/Aichi/02/1968-X31 (H3N2). The control group included uninfected negative control MAID7225 HumIn TMPRSS4 and wild-type mice (black diamonds, solid line).

The survival of MAID7225 HumIn TMPRSS4 mice was compared to WT littermates after challenge with both severe Influenza A group 1 virus [A/Puerto Rico/08/1934 (H1N1)] and a severe, mouse-adapted Influenza A group 2 virus [A/Aichi/02/1968-X31 (H3N2)] (FIG. 4). Survival of MAID7225 HumIn TMPRSS4 mice was no different from wild-type mice with either the H1N1 challenge (25%; n=8 and 20%; n=10, respectively) or the H3N2 challenge (25%; n=8 and 11.1%; n=9, respectively).

The publications, websites and other reference materials referenced herein to describe the background of the invention and to provide additional detail regarding its practice are hereby incorporated by reference.

What is claimed is:

1. A rodent whose genome comprises a replacement of a nucleotide sequence of an endogenous rodent Tmprss gene at an endogenous rodent Tmprss locus with a nucleotide sequence of a cognate human TMPRSS gene to form a humanized Tmprss gene, wherein the humanized Tmprss gene is under control of the promoter of the endogenous rodent Tmprss gene at the endogenous rodent Tmprss locus, and wherein the humanized Tmprss gene encodes a humanized Tmprss protein that comprises (i) an ectodomain substantially identical to the ectodomain of the human TMPRSS protein encoded by the cognate human TMPRSS gene, and (ii) a cytoplasmic and transmembrane portion that is substantially identical to the cytoplasmic and transmembrane portion of the endogenous rodent Tmprss protein encoded by the endogenous rodent Tmprss gene.

2. The rodent of claim 1, wherein the rodent is a mouse or a rat.

3. The rodent of claim 1, wherein the rodent is heterozygous for the humanized Tmprss gene.

4. The rodent of claim 1, wherein the rodent is homozygous for the humanized Tmprss gene.

5. An isolated rodent cell or tissue whose genome comprises a replacement of a nucleotide sequence of an endogenous rodent Tmprss gene at an endogenous rodent Tmprss locus with a nucleotide sequence of a cognate human TMPRSS gene to form a humanized Tmprss gene, wherein the humanized Tmprss gene is under control of the promoter of the endogenous rodent Tmprss gene at the endogenous rodent Tmprss locus, and wherein the humanized Tmprss gene encodes a humanized Tmprss protein that comprises (i) an ectodomain substantially identical to the ectodomain of the human TMPRSS protein encoded by the cognate human TMPRSS gene, and (ii) a cytoplasmic and transmembrane portion that is substantially identical to the cytoplasmic and transmembrane portion of the endogenous rodent Tmprss protein encoded by the endogenous rodent Tmprss gene.

6. The isolated rodent cell or tissue of claim 5, wherein the rodent cell is a rodent embryonic stem cell.

7. A rodent embryo generated from the rodent embryonic stem cell of claim 6.

8. A vector comprising a human genomic DNA encoding the ectodomain of a human TMPRSS protein, flanked by a 5' nucleotide sequence and a 3' nucleotide sequence that are homologous to genomic DNA sequences flanking a rodent genomic DNA at a rodent Tmprss locus encoding the ectodomain of a cognate rodent Tmprss protein, wherein a homologous recombination-mediated integration of the human genomic DNA into the rodent Tmprss locus results in a replacement of the rodent genomic DNA with the human genomic DNA to form a humanized Tmprss gene which encodes a humanized Tmprss protein that comprises (i) an ectodomain substantially identical to the ectodomain of the human TMPRSS protein encoded by the cognate human TMPRSS gene, and (ii) a cytoplasmic and transmembrane portion that is substantially identical to the cytoplasmic and transmembrane portion of the endogenous rodent Tmprss protein encoded by the endogenous rodent Tmprss gene.

9. A method of providing a rodent whose genome comprises a humanized Tmprss gene, the method comprising:

modifying the genome of a rodent to replace a genomic sequence of an endogenous Tmprss gene at an endogenous rodent Tmprss locus with a genomic sequence of a cognate human TMPRSS gene to form a humanized Tmprss gene, wherein the humanized Tmprss gene is under control of the promoter of the endogenous rodent Tmprss gene at the endogenous rodent Tmprss locus, and wherein the humanized Tmprss gene encodes a humanized Tmprss protein that comprises (i) an ectodomain substantially identical to the ectodomain of the human TMPRSS protein encoded by the cognate human TMPRSS gene, and (ii) a cytoplasmic and transmembrane portion that is substantially identical to the cytoplasmic and transmembrane portion of the endogenous rodent Tmprss protein encoded by the endogenous rodent Tmprss gene.

10. A method of making a rodent having a humanized Tmprss gene, comprising:

(a) inserting a genomic fragment into an endogenous rodent Tmprss locus in a rodent embryonic stem cell, said genomic fragment comprising a nucleotide sequence of a cognate human TMPRSS gene, thereby forming a humanized Tmprss gene, wherein the humanized Tmprss gene is under control of the promoter of the rodent Tmprss gene at the endogenous rodent Tmprss locus, and wherein the humanized Tmprss gene encodes a humanized Tmprss protein that comprises (i) an ectodomain substantially identical to the ectodomain of the human TMPRSS protein encoded by the cognate human TMPRSS gene, and (ii) a cytoplasmic and transmembrane portion that is substantially identical to the cytoplasmic and transmembrane portion of the endogenous rodent Tmprss protein encoded by the endogenous rodent Tmprss gene;

(b) obtaining a rodent embryonic stem cell comprising the humanized Tmprss gene of (a); and, (c) creating a rodent using the rodent embryonic stem cell of (b).

11. A method of assessing the therapeutic efficacy of a compound in treating influenza virus infection, comprising:

administering an influenza virus and a candidate compound to the rodent of claim 1; and monitoring the presence and severity of influenza virus infection in the rodent to determine the therapeutic efficacy of the candidate compound.

12. The rodent of claim 1, wherein the rodent is a mouse.

13. The isolated rodent cell or tissue of claim 6, wherein the rodent cell is a mouse or rat embryonic stem cell.

14. The isolated rodent cell or tissue of claim 6, wherein the rodent cell is a mouse embryonic stem cell.

15. The rodent embryo of claim 7, wherein the rodent embryo is a mouse or rat embryo.

16. The rodent embryo of claim 7, wherein the rodent embryo is a mouse embryo.

17. The method of claim 9, wherein the rodent is a mouse or a rat.

18. The method of claim 9, wherein the rodent is a mouse.

19. The method of claim 10, wherein the rodent is a mouse or a rat.

20. The method of claim 10, wherein the rodent is a mouse.

21. The method of claim 11, wherein the rodent is a mouse or a rat.

22. The method of claim 11, wherein the rodent is a mouse.

23. The method of claim 11, wherein the candidate compound is an antibody or antigen-binding fragment thereof specific for a human TMPRSS protein.

* * * * *

SEQUENCE LISTING

```
<160> NUMBER OF SEQ ID NOS: 72

<210> SEQ ID NO 1
<211> LENGTH: 3175
<212> TYPE: DNA
<213> ORGANISM: Mus musculus

<400> SEQUENCE: 1

gcctttcctg gccgttccct ccttctggcc gaggtgcctg cgtttagggg tgtcaccctg      60

gctcccggga cgccgcctcc ggagatttaa gcgagaactg gagtaggtcg tgtacttgga     120

gcggacgagg aagccaagag ctcggacaga ggcggagagg ggcgggaagc gcaacaggtc     180

acctggagga agccccatac tgacctcctc atgctgctga cacaggcagg atggcattga     240

actcagggtc acctccagga atcggacctt gctatgagaa ccacgggtat cagtctgagc     300

acatctgtcc tccgagacca ccagtggctc ccaatggcta caacttgtat ccagcccagt     360

actacccatc tccagtgcct cagtatgctc cgaggattac aacgcaagcc tcaacatctg     420

tcatccacac acatcccaag tcctcaggag cactgtgcac ctcaaagtct aagaaatcgc     480

tgtgtttagc cctcgccctg ggcactgtcc tcacgggagc tgctgtggct gctgtcttgc     540

tttggaggtt ctgggacagc aactgttcta cgtctgagat ggagtgtggg tcttcaggca     600

catgcatcag ctcttctctc tggtgtgacg ggtagcaca ttgtcccaac ggagaagatg      660

agaaccgttg tgttcgtctc tacggacaaa gcttcatcct ccaggtttac tcatctcaga     720

ggaaagcctg gtatcccgtg tgccaggatg attggagtga gagctacggg agagcagcat     780

gtaaagacat gggatacaag aacaattttt attctagcca agggatacca gaccagagcg     840

gggcaacgag ctttatgaag ctgaatgtga gctcaggcaa cgttgacctc tataaaaaac     900

tctaccacag tgactcatgt tcatcccgca tggtggtttc tttgcgctgt atagaatgcg     960

gggttcgctc agtgaaacgc cagagcagga ttgtgggtgg attgaatgcc tcaccaggag    1020

actggccctg gcaggtcagc ctgcacgtcc aaggcgtcca cgtctgcgga ggctccatca    1080

tcacccccga gtggattgtg acggccgccc actgtgtgga agaacccctc agcagcccga    1140

ggtactggac ggcatttgcg ggaattctga gacagtctct catgttctat ggaagtagac    1200

accaggtaga aaaagtaatt tcccatccaa attacgactc taagaccaag aataacgaca    1260

ttgctctcat gaagctgcag acacctttgg cttttaatga tctagtgaag ccagtgtgtc    1320

tgccgaaccc aggcatgatg ctagacctag accaggaatg ctggatttcg gggtgggggg    1380

ccacctatga gaaagggaag acctcggacg tgttgaatgc tgccatggta cccttgatcg    1440

agccctccaa atgtaatagt aaatacatat acaacaacct aatcacacca gccatgatct    1500

gtgccggctt cctccagggg tctgtcgact cttgccaggg agacagtgga gggccgctgg    1560

ttactttgaa gaatgggatc tggtggctga ttggggacac gagctggggc tcgggctgtg    1620

ccaaggcact cagacctgga gtatacggga acgtgacggt atttacagat tggatctacc    1680

agcaaatgag ggcgaacagc taatccacgt ggctttgtcc cagacttcct ttgtcttcaa    1740

caaccttctg caagaaaacc aagggcctga attttaactt cctgtgcaca atgtaccttt    1800

tgagatgatt cgaagggcct ttcactttta ttaaacagtg acttgtttga ctgtgctccc    1860
```

```
tggtcctgtg agggcttcag tgccccaccc ctgggccact tctgcagctc ccaccagaat   1920

ggatgaccag attctgttgg gtttgggcac atagggccaa aggcagagga gggtggcact   1980

ctcatgttgg aacttctttt gggctcatgc tcaggccttt tttggatcac taaggactat   2040

gacctctgag taacctgatg acctgagaaa gagtaaggag gccaggcagg gccttgggcc   2100

caggaacagg taccttgaga gtgagagcta cccattgcct gtggcctaaa tctgctgtgc   2160

aggttgggct ggtcatactg tcatgatttc attaacagcc tgggtgaaca tggctgggag   2220

taaagggctt gctctcctgc atgttgacat gacggccctt tccaagggtg atggaggctt   2280

tcccaagcta agggcctagg cagatctctc agagcaagaa gctaatgccg gcatgtccct   2340

tgggtgagct ctacatggtg ttattcagtc tggttcttgg ctccccacta ctgtttctct   2400

cagcctctca gagcctgaaa cttacctctt agctttggct acaggcatgg cctagtacct   2460

gatggagcct gtatagctca gctaatcaaa tggaggctca ggtccatcag aatcagggac   2520

ttgtgatttc agtcaccttg cttctgggtt gtgtttcttc tcttactacc tcactgcacc   2580

tggacactag agtggatgaa tgtctggagt tcacctgcat ttggactgtg tgattgtgcc   2640

tcagacacta gacctcttcc agatggttag gttgttctgt agactggcaa tgagattaga   2700

agttcctagc ttcagataaa gatgaaagag aggagatcat tgtcttctgt cttcttctgg   2760

ccctgggttt ataccaggaa agccatgcca gaattaccaa atatgaagta tgaatgtctt   2820

acccacggtg aggctctgcc tccttctctc tgcctggttc ttcagaaggc agtgaatggg   2880

tcataactgg gactccatct ttgctgggga aagtctccca cctagggaat ggttaccact   2940

ccatgtaaag aaaactccct catgcgtcct ctgggacctt cttagatgct gtaaggtacc   3000

tacatacaga ctaaatgtgc aagcaccttg aagtgtgaga acctgtcccc tccttagctc   3060

tccttgtctt tgctgttggt tggttatttc ctgctttgtg tctgttctga gctgtgagat   3120

tccactgtga aatatatgaa taaagtatat aattctttta aaaaaaaaaa aaaaa        3175
```

```
<210> SEQ ID NO 2
<211> LENGTH: 490
<212> TYPE: PRT
<213> ORGANISM: Mus musculus

<400> SEQUENCE: 2

Met Ala Leu Asn Ser Gly Ser Pro Pro Gly Ile Gly Pro Cys Tyr Glu
1               5                   10                  15

Asn His Gly Tyr Gln Ser Glu His Ile Cys Pro Pro Arg Pro Pro Val
            20                  25                  30

Ala Pro Asn Gly Tyr Asn Leu Tyr Pro Ala Gln Tyr Tyr Pro Ser Pro
        35                  40                  45

Val Pro Gln Tyr Ala Pro Arg Ile Thr Thr Gln Ala Ser Thr Ser Val
    50                  55                  60

Ile His Thr His Pro Lys Ser Ser Gly Ala Leu Cys Thr Ser Lys Ser
65                  70                  75                  80

Lys Lys Ser Leu Cys Leu Ala Leu Ala Leu Gly Thr Val Leu Thr Gly
                85                  90                  95

Ala Ala Val Ala Ala Val Leu Leu Trp Arg Phe Trp Asp Ser Asn Cys
            100                 105                 110

Ser Thr Ser Glu Met Glu Cys Gly Ser Ser Gly Thr Cys Ile Ser Ser
        115                 120                 125

Ser Leu Trp Cys Asp Gly Val Ala His Cys Pro Asn Gly Glu Asp Glu
    130                 135                 140
```

```
Asn Arg Cys Val Arg Leu Tyr Gly Gln Ser Phe Ile Leu Gln Val Tyr
145                 150                 155                 160

Ser Ser Gln Arg Lys Ala Trp Tyr Pro Val Cys Gln Asp Asp Trp Ser
                165                 170                 175

Glu Ser Tyr Gly Arg Ala Ala Cys Lys Asp Met Gly Tyr Lys Asn Asn
            180                 185                 190

Phe Tyr Ser Ser Gln Gly Ile Pro Asp Gln Ser Gly Ala Thr Ser Phe
        195                 200                 205

Met Lys Leu Asn Val Ser Ser Gly Asn Val Asp Leu Tyr Lys Lys Leu
    210                 215                 220

Tyr His Ser Asp Ser Cys Ser Ser Arg Met Val Val Ser Leu Arg Cys
225                 230                 235                 240

Ile Glu Cys Gly Val Arg Ser Val Lys Arg Gln Ser Arg Ile Val Gly
                245                 250                 255

Gly Leu Asn Ala Ser Pro Gly Asp Trp Pro Trp Gln Val Ser Leu His
            260                 265                 270

Val Gln Gly Val His Val Cys Gly Gly Ser Ile Ile Thr Pro Glu Trp
        275                 280                 285

Ile Val Thr Ala Ala His Cys Val Glu Glu Pro Leu Ser Ser Pro Arg
    290                 295                 300

Tyr Trp Thr Ala Phe Ala Gly Ile Leu Arg Gln Ser Leu Met Phe Tyr
305                 310                 315                 320

Gly Ser Arg His Gln Val Glu Lys Val Ile Ser His Pro Asn Tyr Asp
                325                 330                 335

Ser Lys Thr Lys Asn Asn Asp Ile Ala Leu Met Lys Leu Gln Thr Pro
            340                 345                 350

Leu Ala Phe Asn Asp Leu Val Lys Pro Val Cys Leu Pro Asn Pro Gly
        355                 360                 365

Met Met Leu Asp Leu Asp Gln Glu Cys Trp Ile Ser Gly Trp Gly Ala
    370                 375                 380

Thr Tyr Glu Lys Gly Lys Thr Ser Asp Val Leu Asn Ala Ala Met Val
385                 390                 395                 400

Pro Leu Ile Glu Pro Ser Lys Cys Asn Ser Lys Tyr Ile Tyr Asn Asn
                405                 410                 415

Leu Ile Thr Pro Ala Met Ile Cys Ala Gly Phe Leu Gln Gly Ser Val
            420                 425                 430

Asp Ser Cys Gln Gly Asp Ser Gly Gly Pro Leu Val Thr Leu Lys Asn
        435                 440                 445

Gly Ile Trp Trp Leu Ile Gly Asp Thr Ser Trp Gly Ser Gly Cys Ala
    450                 455                 460

Lys Ala Leu Arg Pro Gly Val Tyr Gly Asn Val Thr Val Phe Thr Asp
465                 470                 475                 480

Trp Ile Tyr Gln Gln Met Arg Ala Asn Ser
                485                 490
```

<210> SEQ ID NO 3
<211> LENGTH: 3212
<212> TYPE: DNA
<213> ORGANISM: Homo sapiens

<400> SEQUENCE: 3

```
gagtaggcgc gagctaagca ggaggcggag gcggaggcgg agggcgaggg gcggggagcg      60

ccgcctggag cgcggcaggt catattgaac attccagata cctatcatta ctcgatgctg     120

ttgataacag caagatggct ttgaactcag ggtcaccacc agctattgga ccttactatg     180
```

```
aaaaccatgg ataccaaccg gaaaacccct atcccgcaca gcccactgtg gtccccactg    240
tctacgaggt gcatccggct cagtactacc cgtcccccgt gccccagtac gccccgaggg    300
tcctgacgca ggcttccaac cccgtcgtct gcacgcagcc caaatcccca tccgggacag    360
tgtgcacctc aaagactaag aaagcactgt gcatcacctt gaccctgggg accttcctcg    420
tgggagctgc gctggccgct ggcctactct ggaagttcat gggcagcaag tgctccaact    480
ctgggataga gtgcgactcc tcaggtacct gcatcaaccc ctctaactgg tgtgatggcg    540
tgtcacactg ccccggcggg gaggacgaga atcggtgtgt tcgcctctac ggaccaaact    600
tcatccttca ggtgtactca tctcagagga agtcctggca ccctgtgtgc caagacgact    660
ggaacgagaa ctacgggcgg gcggcctgca gggacatggg ctataagaat aatttttact    720
ctagccaagg aatagtggat gacagcggat ccaccagctt tatgaaactg aacacaagtg    780
ccggcaatgt cgatatctat aaaaaactgt accacagtga tgcctgttct tcaaaagcag    840
tggtttcttt acgctgtata gcctgcgggg tcaacttgaa ctcaagccgc cagagcagga    900
ttgtgggcgg cgagagcgcg ctcccggggg cctggccctg gcaggtcagc ctgcacgtcc    960
agaacgtcca cgtgtgcgga ggctccatca tcacccccga gtggatcgtg acagccgccc   1020
actgcgtgga aaaacctctt aacaatccat ggcattggac ggcatttgcg gggattttga   1080
gacaatcttt catgttctat ggagccggat accaagtaga aaaagtgatt tctcatccaa   1140
attatgactc caagaccaag aacaatgaca ttgcgctgat gaagctgcag aagcctctga   1200
ctttcaacga cctagtgaaa ccagtgtgtc tgcccaaccc aggcatgatg ctgcagccag   1260
aacagctctg ctggatttcc gggtgggggg ccaccgagga gaaagggaag acctcagaag   1320
tgctgaacgc tgccaaggtg cttctcattg agacacagag atgcaacagc agatatgtct   1380
atgacaacct gatcacacca gccatgatct gtgccggctt cctgcagggg aacgtcgatt   1440
cttgccaggg tgacagtgga gggcctctgg tcacttcgaa gaacaatatc tggtggctga   1500
taggggatac aagctggggt tctggctgtg ccaaagctta cagaccagga gtgtacggga   1560
atgtgatggt attcacggac tggatttatc gacaaatgag ggcagacggc taatccacat   1620
ggtcttcgtc cttgacgtcg ttttacaaga aaacaatggg gctggttttg cttccccgtg   1680
catgatttac tcttagagat gattcagagg tcacttcatt tttattaaac agtgaacttg   1740
tctggctttg gcactctctg ccattctgtg caggctgcag tggctcccct gcccagcctg   1800
ctctccctaa ccccttgtcc gcaaggggtg atggccggct ggttgtgggc actggcggtc   1860
aagtgtggag gagaggggtg gaggctgccc cattgagatc ttcctgctga gtcctttcca   1920
ggggccaatt ttggatgagc atggagctgt cacctctcag ctgctggatg acttgagatg   1980
aaaaaggaga gacatggaaa gggagacagc caggtggcac ctgcagcggc tgccctctgg   2040
ggccacttgg tagtgtcccc agcctacctc tccacaaggg gattttgctg atgggttctt   2100
agagccttag cagccctgga tggtggccag aaataaaggg accagccctt catgggtggt   2160
gacgtggtag tcacttgtaa ggggaacaga aacatttttg ttcttatggg gtgagaatat   2220
agacagtgcc cttggtgcga gggaagcaat tgaaaaggaa cttgccctga gcactcctgg   2280
tgcaggtctc cacctgcaca ttgggtgggg ctcctgggag ggagactcag ccttcctcct   2340
catcctccct gaccctgctc ctagcaccct ggagagtgca catgcccctt ggtcctggca   2400
gggcgccaag tctggcacca tgttggcctc ttcaggcctg ctagtcactg gaaattgagg   2460
tccatggggg aaatcaagga tgctcagttt aaggtacact gtttccatgt tatgtttcta   2520
```

```
cacattgcta cctcagtgct cctggaaact tagcttttga tgtctccaag tagtccacct   2580

tcatttaact ctttgaaact gtatcatctt tgccaagtaa gagtggtggc ctatttcagc   2640

tgctttgaca aaatgactgg ctcctgactt aacgttctat aaatgaatgt gctgaagcaa   2700

agtgcccatg gtggcggcga agaagagaaa gatgtgtttt gttttggact ctctgtggtc   2760

ccttccaatg ctgtgggttt ccaaccaggg gaagggtccc ttttgcattg ccaagtgcca   2820

taaccatgag cactactcta ccatggttct gcctcctggc caagcaggct ggtttgcaag   2880

aatgaaatga atgattctac agctaggact taaccttgaa atggaaagtc atgcaatccc   2940

atttgcagga tctgtctgtg cacatgcctc tgtagagagc agcattccca gggaccttgg   3000

aaacagttgg cactgtaagg tgcttgctcc ccaagacaca tcctaaaagg tgttgtaatg   3060

gtgaaaacgt cttccttctt tattgcccct tcttatttat gtgaacaact gtttgtcttt   3120

ttttgtatct tttttaaact gtaaagttca attgtgaaaa tgaatatcat gcaaataaat   3180

tatgcaattt ttttttcaaa gtaaaaaaaa aa                                 3212
```

<210> SEQ ID NO 4
<211> LENGTH: 492
<212> TYPE: PRT
<213> ORGANISM: Homo sapiens

<400> SEQUENCE: 4

```
Met Ala Leu Asn Ser Gly Ser Pro Pro Ala Ile Gly Pro Tyr Tyr Glu
1               5                   10                  15

Asn His Gly Tyr Gln Pro Glu Asn Pro Tyr Pro Ala Gln Pro Thr Val
            20                  25                  30

Val Pro Thr Val Tyr Glu Val His Pro Ala Gln Tyr Tyr Pro Ser Pro
        35                  40                  45

Val Pro Gln Tyr Ala Pro Arg Val Leu Thr Gln Ala Ser Asn Pro Val
    50                  55                  60

Val Cys Thr Gln Pro Lys Ser Pro Ser Gly Thr Val Cys Thr Ser Lys
65                  70                  75                  80

Thr Lys Lys Ala Leu Cys Ile Thr Leu Thr Leu Gly Thr Phe Leu Val
                85                  90                  95

Gly Ala Ala Leu Ala Ala Gly Leu Leu Trp Lys Phe Met Gly Ser Lys
            100                 105                 110

Cys Ser Asn Ser Gly Ile Glu Cys Asp Ser Ser Gly Thr Cys Ile Asn
        115                 120                 125

Pro Ser Asn Trp Cys Asp Gly Val Ser His Cys Pro Gly Gly Glu Asp
    130                 135                 140

Glu Asn Arg Cys Val Arg Leu Tyr Gly Pro Asn Phe Ile Leu Gln Val
145                 150                 155                 160

Tyr Ser Ser Gln Arg Lys Ser Trp His Pro Val Cys Gln Asp Asp Trp
                165                 170                 175

Asn Glu Asn Tyr Gly Arg Ala Ala Cys Arg Asp Met Gly Tyr Lys Asn
            180                 185                 190

Asn Phe Tyr Ser Ser Gln Gly Ile Val Asp Asp Ser Gly Ser Thr Ser
        195                 200                 205

Phe Met Lys Leu Asn Thr Ser Ala Gly Asn Val Asp Ile Tyr Lys Lys
    210                 215                 220

Leu Tyr His Ser Asp Ala Cys Ser Ser Lys Ala Val Val Ser Leu Arg
225                 230                 235                 240

Cys Ile Ala Cys Gly Val Asn Leu Asn Ser Ser Arg Gln Ser Arg Ile
                245                 250                 255
```

```
Val Gly Gly Glu Ser Ala Leu Pro Gly Ala Trp Pro Trp Gln Val Ser
            260                 265                 270

Leu His Val Gln Asn Val His Val Cys Gly Gly Ser Ile Ile Thr Pro
        275                 280                 285

Glu Trp Ile Val Thr Ala Ala His Cys Val Glu Lys Pro Leu Asn Asn
    290                 295                 300

Pro Trp His Trp Thr Ala Phe Ala Gly Ile Leu Arg Gln Ser Phe Met
305                 310                 315                 320

Phe Tyr Gly Ala Gly Tyr Gln Val Glu Lys Val Ile Ser His Pro Asn
                325                 330                 335

Tyr Asp Ser Lys Thr Lys Asn Asn Asp Ile Ala Leu Met Lys Leu Gln
            340                 345                 350

Lys Pro Leu Thr Phe Asn Asp Leu Val Lys Pro Val Cys Leu Pro Asn
        355                 360                 365

Pro Gly Met Met Leu Gln Pro Glu Gln Leu Cys Trp Ile Ser Gly Trp
    370                 375                 380

Gly Ala Thr Glu Glu Lys Gly Lys Thr Ser Glu Val Leu Asn Ala Ala
385                 390                 395                 400

Lys Val Leu Leu Ile Glu Thr Gln Arg Cys Asn Ser Arg Tyr Val Tyr
                405                 410                 415

Asp Asn Leu Ile Thr Pro Ala Met Ile Cys Ala Gly Phe Leu Gln Gly
            420                 425                 430

Asn Val Asp Ser Cys Gln Gly Asp Ser Gly Gly Pro Leu Val Thr Ser
        435                 440                 445

Lys Asn Asn Ile Trp Trp Leu Ile Gly Asp Thr Ser Trp Gly Ser Gly
    450                 455                 460

Cys Ala Lys Ala Tyr Arg Pro Gly Val Tyr Gly Asn Val Met Val Phe
465                 470                 475                 480

Thr Asp Trp Ile Tyr Arg Gln Met Arg Ala Asp Gly
                485                 490
```

<210> SEQ ID NO 5
<211> LENGTH: 27947
<212> TYPE: DNA
<213> ORGANISM: Artificial Sequence
<220> FEATURE:
<223> OTHER INFORMATION: Recombinant polynucleotide

<400> SEQUENCE: 5

```
gcagagtcta agaaatcgct gtgtttagcc ctcgccctgg gcactgtcct cacgggagct      60

gctgtggctg ctgtcttgct ttggaagttc agtaagtgca gggagcctcg atcccaccat     120

gtgctcctgc agtccccagt gctctgagcc agaccctgct ctctgggcta ttgagacctc     180

tggaggccct ccgtgaggtt cctctcttac ataacgaggc tgtctctctt cccttctctt     240

gtttagctat gagattgaca catcatgggg aaagcattta gaatgtaccc agtgctttgg     300

ggtgcttggt gccacccagc actgtgagca caggttcttc taccttgggg ccacacccag     360

ttacctgtat ctcactgcac agcagtggct gttggggacc aggcccaccc ctccatgtcc     420

cacctcctgc aactgcagcc tgagccttcc catcagcctg ggtggtgca gacccatgtg      480

ccattgtgga tccttcaagt tacctgtgtg gcagagagga cgtgtgagtg ccgtccaaac     540

ccaaacactg agagggtcct tcccattgcc cccacggaag taaggtgccc cagtgctaat     600

tccacttata cttgctggtg gcaaggacac ttctcctcct tattaaagtg ggggattggc     660

tgggtgaggt ggctcacgcc tgttatccca gcactttaag aggccaaggc aggtggacca     720
```

```
cctgaggtca ggagtttgag accacaagcc tggccaacat gttgaaactc catctctact    780

aaaaatacaa aaattagtca ggcgtggtgg cgtgcacctg taatcccagc tacttaggag    840

gctggggcag gaggatcact tgaacccagg agttggaggt tgcagtgagc caagattgtg    900

cccctgcact ccagcctggg tgacagaatg agacttcatc tcaaaaacaa aacaaaacaa    960

aacacagtgg ggccaggagt tggaggctgc agcgagctac agtaatgcca cggtgttcct   1020

cactccatga ggctcattgc gtttctcagc ctgaagggca cctctcttct gttttctctg   1080

caagtgggca gcaagtgctc caactctggg atagagtgcg actcctcagg tacctgcatc   1140

aacccctcta actggtgtga tggcgtgtca cactgccccg gcggggagga cgagaatcgg   1200

tgtggtgagt cagccttgac cttgggaagg gactcctctg ctcaccttgg agacagcagc   1260

cgggtccagg ggcctttggg tgactgggcc tggcgtgcgt ccagtacgct gacacatgat   1320

gtcattgaat ccctgctcca ggctgagccc tggggctcag agaggttgtg tttccggccc   1380

aacctcaccc agcaggtggg agatgacagg gccaccgagg actgtgtcat tggaaccaca   1440

cgtgctctga actgccacag gaagtcagtt aagatgagca aactgtttat aaagttggag   1500

atgcaggcta ggaacggtgg ctcatgcctg taatcccagc actttgggag gccgaggcag   1560

atggatcacc tgaggtcagg agtttgagac cagcctgacc aatatggtga aaccttatct   1620

ccactaaaaa tacaaaaatt agccaagcgc ggtggcgggt gcctgtaatt ccagctattc   1680

aggaggctga ggcaggagaa tcacttgaac ctgggaggcg gaggttgcag tgagctgaga   1740

tcacgccact gcattccagc ctgggagaca gagctggctc aaaaaataaa ttaattaatt   1800

aaaaacaaaa ttggagatgc actatgttat tttcaaaaca agctgccttt aaagatctat   1860

ctgttgtcac agggtgggct catctgtttc attttatttt ctgtggttta tctatttatt   1920

cattttaatg aactaggaag cattgctcct atttatggca taccacatga tgtttggata   1980

cgtgtatgcc tgtggcatgg ctaagtcaag ctagaacatg ggccttacct catatacgtg   2040

tcttattaag aacacataaa acctactctt gtagtgattt tcaaatatgc aacatatagt   2100

ttattaactg cagtcactat gatgtacaat agattgctcg aacttattcc tcctgtctaa   2160

ctaagatttt gtgacctctg accaacatct ccccagtgtt gtcaccccccc gcccccagcc   2220

tctgatagct gcctttctac tctctgcttc tgtgagtttg atgtttatac attccacatg   2280

taagtggcct catgcagtgt ttctgtctct gtgtctggct tgttcactta gcgtaatgtc   2340

ctccagcttc atctatgttg ttggaaatga caggatttcc ttctttcttg tggctgaata   2400

gtattgcctt gtgcatatac accacatttt ctttatccct tcattcactg atggactctt   2460

aggttgatgt catgtcttgg ctgttgtgaa aaatgccgca gtgagcgtgg gcgtgcaggt   2520

ccctcttcaa cacacggatt tcctttcctt tggatataaa cccagcagtg agattgctgg   2580

atcacatggc agttctgttt ctcacctttt gaggaaactc catactgttt tccataatgg   2640

ctgtagcaac ttccactccc acccccacgg tgcaaagtct ccatttctct tctacaacct   2700

caccaactcc tgttattttc catctttctg atagtagcca tttgaagagg tatgagatga   2760

tacctcattg tggttttcat ttgcattttt atttgtattt ttcatgaatt tttgagggtg   2820

atttcaaggg tagttagtga ctcgaacagg gaaacgatcc tgagtatgag ggttgtgcta   2880

atcatccccc tcctgccagc tgcgtacgga atggggctct gcagatggca gggagctggc   2940

tcgtttctct ttaagagctg ccttttactt ttcttcctct tcctttaaaa cttatttcct   3000

ggccggacgc agtggctcat gcctgtaatc ccagcacttt gggaggccga ggtgggcgga   3060
```

```
tcacgaggtc aggaattcca gaccagcctg gccaacatgg tgaaaccccg tctctactaa   3120
aaatacaaaa attagccaga cgtggtggtg cgggcctata gtcccagcta ctcgggaggc   3180
tgaggcagga gaatcacttg aacctgggag gagggggttg cagtgagccg agattgcgcc   3240
actgcactcc agcctgggcg acagagccag actccatctc aaaaaacaaa aaaaagttat   3300
ttcccaagca cagccatgta ttccaggctt gtggatcagc gttggtggtg gtgtgtgctc   3360
tcatatctta gttccagcta agcacactct gacatgttta cactagaacc atttgttttt   3420
tctagaaata gaaatttcag aattgtagag tcagaggact taccagaaat ctcttaggta   3480
gttctcctcc cctccctcaa gtgcagtcct aacctcctgg agttttctgt agaaaccaca   3540
agcctcagag ctggccgaga attctagcca aagatttttc catgccaaag taatcccccc   3600
tctcctaagg gccatccttg gtggggactg gtttcctgtt aagccctcgc tgtcagtcct   3660
ggctgtggaa tttcctggtg aggagcactg gcccgtggag ctcggccctc gtgccggcct   3720
tgagcaggcc caagtgttcc gtgttcttga tacctttcct ccagcacagt cttgcttccc   3780
agaaaaaggt ttgcacttga aaatgatgca tttgctgatt aaacatagtt cttttgcttt   3840
atttggtttc taaaataaag tgggagtttt tgagattgag taacgtgagg ttaagatagc   3900
acgtggaatg gctttttctt ttctttctat tttttttttt tttttcctgg agacagggtt   3960
tcactctgtt gcccaggctg gagtgcagag gcatgaccat ggctcactgc aacttcgatg   4020
tcctggggtt aagcgatccc ccagcctcag ccccccaagt ggctgggact acaggtgctc   4080
gccaccacac ctggctaatt tttgtatttt ttgtagaaaa tgggtttcat caatgttgtc   4140
cagactggtc tcgaactcct gacctcaagc aattctcctg cctcagcctc ccagactgct   4200
gggattacag gcgtgaacta ccacgcctgg cctggaatgg cttttgatgt tctcctatgt   4260
gcacatgtgg gtgaataaac accaacaaag tccttatgtt acctgaagag ttgctctctt   4320
cttaatattt aagtcgtatt tatttaaata ctttaatagt tgtacactat taaagtatta   4380
ttaggtcaaa atcaaggaag tacaaaaggg tatgctgtga aaaatctctt cttccttgct   4440
ctgcttactt acctaccccg catccccccca tacaccccag acacacacac acacacacac   4500
acacacacac acacacgcat cactcccata catgcccacc tgtttaccag ccaatcacat   4560
ttcttggggc aactcatctg agttgcttct ctttccagag agtttttgca taaagaagca   4620
caggtatttc tgcgttacca tgaccctatt tcccagtggt tcctagccag ttgactctcc   4680
tgcactggat accatcctgg acagcattcc ttagggaaat gagcccccctg tttttcccca   4740
ccatggcaca gttggtcctt tgcatggacg caccattatt gcccctgtct cttcttggtg   4800
gaccttaagg ttttctccat ccttttgctg taacacacac tgctccaagt gtgtgagcat   4860
atcagtagga aacgcttcca ggagtagaac tgctaggtca gagggcgtgt ggatctgtaa   4920
cctgacagac ctagaccggc ttcagtttgg ttttatccag tttccatatt gattattcat   4980
ataaaaggaa acagacaaac ataacgctgt gcatgtattc tctcttagac cagaacaggc   5040
atagggtgca cttttaattt gtccatttcg tagagtagaa attgtttttg ctgaaatgaa   5100
caccttagga tgctgaagaa tatgacccgt cccatggaaa acattcaaaa atgtgtgtag   5160
cgctttcttc ccaagggtgt gtgtgcgcat attttaacac taattcactt tctacttccg   5220
ttgctatcct ttctgtgagt ctttctcaga atctcagaaa agaaactaaa ttgttcactc   5280
tagttatcaa tgctgtactc tatacctgga atttgctaaa agggcagatt ttaagtattc   5340
tcaccacaga aaagagaaaa gaaaatggta attatgtgac gtggtggaca tgttaactag   5400
ctttattatg gtgagcattt cacagcggat atccagtcat cacgctgtac acattaaaca   5460
```

```
tgtacaattg ggttttttttg agacaaggtc tccttctgtc acccagtctg gagtgcagtg   5520
gctcagtcat ggctcattgc agcctcgacc tcctgggctc aatccatcct tccccctcag   5580
cctcctgaaa agctggggcc acaggcatgt accatcatgc caggctaatg catatatatt   5640
tatatttttt ggtggagatg gggttggtct cgaactctgg gctcaagtga tcctcccgcc   5700
ttgcccttcc aaagtgctga gattacaggc atgaaccaca gcaccaggcc tacatgtaaa   5760
atttttattt gtcaactata ctttgacaaa gctgagaaaa aaaatcctaa tatttaaaaa   5820
aaaaaaaaaa aggactagct tgagaccttt tccagctctc tggcttatca gctgccgtct   5880
cttccgggtg cagatagctg gaagggaaag aaaatcccta aaattaccca caagccaaga   5940
atgaagtgtc tccctttgag ccacagtggc agttttgttt ttaatcatag aagtgtattt   6000
tgagccgggt gtgctggctc acgcctgtaa tccccgcact ttgggaggcc gaggtggggg   6060
gcggaggggg tggggatcgc ctgaggtcag gagttcgaga ccagcctgac caacatggag   6120
aaaccccgtc tctactaaaa atacaaaatt agccggcgtg gtggtgcatg cctgtaatcc   6180
cagctactca tgaggctgag tcaggagaat ctcttgaacc caggaggtgg aggttgcggt   6240
gagctgagat catgccattg cactccagcc tgggaacaag aaaaaaaaag aagaagaaga   6300
agaagtgtat tcatttcagt tacttttaaa aaagtgaaca gactttatat tttagagcgg   6360
ttttaggttt acagaaaatg aaacagacag ggcagcgagc tccttgtact cctccccagc   6420
acacagttgc cctgttatga acatcccaca tcagtgctgt gcgttcatta acaccgatga   6480
acctgatgca tacattatga tgaactgaag tcctggactt caccctttct cttgtacagt   6540
tctgtgggat ttgacaaatg cataatgctg tacagccaca atgatagtat cgtccagagt   6600
agttctcctg ccttaaaacc tcttttgctg cacctgtttc tctctcccca ctcaccccag   6660
ctatctgatc ttcttagtgc ctccgaagtt ttggtctttt caggatgttg tagcgttgga   6720
atcatggagt atgtagcctt caccacatac accttccttc actttgttgg cttcctttac   6780
ttagtaatat gcattcaagt ttcctccatg ccttttcatg gcttgatagc tcatttcttt   6840
ttagcaccaa ataatattcc gttgtccaga tgtagcacaa tgtttatcca ttcatgtaac   6900
ctgtgaccga ctcacagata ggatgtggaa tcactcacca cagaggcatt agacaataat   6960
cagacccaag tcatttcatg gggggaacaag cccacaggta ccagactgtc cagtgagtca   7020
gggccactcg taggaagtaa gaagagaggc tagagcatag ccaggtcctc actttatact   7080
ttaagcccat gtgtatttct cccaaaccac acagcattgt ttccatgctt tcagctttgc   7140
atgaataacg tgatacttga acgcatcatt tatcacttgc tctctttccc acagcgctgt   7200
tttcaagctt cttcctgttc atgatgctct gcttaaccct taagctgcat gggattctgt   7260
tctgtgaata cgcccacccc atgtattatc ctgcccagca aaaagtcccc aaaactctgg   7320
atggtggtta cctctaggga gggagagaag agattgggaa tagggagcga cttcaacggt   7380
gtttgtaatg ttttgtttct ttaaataaaa gagctgagat catttcagca gaatgttgat   7440
ttagagtctc ctggacaatt tgttgctcaa agtgctctct taaagagcac tttaaaaaaa   7500
aaaacctttt atcttattat ttatttattt atttattgag acggagtttt gctctgtcac   7560
ccaggctgga gtggagtggt gtgatctcag ctcactgcaa cctttacctc ctgggttcaa   7620
gcaattcccc tgcctcagcc tcccaagtag gtgggattac agatgcgtgc caccacactt   7680
ggctaatttt tgcattttag tagagatcgg tttctccatg ttggccaggc tgatctcaaa   7740
cgcctgacct caggtgatct gcccgccttg gcctcccaaa gtgctggtat tacaggcgtg   7800
```

-continued

```
agctaccatg cctggcttat cttatatatt tttaaaaaca gcttattgag atctaattta   7860
tgtaccataa aattcaagta tataattcag tgcttttata tataaaacat atatatgaaa   7920
tagcttattg agatataatt ttttatataa aacagcttat tgatatgtaa tgtatgtacc   7980
ataaaattta aatatataat tcactggctt ttatatattc acgaatatgt gcaactatca   8040
ccacagtcaa ttttagcata ttttcatcag ctcataaaga aaccccaagc ccttgaacta   8100
tcaccccata tccctcctcc cagcccgtcc ctcctactca taagcaacca ctaatctact   8160
tagtgtctat agatttccta ctctaggcat tccatgtgag cgggatcatg caatacgtgg   8220
gctcacacaa tataagtggc attccatgtg agtcggctca tgcagtatgt ccggctcctt   8280
tcactgagca taaggtcttc agcactcatc caggttgcag cctgtgtctg aatttcattc   8340
cctcttctgg ctgaatcgta ttccattgtg tatcttggac atatcctatt ctgctcaccc   8400
agccgttggt gggcgtttgg agtgttttcg cctttcagct gttttaagag ggttgcagtg   8460
aacatttgta caagttttgg acccaatgcc tgttttcaat tctcttgtgt agagagcact   8520
ttttagcaga aaaagaatag atttgtggcc tccctttgtg tgcggtcagt gccttgagaa   8580
gagtgaactg tgctgccacc tccggagccg tggagagcgc ggggcttggg tagcagctag   8640
gacgatacaa gttgggacaa ggccaggtgc aatggctcac gcctgtaatt ccaacacttt   8700
gggagaccga ggcaggggga tcacctgagg tcaggagttc aagaccagcc tggccaacat   8760
ggtgaaaccc catctctaat aaaacagaaa aattaactgg acggggtggt ggacgcctgt   8820
aatcccagct actcgggagg ctgaggcagg agaatcactt gaacctggga ggcggaggct   8880
gcagtgagtg gagatcagac cactgcactt cagcctaggt gacagagcga gactccgtct   8940
caaaaaaaag aaaaaaaaag aaagaaactc atggataatc ctccctctcg tgcagttcgc   9000
ctctacggac caaacttcat ccttcaggtg tactcatctc agaggaagtc ctggcaccct   9060
gtgtgccaag acgactggaa cgagaactac gggcgggcgg cctgcaggga catgggctat   9120
aagtgagtat ggggcagcac ccgccgagtg acagtaacag acagcagaaa cacgagaaga   9180
ccctctctct gcctccctgt gaaagcaccg gcacatgagt gctggggaca attgtcacct   9240
tccaaaagct gagccctata accagcaggt ggaatttgtc ctgctagggc tgtgcccagc   9300
acacagacct tggctcactg ccaccttgcc ctgcctcctc cttggcctct atagactcct   9360
ggttgctcgg gagtgcccag tgctgtggtc atctggtcag aggggtaggc tgagggcgtt   9420
aggtgcctct ttttccaagg tgcctctcag ccagggtcca ttcacctccc tgggtagagg   9480
ttggaccaga acagctggcg aggagggttg ggctggggag agcagcagag acaaatcctg   9540
tgccagtttc acttcattcg ggagccatgg aagccttttg agctggggag agaatcaatc   9600
aatcagactg atacttaaaa aatgtcattc ctgctcgtag ctctgaggga aggtgggaag   9660
gcttaacagg gtgtgtgtcg cctgacagtg attcctaacg gggtggggc ggtggttacc    9720
atttaccagc actgcctggg gagatgcggc agccctcagg catcggggga gagggtggta   9780
ggatgctact gccactttgt tttccatggg agggtcccca ggtgatttct atgcaacttt   9840
agggtattca atatgccagt tttcagaatg aattaccact cggtgagaaa gttggcatct   9900
tagctagtca ctgtgacatc cctaaacagc aggggtgaat tacacagcaa agccccccca   9960
tcacagtcca ggaacctggt ggaattgata actggggcca tgttaacatc tgtacctttt  10020
attagattaa atgtgtgtat gattatacaa tcctatgtcc ttctcatagt ttcttgatcc  10080
taacctggat aagaaacacg accaatgaag gaattttgtc tgacacttta gggttattga  10140
atcgaaaaat cgttacaata ttctagcact tggttagaac gtgtgatttt ttttcctaaa  10200
```

```
tgctaaggtt tttccctctt attctgaatg tcgtatgagc ggtattatga catagtatag  10260
gatttgtgtt tgcttatgcc ttaaccatta tcacaaataa ggttttcttt tttaggaata  10320
atttttactc tagccaagga atagtggatg acagcggatc caccagcttt atgaaactga  10380
acacaagtgc cggcaatgtc gatatctata aaaaactgta ccacaggtat gcagcaattt  10440
cttcttgaaa aattttggaa tgaaatcaac taggagacac catggggaat cgttgtcctg  10500
agtctgattt ctctgagctg caatactcgg tctggatggg ttttgcattg ggaggagatt  10560
agagtctgac caggcctggt tactctaagc agcccttggt ttattcatag gaagtggctg  10620
aggtttctct gctatttcat tttcagcctc taccgtctgc ccttgttggt agcggctcac  10680
acttgcaaca tcgacattca actctattta gttttctttc ctcttcagac atttagaggt  10740
gtacctattt tgtcagggcg tggttctagg aatccaagat aatgtctcag tgtcccagcc  10800
agggtgaccg gctcattcca gtttgccagg gacttcactg gcttgagcaa gggaagtcct  10860
gctccattcc aggcagctgg gctggctggt cccgttagcc ccaaccccgg gacagcagtg  10920
ccagagggtg ctctgtgagg gatgggcagc attctggcgg cctgggaatg agttgtggtg  10980
tttccagggg gtagaagtgg gtacaagcca caggtcacat gatgagtggc tgacctggct  11040
gggagggcag aagaggggat ggacttaggc tcttcctttt gctttgcaca tatttaggat  11100
gtttgcagac ttgctatgat tgttgctgtt atgtgttttc tgatgtgaaa gatacacagt  11160
gtcctttgcc catgagctct ccttgcctcc caggtcccca gggcttatgc ctggtgtcta  11220
ggcatcacct ccctgcctgc caggtgccag gtgctgcatt tcgggggagg atgaactaat  11280
caccccgcgc cacctttcct ctgagtggga gcctggggca ggtttgcatt cctggaggcc  11340
gctggtggag ggtctgggg gcctgacttc cactgcagcc tgctgtcctg gggaatgtgg  11400
cagggcaagc ccagtgggga gggctgtgca cggccaggtg cacccatcaa aacagcaggg  11460
ctgcggtttg tccctgtgga gaagctaaac acagctgcct gggcactttg taaatgctga  11520
gtggttcttt gtctttctgg gttacacacg gaatcaggga gccaagtcca gccgggcagg  11580
gacgggggga ggggaggagg tgctgccgtc ccttggcaag agccttggga actcacaagg  11640
aggctggagg gcttggaaga aagaagagaa ggccattgtc tggtaggctc tattctatct  11700
cggtggtggt ggtgggggga ggcgcacttc ttttcctctt tctgtgcagc agttgccctt  11760
tgatgcctga gttcttggct tgttttctgt cgggcttctg tgaataacca catgtgccct  11820
ggcgctgtga ccacacaggg ctatccctac cgaccttagg attcttagga aatgtcttct  11880
cttaaagggg acatgtcttc acttggccgt gtcagtgccc cagagccaga gtccacctgg  11940
aatgcacctg tagtcactga gaacccgggg ggtgtgcctt agtaagaagg tgtcaggaag  12000
gacctattat tgtagggcct gggctcctgc aaggtggttt gggggtggtt ggaggaagca  12060
gagatttgct ctggattgga tgctgtcagg aagcaggggt aattctgtga ggctgcttta  12120
ttattttttt tctaggagga ggttggaatg aggctaggct aaagctgtga ttggtaaaga  12180
aacgtccgtc gctcaagtta gccaggacag gaggagacat cagatcgtga ttttgtggtt  12240
gtgagcacaa ggttcctgtt ctgtctgttc agacatcatt tcggaggagg ctccttgtgt  12300
cttgccccat ctcaggcatg gaggggccta gtccgatatt gacgctcagt gaaataattc  12360
aggttccgca gagcacacgg cccagctatc agggcgggcc agctctgcat gccaggggcc  12420
gcgtcttccc ttctcagcat agcctgggaa attcactgca ggacaaaatg catcagttac  12480
ttcctcttca tccataacct gggatgtttg actcccaaat gagtaactct tacgtttctt  12540
```

```
ctaatcctag ggaaactatt ggttatattg ctttcaacac tacaaattta aagcagttat  12600
aggagcccag aggtttccaa atggcttcct taaaaattag aagatgattt taaattccaa  12660
gaggaaaaac aaaactagca ttattgtata cttaccctca caaccgtcct aggagctggt  12720
acaattttaa gagaggttaa gtaacttgcc caaggtcaca ctgtggggat gtgagccgcg  12780
taccttggct cagtgtctgg tctttgccac tgtccctata tggatttact taccttattg  12840
gagttgtaac tagcagaccc ttctatgtct cagaagacag gagagggaac atcggaagaa  12900
atgactgatt tctaagcatg tgagaggcag gtgactccgc actatcgtga ccagaatttc  12960
ccctgttctt tttgcagtga tgcctgttct tcaaaagcag tggtttcttt acgctgtata  13020
ggtaagttca tctggagtcc cccttttgat acttctaact aggaaaagct ctctactttc  13080
agaacagtac tccctgtgtc tctgggggcg tgggagggaa gaaggtgggg tcacgggttg  13140
gaatgtgccc agcggcgtct cgctctttcc aaggagctcc tggtttagat ttccatggcc  13200
tgtagacacc ttcagccttg ggtccaaggg acacccccctg agatcaggca cgctcaagaa  13260
gctgacaaag ccctacactt tatgccaccc atgagctgga ggcccggcag gtctctttct  13320
ccagaaagca aaggggggtg gcgttagtga gccctggcag ccacctaacg tggacttgga  13380
gcatctgcgg ggctgtggtc cagcaccacc gtgtggccac caggtgctca tcagccagtg  13440
ggacccggga ggagggacaa gaccagagaa caacagtgct cttgcctctt ctctcctgaa  13500
ttttggacgg tggcttagac ttgggtgtcc ccatctctgt gtttagagtg cttacagttt  13560
ccaaactgtt tgcaaatgtg gaagccaccg tccctctcct ctgggatggc ccagtgctgt  13620
cgtggggccg tggtcctgag ctcagctttt catttgaaga ggtggaagga gctgacaccg  13680
tcccatcccg gcagggctgg ctcaggtctt ctttaggtcc tgagtggggg tccagcacag  13740
ccccaagggt gcgtggcacc cgccctgccc tctgcccatg cactcatctc ctggtggaga  13800
agacactcac acacaggaag cagggaaggc agcagacctc actcacccct cacccccctca  13860
ctcacccccct actcaccccc tcaacctctc attcaccacc caccccctcg ccccctcact  13920
caccccctca ctccctcaac cctcactcac ctcctcactc cctcaaccct cactcacctc  13980
ctcacctcct cactctcccc ctcatccctc cctcacccca ccccgtcacc tcctcactca  14040
cctcctcacc ccctcactca cccttcaccc cctcactcac cacctcacct cctcactcac  14100
cccctactca accccctcatt cacccctcac cccctcactc acccctgcac cccctcactc  14160
acccccttcat ccactcaccc acctgctcac ctcctcactc aacccctcac cccctcacta  14220
atccctcact ccctcacccc ctcacgccct cactcacacc ttcacctcct cactcacccc  14280
ctcacccccct caacccctta cttacccccct cactcatccc ttcacccctc actcaccccc  14340
tctctcaccc attcaccccc tcactcatgc cttcaccccc tcactcacct cctcactcac  14400
accttcaccc ctcagtcacc ccctcactca cccccttcacc ccctcaatca tgccttcact  14460
ccctcactca cccccttcacc ctctgaatta ctccctcatc ccctcactca cccccctcact  14520
cacccccttca ccccctcacc caccacctca cccacccctc acccaccccc tcacctcctt  14580
accccctcacc cccctcactc acccctcacc ccctcactca ccacctcacc caccccctcac  14640
ccacccccctc actcactccc tcatcccctc actcaccccc tcaccccctc actcaccccc  14700
tcacccaccc ctcacccacc ccctcacccc ctcactcacc ccttcacccc ctcactcacc  14760
ccctcactca cccccttcacc ccctcactca ccacctcacc caccccctcac ccacccccctc  14820
actcactccc tcaccccctc actcaccccc tcaccccctc actcaccccc tcatctcctc  14880
actcaccccc tcacctcctc actcacccgc tcacctcctc actcaccccc tcgcccccctc  14940
```

```
actcacccct cacccctca cccctcact caccctcac cccctcgccc cctcactcac  15000
cccctcgccc cctcactcac ccctcacccc ctcacccct cactcatccc ctcacctcct  15060
cactcacccc ctcacctcct cactcacccc ctcacctcct cactcacccc ctcacctcct  15120
cacccacccc ctcactcact ccctcacccc ctcacccct cactcacccc ctcacctcct  15180
cactcacccc ctcacctcct cacccacccc ctcactcact ccctcacccc ctcacccct  15240
cactcacccc ctcacctcct cactcacccc ctcacctcct cactcacccc ctcacctcct  15300
cactcatgcc ctcacccct cactcaccct ttcacctcct tgctcatccc ctcacttacc  15360
ccctcacttc gtcaatcacc cccccacctc gtcaatcacc ccctcacctt ttcactcacc  15420
ccctcactca cccccttact tcctcactta cctcctcacc ccccactcac cccctcaccc  15480
cccactcacc ccctcacccc acactcaccc cctcacccc cactcacccc ctcacccctc  15540
tcacctcctc actcacccc tcacctcctc acttatcccc tcacccctc aattaccccc  15600
tcacccctc aattactccc tcatcctttc aattacccac tcacccctc acctcctcac  15660
tcctcactca ctccctcact caccccttca ccttctcact cacctcctcg tctcctcacc  15720
ccctcactca cttccagccc tgcccctccc atcttccttt tctttgtgtg agaatctggg  15780
gtccctgagt ggtgtcagtc cctccaagac tcaaggagtc cccagggcct tgttatccag  15840
aacaccccca cctgggtccc gggagacccc atgggatcac aggagtgttc agggaagtgg  15900
tgcttcctgg gtctgggtgg gctggagggg catcctccct tccccaagag gagaccccca  15960
ggagccccct aagtccatcc ccagcagtgg tgcccctgcc ctgtccttgc agcctgggag  16020
acccttggga ggggcgggcg ctgggtggct gggcggcttc tgctggtctc accccactgg  16080
cctcctgttt gtcatcctca gcctgcgggg tcaacttgaa ctcaagccgc cagagcagga  16140
ttgtgggcgg cgagagcgcg ctcccggggg cctggccctg gcaggtcagc ctgcacgtcc  16200
agaacgtcca cgtgtgcgga ggctccatca tcacccccga gtggatcgtg acagccgccc  16260
actgcgtgga aaagtatgcc aggggcggcg cgggccgggt gggggctcag ggctggccta  16320
cagccaccct gtgaccttga gcaggtctca acccttgcag ccccggcatc cttgtgttta  16380
aatggggaga gtattgcacc tgcttcctag ggctgtgaga catcaagtgc gctcatgcca  16440
ggcagtgcat ggctgtatgc actgagtgtc ccctgcacgc agggcacagg gtgcaggtgg  16500
aacattctcc acgatgtcgc cgtgaccagc gttccttcca gccactgtcc tctgagctct  16560
gtcctgccct tgagcaaagc ccctgccccc tgaggtatcc tgtctccggg acgctagtcc  16620
caggagaggg cacactcaga caggcttcag gctgccctgc tggaaggtcc ctggggttaa  16680
gcgttcttgg ccacagcatt gctcatgcag agggttaggt aggggtgagg ctagccgtga  16740
cagtattagc atttatggac gctaccaccc cctcccctttt tccttaaaca catagtgctt  16800
ttggtcacat gctgctttgg aggaggcctc acttggcgga tgtatttttc tgccttagag  16860
agaggctgaa ctgggtttga ctgttggccc agccctctct tgctgcgtgc ccttagacga  16920
ttcactcaac gtctctgatc catggcatgt acaactataa gatgggcatg cccttctcct  16980
ctcgggctgt tatgaaggtc aaggaagcaa gggctgttac ccaagggtgc tcccttctct  17040
ccccctcttc acaccccag gtgctctggg ccctctagga actgggtttc tctcaagggc  17100
tgttacccaa gggtgctccc ttctctcccc ctcttcacac cactgggtgc tctgggccca  17160
ctaggagctg ggattctctt aagagggaaa ctcttggata aaggaaatgg tttgattgat  17220
atcggacaag tctgttcatt agtatccatt tattaagcac ctaccatgtg ccaggaaatg  17280
```

ctttggcgta caaaggaaaa taagggccag tcctgctaga aatggccttg aaaccccagg 17340
gagggatgtc ggcccattgt gggtgctgca gattccttga aggtgatgca agagccagaa 17400
agaaggatga tgtggggggc tgaggcaggg agtcggggtt gggggagtgt gggggagaag 17460
gggagaccga gcacctcttc cactatctcc ctgtgtggtt tttggtgaac catcctgcct 17520
ctgggtgtct tgcctccagc ttctgacgtt ggaagttcat ccactgagag ctctgtgttt 17580
atggctctga gatactgagt ccttcttctc tcccagacct cttaacaatc catggcattg 17640
gacggcattt gcggggattt tgagacaatc tttcatgttc tatggagccg gataccaagt 17700
agaaaaagtg atttctcatc caaattatga ctccaagacc aagaacaatg acattgcgct 17760
gatgaagctg cagaagcctc tgactttcaa cggtacgtgt ggctcaggct tggcaagcag 17820
gttggcagaa tcttaaagag atgttgattg gaaatgacac ttgtgctatg ccaaatggaa 17880
gggaggcatt tgcgttgagc gagggtagcg tgcagcgggt ggccaatggg agaggctcac 17940
agaggctaag agcacctgcc gcattttggg ggaggcagca gccaccacat ctgttctgta 18000
ctgtactgag tggtggtgat tcaagccagg catggaaaag gctagaacag ggctttccca 18060
ctgcagcacc cttgacatct gggtggttct ctgttgtagg gctctcttgt gccttgtagg 18120
atgtttaaca gcgtccccag cctctaccca ctggaggcca gtagctacca agctgtgaca 18180
accagtgttg cctgctgaca ttgccaaaca tccgctttga ggcaaagtca cttccagttg 18240
agaactactg gcctaaaatg tgtaaagatc cttgattttt aaagatacat tctaaaacca 18300
agttgcttaa ttcaggacaa acatgctttc tcttagcctc ttattcggtc ccactctggt 18360
ccatccaagg gtctggaatg ttctagcccc atgtggatac agaagaagca aaacctcagc 18420
cctccctaca gcatgtctgt attcacattg ggaaatggtt cacatataga agagcgaatg 18480
cctgagcaat ggcgtggtgc ctctggggcg aaagctgact ccattgactc catcggcttt 18540
ttggctgttg cctcctgtgt gtctttcccg tcttgatcac ctggagatat gtaattttgg 18600
aagcagagct agcaaataat tcctcttata agcagagcta gcaaataatt ctacttataa 18660
gtagcataac gtcttgcctg ccagaaggag aggtctggca gggggagaaa gtgagaatgt 18720
gggacttgtt gggatgcagg gtcctctggg cagggtggcc agggtgccag gcccagcagc 18780
ctgcatgtgg gaaggccagg tggagacata ggtgataccc gcctggctca ctgtgttttc 18840
tcttcttgaa acagacctag tgaaaccagt gtgtctgccc aacccaggca tgatgctgca 18900
gccagaacag ctctgctgga tttccgggtg gggggccacc gaggagaaag gtgaggctgc 18960
tcctgggcac acaggactgc agggcccaca gatggagcat tgggttcgga agtgggaggt 19020
ccaggtttta atcccagttc tactactcaa tgactggatg actttggttg attcccccag 19080
tccttgtgcc tcagtttctc catctgctaa gtgggagaaa tcctgcccag cctacctaat 19140
acactgtgtt cttatcgtga tcacacagag cagcatgtgg aatggctttt gaagtatctg 19200
ggccatacga gtttagaggt gcaggatctc ctgtgttgca ctcattgtga gtttagagct 19260
gccctggaga tcccaccaag gcctgcgtgg ctgagtgaca gggggcttgg tgaggacggg 19320
catcctggac ccatggtggc cacatctaag cctgtcctct gccctgataa ccacagagag 19380
aggctctctc cacccacttc ctttgcaatc tgcatttctc tctgacagtc tttcaaatga 19440
agggagcctg gctgcttcat ttttatggag ggttggaagt gcttagtggc aggcacaaag 19500
gttcatttta catattgttt atatccttct caaaagcgtc taggccatac agacaacaaa 19560
tcctttcaaa caaggggaaa agtacaaagg ttgggtgatt tctggggagc gtcagggaag 19620
gtagtggggg gcatcctggc tcctcatcag cagaaactta ctacagtaga gccacaggct 19680

```
gggcaaaaga cctcatggaa tccaagatga agggaatatc gacaaatatt tgtgcgcacc  19740
tgcacctagt acaggctggg tgctactcag gtgctgggaa tgcagaagtg aacagagtaa  19800
gacaaatgtc tctgctgtca ggagctttac ctctcttctg gatgtcggtg gtggggacgg  19860
ggcaggtgtg gtcagacaga tgggagacaa acaactgagc gaggtacttc caaacatctg  19920
agggtgggga tcacaaggtc ccggctattt tgaaggggtg gtcaggaaag gcttctcgga  19980
agaggtggca tttgagctga gactcaaatg gcaaaaatgt gtacacatca aaaaggctag  20040
tgcatgtatc ttcaggtgtg gtcaaggggc caaggaggtg ggctggggcc agattgcata  20100
ggtccttgtg gattatggtg aagacaccag cttctcatct gcttgaggtg gggagatcgt  20160
gagccgggga gtgccatgat ctggcagctg cgtggggagt ggggatgaat ggatggagac  20220
gaggatgatg gtgacaagtc cattgctgtg gttccttgag acaggaagcc agctcatagc  20280
agagtgcggg cgtggatgtg aagagatgag ggtacactag ggctagagcc accagactta  20340
ctgatgggtt gcatgtctgt gggagagaga gtgagaagtc agggacgatg gctttccact  20400
ctgtggctga agccccaggg tggcgggtgg tgccattttt caagccagga aatattggtt  20460
ggtgagaatt tggggtggga gaaggtgtga cggagggttc tggttttgca cactaagccc  20520
acggtgccca gaagatgccc gaggggaggc agcaaagcga gagtgggaaa tgcagaggtg  20580
gcaagtgcag gccgtgtctt gagaagctct aatgtgcagg ggagccgaga agcaggcggc  20640
ctagggaggg tcacgtgtgc tccagaagag tgtgtgcatg ccagagggga aacaggcgcc  20700
tgtgtgtcct gggtggggtt cagtgaggag tgggaaattg gttcagcaga accaagccgt  20760
tgggtgaata agagggggat tccatggcac tgatagagcc ctatagtttc agagctggga  20820
atttctttcc ctgaagctga actccagagc tgcattcagc acaggcaccg ccagttgtaa  20880
ggagaatcca ggtttcccag gagaggggtt ggtgctggga tgagctgacc ggggcagggc  20940
tggaaaatag ggctgtgacc atctgtgtag tgcgtgtgga ggtctcaggg agggaagtgt  21000
gctctccctg cgagagctgc aggcaacact gggagctcaa caagtctccc tgtccttagg  21060
gaagacctca gaagtgctga acgctgccaa ggtgcttctc attgagacac agagatgcaa  21120
cagcagatat gtctatgaca acctgatcac accagccatg atctgtgccg gcttcctgca  21180
ggggaacgtc gattcttgcc aggtaattca acatttttat tctacctttg gtccttacca  21240
gatcctactg aaccccccat gagagagagg gcattcttgg ggtcagcaga gcctcctcag  21300
tgacacggag ccagctcggg gcagtcatgg gaagtgacgg ccacaaacag tgcgaacgct  21360
tctggtggca gaaggaagta cagtcaacaa atcacacaca ccctctgaaa aaccggtatt  21420
tggtaaaagt gccagtggaa cagaaacaag tatttagact attttaaatt atgaacggca  21480
atttatttag taacttttag cttgaacaga ttaaaattca ggatgggggc tatctctttg  21540
ggggttacat ctctgttacc atcacccctt gatggtggag attcgaagcc cacacagtca  21600
ctcgtaactc acactgcgac ccccgccccc caactcctct aggcctggtc agtggtgtgc  21660
ggcagattgt gacttgattt tctgctctct gtaccttgct gtgtcccaca gggtgacagt  21720
ggagggcctc tggtcacttc gaagaacaat atctggtggc tgatagggga tacaagctgg  21780
ggttctggct gtgccaaagc ttacagacca ggagtgtacg ggaatgtgat ggtattcacg  21840
gactggattt atcgacaaat gagggtaact atcctgtcct ccttctgact gtgttctccg  21900
attcctcgag ccaaagccag acatctgtta ggcgtggttc tgctgctgga agctgactgg  21960
tgaccactgg tcagcatgaa gcaaactctg cttcctccag ccacagcccc atccccccag  22020
```

```
tgtccaccca ttgcccattg cctctcactg gcttcacttg catatttccc ctggtgtttg  22080
gatgaaaagc gctggggctc agcttgtgtg aaattccttg gtgctctgcc aaccacactt  22140
cgttctggct cagctgactc agctgttcca cccaggccac ctcacatcaa actttttttt  22200
tttttttttg agatggagtc tcactgtgtc gcccaggctg gagtgcagtg gcacaatctc  22260
gactcactgc aacctttgcc tcctgggttc aagtgattct cctgcctcag cctcccaagt  22320
agctgggact acaggcatgc gccaccacgc ccagctactt tttgtatttt tagtagagat  22380
ggggtttctc catgttggcc aggctggtct cgaagccctg acctcaggtg attcacccac  22440
ctcagcctcc cacagtgctg ggattacaag tgtgaaccac ggtgcccggc ctcacatgaa  22500
acttttgatt tatagagagc agagggaaga gccggctgtg cccatccttt tctggggcca  22560
tcgagtggct cctgggcagc cccaaggtt aggaagggca ggagcagcca gggttctctg  22620
atgccccaga ctcaagcacg agggaaggtc tcaggggttc catgtgagcc tcatggatgt  22680
ctctgcttag cagagccctg gctttgggca ttgtccagat agggggtgag aaccagatct  22740
tctcatctcc aggacctcag acgtatagtt ttctcagatt tctgtgcttt ctggggctgg  22800
gctactagtg gaagaaagca gtctattctg tcttctccca aatctcccag atgcccagtc  22860
tgttgaagga ggagcagaac caggggcct ttcccgctga ggcccgacct gtgtctcctt  22920
caaatgacac gcgggactca gggccttccc atgaccatgg ggcccagggg gcgtcacctg  22980
gcccagggcc cagtgctaga aacagatgac cccaggagga ggaggcaggg caggagggaa  23040
gctggcaggg ctgggatggt cagccaggct gaggggcgga ctcgcaccag gatggagcta  23100
ggaaatgatc caggtgtgtt tggcggctgc aggtgggtcc gcatggctgt gcagggaggg  23160
aagggctgcg tggcaggaga gcagccgggg gaggcccaga ctctgctgaa gagatgcctg  23220
ttgtgccggc ctccacatcc gctgcccgct ccttccggag ctcctgcccc gccatgctca  23280
gcctgactct gaccaacacg ttggagagaa gaatgatccc tttgtgctat taagcttgct  23340
tatttggttt ctaagtgctt catgcgaacc tagaggaaaa aattattttc cacctttgtt  23400
tgtcttaaga aaataacaca cttttttttt tcctatttga acaggcagac ggctaatcca  23460
catggtcttc gtccttgacg tcgttttaca agaaaacaat ggggctggtt ttgcttcccc  23520
gtgcatgatt tactcttaga gatgattcag aggtcacttc atttttatta aacagtgaac  23580
ttgtctggct ttggcactct ctgccattct gtgcaggctg cagtggctcc cctgcccagc  23640
ctgctctccc taacccettg tccgcaaggg gtgatggccg gctggttgtg ggcactggcg  23700
gtcaagtgtg gaggagaggg gtggaggctg ccccattgag atcttcctgc tgagtccttt  23760
ccaggggcca attttggatg agcatggagc tgtcacctct cagctgctgg atgacttgag  23820
atgaaaaagg agagacatgg aaagggagac agccaggtgg cacctgcagc ggctgccctc  23880
tggggccact tggtagtgtc cccagcctac ctctccacaa ggggattttg ctgatgggtt  23940
cttagagcct tagcagccct ggatggtggc cagaaataaa gggaccagcc cttcatgggt  24000
ggtgacgtgg tagtcacttg taaggggaac agaaacattt ttgttcttat ggggtgagaa  24060
tatagacagt gcccttggtg cgagggaagc aattgaaaag gaacttgccc tgagcactcc  24120
tggtgcaggt ctccacctgc acattgggtg gggctcctgg gagggagact cagccttcct  24180
cctcatcctc cctgaccctg ctcctagcac cctggagagt gcacatgccc cttggtcctg  24240
gcagggcgcc aagtctggca ccatgttggc ctcttcaggc ctgctagtca ctggaaattg  24300
aggtccatgg gggaaatcaa ggatgctcag tttaaggtac actgtttcca tgttatgttt  24360
ctacacattg ctacctcagt gctcctggaa acttagcttt tgatgtctcc aagtagtcca  24420
```

ccttcattta actctttgaa actgtatcat ctttgccaag taagagtggt ggcctatttc 24480
agctgctttg acaaaatgac tggctcctga cttaacgttc tataaatgaa tgtgctgaag 24540
caaagtgccc atggtggcgg cgaagaagag aaagatgtgt tttgttttgg actctctgtg 24600
gtcccttcca atgctgtggg tttccaacca ggggaagggt cccttttgca ttgccaagtg 24660
ccataaccat gagcactact ctaccatggt tctgcctcct ggccaagcag gctggtttgc 24720
aagaatgaaa tgaatgattc tacagctagg acttaacctt gaaatggaaa gtcatgcaat 24780
cccatttgca ggatctgtct gtgcacatgc ctctgtagag agcagcattc ccagggacct 24840
tggaaacagt tggcactgta aggtgcttgc tccccaagac acatcctaaa aggtgttgta 24900
atggtgaaaa cgtcttcctt ctttattgcc ccttcttatt tatgtgaaca actgtttgtc 24960
tttttttgta tctttttttaa actgtaaagt tcaattgtga aaatgaatat catgcaaata 25020
aattatgcaa tttttttttc aaagtaacta ctgcatcttt gaagttctgc ctggtgagta 25080
ggaccagcct ccatttcctt ataagggggt gatgttgagg ctgctggtca gaggaccaaa 25140
ggtgaggcaa ggccagactt ggtgctcctg tggttctcga gataacttcg tataatgtat 25200
gctatacgaa gttatatgca tggcctccgc gccgggtttt ggcgcctccc gcgggcgccc 25260
ccctcctcac ggcgagcgct gccacgtcag acgaagggcg cagcgagcgt cctgatcctt 25320
ccgcccggac gctcaggaca gcggcccgct gctcataaga ctcggcctta gaaccccagt 25380
atcagcagaa ggacatttta ggacgggact tgggtgactc tagggcactg gttttctttc 25440
cagagagcgg aacaggcgag gaaaagtagt cccttctcgg cgattctgcg gagggatctc 25500
cgtggggcgg tgaacgccga tgattatata aggacgcgcc gggtgtggca cagctagttc 25560
cgtcgcagcc gggatttggg tcgcggttct tgtttgtgga tcgctgtgat cgtcacttgg 25620
tgagtagcgg gctgctgggc tggccggggc tttcgtggcc gccgggccgc tcggtgggac 25680
ggaagcgtgt ggagagaccg ccaagggctg tagtctgggt ccgcgagcaa ggttgccctg 25740
aactgggggt tgggggggagc gcagcaaaat ggcggctgtt cccgagtctt gaatggaaga 25800
cgcttgtgag gcgggctgtg aggtcgttga aacaaggtgg ggggcatggt gggcggcaag 25860
aacccaaggt cttgaggcct tcgctaatgc gggaaagctc ttattcgggt gagatgggct 25920
ggggcaccat ctggggaccc tgacgtgaag tttgtcactg actggagaac tcggtttgtc 25980
gtctgttgcg gggggcggcag ttatggcggt gccgttgggc agtgcacccg tacctttggg 26040
agcgcgcgcc ctcgtcgtgt cgtgacgtca cccgttctgt tggcttataa tgcagggtgg 26100
ggccacctgc cggtaggtgt gcggtaggct tttctccgtc gcaggacgca gggttcgggc 26160
ctagggtagg ctctcctgaa tcgacaggcg ccggacctct ggtgagggga gggataagtg 26220
aggcgtcagt ttctttggtc ggttttatgt acctatcttc ttaagtagct gaagctccgg 26280
ttttgaacta tgcgctcggg gttggcgagt gtgttttgtg aagtttttta ggcacctttt 26340
gaaatgtaat catttgggtc aatatgtaat tttcagtgtt agactagtaa attgtccgct 26400
aaattctggc cgtttttggc ttttttgtta gacgtgttga caattaatca tcggcatagt 26460
atatcggcat agtataatac gacaaggtga ggaactaaac catgggatcg gccattgaac 26520
aagatggatt gcacgcaggt tctccggccg cttgggtgga gaggctattc ggctatgact 26580
gggcacaaca gacaatcggc tgctctgatg ccgccgtgtt ccggctgtca gcgcaggggc 26640
gcccggttct ttttgtcaag accgacctgt ccggtgccct gaatgaactg caggacgagg 26700
cagcgcggct atcgtggctg gccacgacgg gcgttccttg cgcagctgtg ctcgacgttg 26760

```
tcactgaagc gggaagggac tggctgctat tgggcgaagt gccggggcag gatctcctgt  26820

catctcacct tgctcctgcc gagaaagtat ccatcatggc tgatgcaatg cggcggctgc  26880

atacgcttga tccggctacc tgcccattcg accaccaagc gaaacatcgc atcgagcgag  26940

cacgtactcg gatggaagcc ggtcttgtcg atcaggatga tctggacgaa gagcatcagg  27000

ggctcgcgcc agccgaactg ttcgccaggc tcaaggcgcg catgcccgac ggcgatgatc  27060

tcgtcgtgac ccatggcgat gcctgcttgc cgaatatcat ggtggaaaat ggccgctttt  27120

ctggattcat cgactgtggc cggctgggtg tggcggaccg ctatcaggac atagcgttgg  27180

ctacccgtga tattgctgaa gagcttggcg gcgaatgggc tgaccgcttc ctcgtgcttt  27240

acggtatcgc cgctcccgat tcgcagcgca tcgccttcta tcgccttctt gacgagttct  27300

tctgagggga tccgctgtaa gtctgcagaa attgatgatc tattaaacaa taaagatgtc  27360

cactaaaatg gaagtttttc ctgtcatact ttgttaagaa gggtgagaac agagtaccta  27420

cattttgaat ggaaggattg gagctacggg ggtgggggtg gggtgggatt agataaatgc  27480

ctgctcttta ctgaaggctc tttactattg ctttatgata atgtttcata gttggatatc  27540

ataatttaaa caagcaaaac caaattaagg gccagctcat tcctcccact catgatctat  27600

agatctatag atctctcgtg ggatcattgt ttttctcttg attcccactt tgtggttcta  27660

agtactgtgg tttccaaatg tgtcagtttc atagcctgaa gaacgagatc agcagcctct  27720

gttccacata cacttcattc tcagtattgt tttgccaagt tctaattcca tcagacctcg  27780

acctgcagcc cctagataac ttcgtataat gtatgctata cgaagttatg ctagtaacta  27840

taacggtcct aaggtagcga gctagctcca cgtggctttg tcccagactt cctttgtctt  27900

caacaacctt ctgcaagaaa accaagggcc tgaattttaa cttcctg               27947
```

```
<210> SEQ ID NO 6
<211> LENGTH: 25333
<212> TYPE: DNA
<213> ORGANISM: Artificial Sequence
<220> FEATURE:
<223> OTHER INFORMATION: Recombinant polynucleotide

<400> SEQUENCE: 6

gcagagtcta agaaatcgct gtgtttagcc ctcgccctgg gcactgtcct cacgggagct     60

gctgtggctg ctgtcttgct ttggaagttc agtaagtgca gggagcctcg atcccaccat    120

gtgctcctgc agtccccagt gctctgagcc agaccctgct ctctgggcta ttgagacctc    180

tggaggccct ccgtgaggtt cctctcttac ataacgaggc tgtctctctt cccttctctt    240

gtttagctat gagattgaca catcatgggg aaagcattta gaatgtaccc agtgctttgg    300

ggtgcttggt gccacccagc actgtgagca caggttcttc taccttgggg ccacacccag    360

ttacctgtat ctcactgcac agcagtggct gttggggacc aggcccaccc ctccatgtcc    420

cacctcctgc aactgcagcc tgagccttcc catcagcctg gggtggtgca gacccatgtg    480

ccattgtgga tccttcaagt tacctgtgtg gcagagagga cgtgtgagtg ccgtccaaac    540

ccaaacactg agagggtcct tcccattgcc cccacggaag taaggtgccc cagtgctaat    600

tccacttata cttgctggtg gcaaggacac ttctcctcct tattaaagtg ggggattggc    660

tgggtgaggt ggctcacgcc tgttatccca gcactttaag aggccaaggc aggtggacca    720

cctgaggtca ggagtttgag accacaagcc tggccaacat gttgaaactc catctctact    780

aaaaatacaa aaattagtca ggcgtggtgg cgtgcacctg taatcccagc tacttaggag    840

gctggggcag gaggatcact tgaacccagg agttggaggt tgcagtgagc caagattgtg    900
```

```
cccctgcact ccagcctggg tgacagaatg agacttcatc tcaaaaacaa aacaaaacaa    960
aacacagtgg ggccaggagt tggaggctgc agcgagctac agtaatgcca cggtgttcct   1020
cactccatga ggctcattgc gtttctcagc ctgaagggca cctctcttct gttttctctg   1080
caagtgggca gcaagtgctc caactctggg atagagtgcg actcctcagg tacctgcatc   1140
aacccctcta actggtgtga tggcgtgtca cactgccccg gcggggagga cgagaatcgg   1200
tgtggtgagt cagccttgac cttgggaagg gactcctctg ctcaccttgg agacagcagc   1260
cgggtccagg ggcctttggg tgactgggcc tggcgtgcgt ccagtacgct gacacatgat   1320
gtcattgaat ccctgctcca ggctgagccc tggggctcag agaggttgtg tttccggccc   1380
aacctcaccc agcaggtggg agatgacagg gccaccgagg actgtgtcat tggaaccaca   1440
cgtgctctga actgccacag gaagtcagtt aagatgagca aactgtttat aaagttggag   1500
atgcaggcta ggaacggtgg ctcatgcctg taatcccagc actttgggag gccgaggcag   1560
atggatcacc tgaggtcagg agtttgagac cagcctgacc aatatggtga aaccttatct   1620
ccactaaaaa tacaaaaatt agccaagcgc ggtggcgggt gcctgtaatt ccagctattc   1680
aggaggctga ggcaggagaa tcacttgaac ctgggaggcg gaggttgcag tgagctgaga   1740
tcacgccact gcattccagc ctgggagaca gagctggctc aaaaaataaa ttaattaatt   1800
aaaaacaaaa ttggagatgc actatgttat tttcaaaaca agctgccttt aaagatctat   1860
ctgttgtcac agggtgggct catctgtttc attttatttt ctgtggttta tctatttatt   1920
cattttaatg aactaggaag cattgctcct atttatggca taccacatga tgtttggata   1980
cgtgtatgcc tgtggcatgg ctaagtcaag ctagaacatg ggccttacct catatacgtg   2040
tcttattaag aacacataaa acctactctt gtagtgattt tcaaatatgc aacatatagt   2100
ttattaactg cagtcactat gatgtacaat agattgctcg aacttattcc tcctgtctaa   2160
ctaagatttt gtgacctctg accaacatct ccccagtgtt gtcacccccc gcccccagcc   2220
tctgatagct gcctttctac tctctgcttc tgtgagtttg atgtttatac attccacatg   2280
taagtggcct catgcagtgt ttctgtctct gtgtctggct tgttcactta gcgtaatgtc   2340
ctccagcttc atctatgttg ttggaaatga caggatttcc ttctttcttg tggctgaata   2400
gtattgcctt gtgcatatac accacatttt ctttatccct tcattcactg atggactctt   2460
aggttgatgt catgtcttgg ctgttgtgaa aaatgccgca gtgagcgtgg gcgtgcaggt   2520
ccctcttcaa cacacggatt tcctttcctt tggatataaa cccagcagtg agattgctgg   2580
atcacatggc agttctgttt ctcacctttt gaggaaactc catactgttt tccataatgg   2640
ctgtagcaac ttccactccc acccccacgg tgcaaagtct ccatttctct tctacaacct   2700
caccaactcc tgttattttc catctttctg atagtagcca tttgaagagg tatgagatga   2760
tacctcattg tggttttcat ttgcattttt atttgtattt ttcatgaatt tttgagggtg   2820
atttcaaggg tagttagtga ctcgaacagg gaaacgatcc tgagtatgag ggttgtgcta   2880
atcatccccc tcctgccagc tgcgtacgga atggggctct gcagatggca gggagctggc   2940
tcgtttctct ttaagagctg ccttttactt ttcttcctct tcctttaaaa cttatttcct   3000
ggccggacgc agtggctcat gcctgtaatc ccagcacttt gggaggccga ggtgggcgga   3060
tcacgaggtc aggaattcca gaccagcctg gccaacatgg tgaaaccccg tctctactaa   3120
aaatacaaaa attagccaga cgtggtggtg cgggcctata gtcccagcta ctcgggaggc   3180
tgaggcagga gaatcacttg aacctgggag gagggggttg cagtgagccg agattgcgcc   3240
```

-continued

```
actgcactcc agcctgggcg acagagccag actccatctc aaaaaacaaa aaaaagttat   3300
ttcccaagca cagccatgta ttccaggctt gtggatcagc gttggtggtg gtgtgtgctc   3360
tcatatctta gttccagcta agcacactct gacatgttta cactagaacc atttgttttt   3420
tctagaaata gaaatttcag aattgtagag tcagaggact taccagaaat ctcttaggta   3480
gttctcctcc cctccctcaa gtgcagtcct aacctcctgg agttttctgt agaaaccaca   3540
agcctcagag ctggccgaga attctagcca aagatttttc catgccaaag taatcccccc   3600
tctcctaagg gccatccttg gtggggactg gtttcctgtt aagccctcgc tgtcagtcct   3660
ggctgtggaa tttcctggtg aggagcactg gcccgtggag ctcggccctc gtgccggcct   3720
tgagcaggcc caagtgttcc gtgttcttga tacctttcct ccagcacagt cttgcttccc   3780
agaaaaaggt ttgcacttga aaatgatgca tttgctgatt aaacatagtt cttttgcttt   3840
atttggtttc taaaataaag tgggagtttt tgagattgag taacgtgagg ttaagatagc   3900
acgtggaatg gctttttctt ttctttctat ttttttttt tttttcctgg agacagggtt    3960
tcactctgtt gcccaggctg gagtgcagag gcatgaccat ggctcactgc aacttcgatg   4020
tcctggggtt aagcgatccc ccagcctcag ccccccaagt ggctgggact acaggtgctc   4080
gccaccacac ctggctaatt tttgtatttt ttgtagaaaa tgggtttcat caatgttgtc   4140
cagactggtc tcgaactcct gacctcaagc aattctcctg cctcagcctc ccagactgct   4200
gggattacag gcgtgaacta ccacgcctgg cctggaatgg cttttgatgt tctcctatgt   4260
gcacatgtgg gtgaataaac accaacaaag tccttatgtt acctgaagag ttgctctctt   4320
cttaatattt aagtcgtatt tatttaaata ctttaatagt tgtacactat taaagtatta   4380
ttaggtcaaa atcaaggaag tacaaaaggg tatgctgtga aaaatctctt cttccttgct   4440
ctgcttactt acctaccccg catcccccca tacaccccag acacacacac acacacacac   4500
acacacacac acacacgcat cactcccata catgcccacc tgtttaccag ccaatcacat   4560
ttcttggggc aactcatctg agttgcttct ctttccagag agtttttgca taaagaagca   4620
caggtatttc tgcgttacca tgaccctatt tcccagtggt tcctagccag ttgactctcc   4680
tgcactggat accatcctgg acagcattcc ttagggaaat gagcccccctg tttttttccca   4740
ccatggcaca gttggtcctt tgcatggacg caccattatt gcccctgtct cttcttggtg   4800
gaccttaagg ttttctccat ccttttgctg taacacacac tgctccaagt gtgtgagcat   4860
atcagtagga aacgcttcca ggagtagaac tgctaggtca gagggcgtgt ggatctgtaa   4920
cctgacagac ctagaccggc ttcagtttgg ttttatccag tttccatatt gattattcat   4980
ataaaaggaa acagacaaac ataacgctgt gcatgtattc tctcttagac cagaacaggc   5040
atagggtgca cttttaattt gtccatttcg tagagtagaa attgtttttg ctgaaatgaa   5100
caccttagga tgctgaagaa tatgacccgt cccatggaaa acattcaaaa atgtgtgtag   5160
cgctttcttc ccaagggtgt gtgtgcgcat attttaacac taattcactt tctacttccg   5220
ttgctatcct ttctgtgagt ctttctcaga atctcagaaa agaaactaaa ttgttcactc   5280
tagttatcaa tgctgtactc tatacctgga atttgctaaa agggcagatt ttaagtattc   5340
tcaccacaga aaagagaaaa gaaaatggta attatgtgac gtggtggaca tgttaactag   5400
ctttattatg gtgagcattt cacagcggat atccagtcat cacgctgtac acattaaaca   5460
tgtacaattg ggtttttttg agacaaggtc tccttctgtc acccagtctg gagtgcagtg   5520
gctcagtcat ggctcattgc agcctcgacc tcctgggctc aatccatcct tccccctcag   5580
cctcctgaaa agctggggcc acaggcatgt accatcatgc caggctaatg catatatatt   5640
```

```
tatatttttt ggtggagatg gggttggtct cgaactctgg gctcaagtga tcctcccgcc   5700
ttgcccttcc aaagtgctga gattacaggc atgaaccaca gcaccaggcc tacatgtaaa   5760
atttttattt gtcaactata ctttgacaaa gctgagaaaa aaaatcctaa tatttaaaaa   5820
aaaaaaaaaa aggactagct tgagaccttt tccagctctc tggcttatca gctgccgtct   5880
cttccgggtg cagatagctg gaagggaaag aaaatcccta aaattaccca caagccaaga   5940
atgaagtgtc tccctttgag ccacagtggc agttttgttt ttaatcatag aagtgtattt   6000
tgagccgggt gtgctggctc acgcctgtaa tccccgcact ttgggaggcc gaggtggggg   6060
gcggaggggg tggggatcgc ctgaggtcag gagttcgaga ccagcctgac caacatggag   6120
aaaccccgtc tctactaaaa atacaaaatt agccggcgtg gtggtgcatg cctgtaatcc   6180
cagctactca tgaggctgag tcaggagaat ctcttgaacc caggaggtgg aggttgcggt   6240
gagctgagat catgccattg cactccagcc tgggaacaag aaaaaaaaag aagaagaaga   6300
agaagtgtat tcatttcagt tacttttaaa aaagtgaaca gactttatat tttagagcgg   6360
ttttaggttt acagaaaatg aaacagacag ggcagcgagc tccttgtact cctccccagc   6420
acacagttgc cctgttatga acatcccaca tcagtgctgt gcgttcatta acaccgatga   6480
acctgatgca tacattatga tgaactgaag tcctggactt caccctttct cttgtacagt   6540
tctgtgggat ttgacaaatg cataatgctg tacagccaca atgatagtat cgtccagagt   6600
agttctcctg ccttaaaacc tcttttgctg cacctgtttc tctctcccca ctcaccccag   6660
ctatctgatc ttcttagtgc ctccgaagtt ttggtctttt caggatgttg tagcgttgga   6720
atcatggagt atgtagcctt caccacatac accttccttc actttgttgg cttcctttac   6780
ttagtaatat gcattcaagt ttcctccatg ccttttcatg gcttgatagc tcatttcttt   6840
ttagcaccaa ataatattcc gttgtccaga tgtagcacaa tgtttatcca ttcatgtaac   6900
ctgtgaccga ctcacagata ggatgtggaa tcactcacca cagaggcatt agacaataat   6960
cagacccaag tcatttcatg gggggaacaag cccacaggta ccagactgtc cagtgagtca   7020
gggccactcg taggaagtaa gaagagaggc tagagcatag ccaggtcctc actttatact   7080
ttaagcccat gtgtatttct cccaaaccac acagcattgt ttccatgctt tcagctttgc   7140
atgaataacg tgatacttga acgcatcatt tatcacttgc tctctttccc acagcgctgt   7200
tttcaagctt cttcctgttc atgatgctct gcttaaccct taagctgcat gggattctgt   7260
tctgtgaata cgcccacccc atgtattatc ctgcccagca aaaagtcccc aaaactctgg   7320
atggtggtta cctctaggga gggagagaag agattgggaa tagggagcga cttcaacggt   7380
gtttgtaatg ttttgtttct ttaaataaaa gagctgagat catttcagca gaatgttgat   7440
ttagagtctc ctggacaatt tgttgctcaa agtgctctct taaagagcac tttaaaaaaa   7500
aaaacctttt atcttattat ttatttattt atttattgag acggagtttt gctctgtcac   7560
ccaggctgga gtggagtggt gtgatctcag ctcactgcaa cctttacctc ctgggttcaa   7620
gcaattcccc tgcctcagcc tcccaagtag gtgggattac agatgcgtgc caccacactt   7680
ggctaatttt tgcattttag tagagatcgg tttctccatg ttggccaggc tgatctcaaa   7740
cgcctgacct caggtgatct gcccgccttg gcctcccaaa gtgctggtat tacaggcgtg   7800
agctaccatg cctggcttat cttatatatt tttaaaaaca gcttattgag atctaattta   7860
tgtaccataa aattcaagta tataattcag tgcttttata tataaaacat atatatgaaa   7920
tagcttattg agatataatt ttttatataa aacagcttat tgatatgtaa tgtatgtacc   7980
```

```
ataaaattta aatatataat tcactggctt ttatatattc acgaatatgt gcaactatca   8040
ccacagtcaa ttttagcata ttttcatcag ctcataaaga aaccccaagc ccttgaacta   8100
tcaccccata tccctcctcc cagcccgtcc ctcctactca taagcaacca ctaatctact   8160
tagtgtctat agatttccta ctctaggcat tccatgtgag cgggatcatg caatacgtgg   8220
gctcacacaa tataagtggc attccatgtg agtcggctca tgcagtatgt ccggctcctt   8280
tcactgagca taaggtcttc agcactcatc caggttgcag cctgtgtctg aatttcattc   8340
cctcttctgg ctgaatcgta ttccattgtg tatcttggac atatcctatt ctgctcaccc   8400
agccgttggt gggcgtttgg agtgttttcg cctttcagct gttttaagag ggttgcagtg   8460
aacatttgta caagttttgg acccaatgcc tgttttcaat tctcttgtgt agagagcact   8520
ttttagcaga aaaagaatag atttgtggcc tccctttgtg tgcggtcagt gccttgagaa   8580
gagtgaactg tgctgccacc tccggagccg tggagagcgc ggggcttggg tagcagctag   8640
gacgatacaa gttgggacaa ggccaggtgc aatggctcac gcctgtaatt ccaacacttt   8700
gggagaccga ggcaggggga tcacctgagg tcaggagttc aagaccagcc tggccaacat   8760
ggtgaaaccc catctctaat aaaacagaaa aattaactgg acggggtggt ggacgcctgt   8820
aatcccagct actcgggagg ctgaggcagg agaatcactt gaacctggga ggcggaggct   8880
gcagtgagtg gagatcagac cactgcactt cagcctaggt gacagagcga gactccgtct   8940
caaaaaaaag aaaaaaaaag aaagaaactc atggataatc ctccctctcg tgcagttcgc   9000
ctctacggac caaacttcat ccttcaggtg tactcatctc agaggaagtc ctggcaccct   9060
gtgtgccaag acgactggaa cgagaactac gggcgggcgg cctgcaggga catgggctat   9120
aagtgagtat ggggcagcac ccgccgagtg acagtaacag acagcagaaa cacgagaaga   9180
ccctctctct gcctccctgt gaaagcaccg gcacatgagt gctggggaca attgtcacct   9240
tccaaaagct gagccctata accagcaggt ggaatttgtc ctgctagggc tgtgcccagc   9300
acacagacct tggctcactg ccaccttgcc ctgcctcctc cttggcctct atagactcct   9360
ggttgctcgg gagtgcccag tgctgtggtc atctggtcag aggggtaggc tgagggcgtt   9420
aggtgcctct ttttccaagg tgcctctcag ccagggtcca ttcacctccc tgggtagagg   9480
ttggaccaga acagctggcg aggagggttg ggctggggag agcagcagag acaaatcctg   9540
tgccagtttc acttcattcg ggagccatgg aagccttttg agctggggag agaatcaatc   9600
aatcagactg atacttaaaa aatgtcattc ctgctcgtag ctctgaggga aggtgggaag   9660
gcttaacagg gtgtgtgtcg cctgacagtg attcctaacg gggtggggc ggtggttacc   9720
atttaccagc actgcctggg gagatgcggc agccctcagg catcgggga gagggtggta   9780
ggatgctact gccactttgt tttccatggg agggtcccca ggtgatttct atgcaacttt   9840
agggtattca atatgccagt tttcagaatg aattaccact cggtgagaaa gttggcatct   9900
tagctagtca ctgtgacatc cctaaacagc aggggtgaat tacacagcaa agcccccca   9960
tcacagtcca ggaacctggt ggaattgata actggggcca tgttaacatc tgtacctttt  10020
attagattaa atgtgtgtat gattatacaa tcctatgtcc ttctcatagt ttcttgatcc  10080
taacctggat aagaaacacg accaatgaag gaattttgtc tgacacttta gggttattga  10140
atcgaaaaat cgttacaata ttctagcact tggttagaac gtgtgatttt ttttcctaaa  10200
tgctaaggtt tttccctctt attctgaatg tcgtatgagc ggtattatga catagtatag  10260
gatttgtgtt tgcttatgcc ttaaccatta tcacaaataa ggttttcttt tttaggaata  10320
atttttactc tagccaagga atagtggatg acagcggatc caccagcttt atgaaactga  10380
```

```
acacaagtgc cggcaatgtc gatatctata aaaaactgta ccacaggtat gcagcaattt  10440
cttcttgaaa aattttggaa tgaaatcaac taggagacac catgggggaat cgttgtcctg  10500
agtctgattt ctctgagctg caatactcgg tctggatggg ttttgcattg ggaggagatt  10560
agagtctgac caggcctggt tactctaagc agcccttggt ttattcatag gaagtggctg  10620
aggtttctct gctatttcat tttcagcctc taccgtctgc ccttgttggt agcggctcac  10680
acttgcaaca tcgacattca actctattta gttttctttc ctcttcagac atttagaggt  10740
gtacctattt tgtcagggcg tggttctagg aatccaagat aatgtctcag tgtcccagcc  10800
agggtgaccg gctcattcca gtttgccagg gacttcactg gcttgagcaa gggaagtcct  10860
gctccattcc aggcagctgg gctggctggt cccgttagcc ccaaccccgg gacagcagtg  10920
ccagagggtg ctctgtgagg gatgggcagc attctggcgg cctgggaatg agttgtggtg  10980
tttccagggg gtagaagtgg gtacaagcca caggtcacat gatgagtggc tgacctggct  11040
gggagggcag aagaggggat ggacttaggc tcttcctttt gctttgcaca tatttaggat  11100
gtttgcagac ttgctatgat tgttgctgtt atgtgttttc tgatgtgaaa gatacacagt  11160
gtcctttgcc catgagctct ccttgcctcc caggtcccca gggcttatgc ctggtgtcta  11220
ggcatcacct ccctgcctgc caggtgccag gtgctgcatt tcgggggagg atgaactaat  11280
caccccgcgc cacctttcct ctgagtggga gcctggggca ggtttgcatt cctggaggcc  11340
gctggtggag gggtctgggg gcctgacttc cactgcagcc tgctgtcctg gggaatgtgg  11400
cagggcaagc ccagtgggga gggctgtgca cggccaggtg cacccatcaa aacagcaggg  11460
ctgcggtttg tccctgtgga gaagctaaac acagctgcct gggcactttg taaatgctga  11520
gtggttcttt gtctttctgg gttacacacg gaatcaggga gccaagtcca gccgggcagg  11580
gacgggggga ggggaggagg tgctgccgtc ccttggcaag agccttggga actcacaagg  11640
aggctggagg gcttggaaga aagaagagaa ggccattgtc tggtaggctc tattctatct  11700
cggtggtggt ggtgggggga ggcgcacttc ttttcctctt tctgtgcagc agttgccctt  11760
tgatgcctga gttcttggct tgttttctgt cgggcttctg tgaataacca catgtgccct  11820
ggcgctgtga ccacacaggg ctatccctac cgaccttagg attcttagga aatgtcttct  11880
cttaaagggg acatgtcttc acttggccgt gtcagtgccc cagagccaga gtccacctgg  11940
aatgcacctg tagtcactga gaacccgggg ggtgtgcctt agtaagaagg tgtcaggaag  12000
gacctattat tgtagggcct gggctcctgc aaggtggttt gggggtggtt ggaggaagca  12060
gagatttgct ctggattgga tgctgtcagg aagcaggggt aattctgtga ggctgcttta  12120
ttattttttt tctaggagga ggttggaatg aggctaggct aaagctgtga ttggtaaaga  12180
aacgtccgtc gctcaagtta gccaggacag gaggagacat cagatcgtga ttttgtggtt  12240
gtgagcacaa ggttcctgtt ctgtctgttc agacatcatt tcggaggagg ctccttgtgt  12300
cttgccccat ctcaggcatg gaggggccta gtccgatatt gacgctcagt gaaataattc  12360
aggttccgca gagcacacgg cccagctatc agggcgggcc agctctgcat gccaggggcc  12420
gcgtcttccc ttctcagcat agcctgggaa attcactgca ggacaaaatg catcagttac  12480
ttcctcttca tccataacct gggatgtttg actcccaaat gagtaactct tacgtttctt  12540
ctaatcctag ggaaactatt ggttatattg ctttcaacac tacaaattta aagcagttat  12600
aggagcccag aggtttccaa atggcttcct taaaaattag aagatgattt taaattccaa  12660
gaggaaaaac aaaactagca ttattgtata cttaccctca caaccgtcct aggagctggt  12720
```

```
acaattttaa gagaggttaa gtaacttgcc caaggtcaca ctgtggggat gtgagccgcg  12780
taccttggct cagtgtctgg tctttgccac tgtccctata tggatttact taccttattg  12840
gagttgtaac tagcagaccc ttctatgtct cagaagacag gagagggaac atcggaagaa  12900
atgactgatt tctaagcatg tgagaggcag gtgactccgc actatcgtga ccagaatttc  12960
ccctgttctt tttgcagtga tgcctgttct tcaaaagcag tggtttcttt acgctgtata  13020
ggtaagttca tctggagtcc cccttttgat acttctaact aggaaaagct ctctactttc  13080
agaacagtac tccctgtgtc tctgggggcg tgggagggaa gaaggtgggg tcacgggttg  13140
gaatgtgccc agcggcgtct cgctctttcc aaggagctcc tggtttagat ttccatggcc  13200
tgtagacacc ttcagccttg ggtccaaggg acaccccctg agatcaggca cgctcaagaa  13260
gctgacaaag ccctacactt tatgccaccc atgagctgga ggcccggcag gtctctttct  13320
ccagaaagca aagggggggtg gcgttagtga gccctggcag ccacctaacg tggacttgga  13380
gcatctgcgg ggctgtggtc cagcaccacc gtgtggccac caggtgctca tcagccagtg  13440
ggacccggga ggagggacaa gaccagagaa caacagtgct cttgcctctt ctctcctgaa  13500
ttttggacgg tggcttagac ttgggtgtcc ccatctctgt gtttagagtg cttacagttt  13560
ccaaactgtt tgcaaatgtg gaagccaccg tccctctcct ctgggatggc ccagtgctgt  13620
cgtggggccg tggtcctgag ctcagctttt catttgaaga ggtggaagga gctgacaccg  13680
tcccatcccg gcagggctgg ctcaggtctt ctttaggtcc tgagtggggg tccagcacag  13740
ccccaagggt gcgtggcacc cgccctgccc tctgcccatg cactcatctc ctggtggaga  13800
agacactcac acacaggaag cagggaaggc agcagacctc actcacccct cacccccctca  13860
ctcacccct actcaccccc tcaacctctc attcaccacc caccccctcg ccccctcact  13920
caccccctca ctccctcaac cctcactcac ctcctcactc cctcaaccct cactcacctc  13980
ctcacctcct cactctcccc ctcatccctc cctcacccca ccccgtcacc tcctcactca  14040
cctcctcacc ccctcactca cccttcaccc cctcactcac cacctcacct cctcactcac  14100
cccctactca acccctcatt caccccctcac cccctcactc acccctgcac cccctcactc  14160
acccccttcat ccactcaccc acctgctcac ctcctcactc aacccctcac cccctcacta  14220
atccctcact ccctcacccc ctcacgccct cactcacacc ttcacctcct cactcacccc  14280
ctcacccct caacccctta cttacccct cactcatccc ttcaccccctc actcaccccc  14340
tctctcaccc attcaccccc tcactcatgc cttcaccccc tcactcacct cctcactcac  14400
accttcaccc ctcagtcacc ccctcactca cccccttcacc ccctcaatca tgccttcact  14460
ccctcactca cccccttcacc ctctgaatta ctccctcatc ccctcactca cccccctcact  14520
caccccttca ccccctcacc caccacctca cccacccctc acccaccccc tcacctcctt  14580
accccctcacc cccctcactc acccctcacc ccctcactca ccacctcacc caccccctcac  14640
ccaccccctc actcactccc tcatcccctc actcaccccc tcacccccctc actcaccccc  14700
tcacccaccc ctcacccacc ccctcacccc ctcactcacc ccttcacccc ctcactcacc  14760
ccctcactca cccccttcacc ccctcactca ccacctcacc caccccctcac ccacccccctc  14820
actcactccc tcacccccctc actcaccccc tcacccccctc actcaccccc tcatctcctc  14880
actcaccccc tcacctcctc actcacccgc tcacctcctc actcaccccc tcgcccccctc  14940
actcacccct caccccctca cccccctcact caccccctcac cccctcgccc cctcactcac  15000
cccctcgccc cctcactcac ccctcacccc ctcaccccct cactcatccc ctcacctcct  15060
cactcacccc ctcacctcct cactcacccc ctcacctcct cactcacccc ctcacctcct  15120
```

```
cacccacccc ctcactcact ccctcacccc ctcacccccct cactcacccc ctcacctcct  15180
cactcacccc ctcacctcct cacccacccc ctcactcact ccctcacccc ctcaccccct  15240
cactcacccc ctcacctcct cactcacccc ctcacctcct cactcacccc ctcacctcct  15300
cactcatgcc ctcaccccct cactcaccct ttcacctcct tgctcatccc ctcacttacc  15360
ccctcacttc gtcaatcacc cccccacctc gtcaatcacc ccctcacctt ttcactcacc  15420
ccctcactca ccccccttact tcctcactta cctcctcacc ccccactcac cccctcaccc  15480
cccactcacc ccctcacccc acactcaccc cctcaccccc cactcacccc ctcacccctc  15540
tcacctcctc actcaccccc tcacctcctc acttatcccc tcaccccctc aattacccccc  15600
tcaccccctc aattactccc tcatcctttc aattacccac tcaccccctc acctcctcac  15660
tcctcactca ctccctcact cacccccttca ccttctcact cacctcctcg tctcctcacc  15720
ccctcactca cttccagccc tgcccctccc atcttccttt tctttgtgtg agaatctggg  15780
gtccctgagt ggtgtcagtc cctccaagac tcaaggagtc cccagggcct tgttatccag  15840
aacaccccca cctgggtccc gggagacccc atgggatcac aggagtgttc agggaagtgg  15900
tgcttcctgg gtctgggtgg gctggagggg catcctccct tccccaagag gagaccccca  15960
ggagccccct aagtccatcc ccagcagtgg tgcccctgcc ctgtccttgc agcctgggag  16020
acccttggga ggggcgggcg ctgggtggct gggcggcttc tgctggtctc accccactgg  16080
cctcctgttt gtcatcctca gcctgcgggg tcaacttgaa ctcaagccgc cagagcagga  16140
ttgtgggcgg cgagagcgcg ctcccggggg cctggccctg gcaggtcagc ctgcacgtcc  16200
agaacgtcca cgtgtgcgga ggctccatca tcacccccga gtggatcgtg acagccgccc  16260
actgcgtgga aaagtatgcc aggggcggcg cgggccgggt gggggctcag ggctggccta  16320
cagccaccct gtgaccttga gcaggtctca acccttgcag ccccggcatc cttgtgttta  16380
aatggggaga gtattgcacc tgcttcctag ggctgtgaga catcaagtgc gctcatgcca  16440
ggcagtgcat ggctgtatgc actgagtgtc ccctgcacgc agggcacagg gtgcaggtgg  16500
aacattctcc acgatgtcgc cgtgaccagc gttccttcca gccactgtcc tctgagctct  16560
gtcctgccct tgagcaaagc ccctgccccc tgaggtatcc tgtctccggg acgctagtcc  16620
caggagaggg cacactcaga caggcttcag gctgccctgc tggaaggtcc ctggggttaa  16680
gcgttcttgg ccacagcatt gctcatgcag agggttaggt aggggtgagg ctagccgtga  16740
cagtattagc atttatggac gctaccaccc cctccccttt tccttaaaca catagtgctt  16800
ttggtcacat gctgctttgg aggaggcctc acttggcgga tgtatttttc tgccttagag  16860
agaggctgaa ctgggtttga ctgttggccc agccctctct tgctgcgtgc ccttagacga  16920
ttcactcaac gtctctgatc catggcatgt acaactataa gatgggcatg cccttctcct  16980
ctcgggctgt tatgaaggtc aaggaagcaa gggctgttac ccaagggtgc tcccttctct  17040
ccccctcttc acacccccag gtgctctggg ccctctagga actgggtttc tctcaagggc  17100
tgttacccaa gggtgctccc ttctctcccc ctcttcacac cactgggtgc tctgggccca  17160
ctaggagctg ggattctctt aagagggaaa ctcttggata aaggaaatgg tttgattgat  17220
atcggacaag tctgttcatt agtatccatt tattaagcac ctaccatgtg ccaggaaatg  17280
ctttggcgta caaaggaaaa taagggccag tcctgctaga aatggccttg aaaccccagg  17340
gagggatgtc ggcccattgt gggtgctgca gattccttga aggtgatgca agagccagaa  17400
agaaggatga tgtggggggc tgaggcaggg agtcggggtt gggggagtgt gggggagaag  17460
```

```
gggagaccga gcacctcttc cactatctcc ctgtgtggtt tttggtgaac catcctgcct  17520
ctgggtgtct tgcctccagc ttctgacgtt ggaagttcat ccactgagag ctctgtgttt  17580
atggctctga gatactgagt ccttcttctc tcccagacct cttaacaatc catggcattg  17640
gacggcattt gcggggattt tgagacaatc tttcatgttc tatggagccg gataccaagt  17700
agaaaaagtg atttctcatc caaattatga ctccaagacc aagaacaatg acattgcgct  17760
gatgaagctg cagaagcctc tgactttcaa cggtacgtgt ggctcaggct tggcaagcag  17820
gttggcagaa tcttaaagag atgttgattg gaaatgacac ttgtgctatg ccaaatggaa  17880
gggaggcatt tgcgttgagc gagggtagcg tgcagcgggt ggccaatggg agaggctcac  17940
agaggctaag agcacctgcc gcattttggg ggaggcagca gccaccacat ctgttctgta  18000
ctgtactgag tggtggtgat tcaagccagg catggaaaag gctagaacag ggctttccca  18060
ctgcagcacc cttgacatct gggtggttct ctgttgtagg gctctcttgt gccttgtagg  18120
atgtttaaca gcgtccccag cctctaccca ctggaggcca gtagctacca agctgtgaca  18180
accagtgttg cctgctgaca ttgccaaaca tccgctttga ggcaaagtca cttccagttg  18240
agaactactg gcctaaaatg tgtaaagatc cttgattttt aaagatacat tctaaaacca  18300
agttgcttaa ttcaggacaa acatgctttc tcttagcctc ttattcggtc ccactctggt  18360
ccatccaagg gtctggaatg ttctagcccc atgtggatac agaagaagca aaacctcagc  18420
cctccctaca gcatgtctgt attcacattg ggaaatggtt cacatataga agagcgaatg  18480
cctgagcaat ggcgtggtgc ctctggggcg aaagctgact ccattgactc catcggcttt  18540
ttggctgttg cctcctgtgt gtctttcccg tcttgatcac ctggagatat gtaattttgg  18600
aagcagagct agcaaataat tcctcttata agcagagcta gcaaataatt ctacttataa  18660
gtagcataac gtcttgcctg ccagaaggag aggtctggca gggggagaaa gtgagaatgt  18720
gggacttgtt gggatgcagg gtcctctggg cagggtggcc agggtgccag gcccagcagc  18780
ctgcatgtgg gaaggccagg tggagacata ggtgataccc gcctggctca ctgtgttttc  18840
tcttcttgaa acagacctag tgaaaccagt gtgtctgccc aacccaggca tgatgctgca  18900
gccagaacag ctctgctgga tttccgggtg gggggccacc gaggagaaag gtgaggctgc  18960
tcctgggcac acaggactgc agggcccaca gatggagcat tgggttcgga agtgggaggt  19020
ccaggtttta atcccagttc tactactcaa tgactggatg actttggttg attcccccag  19080
tccttgtgcc tcagtttctc catctgctaa gtgggagaaa tcctgcccag cctacctaat  19140
acactgtgtt cttatcgtga tcacacagag cagcatgtgg aatggctttt gaagtatctg  19200
ggccatacga gtttagaggt gcaggatctc ctgtgttgca ctcattgtga gtttagagct  19260
gccctggaga tcccaccaag gcctgcgtgg ctgagtgaca gggggcttgg tgaggacggg  19320
catcctggac ccatggtggc cacatctaag cctgtcctct gccctgataa ccacagagag  19380
aggctctctc cacccacttc ctttgcaatc tgcatttctc tctgacagtc tttcaaatga  19440
agggagcctg gctgcttcat ttttatggag ggttggaagt gcttagtggc aggcacaaag  19500
gttcatttta catattgttt atatccttct caaaagcgtc taggccatac agacaacaaa  19560
tcctttcaaa caaggggaaa agtacaaagg ttgggtgatt tctggggagc gtcagggaag  19620
gtagtggggg gcatcctggc tcctcatcag cagaaactta ctacagtaga gccacaggct  19680
gggcaaaaga cctcatggaa tccaagatga agggaatatc gacaaatatt tgtgcgcacc  19740
tgcacctagt acaggctggg tgctactcag gtgctgggaa tgcagaagtg aacagagtaa  19800
gacaaatgtc tctgctgtca ggagctttac ctctcttctg gatgtcggtg gtggggacgg  19860
```

```
ggcaggtgtg gtcagacaga tgggagacaa acaactgagc gaggtacttc caaacatctg  19920
agggtgggga tcacaaggtc ccggctattt tgaaggggtg gtcaggaaag gcttctcgga  19980
agaggtggca tttgagctga gactcaaatg gcaaaaatgt gtacacatca aaaaggctag  20040
tgcatgtatc ttcaggtgtg gtcaaggggc caaggaggtg ggctggggcc agattgcata  20100
ggtccttgtg gattatggtg aagacaccag cttctcatct gcttgaggtg gggagatcgt  20160
gagccgggga gtgccatgat ctggcagctg cgtggggagt ggggatgaat ggatggagac  20220
gaggatgatg gtgacaagtc cattgctgtg gttccttgag acaggaagcc agctcatagc  20280
agagtgcggg cgtggatgtg aagagatgag ggtacactag ggctagagcc accagactta  20340
ctgatgggtt gcatgtctgt gggagagaga gtgagaagtc agggacgatg gctttccact  20400
ctgtggctga agccccaggg tggcgggtgg tgccattttt caagccagga aatattggtt  20460
ggtgagaatt tggggtggga gaaggtgtga cggagggttc tggttttgca cactaagccc  20520
acggtgccca gaagatgccc gaggggaggc agcaaagcga gagtgggaaa tgcagaggtg  20580
gcaagtgcag gccgtgtctt gagaagctct aatgtgcagg ggagccgaga agcaggcggc  20640
ctagggaggg tcacgtgtgc tccagaagag tgtgtgcatg ccagagggga aacaggcgcc  20700
tgtgtgtcct gggtggggtt cagtgaggag tgggaaattg gttcagcaga accaagccgt  20760
tgggtgaata agagggggat tccatggcac tgatagagcc ctatagtttc agagctggga  20820
atttctttcc ctgaagctga actccagagc tgcattcagc acaggcaccg ccagttgtaa  20880
ggagaatcca ggtttcccag gagaggggtt ggtgctggga tgagctgacc ggggcagggc  20940
tggaaaatag ggctgtgacc atctgtgtag tgcgtgtgga ggtctcaggg agggaagtgt  21000
gctctccctg cgagagctgc aggcaacact gggagctcaa caagtctccc tgtccttagg  21060
gaagacctca gaagtgctga acgctgccaa ggtgcttctc attgagacac agagatgcaa  21120
cagcagatat gtctatgaca acctgatcac accagccatg atctgtgccg gcttcctgca  21180
ggggaacgtc gattcttgcc aggtaattca acatttttat tctacctttg gtccttacca  21240
gatcctactg aaccccccat gagagagagg gcattcttgg ggtcagcaga gcctcctcag  21300
tgacacggag ccagctcggg gcagtcatgg gaagtgacgg ccacaaacag tgcgaacgct  21360
tctggtggca gaaggaagta cagtcaacaa atcacacaca ccctctgaaa aaccggtatt  21420
tggtaaaagt gccagtggaa cagaaacaag tatttagact attttaaatt atgaacggca  21480
atttatttag taacttttag cttgaacaga ttaaaattca ggatgggggc tatctctttg  21540
ggggttacat ctctgttacc atcacccctt gatggtggag attcgaagcc cacacagtca  21600
ctcgtaactc acactgcgac ccccgccccc caactcctct aggcctggtc agtggtgtgc  21660
ggcagattgt gacttgattt tctgctctct gtaccttgct gtgtcccaca gggtgacagt  21720
ggagggcctc tggtcacttc gaagaacaat atctggtggc tgatagggga tacaagctgg  21780
ggttctggct gtgccaaagc ttacagacca ggagtgtacg ggaatgtgat ggtattcacg  21840
gactggattt atcgacaaat gagggtaact atcctgtcct ccttctgact gtgttctccg  21900
attcctcgag ccaaagccag acatctgtta ggcgtggttc tgctgctgga agctgactgg  21960
tgaccactgg tcagcatgaa gcaaactctg cttcctccag ccacagcccc atccccccag  22020
tgtccaccca ttgcccattg cctctcactg gcttcacttg catatttccc ctggtgtttg  22080
gatgaaaagc gctggggctc agcttgtgtg aaattccttg gtgctctgcc aaccacactt  22140
cgttctggct cagctgactc agctgttcca cccaggccac ctcacatcaa actttttttt  22200
```

```
ttttttttttg agatggagtc tcactgtgtc gcccaggctg gagtgcagtg gcacaatctc  22260
gactcactgc aacctttgcc tcctgggttc aagtgattct cctgcctcag cctcccaagt  22320
agctgggact acaggcatgc gccaccacgc ccagctactt tttgtatttt tagtagagat  22380
ggggtttctc catgttggcc aggctggtct cgaagccctg acctcaggtg attcacccac  22440
ctcagcctcc cacagtgctg ggattacaag tgtgaaccac ggtgcccggc ctcacatgaa  22500
acttttgatt tatagagagc agagggaaga gccggctgtg cccatccttt tctggggcca  22560
tcgagtggct cctgggcagc cccaaggtt aggaagggca ggagcagcca gggttctctg  22620
atgccccaga ctcaagcacg agggaaggtc tcaggggttc catgtgagcc tcatggatgt  22680
ctctgcttag cagagccctg gctttgggca ttgtccagat agggggtgag aaccagatct  22740
tctcatctcc aggacctcag acgtatagtt ttctcagatt tctgtgcttt ctggggctgg  22800
gctactagtg gaagaaagca gtctattctg tcttctccca aatctcccag atgcccagtc  22860
tgttgaagga ggagcagaac caggggggcct ttcccgctga ggcccgacct gtgtctcctt  22920
caaatgacac gcgggactca gggccttccc atgaccatgg ggcccagggg gcgtcacctg  22980
gcccagggcc cagtgctaga aacagatgac cccaggagga ggaggcaggg caggagggaa  23040
gctggcaggg ctgggatggt cagccaggct gaggggcgga ctcgcaccag gatggagcta  23100
ggaaatgatc caggtgtgtt tggcggctgc aggtgggtcc gcatggctgt gcagggaggg  23160
aagggctgcg tggcaggaga gcagccgggg gaggcccaga ctctgctgaa gagatgcctg  23220
ttgtgccggc ctccacatcc gctgcccgct ccttccggag ctcctgcccc gccatgctca  23280
gcctgactct gaccaacacg ttggagagaa gaatgatccc tttgtgctat taagcttgct  23340
tatttggttt ctaagtgctt catgcgaacc tagaggaaaa aattattttc cacctttgtt  23400
tgtcttaaga aaataacaca cttttttttt tcctatttga acaggcagac ggctaatcca  23460
catggtcttc gtccttgacg tcgttttaca agaaaacaat ggggctggtt ttgcttcccc  23520
gtgcatgatt tactcttaga gatgattcag aggtcacttc atttttatta aacagtgaac  23580
ttgtctggct ttggcactct ctgccattct gtgcaggctg cagtggctcc cctgcccagc  23640
ctgctctccc taacccettg tccgcaaggg gtgatggccg gctggttgtg ggcactggcg  23700
gtcaagtgtg gaggagaggg gtggaggctg ccccattgag atcttcctgc tgagtccttt  23760
ccaggggcca attttggatg agcatggagc tgtcacctct cagctgctgg atgacttgag  23820
atgaaaaagg agagacatgg aaagggagac agccaggtgg cacctgcagc ggctgccctc  23880
tggggccact tggtagtgtc cccagcctac ctctccacaa ggggattttg ctgatgggtt  23940
cttagagcct tagcagccct ggatggtggc cagaaataaa gggaccagcc cttcatgggt  24000
ggtgacgtgg tagtcacttg taaggggaac agaaacattt ttgttcttat ggggtgagaa  24060
tatagacagt gcccttggtg cgagggaagc aattgaaaag gaacttgccc tgagcactcc  24120
tggtgcaggt ctccacctgc acattgggtg gggctcctgg gagggagact cagccttcct  24180
cctcatcctc cctgaccctg ctcctagcac cctggagagt gcacatgccc cttggtcctg  24240
gcagggcgcc aagtctggca ccatgttggc ctcttcaggc ctgctagtca ctggaaattg  24300
aggtccatgg gggaaatcaa ggatgctcag tttaaggtac actgtttcca tgttatgttt  24360
ctacacattg ctacctcagt gctcctggaa acttagcttt tgatgtctcc aagtagtcca  24420
ccttcattta actctttgaa actgtatcat ctttgccaag taagagtggt ggcctatttc  24480
agctgctttg acaaaatgac tggctcctga cttaacgttc tataaatgaa tgtgctgaag  24540
caaagtgccc atggtggcgg cgaagaagag aaagatgtgt tttgttttgg actctctgtg  24600
```

```
gtcccttcca atgctgtggg tttccaacca ggggaagggt cccttttgca ttgccaagtg  24660

ccataaccat gagcactact ctaccatggt tctgcctcct ggccaagcag gctggtttgc  24720

aagaatgaaa tgaatgattc tacagctagg acttaacctt gaaatggaaa gtcatgcaat  24780

cccatttgca ggatctgtct gtgcacatgc ctctgtagag agcagcattc ccagggacct  24840

tggaaacagt tggcactgta aggtgcttgc tccccaagac acatcctaaa aggtgttgta  24900

atggtgaaaa cgtcttcctt ctttattgcc ccttcttatt tatgtgaaca actgtttgtc  24960

tttttttgta tctttttttaa actgtaaagt tcaattgtga aaatgaatat catgcaaata  25020

aattatgcaa tttttttttc aaagtaacta ctgcatcttt gaagttctgc ctggtgagta  25080

ggaccagcct ccatttcctt ataagggggt gatgttgagg ctgctggtca gaggaccaaa  25140

ggtgaggcaa ggccagactt ggtgctcctg tggttctcga gataacttcg tataatgtat  25200

gctatacgaa gttatgctag taactataac ggtcctaagg tagcgagcta gctccacgtg  25260

gctttgtccc agacttcctt tgtcttcaac aaccttctgc aagaaaacca agggcctgaa  25320

ttttaacttc ctg                                                     25333
```

<210> SEQ ID NO 7
<211> LENGTH: 491
<212> TYPE: PRT
<213> ORGANISM: Artificial Sequence
<220> FEATURE:
<223> OTHER INFORMATION: Recombinant protein

<400> SEQUENCE: 7

```
Met Ala Leu Asn Ser Gly Ser Pro Pro Gly Ile Gly Pro Cys Tyr Glu
1               5                   10                  15

Asn His Gly Tyr Gln Ser Glu His Ile Cys Pro Pro Arg Pro Pro Val
            20                  25                  30

Ala Pro Asn Gly Tyr Asn Leu Tyr Pro Ala Gln Tyr Tyr Pro Ser Pro
        35                  40                  45

Val Pro Gln Tyr Ala Pro Arg Ile Thr Thr Gln Ala Ser Thr Ser Val
    50                  55                  60

Ile His Thr His Pro Lys Ser Ser Gly Ala Leu Cys Thr Ser Lys Ser
65                  70                  75                  80

Lys Lys Ser Leu Cys Leu Ala Leu Ala Leu Gly Thr Val Leu Thr Gly
                85                  90                  95

Ala Ala Val Ala Ala Val Leu Leu Trp Lys Phe Met Gly Ser Lys Cys
            100                 105                 110

Ser Asn Ser Gly Ile Glu Cys Asp Ser Ser Gly Thr Cys Ile Asn Pro
        115                 120                 125

Ser Asn Trp Cys Asp Gly Val Ser His Cys Pro Gly Gly Glu Asp Glu
    130                 135                 140

Asn Arg Cys Val Arg Leu Tyr Gly Pro Asn Phe Ile Leu Gln Val Tyr
145                 150                 155                 160

Ser Ser Gln Arg Lys Ser Trp His Pro Val Cys Gln Asp Asp Trp Asn
                165                 170                 175

Glu Asn Tyr Gly Arg Ala Ala Cys Arg Asp Met Gly Tyr Lys Asn Asn
            180                 185                 190

Phe Tyr Ser Ser Gln Gly Ile Val Asp Asp Ser Gly Ser Thr Ser Phe
        195                 200                 205

Met Lys Leu Asn Thr Ser Ala Gly Asn Val Asp Ile Tyr Lys Lys Leu
    210                 215                 220
```

```
Tyr His Ser Asp Ala Cys Ser Ser Lys Ala Val Val Ser Leu Arg Cys
225                 230                 235                 240

Ile Ala Cys Gly Val Asn Leu Asn Ser Ser Arg Gln Ser Arg Ile Val
                245                 250                 255

Gly Gly Glu Ser Ala Leu Pro Gly Ala Trp Pro Trp Gln Val Ser Leu
            260                 265                 270

His Val Gln Asn Val His Val Cys Gly Gly Ser Ile Ile Thr Pro Glu
        275                 280                 285

Trp Ile Val Thr Ala Ala His Cys Val Glu Lys Pro Leu Asn Asn Pro
    290                 295                 300

Trp His Trp Thr Ala Phe Ala Gly Ile Leu Arg Gln Ser Phe Met Phe
305                 310                 315                 320

Tyr Gly Ala Gly Tyr Gln Val Glu Lys Val Ile Ser His Pro Asn Tyr
                325                 330                 335

Asp Ser Lys Thr Lys Asn Asn Asp Ile Ala Leu Met Lys Leu Gln Lys
            340                 345                 350

Pro Leu Thr Phe Asn Asp Leu Val Lys Pro Val Cys Leu Pro Asn Pro
        355                 360                 365

Gly Met Met Leu Gln Pro Glu Gln Leu Cys Trp Ile Ser Gly Trp Gly
    370                 375                 380

Ala Thr Glu Glu Lys Gly Lys Thr Ser Glu Val Leu Asn Ala Ala Lys
385                 390                 395                 400

Val Leu Leu Ile Glu Thr Gln Arg Cys Asn Ser Arg Tyr Val Tyr Asp
                405                 410                 415

Asn Leu Ile Thr Pro Ala Met Ile Cys Ala Gly Phe Leu Gln Gly Asn
            420                 425                 430

Val Asp Ser Cys Gln Gly Asp Ser Gly Gly Pro Leu Val Thr Ser Lys
        435                 440                 445

Asn Asn Ile Trp Trp Leu Ile Gly Asp Thr Ser Trp Gly Ser Gly Cys
    450                 455                 460

Ala Lys Ala Tyr Arg Pro Gly Val Tyr Gly Asn Val Met Val Phe Thr
465                 470                 475                 480

Asp Trp Ile Tyr Arg Gln Met Arg Ala Asp Gly
                485                 490


<210> SEQ ID NO 8
<211> LENGTH: 2267
<212> TYPE: DNA
<213> ORGANISM: Mus musculus

<400> SEQUENCE: 8

ccggttgtgt tataggactt gaccagcccc aatagtcctc aagtcactcc tagatacagt      60

ggcaggtggt agctggcttg cggaaggaag aggaagaaga gaatgtgggc catcaaggag     120

caaggccagc cttgcacttg ggccccctct gctcagtgct gaccagggct ttctgagccg     180

cttcctaatg aggctcattt gaagaccccc ccccaccccc ctcctgctgt cttgggtggc     240

agagctagct ccaggctgta agaaaattag gaggattacc aaagcagtat ggagtcagac     300

agtggccaac ccctcaacaa ccgtgatatt gttccctttc gcaaaccccg aaggccccag     360

gagaccttca aaaaggtggg gatccccatc attgcagtgc tgctgagcct gatagccctc     420

gtgattgtgg cccttctcat caaggtgatt ctggataaat actacttcat ctgcggcagt     480

cccctgacct tcattcagag ggccagttg tgtgacggcc accttgactg cgcctcaggg     540

gaggatgagg aacactgtgt caaggacttc cctgaaaagc ccggagtggc agtccggctc     600
```

```
tccaaggaca gatccaccct gcaggtgctg gatgcagcca cagggacctg ggcctcagtc    660

tgtttcgaca acttcacaga agcactggcc aagacagcct gcagacagat gggctatgac    720

agccagcccg ctttcagagc agtggagatc cgtccagatc agaacctccc tgttgctcaa    780

gtcacaggaa acagccagga acttcaggtg cagaatggaa gcagatcctg cctctcaggc    840

tccctggttt ccttgcgctg ccttgactgt ggaaagagcc tgaagactcc tcgtgtggtg    900

ggtggggtgg aggcccctgt ggattcttgg ccgtggcagg tcagcatcca gtacaacaag    960

cagcatgtct gtggtgggag catcctggat ccccactgga tcctcacagc agcccactgc   1020

ttcaggaagt atcttgatgt gtcaagctgg aaggtcaggg caggctcaaa catactgggt   1080

aactctccat ccttgcctgt ggccaagatc ttcatcgctg aacccaatcc tctgtacccc   1140

aaagagaagg acattgccct tgttaagctg cagatgccac tcacattctc aggctcagtc   1200

aggcccatct gcctgccctt ctctgatgag gtgcttgtcc cagccacacc agtctgggtc   1260

attggatggg gctttacaga agaaaacgga ggaaagatgt ctgacatgct actgcaggca   1320

tcagtccagg tcattgacag cacacggtgc aatgcagagg atgcctacga aggggaagtg   1380

accgctgaga tgctgtgtgc aggtacccca cagggtggca aggacacctg ccagggtgac   1440

agtggtgggc ctttgatgta ccattctgac aagtggcagg tagtaggcat cgtgagctgg   1500

ggccatggat gcggcggccc aagtactcct ggagtgtata ccaaggtcac tgcctatctc   1560

aactggatct acaatgttcg gaagtctgag atgtaacgct gccgtccccc acatccagaa   1620

gctgcttccc ttcagaccta cctacggcat gacccctcaa agtcagatat gggacaagag   1680

cctccttgaa caaactctgg tatccctgca gcaagcaagg atacattgca gaggtgcccg   1740

gagtggagtc agatgggcta gctcagccac ccctgcatct cccaaaccct gggagacatg   1800

tggcccatgg gagtaaatcc aggacattga ctcaactctc agaagtgtta ttcagtcaag   1860

gaggctctcc cttccactga aggaaggaaa gtcagctctc tcctgaaagg ccagatcact   1920

ggctgagtag atgagacaag ggtatgaaag gcctttgcca tcttctttgc ccagtcctga   1980

aagcactgac gtaagagacc agtcagttct aatgtaaggt gtatatttta gtgtcagggt   2040

attgcaattg tcacctctgt ggtcaatatc attaaacagg tatgagaatt cgctggcata   2100

gacttcctgg tctgcttaat aagaatccaa ctaaggatgt cacatgacag tttcccagaa   2160

aatgtgaaca agtgtccatc tgacacacgg caccaatgac aaaccaaaga agttattctg   2220

cctgagtctc agttgctgaa ctaataaatt agctgcggtt tcttgca                 2267
```

```
<210> SEQ ID NO 9
<211> LENGTH: 435
<212> TYPE: PRT
<213> ORGANISM: Mus musculus

<400> SEQUENCE: 9

Met Glu Ser Asp Ser Gly Gln Pro Leu Asn Asn Arg Asp Ile Val Pro
1               5                   10                  15

Phe Arg Lys Pro Arg Arg Pro Gln Glu Thr Phe Lys Lys Val Gly Ile
            20                  25                  30

Pro Ile Ile Ala Val Leu Leu Ser Leu Ile Ala Leu Val Ile Val Ala
        35                  40                  45

Leu Leu Ile Lys Val Ile Leu Asp Lys Tyr Tyr Phe Ile Cys Gly Ser
    50                  55                  60

Pro Leu Thr Phe Ile Gln Arg Gly Gln Leu Cys Asp Gly His Leu Asp
65                  70                  75                  80
```

```
Cys Ala Ser Gly Glu Asp Glu Glu His Cys Val Lys Asp Phe Pro Glu
                85                  90                  95

Lys Pro Gly Val Ala Val Arg Leu Ser Lys Asp Arg Ser Thr Leu Gln
            100                 105                 110

Val Leu Asp Ala Ala Thr Gly Thr Trp Ala Ser Val Cys Phe Asp Asn
        115                 120                 125

Phe Thr Glu Ala Leu Ala Lys Thr Ala Cys Arg Gln Met Gly Tyr Asp
    130                 135                 140

Ser Gln Pro Ala Phe Arg Ala Val Glu Ile Arg Pro Asp Gln Asn Leu
145                 150                 155                 160

Pro Val Ala Gln Val Thr Gly Asn Ser Gln Glu Leu Gln Val Gln Asn
                165                 170                 175

Gly Ser Arg Ser Cys Leu Ser Gly Ser Leu Val Ser Leu Arg Cys Leu
            180                 185                 190

Asp Cys Gly Lys Ser Leu Lys Thr Pro Arg Val Val Gly Gly Val Glu
        195                 200                 205

Ala Pro Val Asp Ser Trp Pro Trp Gln Val Ser Ile Gln Tyr Asn Lys
    210                 215                 220

Gln His Val Cys Gly Gly Ser Ile Leu Asp Pro His Trp Ile Leu Thr
225                 230                 235                 240

Ala Ala His Cys Phe Arg Lys Tyr Leu Asp Val Ser Ser Trp Lys Val
                245                 250                 255

Arg Ala Gly Ser Asn Ile Leu Gly Asn Ser Pro Ser Leu Pro Val Ala
            260                 265                 270

Lys Ile Phe Ile Ala Glu Pro Asn Pro Leu Tyr Pro Lys Glu Lys Asp
        275                 280                 285

Ile Ala Leu Val Lys Leu Gln Met Pro Leu Thr Phe Ser Gly Ser Val
    290                 295                 300

Arg Pro Ile Cys Leu Pro Phe Ser Asp Glu Val Leu Val Pro Ala Thr
305                 310                 315                 320

Pro Val Trp Val Ile Gly Trp Gly Phe Thr Glu Glu Asn Gly Gly Lys
                325                 330                 335

Met Ser Asp Met Leu Leu Gln Ala Ser Val Gln Val Ile Asp Ser Thr
            340                 345                 350

Arg Cys Asn Ala Glu Asp Ala Tyr Glu Gly Glu Val Thr Ala Glu Met
        355                 360                 365

Leu Cys Ala Gly Thr Pro Gln Gly Gly Lys Asp Thr Cys Gln Gly Asp
    370                 375                 380

Ser Gly Gly Pro Leu Met Tyr His Ser Asp Lys Trp Gln Val Val Gly
385                 390                 395                 400

Ile Val Ser Trp Gly His Gly Cys Gly Gly Pro Ser Thr Pro Gly Val
                405                 410                 415

Tyr Thr Lys Val Thr Ala Tyr Leu Asn Trp Ile Tyr Asn Val Arg Lys
            420                 425                 430

Ser Glu Met
        435

<210> SEQ ID NO 10
<211> LENGTH: 3543
<212> TYPE: DNA
<213> ORGANISM: Homo sapiens

<400> SEQUENCE: 10

atcattccag tttggcaact tcacttgtag ggctgtttta atcaagctgc ccaaagtccc      60
```

-continued

```
ccaatcactc ctggaataca cagagagagg cagcagcttg ctcagcggac aaggatgctg    120
ggcgtgaggg accaaggcct gccctgcact cgggcctcct ccagccagtg ctgaccaggg    180
acttctgacc tgctggccag ccaggacctg tgtggggagg ccctcctgct gccttggggt    240
gacaatctca gctccaggct acagggagac cgggaggatc acagagccag catggatcct    300
gacagtgatc aacctctgaa cagcctcgat gtcaaacccc tgcgcaaacc ccgtatcccc    360
atggagacct tcagaaaggt ggggatcccc atcatcatag cactactgag cctggcgagt    420
atcatcattg tggttgtcct catcaaggtg attctggata aatactactt cctctgcggg    480
cagcctctcc acttcatccc gaggaagcag ctgtgtgacg gagagctgga ctgtcccttg    540
ggggaggacg aggagcactg tgtcaagagc ttccccgaag ggcctgcagt ggcagtccgc    600
ctctccaagg accgatccac actgcaggtg ctggactcgg ccacagggaa ctggttctct    660
gcctgtttcg acaacttcac agaagctctc gctgagacag cctgtaggca gatgggctac    720
agcagcaaac ccactttcag agctgtggag attggcccag accaggatct ggatgttgtt    780
gaaatcacag aaaacagcca ggagcttcgc atgcggaact caagtgggcc ctgtctctca    840
ggctccctgg tctccctgca ctgtcttgcc tgtgggaaga gcctgaagac cccccgtgtg    900
gtgggtgggg aggaggcctc tgtggattct tggccttggc aggtcagcat ccagtacgac    960
aaacagcacg tctgtggagg gagcatcctg gacccccact gggtcctcac ggcagcccac   1020
tgcttcagga aacataccga tgtgttcaac tggaaggtgc gggcaggctc agacaaactg   1080
ggcagcttcc catccctggc tgtggccaag atcatcatca ttgaattcaa ccccatgtac   1140
cccaaagaca atgacatcgc cctcatgaag ctgcagttcc cactcacttt ctcaggcaca   1200
gtcaggccca tctgtctgcc cttctttgat gaggagctca ctccagccac cccactctgg   1260
atcattggat ggggctttac gaagcagaat ggagggaaga tgtctgacat actgctgcag   1320
gcgtcagtcc aggtcattga cagcacacgg tgcaatgcag acgatgcgta ccagggggaa   1380
gtcaccgaga agatgatgtg tgcaggcatc ccggaagggg gtgtggacac ctgccagggt   1440
gacagtggtg ggcccctgat gtaccaatct gaccagtggc atgtggtggg catcgttagt   1500
tggggctatg gctgcggggg cccgagcacc ccaggagtat acaccaaggt ctcagcctat   1560
ctcaactgga tctacaatgt ctggaaggct gagctgtaat gctgctgccc ctttgcagtg   1620
ctgggagccg cttccttcct gccctgccca cctggggatc ccccaaagtc agacacagag   1680
caagagtccc cttgggtaca cccctctgcc cacagcctca gcatttcttg gagcagcaaa   1740
gggcctcaat tcctataaga gaccctcgca gcccagaggc gcccagagga agtcagcagc   1800
cctagctcgg ccacacttgg tgctcccagc atcccaggga gagacacagc ccactgaaca   1860
aggtctcagg ggtattgcta agccaagaag gaactttccc acactactga atggaagcag   1920
gctgtcttgt aaaagcccag atcactgtgg gctggagagg agaaggaaag ggtctgcgcc   1980
agccctgtcc gtcttcaccc atccccaagc ctactagagc aagaaaccag ttgtaatata   2040
aaatgcactg ccctactgtt ggtatgacta ccgttaccta ctgttgtcat tgttattaca   2100
gctatggcca ctattattaa agagctgtgt aacatctctg gcataggcta gctggaatgc   2160
ttgataagaa ctgagctggg atgattgaac tttcattctt tggcttgggg agaaaagaag   2220
tcctggggaa gcaattgagt ctcaaagtag aggcagggga aaaaagagtt agggagacca   2280
gatctgctga gtggcagcaa gagtgagctg cagattacag aaaccagggt gagcaagttt   2340
gagtcccaca cagggccttc tccctttgcc tctttccctc cctccctgcc tgtgataatc   2400
agccaggagc cagggataac ctatgacttg ggaaagagat gagttaggca gtcaagggtg   2460
```

```
acattcaatc agggatccac aagtggctgg aaagaaatgc tggtcctgtg tcctaacttt   2520

ttccgcctgg agagccctca gtgtggcttc ttacatttaa aaaacaaaaa ggatcagctg   2580

ccaggtgtga ggcagtcccc aagctgagtt gtgaggatgt aagcatgaat aagtccctgc   2640

actcaaaatg gtcaaagaat taaaccccat ggactttttt ggcatctgta tgaaagcttg   2700

ggttttctga ggactgtctt gctatagtta agtcagatcc tagatgaaat atacttgttc   2760

atactgtact aggttcttag gaaacaacag aattcctcaa atgccaaaaa caaagaaaat   2820

agaaacccag aaaacaaaac aaaataaaac aaaaccatca gaactgtgag tggaaactaa   2880

ggtgatgatc tgggagcaat acactaaaat cttgggtcga gacctatatg aaggctggca   2940

gtggagctaa acctggacac actgaagaca agggagctga accagggctc ctacatgaag   3000

cagggataac tgatggcagt aaatgtggtc tcaaattgca gatggtctgg aggaaaattt   3060

cccaaattta gagcctcagg attcccaaag atcctccaaa tatgagctca caatcaaaga   3120

tcagagacgt tgaaaaataa aaaacacctt aagtgggcag cataaaaaac agctaattta   3180

gaaccccaaa ggcttcagat gtcagaatat tagagactta tgataataag caatatttgc   3240

agagtatttg tatgtgccag acactattgt aagtgcttca tcatgtactg attcatttaa   3300

tactcacaga aatctgtgag atgggtatta ttcttatcct cactctatgg attaaaaaaa   3360

ctaaggcaca aagtggttaa gctccttgcc tgagattata gactgtaagt tgaacgtgag   3420

cacttggaat acagagttca tgctgtaaac taccacacta tagggcctcc aatatgataa   3480

tttataaaat atttgaataa aaaatgaata ctagttccac attttaaaaa aaaaaaaaaa   3540

aaa                                                                 3543
```

```
<210> SEQ ID NO 11
<211> LENGTH: 437
<212> TYPE: PRT
<213> ORGANISM: Homo sapiens

<400> SEQUENCE: 11

Met Leu Gln Asp Pro Asp Ser Asp Gln Pro Leu Asn Ser Leu Asp Val
1               5                   10                  15

Lys Pro Leu Arg Lys Pro Arg Ile Pro Met Glu Thr Phe Arg Lys Val
            20                  25                  30

Gly Ile Pro Ile Ile Ile Ala Leu Leu Ser Leu Ala Ser Ile Ile Ile
        35                  40                  45

Val Val Val Leu Ile Lys Val Ile Leu Asp Lys Tyr Tyr Phe Leu Cys
    50                  55                  60

Gly Gln Pro Leu His Phe Ile Pro Arg Lys Gln Leu Cys Asp Gly Glu
65                  70                  75                  80

Leu Asp Cys Pro Leu Gly Glu Asp Glu Glu His Cys Val Lys Ser Phe
                85                  90                  95

Pro Glu Gly Pro Ala Val Ala Val Arg Leu Ser Lys Asp Arg Ser Thr
            100                 105                 110

Leu Gln Val Leu Asp Ser Ala Thr Gly Asn Trp Phe Ser Ala Cys Phe
        115                 120                 125

Asp Asn Phe Thr Glu Ala Leu Ala Glu Thr Ala Cys Arg Gln Met Gly
    130                 135                 140

Tyr Ser Ser Lys Pro Thr Phe Arg Ala Val Glu Ile Gly Pro Asp Gln
145                 150                 155                 160

Asp Leu Asp Val Val Glu Ile Thr Glu Asn Ser Gln Glu Leu Arg Met
                165                 170                 175
```

```
Arg Asn Ser Ser Gly Pro Cys Leu Ser Gly Ser Leu Val Ser Leu His
            180                 185                 190

Cys Leu Ala Cys Gly Lys Ser Leu Lys Thr Pro Arg Val Val Gly Gly
        195                 200                 205

Glu Glu Ala Ser Val Asp Ser Trp Pro Trp Gln Val Ser Ile Gln Tyr
    210                 215                 220

Asp Lys Gln His Val Cys Gly Gly Ser Ile Leu Asp Pro His Trp Val
225                 230                 235                 240

Leu Thr Ala Ala His Cys Phe Arg Lys His Thr Asp Val Phe Asn Trp
                245                 250                 255

Lys Val Arg Ala Gly Ser Asp Lys Leu Gly Ser Phe Pro Ser Leu Ala
            260                 265                 270

Val Ala Lys Ile Ile Ile Ile Glu Phe Asn Pro Met Tyr Pro Lys Asp
        275                 280                 285

Asn Asp Ile Ala Leu Met Lys Leu Gln Phe Pro Leu Thr Phe Ser Gly
    290                 295                 300

Thr Val Arg Pro Ile Cys Leu Pro Phe Phe Asp Glu Glu Leu Thr Pro
305                 310                 315                 320

Ala Thr Pro Leu Trp Ile Ile Gly Trp Gly Phe Thr Lys Gln Asn Gly
                325                 330                 335

Gly Lys Met Ser Asp Ile Leu Leu Gln Ala Ser Val Gln Val Ile Asp
            340                 345                 350

Ser Thr Arg Cys Asn Ala Asp Asp Ala Tyr Gln Gly Glu Val Thr Glu
        355                 360                 365

Lys Met Met Cys Ala Gly Ile Pro Glu Gly Gly Val Asp Thr Cys Gln
    370                 375                 380

Gly Asp Ser Gly Gly Pro Leu Met Tyr Gln Ser Asp Gln Trp His Val
385                 390                 395                 400

Val Gly Ile Val Ser Trp Gly Tyr Gly Cys Gly Gly Pro Ser Thr Pro
                405                 410                 415

Gly Val Tyr Thr Lys Val Ser Ala Tyr Leu Asn Trp Ile Tyr Asn Val
            420                 425                 430

Trp Lys Ala Glu Leu
        435


<210> SEQ ID NO 12
<211> LENGTH: 20078
<212> TYPE: DNA
<213> ORGANISM: Artificial Sequence
<220> FEATURE:
<223> OTHER INFORMATION: Recombinant polynucleotide

<400> SEQUENCE: 12

ccacccgcac acactacagt cgagataact tcgtataatg tatgctatac gaagttatat     60

gcatggcctc cgcgccgggt tttggcgcct cccgcgggcg ccccccctcct cacggcgagc    120

gctgccacgt cagacgaagg gcgcagcgag cgtcctgatc cttccgcccg gacgctcagg    180

acagcggccc gctgctcata agactcggcc ttagaacccc agtatcagca gaaggacatt    240

ttaggacggg acttgggtga ctctagggca ctggttttct ttccagagag cggaacaggc    300

gaggaaaagt agtcccttct cggcgattct gcggagggat ctccgtgggg cggtgaacgc    360

cgatgattat ataaggacgc gccgggtgtg gcacagctag ttccgtcgca gccgggattt    420

gggtcgcggt tcttgtttgt ggatcgctgt gatcgtcact tggtgagtag cgggctgctg    480

ggctggccgg ggctttcgtg gccgccgggc cgctcggtgg gacggaagcg tgtggagaga    540
```

```
ccgccaaggg ctgtagtctg ggtccgcgag caaggttgcc ctgaactggg ggttgggggg    600
agcgcagcaa aatggcggct gttcccgagt cttgaatgga agacgcttgt gaggcgggct    660
gtgaggtcgt tgaaacaagg tgggggggcat ggtgggcggc aagaacccaa ggtcttgagg    720
ccttcgctaa tgcgggaaag ctcttattcg ggtgagatgg gctggggcac catctgggga    780
ccctgacgtg aagtttgtca ctgactggag aactcggttt gtcgtctgtt gcgggggcgg    840
cagttatggc ggtgccgttg ggcagtgcac ccgtaccttt gggagcgcgc gccctcgtcg    900
tgtcgtgacg tcacccgttc tgttggctta taatgcaggg tggggccacc tgccggtagg    960
tgtgcggtag gcttttctcc gtcgcaggac gcagggttcg ggcctagggt aggctctcct   1020
gaatcgacag gcgccggacc tctggtgagg ggagggataa gtgaggcgtc agtttctttg   1080
gtcggtttta tgtacctatc ttcttaagta gctgaagctc cggttttgaa ctatgcgctc   1140
ggggttggcg agtgtgtttt gtgaagtttt ttaggcacct tttgaaatgt aatcatttgg   1200
gtcaatatgt aattttcagt gttagactag taaattgtcc gctaaattct ggccgttttt   1260
ggcttttttg ttagacgtgt tgacaattaa tcatcggcat agtatatcgg catagtataa   1320
tacgacaagg tgaggaacta aaccatggga tcggccattg aacaagatgg attgcacgca   1380
ggttctccgg ccgcttgggt ggagaggcta ttcggctatg actgggcaca acagacaatc   1440
ggctgctctg atgccgccgt gttccggctg tcagcgcagg ggcgcccggt tctttttgtc   1500
aagaccgacc tgtccggtgc cctgaatgaa ctgcaggacg aggcagcgcg gctatcgtgg   1560
ctggccacga cgggcgttcc ttgcgcagct gtgctcgacg ttgtcactga agcgggaagg   1620
gactggctgc tattgggcga agtgccgggg caggatctcc tgtcatctca ccttgctcct   1680
gccgagaaag tatccatcat ggctgatgca atgcggcggc tgcatacgct tgatccggct   1740
acctgcccat tcgaccacca agcgaaacat cgcatcgagc gagcacgtac tcggatggaa   1800
gccggtcttg tcgatcagga tgatctggac gaagagcatc aggggctcgc gccagccgaa   1860
ctgttcgcca ggctcaaggc gcgcatgccc gacggcgatg atctcgtcgt gacccatggc   1920
gatgcctgct tgccgaatat catggtggaa aatggccgct tttctggatt catcgactgt   1980
ggccggctgg gtgtggcgga ccgctatcag gacatagcgt tggctacccg tgatattgct   2040
gaagagcttg gcggcgaatg ggctgaccgc ttcctcgtgc tttacggtat cgccgctccc   2100
gattcgcagc gcatcgcctt ctatcgcctt cttgacgagt tcttctgagg ggatccgctg   2160
taagtctgca gaaattgatg atctattaaa caataaagat gtccactaaa atggaagttt   2220
ttcctgtcat actttgttaa gaagggtgag aacagagtac ctacattttg aatggaagga   2280
ttggagctac gggggtgggg gtggggtggg attagataaa tgcctgctct ttactgaagg   2340
ctctttacta ttgctttatg ataatgtttc atagttggat atcataattt aaacaagcaa   2400
aaccaaatta agggccagct cattcctccc actcatgatc tatagatcta tagatctctc   2460
gtgggatcat tgtttttctc ttgattccca ctttgtggtt ctaagtactg tggtttccaa   2520
atgtgtcagt ttcatagcct gaagaacgag atcagcagcc tctgttccac atacacttca   2580
ttctcagtat tgttttgcca agttctaatt ccatcagacc tcgacctgca gcccctagcc   2640
cgggcgccag tagcagcacc cacgtccacc ttctgtctag taatgtccaa cacctccctc   2700
agtccaaaca ctgctctgca tccatgtggc tcccatttat acctgaagca cttgatgggg   2760
cctcaatgtt ttactagagc ccacccccct gcaactctga gaccctctgg atttgtctgt   2820
cagtgcctca ctggggcgtt ggataatttc ttaaaaggtc aagttccctc agcagcattc   2880
```

-continued

```
tctgagcagt ctgaagatgt gtgcttttca cagttcaaat ccatgtggct gtttcaccca   2940
cctgcctggc cttgggttat ctatcaggac ctagcctaga agcaggtgtg tggcacttaa   3000
cacctaagct gagtgactaa ctgaacactc aagtggatgc catctttgtc acttcttgac   3060
tgtgacacaa gcaactcctg atgccaaagc cctgcccacc cctctcatgc ccatatttgg   3120
acatggtaca ggtcctcact ggccatggtc tgtgaggtcc tggtcctctt tgacttcata   3180
attcctaggg gccactagta tctataagag gaagagggtg ctggctccca ggccacagcc   3240
cacaaaattc cacctgctca caggttggct ggctcgaccc aggtggtgtc ccctgctctg   3300
agccagctcc cggccaagcc agcaccatgg gtacccccaa gaagaagagg aaggtgcgta   3360
ccgatttaaa ttccaattta ctgaccgtac accaaaattt gcctgcatta ccggtcgatg   3420
caacgagtga tgaggttcgc aagaacctga tggacatgtt cagggatcgc caggcgtttt   3480
ctgagcatac ctggaaaatg cttctgtccg tttgccggtc gtgggcggca tggtgcaagt   3540
tgaataaccg gaaatggttt cccgcagaac ctgaagatgt tcgcgattat cttctatatc   3600
ttcaggcgcg cggtctggca gtaaaaacta tccagcaaca tttgggccag ctaaacatgc   3660
ttcatcgtcg gtccgggctg ccacgaccaa gtgacagcaa tgctgtttca ctggttatgc   3720
ggcggatccg aaaagaaaac gttgatgccg gtgaacgtgc aaaacaggct ctagcgttcg   3780
aacgcactga tttcgaccag gttcgttcac tcatggaaaa tagtgatcgc tgccaggata   3840
tacgtaatct ggcatttctg gggattgctt ataacaccct gttacgtata gccgaaattg   3900
ccaggatcag ggttaaagat atctcacgta ctgacggtgg gagaatgtta atccatattg   3960
gcagaacgaa aacgctggtt agcaccgcag gtgtagagaa ggcacttagc ctgggggtaa   4020
ctaaactggt cgagcgatgg atttccgtct ctggtgtagc tgatgatccg aataactacc   4080
tgttttgccg ggtcagaaaa aatggtgttg ccgcgccatc tgccaccagc cagctatcaa   4140
ctcgcgccct ggaagggatt tttgaagcaa ctcatcgatt gatttacggc gctaaggtaa   4200
atataaaatt tttaagtgta taatgtgtta aactactgat tctaattgtt tgtgtatttt   4260
aggatgactc tggtcagaga tacctggcct ggtctggaca cagtgcccgt gtcggagccg   4320
cgcgagatat ggcccgcgct ggagtttcaa taccggagat catgcaagct ggtggctgga   4380
ccaatgtaaa tattgtcatg aactatatcc gtaacctgga tagtgaaaca ggggcaatgg   4440
tgcgcctgct ggaagatggc gattgatcta gataagtaat gatcataatc agccatatca   4500
catctgtaga ggttttactt gctttaaaaa acctcccaca cctccccctg aacctgaaac   4560
ataaaatgaa tgcaattgtt gttgttaaac ctgccctagt tgcggccaat tccagctgag   4620
cgtgcctccg caccattacc agttggtctg gtgtcaaaaa taataataac cgggcagggg   4680
ggatctaagc tctagataag taatgatcat aatcagccat atcacatctg tagaggtttt   4740
acttgcttta aaaaacctcc cacacctccc cctgaacctg aaacataaaa tgaatgcaat   4800
tgttgttgtt aacttgttta ttgcagctta taatggttac aaataaagca atagcatcac   4860
aaatttcaca aataaagcat ttttttcact gcattctagt tgtggtttgt ccaaactcat   4920
caatgtatct tatcatgtct ggaataactt cgtataatgt atgctatacg aagttatgct   4980
agtaactata acggtcctaa ggtagcgagc tagccaagtc tgtgtgctac caagtagcaa   5040
aactgagcct ggaactcaca catgcgtgtc tgagagccca gcactatcgc caggaaaacc   5100
cagcgtctcc ctgctcaagc ctgaccctca gccctctctg cctctccctg cacttgcctt   5160
ccagtcaagg tgattctgga taaatactac ttcctctgcg ggcagcctct ccacttcatc   5220
ccgaggaagc agctgtgtga cggagagctg gactgtccct tgggggagga cgaggagcac   5280
```

```
tgtgtcaaga gcttccccga agggcctgca gtggcaggtg agtgcagggt ctgaggcaca   5340
agagaagtgg gcccagcagg aggtctgctc aggcccccac ggcccactgc atagtatctg   5400
ccccctactt gtcacttttc atccttgttg tataaggttc tttgtttgtt tgtttgttgt   5460
tgttttgagg cagagtgctc tgtggcccaa gatggagtgc agtgtcttgg tctcggctca   5520
ctgcaacctc tgcctcccag tttcaagtga ttcttctgcc tcagcctcat gagtagctgg   5580
gattacaggt gccagccacc acgcctggct aatttttata tttttagtag agacggggtt   5640
ttgccacatt ggtcaggctg atcttgaact cctgacctca ggtgatctgc ccgcctcagc   5700
ctcccaaagt gctgggatta caggcgtgag ccaccgtgcc cagctgtgta agtttcttga   5760
gagcaggacc ctgtcttgtc tacctttaaa tcctagtact taacacacag caaacagtaa   5820
ctatttgatg accaaatgtg agccagaaag gacaggaaat tgtaactgag gctgccccat   5880
gcgtgctgcg cctggtggat ttcaggcaga gggctagact gggtgacctt ggggcattcc   5940
tcctttctat gaaatttgtt atttcaagga gactagaaaa gagacttctc agccacttcg   6000
ccagctattg gtccttctat tcattagtgt ttgctgagac atgctatgtg acaggactga   6060
gccaggtcct ttcaatggat aggagatgtt ttgagcataa aatccacgtt ctctcttggg   6120
ctgggctctt ctaccttctt ccccctggtg cttgggctct gaagaaaaaa agataggtag   6180
gagatgagtg atggggcttc tgagggcagg gctgagtgac tttctgtgta tttgctcttt   6240
ctttatcaga agtcaaatgc ccacaggcac ctgtcatcct actgccagta ggacttctca   6300
ctcaaccttc ccctctgacc ttacttggag aaggacttag gtccctctct cagacatttc   6360
cccaggctgg gcaagttgtg tggaccatgg atgggtatgt ggtccataca atttaaacaa   6420
gctgtatatg gtcgctgggt agagtgacca cataattgat catcaaaact gatacctgta   6480
agagcaaaag ggggcactat taaccattgg gtcagggcaa caggtcaaaa tggagaccta   6540
ccctgggact tctggtcaca ctagctactg tcaaaatggg gcccaaatag acaaagccaa   6600
atggaagaaa ttcccttgac attgaaagtg ttggggctct gtggcacccc cagttctagg   6660
ttgggggagc ttgggctggt ctcatgatga gttctgaggg ggatgggcca gttgggcccc   6720
ccgttccatc taactcaggt tcctttcctc ccagtccgcc tctccaagga ccgatccaca   6780
ctgcaggtgc tggactcggc cacagggaac tggttctctg cctgtttcga caacttcaca   6840
gaagctctcg ctgagacagc ctgtaggcag atgggctaca gcaggtaacc aacctgggcc   6900
tctctccttt ttccctcctt cctccttcct cctcttcctc ctttccttcc tcccttcttc   6960
tctctttcct aaaaattacg ggcattggag ccaggcagaa tggcttttga atcccagcat   7020
ttcacttata agcaacatga agttaaattt cctaagcctc aggttcctca ggagttaatt   7080
gggggaacta atgccaacct cataggatag ttttgcaatg ccagtgagag aatgtgtgct   7140
gccctccaac acacacacac acacttctag cgtctatgca gtcctctcct ttcctttact   7200
cctcaacctt cactcctttg tgctggcttt gcaagaaact gttcctgccc agtaatacaa   7260
aagctaagtt aacttattca aagtttcgtt agttaagatt tagcttaagt gagcctagtt   7320
tcagtggggc cccatcttca gcaatcccag ctctctctgc aaatttcaaa agcagttcca   7380
aatctggagt ggatgaaaag gtgtaagatg atagtaagag taatttgcat tctatatatt   7440
tatattcact tgattttggc agaaaaccaa aaagatagtt attatatctt atatatagat   7500
atatattata tctatttcat aaataggctc aaacaaagta agtaacttgc tagggtacta   7560
gctgggaggt agagggctag aatttgagcc caagacccct aattcttgcg cattaggagt   7620
```

```
tcccacattg tttctgtttc tagactgagt aattctttat tctcatgtag gacatcatct   7680
ctaagggaag gggctaatga gatggttgat cactcagaga gtttagctgg agaggatgga   7740
aaagaaccca tacattcagt tgcagattga gatagcctat ctctggcagg cctcagattt   7800
cttcaggatt ctaacagact ggacccagag actaggccaa acaaacaaac aaacaaaaac   7860
tctactaggc agacatcacc aaccaatcac agaactctct cccatggatc cctaatacag   7920
cctcaaagtc cttttcagta aatgctccag gcagccatta caaatcaatc agaattattt   7980
gcctttctct tctctgctca acgggcttct gctgctctct actttccata gggggcaact   8040
tccattaccc tctagaaagc acaccccacc accttcattt caaggagagt gaggaactca   8100
tgcccagcac ctgctattct cccctcttcc tgcagccacg gagcccagcc tcgctgcagc   8160
cagccctgcc tccccactgt agtccagtca actgctgcat cagccgttcc tggcacagca   8220
ggctgagcct tgattatgaa acctgggtgt ctccaggggt tcttaagatg ataggctcct   8280
ggaatttctg tccttttgga gctcagtaag gcaccaaacc acctgagtct tgtgcttcac   8340
aaaatcaaag ttcatcagaa tcattcattg ggatggaatt ggtgaacaga agttaacttt   8400
cctgggaatg tccatttcca ccatattccg tccttctagg tctcagactt ctctactttc   8460
tttcctctct ctagatcgga ggcccttctt gtcctagaac cataggcatt tcaagatgtg   8520
ggagacccta gggatcatct agtccacgca tctttttttt ttttttttga cagagtctca   8580
ctctgtcacc caggctggag tgcaatggca ccatctctgc ttactgcaac ctccacctcc   8640
caggttcaag tgattctttc gcctcagcct cccaagtagc tgggattaca ggcacgcacc   8700
atcatgccca gctaattttt atatttttgt agagaccgag tttcaccatg ttggccaggc   8760
tggtcttgaa ctcctgacct caggtgatcc acccacctcg gcctcccaaa gtgctgggat   8820
tacaggcgtg agccactgca cccagccccg tgcatctttt tatagagggg gaaactgagg   8880
cttggagaga cccagaaaaa gaatatgacc tgcccaaggc cacacatcaa actagtgcca   8940
gagccaggga cagaacctag atcatgagga ctcttaaaat gcactctagt cctcccaggt   9000
ctgagacttg ggtccttcca ggaagtgcca gcattcctgc ctgagaatgt gccaatccac   9060
cagtattgcc aatgactcag ccctccatgg agagcttcta ctaacattac tagcatagtt   9120
agggatggaa ggaaaagatt tagaagaggc agattcagta aaggaacaat cagagagatg   9180
gaattaatca aggaaggctt cctggaggag gaaaaacttc aacccaaggt ttgaaagtag   9240
caagcatgga ttagcaggga gaaagaggga gagtggtcca gttgagagaa acgtttgtct   9300
ggattcatat gaagacagat ctagtcctgt tctattaaat atctctaagg gggccaaaaa   9360
catacccccg ctatcaaagt cagaccagat gctttgtttg gagaacgaaa tatccacatt   9420
ccaactccct cccaggtgag aagggagcta acctgagccc ctatgcctct ttgtttccct   9480
gctgtgaacc agaagacatt gctgggatat ttgaaatagg gacagagctg ggaatatgga   9540
aaggagaccc ctaacatttc tccagggctc tgggttctgg atttggattc cccacccaag   9600
aaagcaagtt acatcagcaa tgcactgagg gttgagtcct gggatgccaa gggtcggttc   9660
tttattgtat agcaaagcag gccccatctt cactgactaa gaccatctcc actccctggc   9720
cactccccac caagcattct ctgccactct ttctcctgaa agtgggggcc aactctacca   9780
tcttgttcta accccctgcc ccagctcaca actctctctc cctcttgatg tgagcagcaa   9840
acccactttc agagctgtgg agattggccc agaccaggat ctggatgttg ttgaaatcac   9900
agaaaacagc caggagcttc gcatgcggaa ctcaagtggg taagtgaggg gacaccttct   9960
ggcctacaga aggcccccac atggacgctg ctcttcaggt tgcaaccagc tcacctggaa  10020
```

```
ccccaagcag ccaggggaat gtaagcagac atcaggaaga actcctagcc agatggatca  10080
ttcaatgcca agagctatag actcacattt tggagaggtt ttctgtgttg acttgttttt  10140
aatacaatgg acagctggac aaagtgtgtt gtcctactca gagccagagg gatggataat  10200
gtgacctttc catcaatctg gatagtaaat agtttttgct actgctgtag gttttctaat  10260
aaattgccca ataggcaaga ttccaaagtc actttgtcct tccctaccac ttacccagcc  10320
agagctcccc accttcttga tgctccaggg aagaggctcc atggcccttg tgggtggcct  10380
gttcctgagc ctcgccaccc tgtgttagag cagagcatcc agatgaaatc tgtcacactg  10440
tggcaaagtg gctcagagag gaggctggct tcctagcatt cagggacgtt gctgagggcc  10500
gcttattcac cgaaaataaa tcttgaaaag gacagggctg gtagcagaat gatcctttac  10560
ctaaaattct atcaaaatcc cattcttcca tttggaaagc ccacagtgtc acagactctg  10620
ttccgggctc tgtcctcttc cctcttgggt cccaggagcc caggctgggc tttgaagcag  10680
gcagggccca gcacacagta ggtactcagc agtgggggtg ttgaatccaa tcaaacggaa  10740
gtgtcaatgc aggaaatgca atggatgtca atgcagtctc caaatgttcc ccactgtgca  10800
gcttccacat tcccgaggta ttgggagggg acttgaatta acagcttcgg gaggcctgag  10860
tccctgcctc ccagctgagg aagaagctta aatcacaggg cgctgtgtct gtcttccagg  10920
ccctgtctct caggctccct ggtctccctg cactgtcttg gtgagtaccc ccaatctctg  10980
agggtttggg gcctgggcca gcaatgagca gggaggaaga ccttcatctt cactcctaaa  11040
tttctgggac tccaagtttc attctgcctt ggtctacagc ccttgggctt gtcggtcaat  11100
gccccctcga gttgttggtg gccttgggca ggtcacattc tttttctggg tctttccaag  11160
ccccagtttc cccctctac catctgtgca tggctccatg acctaagtgg agacctggga  11220
gagagtgtta ggaagaccga aaagggcagg acggggcctc cactgcctcc catccctggt  11280
ccgggcccac atagccttct ttgtcacaat cagctcaggt atccaagatc agattaccca  11340
cattcattat ttgagcaact attcattgaa cagttagaat atgtctcact ctgtcagttg  11400
ctggctagaa gtagaaagta ccagatgagt gaaataattg gccactatcc ttggtagctg  11460
atgactaagt aagagagaga tgcaagacaa catgtggaaa atgccaaact gagtagcagt  11520
cacagttgac atgctgcaga gagagctggc cgggggtcag aagacctggg caccagtcct  11580
gttcatttcc agtgtggcct cgagtcattc acctgacctc cctgaagttc attttcccaa  11640
gaagttgttt agtccaactg cccatcaagg atctttaggg acccttctag ctctaacaga  11700
ggagatcaga aaagaaaaca agcaatgtgg ctcagctcat cctacaagct tcatagagaa  11760
ctgagactgg cctggaagca tagccagaaa ttagaacgcc taagggaaga aggtcacaac  11820
gctgcctctg caatttagga gtgtatatgc tttcctgcag gatgttgaga gtttcattca  11880
ttatcgtatg ccccctaccc cggccccaca atacctagtg cgtgggatct gacacgtggt  11940
ggctggtcaa tgaatgaatg aatgaatggt cacaccatct gaggttctgc actgagtagc  12000
cctgaaggct tgaagcagca taagtgacag gtcctccctt gaggggcctc tgttttacca  12060
ataagccaag acctaagctc aacaacactg aaagggtggc caatacccag gacagcctgt  12120
gggaattcca gagaaaggga gattcccagg gactgggggc ccaggctaaa cactgaaaaa  12180
tgcatctgta ggctcaagga ggaaaagccc atgtctgtct gtcttgccca ccactctctc  12240
ccagcaccca gcactgcccc aggacagaga gcacttgaca caagttggtt agattaatga  12300
atgatttaga gttcagtggt ccccaacctt tttggcacaa gagactggtt gcatggaaga  12360
```

```
caatttttcc gcaaaccaag agggggatag agagcattag attctctctt tttttttttt  12420
ttgagaccaa gtctggctct tgtcactcag cctggagtaa agtgttgcga tctcggctca  12480
ctgcaacctc cgcctcctgg attcaagcga ttctcctgcc tcagcccccct aaatagctgg  12540
gattacaggc acccgtcacc agcccagctg ggactatagg catgtgccac catgcccggc  12600
taatttttgt atttttagta gagacggcgt ttcaccatgt tggccaggct agtctcgaac  12660
tcctgacctc aggtgatctg cccgcctgag cctcccaaag tgctgggatt acaggcatga  12720
gctgcctcac ccagcctaaa gtctcataag gaacgtacag catagatccc tcacatgtgc  12780
agttcacaat aaggttgtgc tcctacaaga atctaacgcc acctctgatc tgacaggagg  12840
tgaagctcag gtggtcatgc tcgcttgtcc ctgccactca cttcctaatg tacagccagg  12900
ttcctaacag gccacgaacc agtgggaagg gcatcttttt ggatcaaaaa cagaattact  12960
ttttagagaa ctacaagcag atcaatttgg ctagacagag actttatatg aaacagcagg  13020
aggctgctag gaggagtgga aactctactt tgccctcaag ggagatcccg aagggctttg  13080
caggagcggg caaggtggca tgaagaaagc agtgtttgaa atcaggtggt atttgaaaag  13140
cccagccctt cccccttagaa tggcccttct accatctgtg catggctcca caaccgtggt  13200
ggtggctgcc agaagaattg gaaaggcaga gcatgggtgg agaggggggga cctgagggct  13260
ttacaggagt tccgggggtg gtgagggtgt gaaagccagg tcagtcagta ggaagacagg  13320
atgtcagatt gagagactcc cctggccggg gaaacagact tggagaaggg ggagttttgg  13380
atgagacagt ccacttccga gtcacaaaat agcttgtggg tgtctgttta ctgttactca  13440
gtgggagtgg ctggggacac gccacctggg cagggctttc gtaattctgc atcacttgtg  13500
aaggtcacag attcccagca caacggacac acccatgttc atagtctgaa ctcctaaaca  13560
catcttaaac caaaataaaa aaaaaagaaa gaaagaaaga aaaaggagag ggaggtttga  13620
ggaaagccta tggtctggga cactcaatac ctcccatgaa tatctcatat tgggctggtc  13680
ctctctccac tctggcccca gccataaggg ccctgcttag agcagatttt gggtgctgag  13740
tggaggcagc ctcatcccca acagcctgac ttcctgcctc ctccctgcct ctgcctgtgt  13800
ccagcctgtg ggaagagcct gaagaccccc cgtgtggtgg gtgtggagga ggcctctgtg  13860
gattcttggc cttggcaggt cagcatccag tacgacaaac agcacgtctg tggagggagc  13920
atcctggacc cccactgggt cctcacggca gcccactgct tcaggtaaga ccccagctgt  13980
aaggaggtct ctggggacca aggccagtca gggaccagag agcttggggt cctgtctcct  14040
ggcaccgtcc ttctcttcac tctcccacta gagacgtttt ccaggttgtg gtggccccaa  14100
tgagacaatg gccatgatgc cctttgttag gcttttgggt gtctgagcag agggtgctgg  14160
tcaccaagca tggcctcttc ctggtgggac accagcagat acccagagtc ctcaccccac  14220
ccccatatcg ttcaagctac aaaagctctt cccacctgcc tcaacttcca agaactcact  14280
ctctttttgc ttgtttccag gaagttgttc cagggtctag agtcatagcc acgtcctcat  14340
tatgtctgga aactttaaaa aaattaaaga gcataggttc ctttcagtcc acagagaagc  14400
ctggccttac ctcagggaag ggctactccc agaccccctt cacttttttt tttttttttt  14460
tttttttttt ttttgagaca gagtcttgct ctgttgctta ggctggagcg cagcagcatg  14520
atcttggctc actgcaacct ccgcctcctg agttcaagca attctcctgc ctcagcttcc  14580
caagtagctg ggactatagg catgggccac catgcccggc taatttttgt atttttggta  14640
gagacagggt ttcaccatgt tggccaggct gatctctaac tcctgacctc aagtgatctg  14700
cccacctcag cctcccaaac tgctgggatt acaggcatga gccagggcat ccggctttta  14760
```

```
tttattcatt cattcaatat ctaatgagca cctaccaggt accaaacacc agatgatgcg  14820
cccaagttca ttagacccca ccgctgtctt caaggcactc atgatctagg ccagcgtttt  14880
ttaaccactt tttttttttt tttttttgag attctggtga gagctataaa ttctttcctg  14940
gaaaaacatc tctgcacact aagctgtgcc tggcattggg aaaaagaaag cacgtaatgt  15000
aactgacagc atgagtaaca cagtgagaaa ggttggagga gagagcgcca ggacctcaga  15060
actcaggcat tagaggagcc ccttccccag ccctccttga ggtttcgttg ggcaggtttc  15120
actgaggaaa aagggtcaaa tccctttttc gaatttgact tcttgtaagt gccagaagac  15180
tgccccttct ccaccatccc tgcctcacca tcatctttcc tcccaaggca gtgacatcca  15240
gcaccccgat ccctagggcc ctggggaccc agcctttggc aaagtctcct caggcttgga  15300
tcaggcctga acccagctgt ctctaccccc aggaaacata ccgatgtgtt caactggaag  15360
gtgcgggcag gctcagacaa actgggcagc ttcccatccc tggctgtggc caagatcatc  15420
atcattgaat tcaaccccat gtaccccaaa gacaatgaca tcgccctcat gaagctgcag  15480
ttcccactca ctttctcagg tgagaagcag ggcccaaggc cactcaagcc tcttacatca  15540
gttttcacgc ccactctgct attagctcac tgaccgccct tggcacataa tgtctcctct  15600
caagtcctca gcttgcccat ttgtctctaa tacgtcagcc taacatcact gatgccatga  15660
ggcctcctca agctgtcagc taacacctcc actccattcc ctgccagaga ttcttccaag  15720
gcctgtcttc cctatgtgga gcccctcgag tgagaactgg agtttcatcc aatcttggag  15780
ttttaggaga ccttttaaaa agattatcga gctaattccc caccactgac caacacgcaa  15840
gagcctgctc agtatccctg ccaaggagtc attgtgcccc tgtttgctct cctccagggg  15900
cagggaaccc attacctgtg aggcagccca cagagtcttt gaacagctct gttggatgcc  15960
ttgtgcttat actgaaatgt atttagatca ggattcccaa ctgtggggtc cacaagacac  16020
tggccccttg gagaagagag gattccattg tcaaataagt ttggggaaca ttttcatact  16080
acagctccct tcttggaaca cattagttta ttaaaggtag gagaagtttt taaaataatc  16140
tgttttattg cgtttaacct acatttttta aatttatttg accacagaat cctttttttca  16200
tgctacttct attagcatcc catagaacaa gtgttctaga gaccctggtg tgacccccttt  16260
cagagagctt aactgccagg ctctcctgag ccctggtgtg tgtttcaaga tttgtgcctg  16320
ggaattgttt taatcaggta tggcaaggtg acagatacag acacagctat ctttgaaaga  16380
agagtttatt atttataatt cctgagagaa agggacatac cccaccccc aacacaggga  16440
cacccgggga agcagctggg tccaccagga ggcaggagtg aggggaaggc atggcccaga  16500
gccacctgtg gcttccatgg gcaggtctgg ccaaggtagg gtaggcaaga ttgagcatgc  16560
tcaggattgg atagtgtgga caattctcta ggctatagat gtcagcctct ggttgtctag  16620
tatctgtccc tggggtgatt tagggcaggg aaaatattgg cttggtgtct gagagtcaga  16680
taaaggaagt ggttggggat atgggctttg ggttggctgg tttgcctatt aaaggcgtgc  16740
ccaaagccaa gttgtttact atctgcagga attagctaac ccagtctctc ccagaccagc  16800
aagatcccca taatcataaa gcatcataat ttacagaaaa ttaacactta tgatgaataa  16860
aagatctcct tcttcctctg tgctcctggc aggcacagtc aggcccatct gtctgccctt  16920
ctttgatgag gagctcactc cagccacccc actctggatc attggatggg gctttacgaa  16980
gcagaatgga ggtaagtcct gggtgcagga ccacagggca ggagatgccc ttgtatgagg  17040
gagcagcttc cagaagtaat gggaaggagg accacccttc agagaaaccc atcctggagg  17100
```

```
accaagcacc aaggcgccag gcagaaagca aagtggtttg gcaatccagg gctgggggat  17160
agaaggcaag gatgggaatg tgagtgtttt taccctccca gggaagatgt ctgacatact  17220
gctgcaggcg tcagtccagg tcattgacag cacacggtgc aatgcagacg atgcgtacca  17280
gggggaagtc accgagaaga tgatgtgtgc aggcatcccg gaagggggtg tggacacctg  17340
ccaggtgggg cctccaagaa tcatggggag ttctaagaat agggtttagg tcctagagag  17400
atgagaaaac ccagaggctg catgccctac aggaagcctt gcatatcatg ggcactcaat  17460
gtgtgatgat gggaggaaga gagggaggga aggaaaggat agtcagataa aagtgtacca  17520
atagatgagt gggtggatgg atggatgcag acaagcagag agatttcaaa tgtctctttc  17580
acattcgaag atgatgttac tggcctggca tggtggctca cgcttgtaat cccagcactt  17640
tgggaggctg aggcgggcag gtgatttgag gtcaggaatt caagaccagc ctggccaaca  17700
tggtgaaatc ccatctctac taaaaagaat acaaaaatta gctgggcgtg gtggcacgtg  17760
cctgtaatcc cagctacttg ggaggctgag gcaggagaat tgcttgaacc caggaggcag  17820
aggttgcagt aagctgagat tgcgccactg cactccagcc tgggtgaccc agcaagactc  17880
catctgaaaa caacaacaac aacaaagatg acattactca tccaccccac ccacccttct  17940
cactagctac agaatgatta gccccttgag gtcaggaatc ccaggtctat tttctctgtg  18000
actctcccca agctgctgaa ctacactagg aaagaattac cgcctgcaga atgctggaag  18060
cacatctgtg tgtgccctca ccccggcctc attggccatc aggactgctt agcaatccct  18120
gtagaccttc ttcctccccc atacttccag aggatcttct gaactatttt cttttttat  18180
tttttctttt atgtttttta acagagacag ggtcactatg ttgcccagtc tggtctcaaa  18240
ctcctgggtt caagggattc tcccacctca gctttccaaa atgctgggat tacaggcatg  18300
agccatcgtg cttggcctga accattttca ttaaaacccc taccctactc tcacctccat  18360
ttccagtcat taaattcctt catttaagag gcatctctta gtcatcgcat gtgtgccatg  18420
aacatggtag tctttggaga cccctcaggg agctcacagt ggttggggga aagggggca  18480
ttaaacagac atttaagcta tagttttggg ttcagaggga ggaagcccca ggggctaaaa  18540
cagctgataa ggactcccag ataagtgcac ttttcactat ctggcatttt cttgttttgt  18600
tatttgcttg ttcactgtct ctcaccccat ttgatcctaa gctttctgag ggcagggatc  18660
tttgtttttt ttcatcagtt ggatcccaat tgcttagaac actacctggc acaaaatagg  18720
cactctataa gtgattacac aaattttgga acgactaggt taaacaatga taaccaggct  18780
ttttttttt tttttgagac tgagtctcac tctgttgccc aggctagagt gaagtggttt  18840
gatctcggct cactgcagcc tccgcctctg ggttcgaatg attctccacc tcagcctcct  18900
gagtagctgg gattacaggt gcctgccact atgcccagct aatttttgta tttgtagtag  18960
agacgggttt caccatgttg gccaggctgg tcttgaactc ctgacctcaa gtgattcacc  19020
cgcctcagcc tcccaaggtg ctgggattac aggtgtgagc caccgctcct ggccaacaac  19080
caggcttttt taagacatca ctcagagcct ttaatttgct aatgtgagtt gtgaatctct  19140
gagagaaggc taacggcatg cttgcaactt acttgtccac agacaagcct ttctgcccca  19200
gaagagaaga ccattctagg gtgctaatga gcaaagaggg tgagggtgga atatcggaga  19260
gcagcaggga gtgcagggga acagataggc cagttcaggg agcagagaag gagaagcccc  19320
cccacctcac ctgccctccc cagcagtctc tgttctggtc tctcacaggg tgacagtggt  19380
gggcccctga tgtaccaatc tgaccagtgg catgtggtgg gcatcgttag ttggggctat  19440
ggctgcgggg gcccgagcac cccaggagta tacaccaagg tctcagccta tctcaactgg  19500
```

atctacaatg tctggaaggt aaggtacctt tgccctaccc actgtgcctt ccctccagtc 19560
ctctacctgg ggggtgccaa tccatcctca ggtttgattt aaatggttct gacaactctt 19620
tacatcccaa ataactttcc ctccaagcaa gggacagcct gagattgcac tattaaggct 19680
gaaattcctt aggtcagaga tttctgataa atgcaaatac cttagggaat agaacacacc 19740
aagcctttct ttctcttttc tgacagaatg agactatcag atcctttcta gagagaagat 19800
tctgataagg aagagagtgg aaaggctcat gagacctcct ggccctctgc agggtaggga 19860
gagaagcaaa gtgtttcaga aaaggaagac tcacgttaca catgtcacca ctttgtccag 19920
tttcagataa tctgactttc tcttcatcgg tctctcttat tctaggctga gctgtaacgc 19980
tgccgtcccc cacatccaga agctgcttcc cttcagacct acctacggca tgacccctca 20040
aagtcagata tgggacaaga gcctccttga acaaactc 20078

<210> SEQ ID NO 13
<211> LENGTH: 15159
<212> TYPE: DNA
<213> ORGANISM: Artificial Sequence
<220> FEATURE:
<223> OTHER INFORMATION: Recombinant polynucleotide

<400> SEQUENCE: 13
ccacccgcac acactacagt cgagataact tcgtataatg tatgctatac gaagttatgc 60
tagtaactat aacggtccta aggtagcgag ctagccaagt ctgtgtgcta ccaagtagca 120
aaactgagcc tggaactcac acatgcgtgt ctgagagccc agcactatcg ccaggaaaac 180
ccagcgtctc cctgctcaag cctgaccctc agccctctct gcctctccct gcacttgcct 240
tccagtcaag gtgattctgg ataaatacta cttcctctgc gggcagcctc tccacttcat 300
cccgaggaag cagctgtgtg acggagagct ggactgtccc ttgggggagg acgaggagca 360
ctgtgtcaag agcttccccg aagggcctgc agtggcaggt gagtgcaggg tctgaggcac 420
aagagaagtg ggcccagcag gaggtctgct caggccccca cggcccactg catagtatct 480 gcccccctact tgtcactttt catccttgtt gtataaggtt ctttgtttgt ttgtttgttg 540
ttgttttgag gcagagtgct ctgtggccca agatggagtg cagtgtcttg gtctcggctc 600
actgcaacct ctgcctccca gtttcaagtg attcttctgc ctcagcctca tgagtagctg 660
ggattacagg tgccagccac cacgcctggc taatttttat atttttagta gagacggggt 720
tttgccacat tggtcaggct gatcttgaac tcctgacctc aggtgatctg cccgcctcag 780
cctcccaaag tgctgggatt acaggcgtga gccaccgtgc ccagctgtgt aagtttcttg 840
agagcaggac cctgtcttgt ctacctttaa atcctagtac ttaacacaca gcaaacagta 900
actatttgat gaccaaatgt gagccagaaa ggacaggaaa ttgtaactga ggctgcccca 960
tgcgtgctgc gcctggtgga tttcaggcag agggctagac tgggtgacct tggggcattc 1020
ctcctttcta tgaaatttgt tatttcaagg agactagaaa agagacttct cagccacttc 1080
gccagctatt ggtccttcta ttcattagtg tttgctgaga catgctatgt gacaggactg 1140
agccaggtcc tttcaatgga taggagatgt tttgagcata aaatccacgt tctctcttgg 1200
gctgggctct tctaccttct tccccctggt gcttgggctc tgaagaaaaa aagataggta 1260
ggagatgagt gatggggctt ctgagggcag ggctgagtga ctttctgtgt atttgctctt 1320
tctttatcag aagtcaaatg cccacaggca cctgtcatcc tactgccagt aggacttctc 1380
actcaacctt cccctctgac cttacttgga gaaggactta ggtccctctc tcagacattt 1440
ccccaggctg ggcaagttgt gtggaccatg gatgggtatg tggtccatac aatttaaaca 1500
agctgtatat ggtcgctggg tagagtgacc acataattga tcatcaaaac tgatacctgt 1560
aagagcaaaa gggggcacta ttaaccattg ggtcagggca acaggtcaaa atggagacct 1620
accctgggac ttctggtcac actagctact gtcaaaatgg ggcccaaata gacaaagcca 1680
aatggaagaa attcccttga cattgaaagt gttggggctc tgtggcaccc ccagttctag 1740
gttgggggag cttgggctgg tctcatgatg agttctgagg gggatgggcc agttgggccc 1800
cccgttccat ctaactcagg ttcctttcct cccagtccgc ctctccaagg accgatccac 1860
actgcaggtg ctggactcgg ccacagggaa ctggttctct gcctgtttcg acaacttcac 1920
agaagctctc gctgagacag cctgtaggca gatgggctac agcaggtaac caacctgggc 1980
ctctctcctt tttccctcct tcctccttcc tcctcttcct cctttccttc ctcccttctt 2040
ctctctttcc taaaaattac gggcattgga gccaggcaga atggcttttg aatcccagca 2100
tttcacttat aagcaacatg aagttaaatt tcctaagcct caggttcctc aggagttaat 2160
tgggggaact aatgccaacc tcataggata gttttgcaat gccagtgaga gaatgtgtgc 2220
tgccctccaa cacacacaca cacacttcta gcgtctatgc agtcctctcc tttcctttac 2280
tcctcaacct tcactccttt gtgctggctt tgcaagaaac tgttcctgcc cagtaataca 2340
aaagctaagt taacttattc aaagtttcgt tagttaagat ttagcttaag tgagcctagt 2400
ttcagtgggg ccccatcttc agcaatccca gctctctctg caaatttcaa aagcagttcc 2460
aaatctggag tggatgaaaa ggtgtaagat gatagtaaga gtaatttgca ttctatatat 2520
ttatattcac ttgattttgg cagaaaacca aaaagatagt tattatatct tatatataga 2580
tatatattat atctatttca taaataggct caaacaaagt aagtaacttg ctagggtact 2640
agctgggagg tagagggcta gaatttgagc ccaagacccc taattcttgc gcattaggag 2700
ttcccacatt gtttctgttt ctagactgag taattcttta ttctcatgta ggacatcatc 2760
tctaagggaa ggggctaatg agatggttga tcactcagag agtttagctg gagaggatgg 2820
aaaagaaccc atacattcag ttgcagattg agatagccta tctctggcag gcctcagatt 2880
tcttcaggat tctaacagac tggacccaga gactaggcca aacaaacaaa caaacaaaaa 2940
ctctactagg cagacatcac caaccaatca cagaactctc tcccatggat ccctaataca 3000
gcctcaaagt ccttttcagt aaatgctcca ggcagccatt acaaatcaat cagaattatt 3060
tgcctttctc ttctctgctc aacgggcttc tgctgctctc tactttccat agggggcaac 3120
ttccattacc ctctagaaag cacaccccac caccttcatt tcaaggagag tgaggaactc 3180
atgcccagca cctgctattc tcccctcttc ctgcagccac ggagcccagc ctcgctgcag 3240
ccagccctgc ctccccactg tagtccagtc aactgctgca tcagccgttc ctggcacagc 3300
aggctgagcc ttgattatga aacctgggtg tctccagggg ttcttaagat gataggctcc 3360
tggaatttct gtccttttgg agctcagtaa ggcaccaaac cacctgagtc ttgtgcttca 3420
caaaatcaaa gttcatcaga atcattcatt gggatggaat tggtgaacag aagttaactt 3480
tcctgggaat gtccatttcc accatattcc gtccttctag gtctcagact tctctacttt 3540
ctttcctctc tctagatcgg aggcccttct tgtcctagaa ccataggcat ttcaagatgt 3600
gggagaccct agggatcatc tagtccacgc atcttttttt ttttttttg acagagtctc 3660
actctgtcac ccaggctgga gtgcaatggc accatctctg cttactgcaa cctccacctc 3720
ccaggttcaa gtgattcttt cgcctcagcc tcccaagtag ctgggattac aggcacgcac 3780
catcatgccc agctaatttt tatattttg tagagaccga gtttcaccat gttggccagg 3840

```
ctggtcttga actcctgacc tcaggtgatc cacccacctc ggcctcccaa agtgctggga   3900
ttacaggcgt gagccactgc acccagcccc gtgcatcttt ttatagaggg ggaaactgag   3960
gcttggagag acccagaaaa agaatatgac ctgcccaagg ccacacatca aactagtgcc   4020
agagccaggg acagaaccta gatcatgagg actcttaaaa tgcactctag tcctcccagg   4080
tctgagactt gggtccttcc aggaagtgcc agcattcctg cctgagaatg tgccaatcca   4140
ccagtattgc caatgactca gccctccatg gagagcttct actaacatta ctagcatagt   4200
tagggatgga aggaaaagat ttagaagagg cagattcagt aaaggaacaa tcagagagat   4260
ggaattaatc aaggaaggct tcctggagga ggaaaaactt caacccaagg tttgaaagta   4320
gcaagcatgg attagcaggg agaaagaggg agagtggtcc agttgagaga aacgtttgtc   4380
tggattcata tgaagacaga tctagtcctg ttctattaaa tatctctaag gggccaaaa    4440
acatacccc gctatcaaag tcagaccaga tgctttgttt ggagaacgaa atatccacat    4500
tccaactccc tcccaggtga gaagggagct aacctgagcc cctatgcctc tttgtttccc   4560
tgctgtgaac cagaagacat tgctgggata tttgaaatag ggacagagct gggaatatgg   4620
aaaggagacc cctaacattt ctccagggct ctgggttctg gatttggatt ccccacccaa   4680
gaaagcaagt tacatcagca atgcactgag ggttgagtcc tgggatgcca agggtcggtt   4740
ctttattgta tagcaaagca ggccccatct tcactgacta agaccatctc cactccctgg   4800
ccactcccca ccaagcattc tctgccactc tttctcctga aagtgggggc caactctacc   4860
atcttgttct aaccccctgc cccagctcac aactctctct ccctcttgat gtgagcagca   4920
aacccacttt cagagctgtg gagattggcc cagaccagga tctggatgtt gttgaaatca   4980
cagaaaacag ccaggagctt cgcatgcgga actcaagtgg gtaagtgagg ggacaccttc   5040
tggcctacag aaggccccca catggacgct gctcttcagg ttgcaaccag ctcacctgga   5100
accccaagca gccaggggaa tgtaagcaga catcaggaag aactcctagc cagatggatc   5160
attcaatgcc aagagctata gactcacatt ttggagaggt tttctgtgtt gacttgtttt   5220
taatacaatg gacagctgga caaagtgtgt tgtcctactc agagccagag ggatggataa   5280
tgtgaccttt ccatcaatct ggatagtaaa tagtttttgc tactgctgta ggttttctaa   5340
taaattgccc aataggcaag attccaaagt cactttgtcc ttccctacca cttacccagc   5400
cagagctccc caccttcttg atgctccagg gaagaggctc catggccctt gtgggtggcc   5460
tgttcctgag cctcgccacc ctgtgttaga gcagagcatc cagatgaaat ctgtcacact   5520
gtggcaaagt ggctcagaga ggaggctggc ttcctagcat tcagggacgt tgctgagggc   5580
cgcttattca ccgaaaataa atcttgaaaa ggacagggct ggtagcagaa tgatccttta   5640
cctaaaattc tatcaaaatc ccattcttcc atttggaaag cccacagtgt cacagactct   5700
gttccgggct ctgtcctctt ccctcttggg tcccaggagc ccaggctggg ctttgaagca   5760
ggcagggccc agcacacagt aggtactcag cagtgggggt gttgaatcca atcaaacgga   5820
agtgtcaatg caggaaatgc aatggatgtc aatgcagtct ccaaatgttc cccactgtgc   5880
agcttccaca ttcccgaggt attgggaggg gacttgaatt aacagcttcg ggaggcctga   5940
gtccctgcct cccagctgag gaagaagctt aaatcacagg gcgctgtgtc tgtcttccag   6000
gccctgtctc tcaggctccc tggtctccct gcactgtctt ggtgagtacc cccaatctct   6060
gagggtttgg ggcctgggcc agcaatgagc agggaggaag accttcatct tcactcctaa   6120
atttctggga ctccaagttt cattctgcct tggtctacag cccttgggct tgtcggtcaa   6180
```

-continued

```
tgccccctcg agttgttggt ggccttgggc aggtcacatt ctttttctgg gtctttccaa   6240
gccccagttt ccccttcta ccatctgtgc atggctccat gacctaagtg gagacctggg   6300
agagagtgtt aggaagaccg aaaagggcag gacggggcct ccactgcctc ccatccctgg   6360
tccgggccca catagccttc tttgtcacaa tcagctcagg tatccaagat cagattaccc   6420
acattcatta tttgagcaac tattcattga acagttagaa tatgtctcac tctgtcagtt   6480
gctggctaga agtagaaagt accagatgag tgaaataatt ggccactatc cttggtagct   6540
gatgactaag taagagagag atgcaagaca acatgtggaa aatgccaaac tgagtagcag   6600
tcacagttga catgctgcag agagagctgg ccgggggtca gaagacctgg gcaccagtcc   6660
tgttcatttc cagtgtggcc tcgagtcatt cacctgacct ccctgaagtt cattttccca   6720
agaagttgtt tagtccaact gcccatcaag gatctttagg gacccttcta gctctaacag   6780
aggagatcag aaaagaaaac aagcaatgtg gctcagctca tcctacaagc ttcatagaga   6840
actgagactg gcctggaagc atagccagaa attagaacgc ctaagggaag aaggtcacaa   6900
cgctgcctct gcaatttagg agtgtatatg ctttcctgca ggatgttgag agtttcattc   6960
attatcgtat gccccctacc ccggccccac aatacctagt gcgtgggatc tgacacgtgg   7020
tggctggtca atgaatgaat gaatgaatgg tcacaccatc tgaggttctg cactgagtag   7080
ccctgaaggc ttgaagcagc ataagtgaca ggtcctccct tgaggggcct ctgttttacc   7140
aataagccaa gacctaagct caacaacact gaaagggtgg ccaataccca ggacagcctg   7200
tgggaattcc agagaaaggg agattcccag ggactggggg cccaggctaa acactgaaaa   7260
atgcatctgt aggctcaagg aggaaaagcc catgtctgtc tgtcttgccc accactctct   7320
cccagcaccc agcactgccc caggacagag agcacttgac acaagttggt tagattaatg   7380
aatgatttag agttcagtgg tccccaacct ttttggcaca agagactggt tgcatggaag   7440
acaatttttc cgcaaaccaa gagggggata gagagcatta gattctctct ttttttttt   7500
tttgagacca agtctggctc ttgtcactca gcctggagta aagtgttgcg atctcggctc   7560
actgcaacct ccgcctcctg gattcaagcg attctcctgc ctcagccccc taaatagctg   7620
ggattacagg cacccgtcac cagcccagct gggactatag gcatgtgcca ccatgcccgg   7680
ctaatttttg tatttttagt agagacggcg tttcaccatg ttggccaggc tagtctcgaa   7740
ctcctgacct caggtgatct gcccgcctga gcctcccaaa gtgctgggat tacaggcatg   7800
agctgcctca cccagcctaa agtctcataa ggaacgtaca gcatagatcc ctcacatgtg   7860
cagttcacaa taaggttgtg ctcctacaag aatctaacgc cacctctgat ctgacaggag   7920
gtgaagctca ggtggtcatg ctcgcttgtc cctgccactc acttcctaat gtacagccag   7980
gttcctaaca ggccacgaac cagtgggaag ggcatctttt tggatcaaaa acagaattac   8040
tttttagaga actacaagca gatcaatttg gctagacaga gactttatat gaaacagcag   8100
gaggctgcta ggaggagtgg aaactctact ttgccctcaa gggagatccc gaagggcttt   8160
gcaggagcgg gcaaggtggc atgaagaaag cagtgtttga aatcaggtgg tatttgaaaa   8220
gcccagccct tccccttaga atggcccttc taccatctgt gcatggctcc acaaccgtgg   8280
tggtggctgc cagaagaatt ggaaaggcag agcatgggtg gagagggggg acctgagggc   8340
tttacaggag ttccgggggt ggtgagggtg tgaaagccag gtcagtcagt aggaagacag   8400
gatgtcagat tgagagactc ccctggccgg ggaaacagac ttggagaagg gggagttttg   8460
gatgagacag tccacttccg agtcacaaaa tagcttgtgg gtgtctgttt actgttactc   8520
agtgggagtg gctggggaca cgccacctgg gcagggcttt cgtaattctg catcacttgt   8580
```

```
gaaggtcaca gattcccagc acaacggaca cacccatgtt catagtctga actcctaaac   8640
acatcttaaa ccaaaataaa aaaaaaagaa agaaagaaag aaaaaggaga gggaggtttg   8700
aggaaagcct atggtctggg acactcaata cctcccatga atatctcata ttgggctggt   8760
cctctctcca ctctggcccc agccataagg gccctgctta gagcagattt tgggtgctga   8820
gtggaggcag cctcatcccc aacagcctga cttcctgcct cctccctgcc tctgcctgtg   8880
tccagcctgt gggaagagcc tgaagacccc ccgtgtggtg ggtgtggagg aggcctctgt   8940
ggattcttgg ccttggcagg tcagcatcca gtacgacaaa cagcacgtct gtggagggag   9000
catcctggac ccccactggg tcctcacggc agcccactgc ttcaggtaag accccagctg   9060
taaggaggtc tctggggacc aaggccagtc agggaccaga gagcttgggg tcctgtctcc   9120
tggcaccgtc cttctcttca ctctcccact agagacgttt tccaggttgt ggtggcccca   9180
atgagacaat ggccatgatg ccctttgtta ggcttttggg tgtctgagca gagggtgctg   9240
gtcaccaagc atggcctctt cctggtggga caccagcaga tacccagagt cctcacccca   9300
cccccatatc gttcaagcta caaaagctct tcccacctgc ctcaacttcc aagaactcac   9360
tctctttttg cttgtttcca ggaagttgtt ccagggtcta gagtcatagc cacgtcctca   9420
ttatgtctgg aaactttaaa aaaattaaag agcataggtt cctttcagtc cacagagaag   9480
cctggcctta cctcagggaa gggctactcc cagaccccct tcactttttt tttttttttt   9540
tttttttttt tttttgagac agagtcttgc tctgttgctt aggctggagc gcagcagcat   9600
gatcttggct cactgcaacc tccgcctcct gagttcaagc aattctcctg cctcagcttc   9660
ccaagtagct gggactatag gcatgggcca ccatgcccgg ctaatttttg tatttttggt   9720
agagacaggg tttcaccatg ttggccaggc tgatctctaa ctcctgacct caagtgatct   9780
gcccacctca gcctcccaaa ctgctgggat tacaggcatg agccagggca tccggctttt   9840
atttattcat tcattcaata tctaatgagc acctaccagg taccaaacac cagatgatgc   9900
gcccaagttc attagacccc accgctgtct tcaaggcact catgatctag gccagcgttt   9960
tttaaccact tttttttttt tttttttgga gattctggtg agagctataa attctttcct  10020
ggaaaaacat ctctgcacac taagctgtgc ctggcattgg gaaaaagaaa gcacgtaatg  10080
taactgacag catgagtaac acagtgagaa aggttggagg agagagcgcc aggacctcag  10140
aactcaggca ttagaggagc cccttcccca gccctccttg aggtttcgtt gggcaggttt  10200
cactgaggaa aaagggtcaa atccctttt cgaatttgac ttcttgtaag tgccagaaga  10260
ctgcccttc tccaccatcc ctgcctcacc atcatctttc ctcccaaggc agtgacatcc  10320
agcaccccga tccctagggc cctggggacc cagcctttgg caaagtctcc tcaggcttgg  10380
atcaggcctg aacccagctg tctctacccc caggaaacat accgatgtgt tcaactggaa  10440
ggtgcgggca ggctcagaca aactgggcag cttcccatcc ctggctgtgg ccaagatcat  10500
catcattgaa ttcaacccca tgtaccccaa agacaatgac atcgccctca tgaagctgca  10560
gttcccactc actttctcag gtgagaagca gggcccaagg ccactcaagc ctcttacatc  10620
agttttcacg cccactctgc tattagctca ctgaccgccc ttggcacata atgtctcctc  10680
tcaagtcctc agcttgccca tttgtctcta atacgtcagc ctaacatcac tgatgccatg  10740
aggcctcctc aagctgtcag ctaacacctc cactccattc cctgccagag attcttccaa  10800
ggcctgtctt ccctatgtgg agcccctcga gtgagaactg gagtttcatc caatcttgga  10860
gttttaggag accttttaaa aagattatcg agctaattcc ccaccactga ccaacacgca  10920
```

```
agagcctgct cagtatccct gccaaggagt cattgtgccc ctgtttgctc tcctccaggg  10980
gcagggaacc cattacctgt gaggcagccc acagagtctt tgaacagctc tgttggatgc  11040
cttgtgctta tactgaaatg tatttagatc aggattccca actgtggggt ccacaagaca  11100
ctggcccctt ggagaagaga ggattccatt gtcaaataag tttggggaac attttcatac  11160
tacagctccc ttcttggaac acattagttt attaaaggta ggagaagttt ttaaaataat  11220
ctgttttatt gcgtttaacc tacatttttt aaatttattt gaccacagaa tccttttttc  11280
atgctacttc tattagcatc ccatagaaca agtgttctag agaccctggt gtgacccctt  11340
tcagagagct taactgccag gctctcctga gccctggtgt gtgtttcaag atttgtgcct  11400
gggaattgtt ttaatcaggt atggcaaggt gacagataca gacacagcta tctttgaaag  11460
aagagtttat tatttataat tcctgagaga aagggacata ccccaccccc caacacaggg  11520
acacccgggg aagcagctgg gtccaccagg aggcaggagt gaggggaagg catggcccag  11580
agccacctgt ggcttccatg ggcaggtctg gccaaggtag ggtaggcaag attgagcatg  11640
ctcaggattg gatagtgtgg acaattctct aggctataga tgtcagcctc tggttgtcta  11700
gtatctgtcc ctggggtgat ttagggcagg gaaaatattg gcttggtgtc tgagagtcag  11760
ataaaggaag tggttgggga tatgggcttt gggttggctg gtttgcctat taaaggcgtg  11820
cccaaagcca agttgtttac tatctgcagg aattagctaa cccagtctct cccagaccag  11880
caagatcccc ataatcataa agcatcataa tttacagaaa attaacactt atgatgaata  11940
aaagatctcc ttcttcctct gtgctcctgg caggcacagt caggcccatc tgtctgccct  12000
tctttgatga ggagctcact ccagccaccc cactctggat cattggatgg ggctttacga  12060
agcagaatgg aggtaagtcc tgggtgcagg accacagggc aggagatgcc cttgtatgag  12120
ggagcagctt ccagaagtaa tgggaaggag gaccacccctt cagagaaacc catcctggag  12180
gaccaagcac caaggcgcca ggcagaaagc aaagtggttt ggcaatccag ggctggggga  12240
tagaaggcaa ggatgggaat gtgagtgttt ttaccctccc agggaagatg tctgacatac  12300
tgctgcaggc gtcagtccag gtcattgaca gcacacggtg caatgcagac gatgcgtacc  12360
agggggaagt caccgagaag atgatgtgtg caggcatccc ggaagggggt gtggacacct  12420
gccaggtggg gcctccaaga atcatgggga gttctaagaa tagggtttag gtcctagaga  12480
gatgagaaaa cccagaggct gcatgcccta caggaagcct tgcatatcat gggcactcaa  12540
tgtgtgatga tgggaggaag agagggaggg aaggaaagga tagtcagata aaagtgtacc  12600
aatagatgag tgggtggatg gatggatgca gacaagcaga gagatttcaa atgtctcttt  12660
cacattcgaa gatgatgtta ctggcctggc atggtggctc acgcttgtaa tcccagcact  12720
ttgggaggct gaggcgggca ggtgatttga ggtcaggaat tcaagaccag cctggccaac  12780
atggtgaaat cccatctcta ctaaaaagaa tacaaaaatt agctgggcgt ggtggcacgt  12840
gcctgtaatc ccagctactt gggaggctga ggcaggagaa ttgcttgaac ccaggaggca  12900
gaggttgcag taagctgaga ttgcgccact gcactccagc ctgggtgacc cagcaagact  12960
ccatctgaaa acaacaacaa caacaaagat gacattactc atccacccca cccacccttc  13020
tcactagcta cagaatgatt agccccttga ggtcaggaat cccaggtcta ttttctctgt  13080
gactctcccc aagctgctga actacactag gaaagaatta ccgcctgcag aatgctggaa  13140
gcacatctgt gtgtgccctc accccggcct cattggccat caggactgct tagcaatccc  13200
tgtagacctt cttcctcccc catacttcca gaggatcttc tgaactattt tcttttttta  13260
ttttttcttt tatgtttttt aacagagaca gggtcactat gttgcccagt ctggtctcaa  13320
```

```
actcctgggt tcaagggatt ctcccacctc agctttccaa aatgctggga ttacaggcat  13380
gagccatcgt gcttggcctg aaccattttc attaaaaccc ctaccctact ctcacctcca  13440
tttccagtca ttaaattcct tcatttaaga ggcatctctt agtcatcgca tgtgtgccat  13500
gaacatggta gtctttggag acccctcagg gagctcacag tggttggggg aaaggggggc  13560
attaaacaga catttaagct atagttttgg gttcagaggg aggaagcccc aggggctaaa  13620
acagctgata aggactccca gataagtgca cttttcacta tctggcattt tcttgttttg  13680
ttatttgctt gttcactgtc tctcacccca tttgatccta agctttctga gggcagggat  13740
ctttgttttt tttcatcagt tggatcccaa ttgcttagaa cactacctgg cacaaaatag  13800
gcactctata agtgattaca caaattttgg aacgactagg ttaaacaatg ataaccaggc  13860
ttttttttt ttttttgaga ctgagtctca ctctgttgcc caggctagag tgaagtggtt  13920
tgatctcggc tcactgcagc ctccgcctct gggttcgaat gattctccac ctcagcctcc  13980
tgagtagctg ggattacagg tgcctgccac tatgcccagc taatttttgt atttgtagta  14040
gagacgggtt tcaccatgtt ggccaggctg gtcttgaact cctgacctca agtgattcac  14100
ccgcctcagc ctcccaaggt gctgggatta caggtgtgag ccaccgctcc tggccaacaa  14160
ccaggctttt ttaagacatc actcagagcc tttaatttgc taatgtgagt tgtgaatctc  14220
tgagagaagg ctaacggcat gcttgcaact tacttgtcca cagacaagcc tttctgcccc  14280
agaagagaag accattctag ggtgctaatg agcaaagagg gtgagggtgg aatatcggag  14340
agcagcaggg agtgcagggg aacagatagg ccagttcagg gagcagagaa ggagaagccc  14400
ccccacctca cctgccctcc ccagcagtct ctgttctggt ctctcacagg gtgacagtgg  14460
tgggcccctg atgtaccaat ctgaccagtg gcatgtggtg ggcatcgtta gttggggcta  14520
tggctgcggg ggcccgagca ccccaggagt atacaccaag gtctcagcct atctcaactg  14580
gatctacaat gtctggaagg taaggtacct ttgccctacc cactgtgcct tccctccagt  14640
cctctacctg gggggtgcca atccatcctc aggtttgatt taaatggttc tgacaactct  14700
ttacatccca aataactttc cctccaagca agggacagcc tgagattgca ctattaaggc  14760
tgaaattcct taggtcagag atttctgata aatgcaaata ccttagggaa tagaacacac  14820
caagcctttc tttctctttt ctgacagaat gagactatca gatcctttct agagagaaga  14880
ttctgataag gaagagagtg gaaaggctca tgagacctcc tggccctctg cagggtaggg  14940
agagaagcaa agtgtttcag aaaaggaaga ctcacgttac acatgtcacc actttgtcca  15000
gtttcagata atctgacttt ctcttcatcg gtctctctta ttctaggctg agctgtaacg  15060
ctgccgtccc ccacatccag aagctgcttc ccttcagacc tacctacggc atgacccctc  15120
aaagtcagat atgggacaag agcctccttg aacaaactc                         15159
```

<210> SEQ ID NO 14
<211> LENGTH: 435
<212> TYPE: PRT
<213> ORGANISM: Artificial Sequence
<220> FEATURE:
<223> OTHER INFORMATION: Recombinant protein

<400> SEQUENCE: 14

```
Met Glu Ser Asp Ser Gly Gln Pro Leu Asn Asn Arg Asp Ile Val Pro
1               5                   10                  15

Phe Arg Lys Pro Arg Arg Pro Gln Glu Thr Phe Lys Lys Val Gly Ile
            20                  25                  30
```

```
Pro Ile Ile Ala Val Leu Leu Ser Leu Ile Ala Leu Val Ile Val Ala
        35                  40                  45

Leu Leu Ile Lys Val Ile Leu Asp Lys Tyr Tyr Phe Leu Cys Gly Gln
    50                  55                  60

Pro Leu His Phe Ile Pro Arg Lys Gln Leu Cys Asp Gly Glu Leu Asp
65                  70                  75                  80

Cys Pro Leu Gly Glu Asp Glu Glu His Cys Val Lys Ser Phe Pro Glu
                85                  90                  95

Gly Pro Ala Val Ala Val Arg Leu Ser Lys Asp Arg Ser Thr Leu Gln
            100                 105                 110

Val Leu Asp Ser Ala Thr Gly Asn Trp Phe Ser Ala Cys Phe Asp Asn
        115                 120                 125

Phe Thr Glu Ala Leu Ala Glu Thr Ala Cys Arg Gln Met Gly Tyr Ser
    130                 135                 140

Ser Lys Pro Thr Phe Arg Ala Val Glu Ile Gly Pro Asp Gln Asp Leu
145                 150                 155                 160

Asp Val Val Glu Ile Thr Glu Asn Ser Gln Glu Leu Arg Met Arg Asn
                165                 170                 175

Ser Ser Gly Pro Cys Leu Ser Gly Ser Leu Val Ser Leu His Cys Leu
            180                 185                 190

Ala Cys Gly Lys Ser Leu Lys Thr Pro Arg Val Val Gly Val Glu Glu
        195                 200                 205

Ala Ser Val Asp Ser Trp Pro Trp Gln Val Ser Ile Gln Tyr Asp Lys
    210                 215                 220

Gln His Val Cys Gly Gly Ser Ile Leu Asp Pro His Trp Val Leu Thr
225                 230                 235                 240

Ala Ala His Cys Phe Arg Lys His Thr Asp Val Phe Asn Trp Lys Val
                245                 250                 255

Arg Ala Gly Ser Asp Lys Leu Gly Ser Phe Pro Ser Leu Ala Val Ala
            260                 265                 270

Lys Ile Ile Ile Ile Glu Phe Asn Pro Met Tyr Pro Lys Asp Asn Asp
        275                 280                 285

Ile Ala Leu Met Lys Leu Gln Phe Pro Leu Thr Phe Ser Gly Thr Val
    290                 295                 300

Arg Pro Ile Cys Leu Pro Phe Phe Asp Glu Glu Leu Thr Pro Ala Thr
305                 310                 315                 320

Pro Leu Trp Ile Ile Gly Trp Gly Phe Thr Lys Gln Asn Gly Gly Lys
                325                 330                 335

Met Ser Asp Ile Leu Leu Gln Ala Ser Val Gln Val Ile Asp Ser Thr
            340                 345                 350

Arg Cys Asn Ala Asp Asp Ala Tyr Gln Gly Glu Val Thr Glu Lys Met
        355                 360                 365

Met Cys Ala Gly Ile Pro Glu Gly Gly Val Asp Thr Cys Gln Gly Asp
    370                 375                 380

Ser Gly Gly Pro Leu Met Tyr Gln Ser Asp Gln Trp His Val Val Gly
385                 390                 395                 400

Ile Val Ser Trp Gly Tyr Gly Cys Gly Gly Pro Ser Thr Pro Gly Val
                405                 410                 415

Tyr Thr Lys Val Ser Ala Tyr Leu Asn Trp Ile Tyr Asn Val Trp Lys
            420                 425                 430

Ala Glu Leu
        435
```

<210> SEQ ID NO 15
<211> LENGTH: 2046
<212> TYPE: DNA
<213> ORGANISM: Mus musculus

<400> SEQUENCE: 15
cagaaacaag gacctcttca ttattcaaga gtaaaatgta taggccaaga ccaatgctat 60
caccgtcaag attcttcact ccctttgcag tagctttcgt tgtcataata acggtagggc 120
tcctggccat gatggcaggt ctacttattc actttttagc ttttgacaag aaagcttact 180
tttatcatag cagctttcaa atcctaaacg ttgaatacac tgaggcttta aactcaccag 240
ctacacacga atacagaacc ttgagtgaaa gaattgaggc tatgattact gatgaatttc 300
gaggatcaag tctaaaaagt gagtttatca ggacacatgt tgtcaaacta agaaaagaag 360
ggactggtgt ggttgcggat gttgtcatga aatttcgatc tagtaaacgt aacaacagaa 420
aggtaatgaa aaccagaatt caatctgtgc tacgaagact cagcagctct ggaaacttgg 480
aaatagcccc ttcgaatgag ataacatcac tcactgacca ggatacagaa aatgttttga 540
ctcaagaatg tggagcacgt ccagacctta taacactgtc agaagagaga atcattggag 600
gcatgcaagc tgagcccggt gactggccct ggcaagtcag tctacagctc aataatgtcc 660
accactgtgg aggtgccctg atcagtaaca tgtgggtcct gacagcagct cattgcttca 720
aaagctatcc taatcctcaa tattggacag ccacctttgg ggtttctaca atgagcccta 780
ggctgagagt gagagtaagg gctattttag cccacgacgg gtacagctcc gtaactcgtg 840
acaatgacat cgcagttgta caacttgaca gatctgtcgc cttttccaga aatatccata 900
gggtatgtct cccagcagca acccaaaata tcatccctgg ttctgtcgca tatgttacag 960
gatggggatc tctcacatat ggaggcaacg cagtcacaaa tctacggcaa ggagaggtca 1020
gaataataag ttcagaggaa tgcaatacgc cagctggtta cagtggaagt gtcttgccag 1080
gaatgctgtg tgctggaatg cgttcagggg ccgtggatgc atgccagggt gattcaggtg 1140
gcccgctagt acaagaagac tcaaggcggc tttggtttgt tgtgggcatt gtgagctggg 1200
gatatcagtg tggcctccca aataagccag gcgtgtatac tcgagtgaca gcctaccgca 1260
actggatcag acagcagacg ggaatctagt gcaaccgagg aaaaaacgtg ccatgaggtc 1320
tctgtatcca agtgtgactg actcggatgc catggcttca catttcaact gcaaaggaga 1380
ctggaaatgc cccttctgaa cgtcccatta cataaatatg gtttaactgt ttagtatttc 1440
tttgtcggta cagattttta ctttcttgag gaaaaaaaaa acatgaacat ggctaagtaa 1500
gaattatgtt aggctagtaa caggaagaca tttattacat gggtggtcag gtgtagtagt 1560
gagaagtcag gtaagttaag tcaataattt acagaaaata atgtcaggta gtcctaacgt 1620
taaatatgtg aggccacaga acaaatagtg ttagaactga agccatccca agtatttaac 1680
atttgttttc aagtgaaact aagaaacaga cttacatata gttttaatgg tgaattttca 1740
ttttaaatat tttatctaca tagaaaagac atatctcctt catgaagaag ctgaggtgat 1800
gaatcaacac agcctcttca gctatgtttg caaccacaag atttgtggga aagaaatccc 1860
tactaccaac ttcctactgt tggcattatt ttttagagta acacgacgca caatagcaaa 1920
atttaagtaa caaattaaaa gttaatgatg aagaagaagt aaagagtttg tttgcaaaga 1980
caaaaattaa acagattaat atcaataaat ctggagacag aagggtctca gattcatatt 2040
ctctct 2046

<210> SEQ ID NO 16

<211> LENGTH: 417
<212> TYPE: PRT
<213> ORGANISM: Mus musculus

<400> SEQUENCE: 16

```
Met Tyr Arg Pro Arg Pro Met Leu Ser Pro Ser Arg Phe Phe Thr Pro
1               5                   10                  15

Phe Ala Val Ala Phe Val Val Ile Ile Thr Val Gly Leu Leu Ala Met
            20                  25                  30

Met Ala Gly Leu Leu Ile His Phe Leu Ala Phe Asp Lys Lys Ala Tyr
        35                  40                  45

Phe Tyr His Ser Ser Phe Gln Ile Leu Asn Val Glu Tyr Thr Glu Ala
    50                  55                  60

Leu Asn Ser Pro Ala Thr His Glu Tyr Arg Thr Leu Ser Glu Arg Ile
65                  70                  75                  80

Glu Ala Met Ile Thr Asp Glu Phe Arg Gly Ser Ser Leu Lys Ser Glu
                85                  90                  95

Phe Ile Arg Thr His Val Val Lys Leu Arg Lys Glu Gly Thr Gly Val
            100                 105                 110

Val Ala Asp Val Val Met Lys Phe Arg Ser Ser Lys Arg Asn Asn Arg
        115                 120                 125

Lys Val Met Lys Thr Arg Ile Gln Ser Val Leu Arg Arg Leu Ser Ser
    130                 135                 140

Ser Gly Asn Leu Glu Ile Ala Pro Ser Asn Glu Ile Thr Ser Leu Thr
145                 150                 155                 160

Asp Gln Asp Thr Glu Asn Val Leu Thr Gln Glu Cys Gly Ala Arg Pro
                165                 170                 175

Asp Leu Ile Thr Leu Ser Glu Glu Arg Ile Ile Gly Gly Met Gln Ala
            180                 185                 190

Glu Pro Gly Asp Trp Pro Trp Gln Val Ser Leu Gln Leu Asn Asn Val
        195                 200                 205

His His Cys Gly Gly Ala Leu Ile Ser Asn Met Trp Val Leu Thr Ala
    210                 215                 220

Ala His Cys Phe Lys Ser Tyr Pro Asn Pro Gln Tyr Trp Thr Ala Thr
225                 230                 235                 240

Phe Gly Val Ser Thr Met Ser Pro Arg Leu Arg Val Arg Val Arg Ala
                245                 250                 255

Ile Leu Ala His Asp Gly Tyr Ser Ser Val Thr Arg Asp Asn Asp Ile
            260                 265                 270

Ala Val Val Gln Leu Asp Arg Ser Val Ala Phe Ser Arg Asn Ile His
        275                 280                 285

Arg Val Cys Leu Pro Ala Ala Thr Gln Asn Ile Ile Pro Gly Ser Val
    290                 295                 300

Ala Tyr Val Thr Gly Trp Gly Ser Leu Thr Tyr Gly Gly Asn Ala Val
305                 310                 315                 320

Thr Asn Leu Arg Gln Gly Glu Val Arg Ile Ile Ser Ser Glu Glu Cys
                325                 330                 335

Asn Thr Pro Ala Gly Tyr Ser Gly Ser Val Leu Pro Gly Met Leu Cys
            340                 345                 350

Ala Gly Met Arg Ser Gly Ala Val Asp Ala Cys Gln Gly Asp Ser Gly
        355                 360                 365

Gly Pro Leu Val Gln Glu Asp Ser Arg Arg Leu Trp Phe Val Val Gly
    370                 375                 380

Ile Val Ser Trp Gly Tyr Gln Cys Gly Leu Pro Asn Lys Pro Gly Val
```

```
385                 390                 395                 400

Tyr Thr Arg Val Thr Ala Tyr Arg Asn Trp Ile Arg Gln Gln Thr Gly
                405                 410                 415

Ile


<210> SEQ ID NO 17
<211> LENGTH: 2800
<212> TYPE: DNA
<213> ORGANISM: Homo sapiens

<400> SEQUENCE: 17

atttgagtgg gaatctcaaa gcagttgagt aggcagaaaa aagaacctct tcattaagga     60

ttaaaatgta taggccagca cgtgtaactt cgacttcaag atttctgaat ccatatgtag    120

tatgtttcat tgtcgtcgca ggggtagtga tcctggcagt caccatagct ctacttgttt    180

actttttagc ttttgatcaa aaatcttact tttataggag cagttttcaa ctcctaaatg    240

ttgaatataa tagtcagtta aattcaccag ctacacagga atacaggact ttgagtggaa    300

gaattgaatc tctgattact aaaacattca aagaatcaaa tttaagaaat cagttcatca    360

gagctcatgt tgccaaactg aggcaagatg gtagtggtgt gagagcggat gttgtcatga    420

aatttcaatt cactagaaat aacaatggag catcaatgaa aagcagaatt gagtctgttt    480

tacgacaaat gctgaataac tctggaaacc tggaaataaa cccttcaact gagataacat    540

cacttactga ccaggctgca gcaaattggc ttattaatga atgtggggcc ggtccagacc    600

taataacatt gtctgagcag agaatccttg gaggcactga ggctgaggag ggaagctggc    660

cgtggcaagt cagtctgcgg ctcaataatg cccaccactg tggaggcagc ctgatcaata    720

acatgtggat cctgacagca gctcactgct tcagaagcaa ctctaatcct cgtgactgga    780

ttgccacgtc tggtatttcc acaacatttc ctaaactaag aatgagagta agaaatattt    840

taattcataa caattataaa tctgcaactc atgaaaatga cattgcactt gtgagacttg    900

agaacagtgt cacctttacc aaagatatcc atagtgtgtg tctcccagct gctacccaga    960

atattccacc tggctctact gcttatgtaa caggatgggg cgctcaagaa tatgctggcc   1020

acacagttcc agagctaagg caaggacagg tcagaataat aagtaatgat gtatgtaatg   1080

caccacatag ttataatgga gccatcttgt ctggaatgct gtgtgctgga gtacctcaag   1140

gtggagtgga cgcatgtcag ggtgactctg gtggcccact agtacaagaa gactcacggc   1200

ggctttggtt tattgtgggg atagtaagct ggggagatca gtgtggcctg ccggataagc   1260

caggagtgta tactcgagtg acagcctacc ttgactggat taggcaacaa actgggatct   1320

agtgcaacaa gtgcatccct gttgcaaagt ctgtatgcag gtgtgcctgt cttaaattcc   1380

aaagctttac atttcaactg aaaaagaaac tagaaatgtc ctaatttaac atcttgttac   1440

ataaatatgg tttaacaaac actgtttaac ctttctttat tattaaaggt tttctatttt   1500

ctccagagaa ctatatgaat gttgcatagt actgtggctg tgtaacagaa gaaacacact   1560

aaactaatta caaagttaac aatttcatta cagttgtgct aaatgcccgt agtgagaaga   1620

acaggaacct tgagcatgta tagtagagga acctgcacag gtctgatggg tcagaggggt   1680

cttctctggg tttcactgag gatgagaagt aagcaaactg tggaaacatg caaaggaaaa   1740

agtgatagaa taatattcaa gacaaaaaga acagtatgag gcaagagaaa taatatgtat   1800

ttaaaatttt tggttactca atatcttata cttagtatga gtcctaaaat taaaaatgtg   1860

aaactgttgt actatacgta taacctaacc ttaattattc tgtaagaaca tgcttccata   1920
```

```
ggaaatagtg gataattttc agctatttaa ggcaaaagct aaaatagttc actcctcaac   1980

tgagacccaa agaattatag atatttttca tgatgaccca tgaaaaatat cactcatcta   2040

cataaaggag agactatatc tattttatag agaagctaag aaatatacct acacaaactt   2100

gtcaggtgct ttacaactac atagtacttt ttaacaacaa aataataatt ttaagaatga   2160

aaaatttaat catcgggaag aacgtcccac tacagacttc ctatcactgg cagttatatt   2220

tttgagcgta aaagggtcgt caaacgctaa atctaagtaa cgaattgaaa gtttaaagag   2280

ggggaagagt tggtttgcaa aggaaaagtt taaatagctt aatatcaata gaatgatcct   2340

gaagacagaa aaaactttgt cactcttcct ctctcatttt ctttctctct ctctcccctt   2400

ctcatacaca tgcctccccc accaaagaat ataatgtaaa ttaaatccac taaaatgtaa   2460

tggcatgaaa atctctgtag tctgaatcac taatattcct gagtttttat gagctcctag   2520

tacagctaaa gtttgcctat gcatgatcat ctatgcgtca gagcttcctc cttctacaag   2580

ctaactccct gcatctgggc atcaggactg ctccatacat ttgctgaaaa cttcttgtat   2640

ttcctgatgt aaaattgtgc aaacacctac aataaagcca tctactttta gggaaaggga   2700

gttgaaaatg caaccaactc ttggcgaact gtacaaacaa atctttgcta tactttattt   2760

caaataaatt ctttttaaaa taaaaaaaaa aaaaaaaaaa                         2800


<210> SEQ ID NO 18
<211> LENGTH: 418
<212> TYPE: PRT
<213> ORGANISM: Homo sapiens

<400> SEQUENCE: 18

Met Tyr Arg Pro Ala Arg Val Thr Ser Thr Ser Arg Phe Leu Asn Pro
1               5                   10                  15

Tyr Val Val Cys Phe Ile Val Val Ala Gly Val Val Ile Leu Ala Val
            20                  25                  30

Thr Ile Ala Leu Leu Val Tyr Phe Leu Ala Phe Asp Gln Lys Ser Tyr
        35                  40                  45

Phe Tyr Arg Ser Ser Phe Gln Leu Leu Asn Val Glu Tyr Asn Ser Gln
    50                  55                  60

Leu Asn Ser Pro Ala Thr Gln Glu Tyr Arg Thr Leu Ser Gly Arg Ile
65                  70                  75                  80

Glu Ser Leu Ile Thr Lys Thr Phe Lys Glu Ser Asn Leu Arg Asn Gln
                85                  90                  95

Phe Ile Arg Ala His Val Ala Lys Leu Arg Gln Asp Gly Ser Gly Val
            100                 105                 110

Arg Ala Asp Val Val Met Lys Phe Gln Phe Thr Arg Asn Asn Asn Gly
        115                 120                 125

Ala Ser Met Lys Ser Arg Ile Glu Ser Val Leu Arg Gln Met Leu Asn
    130                 135                 140

Asn Ser Gly Asn Leu Glu Ile Asn Pro Ser Thr Glu Ile Thr Ser Leu
145                 150                 155                 160

Thr Asp Gln Ala Ala Ala Asn Trp Leu Ile Asn Glu Cys Gly Ala Gly
                165                 170                 175

Pro Asp Leu Ile Thr Leu Ser Glu Gln Arg Ile Leu Gly Gly Thr Glu
            180                 185                 190

Ala Glu Glu Gly Ser Trp Pro Trp Gln Val Ser Leu Arg Leu Asn Asn
        195                 200                 205

Ala His His Cys Gly Gly Ser Leu Ile Asn Asn Met Trp Ile Leu Thr
    210                 215                 220
```

```
Ala Ala His Cys Phe Arg Ser Asn Ser Asn Pro Arg Asp Trp Ile Ala
225                 230                 235                 240

Thr Ser Gly Ile Ser Thr Thr Phe Pro Lys Leu Arg Met Arg Val Arg
                245                 250                 255

Asn Ile Leu Ile His Asn Asn Tyr Lys Ser Ala Thr His Glu Asn Asp
            260                 265                 270

Ile Ala Leu Val Arg Leu Glu Asn Ser Val Thr Phe Thr Lys Asp Ile
        275                 280                 285

His Ser Val Cys Leu Pro Ala Ala Thr Gln Asn Ile Pro Pro Gly Ser
    290                 295                 300

Thr Ala Tyr Val Thr Gly Trp Gly Ala Gln Glu Tyr Ala Gly His Thr
305                 310                 315                 320

Val Pro Glu Leu Arg Gln Gly Gln Val Arg Ile Ile Ser Asn Asp Val
                325                 330                 335

Cys Asn Ala Pro His Ser Tyr Asn Gly Ala Ile Leu Ser Gly Met Leu
            340                 345                 350

Cys Ala Gly Val Pro Gln Gly Gly Val Asp Ala Cys Gln Gly Asp Ser
        355                 360                 365

Gly Gly Pro Leu Val Gln Glu Asp Ser Arg Arg Leu Trp Phe Ile Val
    370                 375                 380

Gly Ile Val Ser Trp Gly Asp Gln Cys Gly Leu Pro Asp Lys Pro Gly
385                 390                 395                 400

Val Tyr Thr Arg Val Thr Ala Tyr Leu Asp Trp Ile Arg Gln Gln Thr
                405                 410                 415

Gly Ile
```

<210> SEQ ID NO 19
<211> LENGTH: 38992
<212> TYPE: DNA
<213> ORGANISM: Artificial Sequence
<220> FEATURE:
<223> OTHER INFORMATION: Recombinant polynucleotide

<400> SEQUENCE: 19

```
gagggagggt ggtgctttgc taatggtgaa ttactaactc ctcaataaag aatattattt     60

gaaataattt ttgaaatttc ataattactt tgggttcttt cttaatgata aataaataat    120

agtatattac aaacatacat taatatttcc tgaatgaata caccacaaat ctcccttaaa    180

atatagcaag aataaaaatt atactatttc tgacaatttt taatttctca aataataata    240

ccactctgat ttttaaacat ctacaccact ctggctttgc caatcttttt aaaaattgaa    300

aagataataa ttttatcata attacactga agcatagaac tttttctttc aaggaaagca    360

aatttttgaa attctataat ataacctccc ataatcctga ataaattaaa ggttcaacaa    420

cttagtaaag taagactgac cttccctttt atttcttttt cagatcaaaa atcttacttt    480

tataggagca gttttcaact cctaaatgtt gaatataata gtcagttaaa ttcaccagct    540

acacaggaat acaggacttt gagtggaaga attgaatctc tggtaagtta atatttgtct    600

ttgctcttta ttccattata aaatgaatat gataataaac ctaatgtttt gtaatatatt    660

ttcagttgct aagtgctcta catattttcc ttccttgaat ggtgaaacat gtgtttctct    720

ctgcttttat ccagttagtt tactcatata ctggttctta ttcacatctt tgtcatgagt    780

aaaaagtgtt agaaaggcca cgagtaaata tgcattttat ttgtttatga attcaaatac    840

taaaagtttt ttatttgttt aattaagcat tgacattgtc tttttaaatt cttttcattt    900
```

```
taccttcttc cctcttcctt atccaactaa agacgcaaag caggaggtgt taaaaaacag    960
gtttaccata tcagcagtaa catagtttgg acaacattac actttggttc aatgatagac   1020
atagaagttt gaacagaaat atgcaaagca agtttgagct ctaacttgaa gagagcctct   1080
gggtgcctgc caggaaacct cacgagtgga cccttaacat tcatgtgtca ccacaaacta   1140
ggggctgccc tttagttttg accagtctca gtgtcactca cttaccctta ccttttcaaa   1200
aaaaagtcct aagaatataa agtaattcaa tggttctaca attttagcat gtaactgagt   1260
cacctggcag ggttgctttg gtgagctcaa gataaaattt tatcagcatt tctacatttt   1320
ctggaatatt ccttaatcca ggcttttaat cccttggtgc ttttctgaac cactgcaatg   1380
agcttctaac tgttctcact gtgtgcaggc tcttttcctt ctaatctaat ttacacactt   1440
ctgaacacaa atctctcaca gcctgtttcc ttcatgttac ctccagctca agactttttg   1500
cctacaaaat aaaattcaaa cttgttagct aagcaccttc tcatgtctat gctttggctc   1560
atatttcagc catcgtgtgc cccacttatt cttatagcca acctgaaaag ccatctttta   1620
taagaaacta cctctgctct ccatgattgg atataattaa tcctccttcc acatcacctc   1680
gccacaaaat tgtatctgtg ttgatctcat gccacatacc tgtatgtatt ttatattata   1740
aatatttgca gacttgttta atttgccatg ttagactaag ttccatgaag acagctccat   1800
atccattcca tttttatata tccacaacat ttggtcgggt tgatgcttaa taaatgttta   1860
ttgaaggaac aggagtctcc cacttctgac ataatgaact tatttccccc agtgttaacc   1920
ctacatctgg ttcctgtcca agagtctctt cccaaatcat tctgattcaa ctgttcattc   1980
tgatctcatt aaacatttaa atgatatatc taacttcgct tgctttattc tatgctcatc   2040
ctgcagtctc ctcataactt ggtttcaatg atgcttgctt ctagagaaaa aaatgtatta   2100
aataagctta tgattcagtc ctccagctgt gatggttctc actgaacatt agctcagtgg   2160
ttttcgaagt atggtctcta gcataaccta gaaacttgtt agaaatgcaa attcttgggc   2220
tcaccaagac atactaaatc aaaaattctg acattggggc ctagaaatct gtgttttaac   2280
aagcctgcca gtgcagcctg gtcccttttc ttctcggagc cccactcaaa gctttcagtg   2340
ctcatctccc accaatgaca gggtcctcta tggaaaccgg caggacggtt tccaactcta   2400
actacgtttt agagtttgct tcctagggct atccaggcac caagtatcac aggttagttt   2460
cccagggaag cagactctga gacttgcatg cagggagtgt ctctggggtg ctctcaacca   2520
acaccttcag gaagagaagg aagcagcatt gggcagaggc atagtcaaac tacagtgctg   2580
ttggcacaga agactgaagg gagtcagagc caggggggtag aggtgggccc ttagcatcca   2640
tccttcacca ttaggtgtga gttgccccac ctccttgatg gtgtaacctc agtcccaagg   2700
tgggtgggag tgcagcagag cagcccctac aagggccaaa ccagagatac accaggcgcc   2760
agaagtgctg ccagggaata gagaggaaag gatgggctta aggtaggatc cacagaactt   2820
ggcaatggat tagaagacag gatgagaagt gacaggttaa cactaacaca gaaatgtcta   2880
acttcggtag ataatggtgc cattggctag aagaggaaac cgaaatgaaa gcaggttgtt   2940
cagggagaca aaagttcact gtggacatct cagcagagtg attcagtggg gaaaggaatg   3000
gatgcccaga ccacctcaga ggaagatcta agctggagcc agcaataaag atacaagatg   3060
aacaatccct aacgaactgc tcctcagcca tgctccccag acacgctgct tcagatttat   3120
agtccgggtg aggctaggag gtgcgcctcc ctcagtggag gacagcaaag caccagtggc   3180
tccagggagt taaaatcttt tgataatttt tgttctagca tctgtctgca gagctgtctc   3240
tcagccattg cctgccttta cacaggagtg cagtccgaaa ttgggagatg agtgaaattt   3300
```

```
attatgccta gagatctgga tccccagttg tttgggagta tattttctga accacttgtt   3360
ggtttaagta atgcagattt attgatgcca cttctcttga atctgtgact ctggacccac   3420
catctaagtg aatgtgcaga gggaacggaa tggctgcaat agatctccat taaaaccagt   3480
gcatcctccc agacacatac agtagtaggg aggtgagtca atgtcaggac agcaccagct   3540
cccgcttcgg tacatttcca aagttctcag tctgtgtaca aaggtttgct ctggggcagc   3600
agaaatagcc ctgggcaggt agtcaaaggc ctggtttgat ttcctccact tccaggcaag   3660
tcactcgaag gctcacaggc tttttcctca cctgccacat gggtccagtg agatctactg   3720
agctgtaaat aatgaaatga gtgtgtgtgc agtcatctat aagttgtaaa gtactagaaa   3780
atggtgaaac tttgggattt gggctattta aggctgaatg ctaaaaatgt caggcattgt   3840
ggagaaagga atttaaatat aagattgatt gactgggatt taaagacaaa tgaaggcaca   3900
cacgcaagtg cacacccaca ctgacactgc acagctcccg ttggaggcat atcctgacca   3960
tgcagacctg ggctctgcc tgtccaagtg cactccttta ctacataaac cctccttctc   4020
ttttggggct gtcaccccac cagagctggc accgagccct tgctgctgcg cttccctggg   4080
gtgtcagctt ttgacagggt gtttcctccc tctgcaggag ccttaacatc ccttggactt   4140
ccttcccccc acccaccccc agcagtttta tctcttccta actcgggacc cttttttttcc   4200
cacacaaagt ttattgtcag ttgctggttt catctgtttg agcggctgca acaaaatacc   4260
atagactggg tggcatatgc acgacaaaaa tttatttctc acaggagaag tcaaagatta   4320
atgcaccagc agatctggtg tctgaggggc caccttctgg tttgtagatg atgctttcta   4380
gttaaaacac ctatttaaca cactattaaa cactaagtgt gttaaatagt gcagttgatg   4440
tatttgtcat gtcaccttta tcatacacta aatccttctt tgtctttttt tctgtactct   4500
aatctctttc tgtaagtaat ctttgcttgc agcagtagga tatttagagt actgtggctt   4560
gacaatatat ttagtatttc aagatttcca tgaaattctt ctgatgtatg agttccctag   4620
ttaatcttac atatgtatcc ctttgtaaaa acactttgaa catttaaaat gatacatgaa   4680
tagtactcta atacaatgcc ataaaaaatta taaatcattt gtatagactg gtaagtaaag   4740
attgtgagat taagaaacgc atcaaaggcc attgagctgg aaagtggtat aatgagaatt   4800
caaaccaggg tctcttgact caaaatctaa ggatcatacc atttctcatg ataatatgag   4860
tattattgtt atctctatcc catagacaaa gtgttaacac tgaatgagca gtgaaatagt   4920
ctcagaattt tttattttat ttagcaattc acttgtcatt tctggtcctc agtttattca   4980
cgagtaaaat aaaatagttg gactagataa tttctatagt acattcttac acaaaaaatc   5040
tatgattttg ttatttttaa tgtgatatac tcatggcact cattcacctc attttcccag   5100
cctgcctcac tggtcattac ttctctgtgt tctttacagg ctccccctcc tctacactgc   5160
cattaaatat tgaaacacct caaagcttta cttatgtcca cctctcctct gacactatca   5220
ttctgtctag atgatcccat acatacatgc ccattacttc aacctgtatt tatacgccaa   5280
tgattcacta tatttccagc ctagacattc ttttgtactc tagttaccag cttgatatcc   5340
ttacatggct gtttcaaaac aactcaaata tattatctct caaaatcaaa ctcatgatgt   5400
ccccacacca tcctagcttt ccaccaacaa tacctatccc tattaatagc aataccattt   5460
attcagttat ccaaatcaaa aacctagaat tcatccttaa aattctacta tcattccaaa   5520
tatcctatcc atcagcagcc actgtattct taatcccctg tatttccttc aaatccattc   5580
acctctctcc atatccattg ctgcatgact atccaagcca tcgcctctac cctagggtac   5640
```

```
caaaatagca acaaacctaa tctgttcatt tgcattattt tttctccaaa actgattatc   5700

tatatgtagc aagacagatt gttctcaaat tgcaaatccc actatattat cctcttgctt   5760

caaacacttc catggtttcc cattgtttat gataaaacca aatgcttcaa gttcgaagac   5820

cggcatgatt gggaatttcc tgtcacccta gcctacttgc tctccatggt acagttgcac   5880

tggctttctt tcattcctta agtacaacct gtttcctccc acctcaggac tgtgcatgtg   5940

ccattcattc tgctgaggag ccttttttcct tccacttcaa tcagctaagt ctgattcttc   6000

ctgacaatct cagctcaata agcatttcct ctaagaaatg tctctaatat cattaattgg   6060

ctcaggtccc tctactgtat tgctgcactt ttcacagtta taattttact taattatgaa   6120

tgattatttg attaggtcta tttccatcca ttagacataa gcttcatgat ggccagatta   6180

ctgttttcta tccatcgttg tattccaata cctgacagaa ggagggcggg aggtggtggc   6240

acacaagaga tgctcaaaaa caattgttga ataagtaaat gaatgaggcc atttagaaat   6300

aacgaaagta cctgtttaca aagtacatgt atcaaaacta tgaatgcatt ctacttacat   6360

ggttttctcc aaataaaaca aaagacttca atcaggatta atacctggga taaactgagt   6420

cattaaatct ctcctttgcc atcaggagtg acattgaaac aaatgtctgc aaacaacaaa   6480

tactttttttc ccaaaatata ttgaatggca tttccataaa caaactagaa catgggagga   6540

gaaagaaagc aatattaatt taaaattaat cttatcacat aacttatacc atcagggatt   6600

tcgggtaaaa ttcctttcag gcacatccat ttaacaagaa ttgattgtta ctgaaagcct   6660

agaagagaat ttggcacata cttggtgttc aaatatttgt tgactgagtg aataaatgat   6720

gcaagtgtct aagaaacaca aaataaggac atgattacag tcacggtgga gttcacagtc   6780

atctccaaaa tgaggatatg catcccaggg aggaccaaca attcattgga gtgctgaaat   6840

aaaatactca aaggtcattt tacatgtatt ttttctctaa attacttttc ttaagacaca   6900

gaaaacaaaa aaagaaactt agctttgtta ctttctaaca aatagttaaa tcattaaaca   6960

ggattgacac tagcatcctt gtttggtctt atgccttagg ggaacatgaa atgtgtgaag   7020

acattctgag atctgaggga agggtagaca gtaatacagt gggactgacc aggcttcagc   7080

acacctttac ctcctctcag cagatttcag tgatgagcag tttacaacta gattgaaaga   7140

ttatattatc tagttctaaa agaaaactaa gcctcccaaa agcaacaagg gaactgagag   7200

gaatcctgca aaacaaaaac aaattttaaa acttgcactt tgtaataacc ctaatatgta   7260

atcacagtaa tgaacagtaa gataatgaca gaactgacat atttccttat ctattaaagc   7320

catattaaca ggtaaagcaa tgccagtcag tggtacactt cttagaagat atttaataca   7380

tactagacac atacacacac acaacatttt ccttcaaggt gtatgtatca gaaaatcact   7440

ttttaaggcc ggatgcagtg gctcaggcct gtaatcccag cactttggga ggccgacgtg   7500

ggcggatcat ctgaggtcag gagttcaaga ccagcctgcc caacatggcg aaaccccatc   7560

tctacaaaaa tacaaaaatt agccagggat gatggtggat gcttgtagtc ccagctactc   7620

aagaggcaga ggcaggagaa tcacttgaac ctgggaggca gaggttgcag tgagccaaga   7680

tcacccattg cactccagcc tgggcaacag agtgagactc tgtctcaaaa aaaaaaaaat   7740

cactttttag ataaaattca tgctatagag agaagactat gaaaatatgt ttagcaatgt   7800

gtccatcatt aggtgattga gtttcctttt gttttgtttt actgaaaatc atataaagta   7860

tgttatctgt aaaagttctc tgacatgcac acataaaaat ttgggagaaa agattaacta   7920

taatgtttaa tagattttgt acacatttct ttaaaaatat ataaaacaca acacctttca   7980

attggtttgc aagaataacc aattgacatc atggaaaatg gaaattcact tgctgaattt   8040
```

```
taacaaaaat ttgcatgatg agtgagactg acaacttagt gtcatgattt aatgaattat   8100
gccaatggta aacttcatgc acatggggcc aggtaattat gtggaaactt tttcaatgct   8160
taaagccaag tattgaaatt aaacttagaa tcagaccttt gaaccatttt atgacaatgt   8220
tcaaaaatta taaattctat ccacttatat tataatatta aaaatatcat tacaaaaaaa   8280
acctgtgttt attttataac tcagcctttt taatttctaa tttcataaat atattataat   8340
ggatattgtt agtaatgtag tattattaca tgtatataat ttataagtaa atatacatgt   8400
tttggctact catgcataaa atgtttcacc cataggagca cataatcaga aatgtctgga   8460
gaccattata gtaatagata gatcatattg ccacatattt tatctcctcc ttgacaactg   8520
agctttccag atcttctggt gaaacgaaag agaaagttgt aacagaagag tgattaaaat   8580
gacaaaagca ttacttctat tacttctatt ctaataatat gagcaaagct ataactatca   8640
agtaataatg cactaaagaa ggtgattaat ctgatatatt cacaggcaac taataagacc   8700
tttctattgc agccatgaaa aatatgtgac aattatagat atcctgtgtg cagtgtttca   8760
acctttatgt gacctgttct actaacagat ttagtgatgt tcactttgtt agaattttct   8820
tacacatgcc ataacttgct tcagtctttt gattatgaat attatggata ttaaggattc   8880
tagactattc tagatttaaa aaataatatt gtcacctcaa tcagaaggga aatattaaat   8940
agttctcatt ttttcaatgt ttactcagtt tttgtccaat gtaatgaaag tgtcagcagt   9000
acaggttaca aaataaaatg tgtattaaag taaactcatt tgaacaggtt aataattgta   9060
gagggaggga aaaggctaaa agattgaatg taaaacttat gaaaagtaga tacatcgtct   9120
ctatgatttg cagtagtcaa ctgcatacag atgaatcatt ttaatacacg ttaactactt   9180
tccttttaca gatggagaaa ctgagaggaa gaaagtttat atggttcatt aaactttgtg   9240
atgcaagcta aactaacctg tctctgtatt ttccatctac tgcccttatc actatctcat   9300
tagaatactc ttcaagcatc tccttactga ttttcttacc aagcatttgt taagttctaa   9360
tgagagttgg tagtaacatt ttcacccact ctgtgaaata tgaaatctta ttcataggcc   9420
tcttctttta ttcttgtatt tgcatatcaa ccaattaatc aacttgcttt ctttatgttg   9480
cttattatct tagtccttac taaattgcct cttaatgttg tccacataac agaaatgtta   9540
aggtggatac ttaacatttt agtccagtct agccggtgcc agtgcaatgc caaatcatga   9600
attaaaatat aattacaaga accacttatc aaattttaac aattccttca gctttgtgac   9660
agttttttct acttcgatta aagtcaagta aaattaaagt taaatatttt tattaaaata   9720
tctcctttaa cattccatat taataaacat attaaagctc atgcttctaa gtagattact   9780
agaagttact ttatcgaatt acagcaatgg ttaattctag atcatagaat ttagaatgac   9840
tttttgcctt cttctttttt ttccttttttt ttaaacagag tcttgctctg ttgtccaggc   9900
tggagtgtac tggcgcgatc ttgactcact gcgacctctg ccctgcaggt tcaagtgatt   9960
ctcctgcccc agcctcttaa gtagttggga ttacaggtgc ctgccaccac acctggctaa  10020
ttttttttt gtatttttag gagagacagg gtttcaccat gttggccaga ctggtctcga  10080
actcctgacc tcaagtgatc cacttgcctc agcctcccaa agtgctggga ttacaggtgt  10140
gagccactgt gcctggcctg actttttgct ttcttcttaa tacttactag tatttcttga  10200
atttttaaaa aagaaacata aagtactttg ataaaaccaa cagtctcatt gttcttaaaa  10260
ttgttcaaag gttctctgga aaaaaaaaag aaaattatca tttggttaag aatcatgttg  10320
gtctgacatc aatcatccta taggagtgaa tattgaaaaa gtaagatata ttgtggtata  10380
```

```
atcgagattg cataaatttt accatttttg agaagaatct gctccaaatc ctggcttaat  10440
gtaatatcca gcatgctact taattttctt gtcttcacct tttcatatcc acatccacct  10500
aggtgccacc tcacagtata agccagcata atccattctt ctcaatgaaa ccacaataca  10560
tctgaccctg catctcagga gaactgtatc agccacagca cttccagttg actatgaatc  10620
tgaatgttat gcctcaggag aaacatcctt gctgggactg agtagtgatt caaggagata  10680
gttatgattc agtcaagaaa ttaataatta gtgttatttt tattattgag acagagtctc  10740
gttctgtagc ccaggctgga gtacagtggc atgatctcgg ctcactgcaa cctctacctc  10800
cccggttcaa gtgattctcc tgcctcagcc tcccaaataa ctgggacagc aggcacttgc  10860
caccacgcct agctaatttt ttgtattttt agtagagacg gagtttcacc gtgttagcca  10920
ggatggtctc gatctcctga cctcaaggtc cacctgcctc agcctcccaa agtgctggga  10980
ttacaggcgt gagccactgc gcccggccat aaattattaa ctgagccagg cacagtggta  11040
cacacttata gtcccagata ctcaggagac tgaggttgga gtatcctttt ttatgttatt  11100
ttatttttaa ttattatggg tacataatag gtgtacatac ccatggagta caagtcatgt  11160
tctgatacag acacataatg tttaataatc acatcagggt aattgggata tccatcacct  11220
caagcattta tctttctttg tgttaggaac attccacctc cactcttgga ataggcaccc  11280
tgttgtgcta ttaaatacga ggtcttattc atttcatcta actatatttt tctacccatt  11340
aaccatcacc tcttttcccc tcttccccac tacctttcct gtgaggctgc aggattctta  11400
agcacaacag ttagaggcca gcctggacaa catagtgaga ctcaatttct aaaaaataaa  11460
aaagaaatta ccaactaatg ctaaaaaaat agtctctgat gcttaggtat gaattagaaa  11520
tgaccaaaaa aaaaaaaaaa aaaaagactg ccctttgctt ccttctcccc ttctcttcaa  11580
gttttccatt gctactcatt ttagtctggt ttaatcaggt ttcatccatt aaaagcaatt  11640
gttgggatca cacattttga gttgtgtcag tggacttccc tcatgctggc atgattcctg  11700
ccccaagccc ttagtaaaag ccaccaagcc atataacata atctctcatt gagtaaaaca  11760
tctgatgtgt ttagaatgac ttctagcaaa aaaccagcct gtccagcatc atctctgtat  11820
aacagataaa ggaataggta ctgcatcaaa aggttataga acctgcccaa atcaatccca  11880
tgtgttttgc aatggaatta ggttgaacta aagtgaaaat tcagttttct actcctcatt  11940
aacatgtctc atgttgcaag gttgagagga aggagaagaa gaactgtatt tacagagaga  12000
ttccccctct ctttctttct acagattact aaaacattca aagaatcaaa tttaagaaat  12060
cagttcatca gagctcatgt tgccaaactg aggtgagtgg aactgtagaa aaaatattta  12120
agtatagata caatgtggca tacttgactt tttgtcacag aatgaatagt aaatgacatg  12180
ttcagataag ttgttgtaat attatgaaaa tagtatttta gtcagcttaa aaaccaatgc  12240
caaaaaagcc aaacatatga tctatttagc tactaatgta aataaccata ttatatctat  12300
tcttattggg aagaggaaga aggggtggag agagagttgg ggtgaaggta cagtaacaag  12360
gccatcctat tgtaaaactc cagtggatat cattcacagt gcagcctatg taaacagtcc  12420
ctcctggagt tgtacaatgc tgtggtttgg gtgtatccat ccaagatcaa gacactatga  12480
ccaacatcaa aagtggcttt ttggttttat ctgcctgatg tgctataata aaagggtatt  12540
atggccaaat ccaaggcatg tctatcatga attaataata ggaggagtag cagcatgcat  12600
gctagttatt tgccattcct gccttagtta aatatgatgt gataaaacca gcctttccaa  12660
ctgaaatagt cacctttact gactctcccg caaatgtctc aaatgaccac attgctctag  12720
tctttaaata atatgcaata gttctttggt agaagaggaa ttatactaat tctttctcaa  12780
```

```
atactagcat cacaagaaaa ttaattcttg ttctctggag agtcacctag taagtatctg  12840
gagcacagat gtctggtcag gtaagttttg atgaggagtt aaagggataa gaagagtcca  12900
tgagaagggt attttccaaa acacctttcg gtcaattcag tgcacattca cttagtactt  12960
tcttgtcagt atctgtatca gccactaatg ttcaaaagtg agtaagccct gaaaacctgt  13020
aggactacat gagccttctg ccttttctct ccttttgttc acttcccact tatcactcaa  13080
tcctctgcaa cctggcttca ataccaccat aaaatatcaa ctgctcttgc cgattcaaca  13140
atgacatcca gataacaaaa tccaaagaaa ccacatcagt cctattcttg gacctttcaa  13200
cagtatttgg tcctgttggc ctgtcactcc ttgaaatagg actatccctt ggtttgcatg  13260
gccttgtata ccctgatttt cccccttacct ccctagctat tccttcttag tttcctttac  13320
taggtcttac ttctttgtat attccttaaa tgttgctgaa catcaggctg tgctctaggc  13380
ctctcatctt ctcaggtcac actctctcct ttccttggcc ttcactgcca cccatatgct  13440
gagtgctctc aaagttgtat ctctaggcca gtcctctttt gcctccaaac atgaatatat  13500
gcagccatct acttggtacc atcacatgga taattctcat gatctcttcc agtatgactg  13560
cttctttatt tttttctggg ctctttttta gcattgcttt acatggaact ttatcatgtc  13620
tctcaacctc tattttatct tttatctatg tatgtagagt ctgtgtaatt tcttcatctc  13680
ttttagataa ctaatatctc ttcagctttg acttgtattc tgtgtaaccc atttattgcg  13740
ttttcaattt caatgagtat gttttcctat ctgcaagttc tatttgtttc ttttgagaat  13800
cttcctggtc ttttaaacac atttcttatt ttaatttttg ggggtaccta gtagttgtat  13860
gtatttttgg agtacatgag atgttttgat acaagcaaac aatgcataat aatcacattg  13920
tgtaaaatgg ggtatccatc ccctcaagca tttatccttt gtgttacaaa caatccaatt  13980
atattctttt agttattttt aaatgtacaa ttaaattatt attgaccata gtgactctgt  14040
tgtgctatca gatactaggt gatcttttaa aaataatgtt ttctacttaa tctcattttt  14100
atgattccct cttttacgtc atttgtcatt tcaaatacag tcacttgtct gttgattcta  14160
ttatgtgaag tttttgagga taatcttttt gttactttga ttccaccttg gtatggtttg  14220
gctgtgcccc cactaaaatc tcatcttgaa ctctggttcc cataataccc acatgttgtg  14280
ggagggacct tgtgggaggt gattagatta tagggacgtt tcccccttt gctctgttct  14340
ttttcctgcc accatgtaag aaagatgtgt ttgcttcccc ttctgccatg attgtaaatt  14400
tcctgaggcc tccgcagcca tgcaggacct cttttctttg taaattaccc agtctccggc  14460
ggttctttat agctccgtga gaaaaaacta atacacacct catgatgtat tgtttaccac  14520
tgaaattgta tgcttaaatt taatctcact tgggaccctg tacaacctag acttaacata  14580
tctacctcca gagcagttac atctgtcaga cattctagag gaatcagcag cacatggact  14640
ttgttgttgt taatttgttg tcgggggagg ggggagggat agcattagga gatacaccta  14700
atgctaaatg acgagttaat gggtgcagca caccaacatg gcacatgtat acatatgtaa  14760
caaacctgca cgttgtgcac atataccctaa aaacttaaag tataataata ataaaattaa  14820
aaaaaaaaag gttctgggag tattcaggta gtattaatga agattcagac atcgtgcagc  14880
caggcccatg cttatgaatt ttcaggtgat acttcttttt cttttttctt aatttaaagc  14940
tggatctcgg aaacagataa atttattttt ttatgacatg acgagcattt ttttcattct  15000
agttcatgct gttattgggt gtttagttct ttgagactcc tggccttttt ctaaaacctc  15060
aagttcaact tcctattttg cactggccca aggtcccatc tccagtctct atgtaaatgc  15120
```

```
taaacataag cctgtggaat attctagtct caccacatac tattcacatt cttctttgtt  15180
tttggtcttc caggattttc cttacttttc tatgaaccca gtcttgcatt tgaaatggaa  15240
tttattatat attatctatc ctttctattt gttttatgca gaaagtgttt tctaaaatta  15300
tttaggcttc catattgcta gacatggaag ttgtaattat ttgttcagtg cctgtttcta  15360
catctaaact gcaagaccca tatggcaact gtgaatctta gtcccagcta atttctgaag  15420
cttagaatag tgcctagcac aagaagttgt ttatctaaca tttttaaaaa taaatattaa  15480
attcatatct ggaatgaata ttaagttaga gctggtcatt gaggtgagag gaggaagcca  15540
agagagaata tgagagcctc aaagccaaat atctttaatg tactttttca gaaaagaaga  15600
cagccaatgt caggtggagg aactggttta tgaggtaact ttcctggaag aaaatagaaa  15660
ttactgaggt tttagataat ccaaatattt aatcaagtca ccaaggttta ttgtggggaa  15720
tctttattat taattaaaat gagtgatgaa atcttaatat acgacaaaag ttaaaatttg  15780
cttttgcagg cagatgaatg gtctaggtat caaaaaatta agttgagtct ctaactcaca  15840
caaatttaca accctatcac tttatgaatt tgtttaggag attattttta ataacactgg  15900
tgaagtctaa gaatagctaa aatttatagt acacttattg tgtgctattg actcttcttt  15960
gaagttttgc atatagtgat tcatctaatc ttcataaccc attttacatg tgaagaaact  16020
tagatataga aagattaaga aacttacata acttatccaa agttacacag taaaactctg  16080
gcattataac ttcaaaatca gctatcctac agtgagtaca gtgttctgtg cattgaaatc  16140
aaataagtga gatagcatcg tgatatagta ttacgtatgc aaacactgtt acagagatct  16200
gtctaaagtt aaattccaca aatgaattct ttaaaagggt ttaatcaaga agaatatata  16260
aacaggatgg tgaaaaattg tcatattatt tgttttttaa aatatcttta tgatttacag  16320
gcaagatggt agtggtgtga gagcggatgt tgtcatgaaa tttcaattca ctagaaataa  16380
caatggagca tcaatgaaaa gcagaattga gtctgtttta cgacaaatgc tgaataactc  16440
tggaaacctg gaaataaacc cttcaactga gataacatgt aagtataatt tttcataaac  16500
aattttattt caatatatcc ctcaagttta ccaattcaaa ttcatatttt aattgagagg  16560
ctgacttttc tttctttgaa actaaactgt gaaaacaatc cattaaaaag ctaaatatac  16620
catatagctc cctaacgtaa atcattctaa gacttaaaga atcatttggc atttatatag  16680
taaattttat ttgctaaaaa ttctcattaa ttatccctgc aacattcctt atgagtgatg  16740
ttactgtcag atgtcattag tggataggcc ataggagggg tacatagatg ctcaaggtca  16800
gagaactatt taattaatga tccacctcag aggcttcttc atttttcttt gtaacattta  16860
tcacaattga aattacaaag ttatctgtgt aaattttgta ttgtttggct tcatcctaca  16920
ctgtaatcat cctaaaagaa agaaccagtc aaccttcttc atcctactac cctcctacca  16980
cccagtctcc atcatataac acatattcaa taaataattc ttgcatgact gaaagaaaag  17040
aaataatata tgcatagaat ttaaggacat tcctccaagt tggttacatt ctgctagttt  17100
aataagccat tatttcttct cgatgagctc aagattaaaa ggattttgat gattcccata  17160
ctagactggt aggtaccagt tacagatgta ctaactgtta aatattgaaa tgctttccta  17220
tttgttggta aacaattact gcatcaggcc cacaaagttg tcttccgaga tgtttcaaat  17280
ccactgcccc tgctgctaaa gagttatgct tagcaaagca aagcactcta agacactgct  17340
ccaactccat ggcctgattg catcttttat gactggccaa tgctcacgca ctgcagtttg  17400
ttaggtagtt gaatattacc tctgcttcca cacattaagg aatgctcccg aacgcacttc  17460
ccaagtgttt atttatttat cattatacta gacaatatgg tgatacgatg gtcacagaat  17520
```

```
agcggtttcc acctccagag cccataatct agttgaaggg aaagatattc caacacaaga  17580
gtgttgacaa tcaagataga atatgatcaa gggcccagtg tgaggcccag gcaatgatca  17640
ctgcaggaat ctggggaaga aagagaccag cgtgcttggg atatctagca aaagtttcat  17700
gaaggagaat ggactttgac tttgaaatat gggtaggatt tacatatttt gagatgagaa  17760
aaagaaagtt cccagagaag gaaagcatga aaaggcaaac agtctgtact gaacgcgatg  17820
ctttgacaga ataatgaaga aagggacctg ctggaatgat tgatcagtgt tcatcattca  17880
caccatcatc atcaaaacac ttatttaatg agaacttact gttttttagg catggcttta  17940
atgccctata tgaatttttt tcttgattaa tccttacaac aaacatatcc catagatagt  18000
tttattgtcc cccttagaaa agataaattg cctaggctga cacagtcagt atatgaggca  18060
gtcaggattc aaactaagtc tgtttgttca aaaaattaag aatggccagc tttttaaaat  18120
tttctgtctc cagaagtatg atttggctcc actgaagttt gcaaaacaaa tgtgataccc  18180
aaaccttgtg aaacttttag tgggaaataa ctttgcataa gtcggtttga gagagcgtgg  18240
aaacctgtct tgaaaagttt taatttaact tgcaggaaat aaaaatgatg ggtttctcaa  18300
ttaaaaattt caatcaagga aggatatgag ctaacataac atttttttaa aaagatcagt  18360
ctggtaaggt agaggtgcat aaactgaaaa ggagcaaaag tggtggaatt cagttagaaa  18420
attattgtaa ctgtactgat gtcaaatgat gaaaccatga actaaagtag taccaaaagg  18480
agtgaggagg atggaataat tcaaaagata gaggacagat gtgcagaacc tggagattat  18540
aagatgtgaa aggaggagtt tgagaaaatt tcagattttg gaagtggtgt cattttacta  18600
aaaggatata ataagtagca aattttggat aaagttgggt cccactgagt ttgagatggc  18660
tgttggacat gcagagaaaa ctgtcttgta tgctgttctt aaattgaaat agacagacct  18720
ttaccctctg atactgacat atttttcctt ccaggctcac cctccatttc cctaaacaca  18780
acacatgcac tagctctcct tactttattg ctccacaaac atcttacacc tccaagcatt  18840
tgtgcccact gtaccttcta tctggaatct cttttgtcct cttgtgtgcc tgaaaaattc  18900
ctttcagatc ttcaaaatac agtgcagatg ctatttcttc tagctcaaat attatctcct  18960
ccatataatt taattactct ctttttcttt ttctctactt tgcacttaca tttatttgaa  19020
tgattgcttg attaatttct acctgtaaat tatgtgaggg caggtcctct atattttgct  19080
cgcagttaaa tctgcagcac ttattataga gtggtatcat tagagtaata tacatatatt  19140
tgaggacatg ataaattaac ttcccctata gtatttatca cattgcatct caatgacttg  19200
cttatgtttc tgttttccca tataaattga gtaacttgaa aaaagagata tctattaagt  19260
atttaatgag aaattaaagt acaaacttta gtatgcataa caacaaattg ggaaaaggtt  19320
gtaaacaaag agatttgtag ggcccatgag ttagagatcg tttcagcagg tctgaaagga  19380
agcctaggaa tctgcatttt agaggaccac ctcccaaccc caacaagtaa ttctgcttct  19440
tgttgtctgg gtactgtact ttaagaaatt atggtgaaat gatatcagcc tttattgtat  19500
ttatcttatt ctcatttttt aatactagca cttactgacc aggctgcagc aaattggctt  19560
attaatggta agttttaata ttattttgta actgtaattt gccaaatcat aaagagtaaa  19620
agtgcaagtc ttttgtgtac ttttggccaa ggcagtatct atcaagttga tgtctttgtt  19680
cttagttcgc tcaggtggtg ttgaaacaag acagtgctga tcccaagtgt cccatggagt  19740
ggactttagg tttccccttt ccttttagaa aaaggaagaa gttgtagtgg aggactaccc  19800
actctgcact caaaattgcc ctcatgaaaa tttctttggc agctttgaga accttttact  19860
```

-continued

```
gccctggttc taaggtggca tttctgtaga cttacaaatt atgtttgatg acaccgttta  19920
tgtagcttct cctaaccacc agagtagctt gctttgttgt gaattcaggt taatcacaaa  19980
gtataataaa aaagaattgt cagaagtctt cccagctttg ggtctataac ctgaaggaaa  20040
agtcactact cttcaacatc atcctatgta ctctcaggct aggatagcag aaatgcaatc  20100
cctagaaaac agcaacttac ttctctgacc aaaaaaatgc agttaaaaat tagttcaatg  20160
tacctggtag ctggcctatc ttaggtactt cagtgatttt acaaagtgat ggtagtccta  20220
tgggtgtttt tcagcttcac tacgtattta attcatgctt attgttaatg aaactgtgat  20280
aagcaattta ctagggtatt tgtttgggag atgccacaaa ggaacacatg tatctcttaa  20340
tggaagcctg gtcctccttt atccaggaaa tttgctagga aaaaaaagcc tttaggtggt  20400
tgtgctatta aaccagggca ctacttaaaa gccagcccag caatagttgt gtgatttacc  20460
attaatttct tagtaataga ccacacaaaa gaagaaaatt atgggaatgc gagttgagag  20520
gaattgggtg atcagcctac cccagcccgt ttcagctctg gccagtagac tattcacgag  20580
ctctttgaaa acatttaaat aaaccttatt tagatactag aaaccctctg tcaccctcaa  20640
gaatattctg tggtatagcg actcctttat gagggcatgt ttggtaatac agcatcagtc  20700
ttggaggtgg actggattct acaaggtgaa ctgcagtcac taaggagtct tttggatgag  20760
accagttttc ctccaacttc aatgtgtgca tgaacctcac atcaaaatgt agctttagat  20820
ttgtcccatg atgtggttcc aagaatcagc acttctaata agtttccagg ggatgcccat  20880
gctgcaggcc cacaaaccac actgagcata gcaagactat tgagaaaaag gaaatttccc  20940
aggagtctgt ggcctgagct ggcacatcca ataatgacct atcttaacct caactcatga  21000
ggaattccag ggaactctga agctgctcaa aatttgaagc ctatatgcca actaaattca  21060
gaaatgttct ccaaaatgct atctataagc aacagtagtc acaaatgcat tgtagaaata  21120
tatcgatcat gctttttgga aaatccagca tgtcctgagg aagaatgtat aagacataaa  21180
agtcataaat tatggaaaga ctcttcagct tcttccaaat gtaaaggaat catgatcttc  21240
ccagcacatt aatgcccttt ctcattagaa tgtggggccg gtccagacct aataacattg  21300
tctgagcaga gaatccttgg aggcactgag gctgaggagg gaagctggcc gtggcaagtc  21360
agtctgcggc tcaataatgc ccaccactgt ggaggcagcc tgatcaataa catgtggatc  21420
ctgacagcag ctcactgctt cagaaggtga ggccaccact acctacccat ctgggaacaa  21480
ttagaataga caggtcatga agactgcacc ctctacccta ggattgaatt gagccagaaa  21540
taattcaatg caaaaaaatc agtaagaatt ttcttcctat tcatgaaagg aaaaggattt  21600
ttccccttta gcatgctaat ttagtgctat ttctctgttt caggtaataa tatattagca  21660
cagtaaagaa caaagattta tatgtcagaa tgttttttaa atcctagcta taaaagctta  21720
agaaatttac taaatctcca taagctttat tttttttcca aattaaggga caacactgtt  21780
atctgtgact tagtgttact ggtagcattg agtacactaa tgtaaacata cgttaaatgt  21840
tagcgaaacg aattgctgtg gaagatttgc acattatatc atgggagctg atggctaacc  21900
tagagactgc cccatgccat taatttattc attcataaag attattgagt atctagtatg  21960
agcacagtgt tatatattgt agaagctact agtataaaca aagtattgcc tctgccttca  22020
aagagcttac actcgaatgt tggaatcaga atgcacaaaa ataatgatca attacaatga  22080
gtagcataaa taaaattaat gtaggcaact tacaagaatt cttaattgag gtgactaaac  22140
tattgccaac actagggtga tatgctacca gtggcgagta ggttgcataa acttacctta  22200
ttggtaaaaa gaaaagttca cattgctcat aaaagaagga ttttagattt cagcataact  22260
```

```
aaaatctgtt tcaaacctgc cttgttactg gggcatcgca gaccacaaca gttgttggga  22320
acttaactca aaaagttcac ccagaaaaat aatggagatt tgaactcgtg tgcccctgac  22380
catatcaatt ttcttctcag actcttactc taaactggac ctccttatca cacacacaaa  22440
gccttccata ggcagatcaa tccagtctta tttctcaaag catgtacctt gagcttcaga  22500
taaacagcat tgttctcttc ccctggactc ttcctacatt tccctaccta tgagtatctg  22560
atcaatctgc ttatccttga aatgttaata tatttaccac atctctattt gaattttatg  22620
aaatttttga taatttctaa gtagtttttt cagatttata ggcactactt catggtacag  22680
tgactgttac aaacgtattt gttaaattta gaaggaataa agatttaaaa gactagggta  22740
gttactgaac taaagtttta ggaaatccca aattatttca aatttttctt atggtaattt  22800
tatgacttaa tatttttata tgcagtgaac aaatttgaaa ctttaaaaga tactcccaga  22860
attatcagtt ttctgatgta gattggcaaa tttattacta tatcccaaat aacccaagag  22920
acaaaattca caaaaacatt tcaattttca ttgccacttg aaaggccaaa aagcagaaat  22980
ggcacgcatt gatttcaatc gtactcttga gtgtgggaac caggaattaa aatacctgga  23040
cttatcaggc acttagcata accaagaacg gaatagaaac ctccctggat tctaagccct  23100
attcagtccc aatcaccaaa aaccaagtaa acgatatcac tataatgaaa gccacagtta  23160
taaatatcga caacgattac caaaggaatc catggaactt tgaattttgc caccccacat  23220
ccttctattc attaccatga ttgatccact aaagctaaca gactctgtga accttgtatt  23280
ggacccctcc ctaaagacct gattgtcact gagaaccatc agtgaggatt tgtttggggc  23340
atgaccagcc ttacatcaaa gtacatagaa gtgatgaggt cttatcaaag aggattattg  23400
aattatcacc tcttctatgt agctttccct gatactctct ttcctctcca ttgagttcca  23460
cagaaatttt tttatctgcc tttaacagtt gtcctcatga tttgtgatat ttgacttacc  23520
tcttgtcagt ttccttcact agtgtagagt tcctcaaaga aagagaccat aattacttat  23580
atttttattc ctggagactc atactattcc ttatacaaag tagacactta acaatggctt  23640
gttgaactat aattaatgaa aataatagct accttcatga aagttcactt tgtgccaaac  23700
actatagttg acataataca tttgtctcat taatacttaa caattgtgtg agaaggtatc  23760
accaatcaca ttttatatgt aaataaaccc cagagctatt aattaacttg tcataaataa  23820
cacttttcat atgtggcata gccaagattt aaatataaat gttactggtt ccaaaatgat  23880
gctctaattc acttgctgga aagaaggaaa ggaagaaaat aaacgagtgg aaggaagaga  23940
gggagggaag agagaaaagg aaggaaagaa aaaagagtct cttcagaacc ttcactgtaa  24000
agactccgag caaaagaagt tgaatataaa aacaacatag gtttgtttgt tttctaatat  24060
tttttcttca aaatttttaa ctcaggttca ctcttacaca aactactgtg tcttataaaa  24120
gtatttccgg tcatagaatt tttattttct gtattaactc cactatctaa tctccataaa  24180
actcctaaat tggtattatc ggtaacattt tgtttttact caacccttag gaacaatgtt  24240
aagttaatca gccctccaca tcacagatcc ttattttcat cagtctgtac aaggcatttc  24300
tctcatttta atttttttc ctcctgtcat ccctggattt cactttcact gccctccttc  24360
cacccatatg cctcatacta atatattcga aatatacatg tcttaaaggt acatgcacgc  24420
acctacaaaa cctatagtgt ttttttgtat gtatatgtct ttaatttaaa taagtagcat  24480
tgtgtaaaag tctaatattg tttcttactg ttttcactca attcttggaa ttttcatctg  24540
atgcactgct gcatagcacc ccatggtatg cagccaccat atttccttca tccaattagg  24600
```

```
ttgcatgacc taccttccca ttgccacaaa gagtacacac aaaatatttg tacttatctt  24660
tctgtaaacc ttcaggaatt tcagaagcac acatgcaggc tgctaaatat accagaatac  24720
tttccagcca cttaaatctt taccagtatt gcaaaagagg ccccatttcc ctccacatca  24780
acatttagta ttattctttt gtttaagttt tatcaatctt ttaaatgtac acaagatgct  24840
catttttata attttaattt ctcagattac tagtttgagt atcttttcat atatctaaga  24900
gctgttttga tctcccctac catgaactgc cactaatatt ctttgcctat tttacaatgg  24960
tttttctgct tatttattac tggtttacag acttttaaaa tatattctac aaaaatttta  25020
gacattaaac attaccaata ttttcccatg gttcctcatc catctggtaa acttgtctat  25080
ggtatatcta attttgattt aatagaattc attctatttt taccttttag tttgtgtttt  25140
tgttgtttag ccaaaaagtc cccattccta ggtcataaag gtaatgtcct tttttttttt  25200
ttaacgctac tgttctctct ctgtctcccc ctatgtatat aggtgcacat atacttgtac  25260
acacatacat atacctatat atgaggggag ttcgataagt ttatggaaaa taaaattaaa  25320
agataaaata aaaaattata aactttattt ctcaacataa gctccttcaa gttcaagaca  25380
cttttgtaag caataatacc agccatatcg tccatcccta aagaactgag ggtcctgaga  25440
atttaactat gtcaatgcag tctttttac attacttttt tacagtactt attgatgaaa  25500
aatgggtgcc ttttaaagat tgttttaaga ttagggaaca aaaataagtc agaggaagtc  25560
aaatcaggac tgaaaggtgg atgcctagtg atttattgct gaaactttca taaaactaac  25620
cttatttgat gagaggaatg agcatgagca tggttgtgat ggagaagaac tctggtggag  25680
ctttcctgga cactttttct actaaagctt tggctaactt tcttactctc ataagaagaa  25740
gatgttattt ttcactgacc ctttagaagg tcaacaagca aaatgccttc agcatcccaa  25800
atgtctgttg tcatgacttt tgttcttgac tagtctggtt ttgctttgac tggaccactt  25860
ctacctcttt atagccattg ctttgatggt gctttgtctt caagattgta ttagtaaagc  25920
catatttcat cttctgttac aattcttcaa agaaatactt cagaatcttg atctgacatg  25980
tttaaaattt ctattggaag ctctgacctt gggtgcagct gatctgggcg aaacagtttt  26040
ggcatccatc aagtagaaag tttgctcaac tttagttttt cagtcagaat tgtataagct  26100
gaaccagttg agatgtctat ggtgttgtct attgtttctc acagttaatt gttggtcctc  26160
tttgagacat gaacaagatg aaatttttcc tagcaaactg atgtggatga tctgttgctg  26220
cgggcttcac cctcaacaac atctctttct ttcttgaaac aaattatcca ttagtaaact  26280
gatgattggg ggagatgctg tccccataaa ctttttgtaa ggcataaata atttcaccat  26340
tcttccagtt tcaccataaa tttgacgttt ttttgcttca attttagcag cattcatgtt  26400
gctttgataa gagctctttt caaattcatg tcttattcct cttagtgcct caaactagat  26460
cttgttcagt atgacaagtt agtatgagtt tatctgcatg caaaaatctt tgaaatccat  26520
gcatagtttg tttataatat acattttcaa tgaacttttg aagaccccat acatacatat  26580
gtatatatat gcacacacac acacacacac acaccaaaat cttcaaccat tatcagactt  26640
agtgcagaaa aattattcat ccattaacaa gataagaatg cccccttatca tcactactat  26700
ttaaatggag ctcctggcta aaggaaaaga cagggattga aaaaaattag ttaaatctaa  26760
aatgtttatt atttcaggtt tcttagttgc ttaaatggga agggaggtat ggacaaaaga  26820
gaaatcaaag atatttgtgt tatgctactt atcattaaag tatcagaata acttcattgg  26880
aatagaaaaa caccaagatc accccacgat atgttttcta aaatcttctc catttcttta  26940
gacaagtgac catgtattcg gccagtgaag aattaaactc acttgccagc ttataatgca  27000
```

ggaaaatata gcaaagagat gtggatccaa tagtttctag atagtggtac aggatggcta 27060
agatgaattt atatatctga aatgttcaca aattccctac tcatatagca tgttttcata 27120
atgttttagc aactctaatc ctcgtgactg gattgccacg tctggtattt ccacaacatt 27180
tcctaaacta agaatgagag taagaaatat tttaattcat aacaattata aatctgcaac 27240
tcatgaaaat gacattgcac ttgtgagact tgagaacagt gtcaccttta ccaaagatat 27300
ccatagtgtg tgtctcccag ctgctaccca gaatattcca cctggctcta ctgcttatgt 27360
aacaggatgg ggcgctcaag aatatgctgg taagtgtctc ggaaaaaaaa attaacaata 27420
gaaatgtctt atatttgcta ttaggtaatt ttttaaatta ggaaacatct ggaataggtg 27480
tttctattct tctacagaca gaaccattct atattctgct cagcccaagc tctggctacc 27540
cctgagtctc cttagcaaag caaagcaatg ctccagaaac tatgggaatt ctcaaatata 27600
gtaataggaa aatgtaaaag aaagttatga agacacgagt tctttaataa tccagagatt 27660
ctataagatt caaatagctt ccctataaac aataaaaaag attttgtttg tttgtttgtt 27720
tgcttgtttt ttagagacaa agactttctc agactggagt gcagtggtgc aatcatggct 27780
tactgcagcc tcaaactctg gtcttaagaa atcctcttgc ttcagcctcc caagtagcta 27840
gaattataaa taagtgtgta ccaccatacc cagctttttt tttttttttc tacagacagg 27900
ttcttgctct gttgcccagg ctggtctgga attcctgccc tcaagccatc ctcctgcctt 27960
gttggcctcc caaagcaatg ggaggattta gattagacat tgtatgaggg cttaataatc 28020
cttaaggtat taactgccct ttaaagtatt ctgggatatg gcaaaaactc gatgtgtata 28080
taaacattgg tcatatttgt ttattgaatg aataaaatgg aaactaaaat gaggacaatg 28140
cacaagagct actagaacca gtaagagtat cagcgaagga gtggaagggt agcattgaca 28200
atttccctgg gcttttaccc atgttgtaga ttgtctctcc aaggaataat acaaagcctt 28260
aatagtccta gaacacattc tattgtgttc ttatggccca aagtaaattg gtgtagtaga 28320
taacatttgc accagtcatg aaaaactatt ggtgtcattc tgagagtaca tcaatataaa 28380
atagactagt tctttagcct tgaaactaga ctggtttctc ttttgctgct aggttaaagg 28440
ttattcaata tgtaatcttc caatccaaaa tctgtcagtg gataatttaa aagcttttag 28500
tcaattttaa gatatttgtt ttcttaaaat tttaaggggc actgtgtcac aaagctaaag 28560
aaaaaaaaga aaaaaaaact gatctgtgaa aggggttatc ctcatctact tggggaattt 28620
tggctgcgaa gaaactccaa agtaaatctt tagaagcctt cattgttaaa tatgaaataa 28680
tgtttggagt acatttattt cttctcaaat ttattatagg gtcaataatg tacacatctt 28740
gaagtccatt tttttcctgc ttttataaca aacaggccac acagttccag agctaaggca 28800
aggacaggtc agaataataa gtaatgatgt atgtaatgca ccacatagtt ataatggagc 28860
catcttgtct ggaatgctgt gtgctggagt acctcaaggt ggagtggacg catgtcaggt 28920
aagctcaaga caatctcatc catgtcatca tccaagaagt gtataagcac ttcctagtat 28980
gtgataatgt gatagacata agtgtaacag ttacaataca cagccctgtt cctctaaaat 29040
ttataatcta gattttagaa ataaattttt ttatgaatga agtttatcta tcatgaaagc 29100
attaactctg agaggccaaa ttacagagta gttaaccatc caaagctcaa gaatcagaaa 29160
gacctcgatt tgaattcctt aacctctatt accaagtctc taactaaaag ctggggataa 29220
tcataatagc acctaacttt ttgggtacta agaaaagtta aatgaagact aaatatatca 29280
ggcacatggt aaacaacaaa gaaatctcat ctatttcact attattaatg tagaccatgg 29340

```
tcactcgtgt taataacttt aacctcaacc ttttaactgc tgtgaaggat taaataaaaa  29400
attaatcact atattataaa aattaattga tatataataa atgaatttta agagatacgt  29460
aataattcat ggactccttg aagatagaaa atttatacaa aatcctagta atttgagtca  29520
caaaagctcc tacaataatg aaacagtatg aatgaaaaag aaaagaaata actattatat  29580
ttggatctag cccataattt ttaaccaaat gcacaaaaac aaacaacaaa tatgaaattc  29640
tcactgtaaa gtgattaaaa tcaaatttga attctaaaat tttaaattaa attatctaaa  29700
cataattgat gcagttatat gttttaatag gttttgttca catatctgaa atccaactcc  29760
acacagtagc aggaacagct ggtgtcagaa attaaatatt cttttagtct ggagttttaa  29820
aaaatcaatc tgtttacttg agtaatttgt tgctgttttc atgggtgaat tgtatacaga  29880
aggataagaa ttattcttcg catcaaaagg tcactgactt tcatatttag tgctcatggt  29940
ctttaaaaag tggataaaaa gtagttctca catttcatgg aaagccccca atccatgagc  30000
acatttccca aaatgaaaca tttttatcaa ctgcaagttg tgtgtaggtg gagatttgtt  30060
tttcaattgt caagatactg ttaattaccc agtcctttat ctccttttgg tggagatgtc  30120
tctgtgctag gaaacccttc ttgctctcct tcctgtttct cttttactac tggccctgaa  30180
acaacaaatt ctcaagtttc atgacagctt tccaaagaat ccatcaatca aataagcaac  30240
acaactcgac actgacaatt ccagacctac taagagcatt aattaagact taaaaataaa  30300
catgagtttt aaaagggtgt tattcattat tttcccattt ataacgtccc ttaccttctg  30360
tccttcagtg catacaaatt attatcttcc ttgaagccca gttcaagccg tacctcacca  30420
tgataccttc catgtatatt ccactctagg cctcactgat ttttaactga aatactataa  30480
tgcatagttc acacttaaaa aaaaaaaaaa aacacagcac tttacataag agcttacagg  30540
atcctatttg ttttatccat tcttttgttc atttttacaa tcattaattc aaaggaatta  30600
tattaattac tttctatgca cccgacgttg tgttaacaca acaatactat ccctgcattc  30660
agcaagtcta tggtctacaa gagaggacac aaattcaaat gtctgtagtc aagcagtgaa  30720
gctggctaga tatggaaaaa ttacaagtcc ctcttgcttt aacatttgct tgcccacatt  30780
tggtcagaca tcatgcaaaa taatttctca ctatagaaaa aaaaacacta caaaaacaat  30840
aatataaaga actgagaact ggttaactga agcatgcata tgtcatctaa aagaagcagg  30900
tgacgaccag cttcatgaag tacttgccat gcatattggc acttcacaca ctgacccttc  30960
tccccaccta gaccagtaat taaacaggta tggatgagct agctactaag agcagccaac  31020
tgaatagctg actaacttag aagcacactt ggtaataata gctgactttt attagtactg  31080
actatactat atgctaagct gtactcaaag tgctttgagt tttaaactga tacaaacatt  31140
atatgaggaa acagaggtac agagagctat tcaccagctt accaaaggtc acatagctgg  31200
taagtggagg acttaaaccc agactatcta gtttcagaac ccacagactt aatccatcgt  31260
gcagaacata agacatactc catctgtctc cccaactagg ttattatgtg cacaaatatt  31320
tattggttgg ttggttcatt attatgactg ggtggtaagt atgtcattag gagtgttttg  31380
cttatgacta tataaatttc ttcaccaaaa gaagactttc tgatgatata ctatgcatca  31440
gacaccacgc agggtgctaa ggttaggaag ataagtgaga cttctagaaa ctcattcatt  31500
caacaaatat ctcctaaggg ctagaagctt aggtttcagc agtgaacaga ataggtatgt  31560
tctctttcgt gttggacctt atagtatatc tgggaaaaca gacattgaat aaatatcaca  31620
aatgcaagtg agtgtttcag agacatgcag ctgctacatc aaaacaaaac agaacaaaac  31680
aaacaaacaa aaactgacca gtgggattaa gtgtaaatag gcacacaaat gcacaaatat  31740
```

```
gcttttataa aatagtgaag cagtgacaga gacacacaca agatataaag acacaatgaa  31800
gaacaattga gcccaaagct ggaaagggtg agagtgtgaa ggaaaaaggt tgatcagaga  31860
agttttcccg aaggagagaa agcctggatg attaggaggc aaccactcgg tgactgaggg  31920
aaatctgaaa aatgtatttg tcatcttctc agacttgctg aaggaatgac ttgggtactt  31980
tgaggatttc agtaattttt ccatgacttg gtataatatt tcaaaaggaa ataggctgac  32040
tttatttgta taatgaatgt gactccttcc tcgactgcca tagaaataaa ctccttaata  32100
ttttgggttt gtctttgcac ttaagtaatc agtcattctg tttttttaca gggtgactct  32160
ggtggcccac tagtacaaga agactcacgg cggctttggt ttattgtggg gatagtaagc  32220
tggggagatc agtgtggcct gccggataag ccaggagtgt atactcgagt gacagcctac  32280
cttgactgga ttaggcaaca aactgggatc tagtgcaaca agtgcatccc tgttgcaaag  32340
tctgtatgca ggtgtgcctg tcttaaattc caaagcttta catttcaact gaaaaagaaa  32400
ctagaaatgt cctaatttaa catcttgtta cataaatatg gtttaacaaa cactgtttaa  32460
cctttcttta ttattaaagg ttttctattt tctccagaga actatatgaa tgttgcatag  32520
tactgtggct gtgtaacaga agaaacacac taaactaatt acaaagttaa caatttcatt  32580
acagttgtgc taaatgcccg tagtgagaag aacaggaacc ttgagcatgt atagtagagg  32640
aacctgcaca ggtctgatgg gtcagagggg tcttctctgg gtttcactga ggatgagaag  32700
taagcaaact gtggaaacat gcaaaggaaa aagtgataga ataatattca agacaaaaag  32760
aacagtatga ggcaagagaa ataatatgta tttaaaattt ttggttactc aatatcttat  32820
acttagtatg agtcctaaaa ttaaaaatgt gaaactgttg tactatacgt ataacctaac  32880
cttaattatt ctgtaagaac atgcttccat aggaaatagt ggataatttt cagctattta  32940
aggcaaaagc taaaatagtt cactcctcaa ctgagaccca aagaattata gatatttttc  33000
atgatgaccc atgaaaaata tcactcatct acataaagga gagactatat ctattttata  33060
gagaagctaa gaaatatacc tacacaaact tgtcaggtgc tttacaacta catagtactt  33120
tttaacaaca aaataataat tttaagaatg aaaaatttaa tcatcgggaa gaacgtccca  33180
ctacagactt cctatcactg gcagttatat ttttgagcgt aaaagggtcg tcaaacgcta  33240
aatctaagta acgaattgaa agtttaaaga gggggaagag ttggtttgca aaggaaaagt  33300
ttaaatagct taatatcaat agaatgatcc tgaagacaga aaaaactttg tcactcttcc  33360
tctctcattt tctttctctc tctctcccct tctcatacac atgcctcccc caccaaagaa  33420
tataatgtaa attaaatcca ctaaaatgta atggcatgaa aatctctgta gtctgaatca  33480
ctaatattcc tgagttttta tgagctccta gtacagctaa agtttgccta tgcatgatca  33540
tctatgcgtc agagcttcct ccttctacaa gctaactccc tgcatctggg catcaggact  33600
gctccataca tttgctgaaa acttcttgta tttcctgatg taaaattgtg caaacaccta  33660
caataaagcc atctactttt agggaaaggg agttgaaaat gcaaccaact cttggcgaac  33720
tgtacaaaca aatctttgct atactttatt tcaaataaat tctttttaaa ataatttccc  33780
tgcctaatta tttatggaag ttatgacttt tgaaggacaa ttcaaaacca tttatttaat  33840
tggttctgca atgaaagaac tgccccatat actctactaa aggcttggca ctttctgctg  33900
ccttttaatc cagcgctata attgaggcaa gcgtccagct tgacacctcg agataacttc  33960
gtataatgta tgctatacga agttatatgc atggcctccg cgccgggttt tggcgcctcc  34020
cgcgggcgcc cccctcctca cggcgagcgc tgccacgtca gacgaagggc gcagcgagcg  34080
```

```
tcctgatcct tccgcccgga cgctcaggac agcggcccgc tgctcataag actcggcctt  34140
agaaccccag tatcagcaga aggacatttt aggacgggac ttgggtgact ctagggcact  34200
ggttttcttt ccagagagcg gaacaggcga ggaaaagtag tcccttctcg gcgattctgc  34260
ggagggatct ccgtggggcg gtgaacgccg atgattatat aaggacgcgc cgggtgtggc  34320
acagctagtt ccgtcgcagc cgggatttgg gtcgcggttc ttgtttgtgg atcgctgtga  34380
tcgtcacttg gtgagtagcg ggctgctggg ctggccgggg ctttcgtggc cgccgggccg  34440
ctcggtggga cggaagcgtg tggagagacc gccaagggct gtagtctggg tccgcgagca  34500
aggttgccct gaactggggg ttggggggag cgcagcaaaa tggcggctgt tcccgagtct  34560
tgaatggaag acgcttgtga ggcgggctgt gaggtcgttg aaacaaggtg gggggcatgg  34620
tgggcggcaa gaacccaagg tcttgaggcc ttcgctaatg cgggaaagct cttattcggg  34680
tgagatgggc tggggcacca tctggggacc ctgacgtgaa gtttgtcact gactggagaa  34740
ctcggtttgt cgtctgttgc gggggcggca gttatggcgg tgccgttggg cagtgcaccc  34800
gtacctttgg gagcgcgcgc cctcgtcgtg tcgtgacgtc acccgttctg ttggcttata  34860
atgcagggtg gggccacctg ccggtaggtg tgcggtaggc ttttctccgt cgcaggacgc  34920
agggttcggg cctagggtag gctctcctga atcgacaggc gccggacctc tggtgagggg  34980
agggataagt gaggcgtcag tttctttggt cggttttatg tacctatctt cttaagtagc  35040
tgaagctccg gttttgaact atgcgctcgg ggttggcgag tgtgttttgt gaagtttttt  35100
aggcaccttt tgaaatgtaa tcatttgggt caatatgtaa ttttcagtgt tagactagta  35160
aattgtccgc taaattctgg ccgtttttgg ctttttttgtt agacgtgttg acaattaatc  35220
atcggcatag tatatcggca tagtataata cgacaaggtg aggaactaaa ccatgggatc  35280
ggccattgaa caagatggat tgcacgcagg ttctccggcc gcttgggtgg agaggctatt  35340
cggctatgac tgggcacaac agacaatcgg ctgctctgat gccgccgtgt tccggctgtc  35400
agcgcagggg cgcccggttc tttttgtcaa gaccgacctg tccggtgccc tgaatgaact  35460
gcaggacgag gcagcgcggc tatcgtggct ggccacgacg ggcgttcctt gcgcagctgt  35520
gctcgacgtt gtcactgaag cgggaaggga ctggctgcta ttgggcgaag tgccggggca  35580
ggatctcctg tcatctcacc ttgctcctgc cgagaaagta tccatcatgg ctgatgcaat  35640
gcggcggctg catacgcttg atccggctac ctgcccattc gaccaccaag cgaaacatcg  35700
catcgagcga gcacgtactc ggatggaagc cggtcttgtc gatcaggatg atctggacga  35760
agagcatcag gggctcgcgc cagccgaact gttcgccagg ctcaaggcgc gcatgcccga  35820
cggcgatgat ctcgtcgtga cccatggcga tgcctgcttg ccgaatatca tggtggaaaa  35880
tggccgcttt tctggattca tcgactgtgg ccggctgggt gtggcggacc gctatcagga  35940
catagcgttg gctacccgtg atattgctga agagcttggc ggcgaatggg ctgaccgctt  36000
cctcgtgctt tacggtatcg ccgctcccga ttcgcagcgc atcgccttct atcgccttct  36060
tgacgagttc ttctgagggg atccgctgta agtctgcaga aattgatgat ctattaaaca  36120
ataaagatgt ccactaaaat ggaagttttt cctgtcatac tttgttaaga agggtgagaa  36180
cagagtacct acattttgaa tggaaggatt ggagctacgg gggtgggggt ggggtgggat  36240
tagataaatg cctgctcttt actgaaggct ctttactatt gctttatgat aatgtttcat  36300
agttggatat cataatttaa acaagcaaaa ccaaattaag ggccagctca ttcctcccac  36360
tcatgatcta tagatctata gatctctcgt gggatcattg tttttctctt gattcccact  36420
ttgtggttct aagtactgtg gtttccaaat gtgtcagttt catagcctga agaacgagat  36480
```

```
cagcagcctc tgttccacat acacttcatt ctcagtattg ttttgccaag ttctaattcc  36540
atcagacctc gacctgcagc ccctagcccg ggcgccagta gcagcaccca cgtccacctt  36600
ctgtctagta atgtccaaca cctccctcag tccaaacact gctctgcatc catgtggctc  36660
ccatttatac ctgaagcact tgatggggcc tcaatgtttt actagagccc accccccctgc  36720
aactctgaga ccctctggat ttgtctgtca gtgcctcact ggggcgttgg ataatttctt  36780
aaaaggtcaa gttccctcag cagcattctc tgagcagtct gaagatgtgt gcttttcaca  36840
gttcaaatcc atgtggctgt ttcacccacc tgcctggcct tgggttatct atcaggacct  36900
agcctagaag caggtgtgtg gcacttaaca cctaagctga gtgactaact gaacactcaa  36960
gtggatgcca tctttgtcac ttcttgactg tgacacaagc aactcctgat gccaaagccc  37020
tgcccacccc tctcatgccc atatttggac atggtacagg tcctcactgg ccatggtctg  37080
tgaggtcctg gtcctctttg acttcataat tcctaggggc cactagtatc tataagagga  37140
agagggtgct ggctcccagg ccacagccca caaaattcca cctgctcaca ggttggctgg  37200
ctcgacccag gtggtgtccc ctgctctgag ccagctcccg gccaagccag caccatgggt  37260
acccccaaga agaagaggaa ggtgcgtacc gatttaaatt ccaatttact gaccgtacac  37320
caaaatttgc ctgcattacc ggtcgatgca acgagtgatg aggttcgcaa gaacctgatg  37380
gacatgttca gggatcgcca ggcgttttct gagcatacct ggaaaatgct tctgtccgtt  37440
tgccggtcgt gggcggcatg gtgcaagttg aataaccgga aatggtttcc cgcagaacct  37500
gaagatgttc gcgattatct tctatatctt caggcgcgcg gtctggcagt aaaaactatc  37560
cagcaacatt tgggccagct aaacatgctt catcgtcggt ccgggctgcc acgaccaagt  37620
gacagcaatg ctgtttcact ggttatgcgg cggatccgaa aagaaaacgt tgatgccggt  37680
gaacgtgcaa aacaggctct agcgttcgaa cgcactgatt tcgaccaggt tcgttcactc  37740
atggaaaata gtgatcgctg ccaggatata cgtaatctgg catttctggg gattgcttat  37800
aacaccctgt tacgtatagc cgaaattgcc aggatcaggg ttaaagatat ctcacgtact  37860
gacggtggga gaatgttaat ccatattggc agaacgaaaa cgctggttag caccgcaggt  37920
gtagagaagg cacttagcct gggggtaact aaactggtcg agcgatggat ttccgtctct  37980
ggtgtagctg atgatccgaa taactacctg ttttgccggg tcagaaaaaa tggtgttgcc  38040
gcgccatctg ccaccagcca gctatcaact cgcgccctgg aagggatttt tgaagcaact  38100
catcgattga tttacggcgc taaggtaaat ataaaatttt taagtgtata atgtgttaaa  38160
ctactgattc taattgtttg tgtattttag gatgactctg gtcagagata cctggcctgg  38220
tctggacaca gtgcccgtgt cggagccgcg cgagatatgg cccgcgctgg agtttcaata  38280
ccggagatca tgcaagctgg tggctggacc aatgtaaata ttgtcatgaa ctatatccgt  38340
aacctggata gtgaaacagg ggcaatggtg cgcctgctgg aagatggcga ttgatctaga  38400
taagtaatga tcataatcag ccatatcaca tctgtagagg ttttacttgc tttaaaaaac  38460
ctcccacacc tccccctgaa cctgaaacat aaaatgaatg caattgttgt tgttaaacct  38520
gccctagttg cggccaattc cagctgagcg tgcctccgca ccattaccag ttggtctggt  38580
gtcaaaaata ataataaccg ggcagggggg atctaagctc tagataagta atgatcataa  38640
tcagccatat cacatctgta gaggttttac ttgctttaaa aaacctccca cacctccccc  38700
tgaacctgaa acataaaatg aatgcaattg ttgttgttaa cttgtttatt gcagcttata  38760
atggttacaa ataaagcaat agcatcacaa atttcacaaa taaagcattt ttttcactgc  38820
```

```
attctagttg tggtttgtcc aaactcatca atgtatctta tcatgtctgg aataacttcg  38880

tataatgtat gctatacgaa gttatgctag taactataac ggtcctaagg tagcgagcta  38940

gctgcaaccg aggaaaaaac gtgccatgag gtctctgtat ccaagtgtga ct          38992


<210> SEQ ID NO 20
<211> LENGTH: 34073
<212> TYPE: DNA
<213> ORGANISM: Artificial Sequence
<220> FEATURE:
<223> OTHER INFORMATION: Recombinant polynucleotide

<400> SEQUENCE: 20

gagggagggt ggtgctttgc taatggtgaa ttactaactc ctcaataaag aatattattt     60

gaaataattt ttgaaatttc ataattactt tgggttcttt cttaatgata aataaataat    120

agtatattac aaacatacat taatatttcc tgaatgaata caccacaaat ctcccttaaa    180

atatagcaag aataaaaatt atactatttc tgacaatttt taatttctca aataataata    240

ccactctgat ttttaaacat ctacaccact ctggctttgc caatcttttt aaaaattgaa    300

aagataataa ttttatcata attacactga agcatagaac tttttctttc aaggaaagca    360

aatttttgaa attctataat ataacctccc ataatcctga ataaattaaa ggttcaacaa    420

cttagtaaag taagactgac cttccctttt atttcttttt cagatcaaaa atcttacttt    480

tataggagca gttttcaact cctaaatgtt gaatataata gtcagttaaa ttcaccagct    540

acacaggaat acaggacttt gagtggaaga attgaatctc tggtaagtta atatttgtct    600

ttgctcttta ttccattata aaatgaatat gataataaac ctaatgtttt gtaatatatt    660

ttcagttgct aagtgctcta catattttcc ttccttgaat ggtgaaacat gtgtttctct    720

ctgcttttat ccagttagtt tactcatata ctggttctta ttcacatctt tgtcatgagt    780

aaaaagtgtt agaaaggcca cgagtaaata tgcattttat ttgtttatga attcaaatac    840

taaaagtttt ttatttgttt aattaagcat tgacattgtc tttttaaatt cttttcattt    900

taccttcttc cctcttcctt atccaactaa agacgcaaag caggaggtgt taaaaaacag    960

gtttaccata tcagcagtaa catagtttgg acaacattac actttggttc aatgatagac   1020

atagaagttt gaacagaaat atgcaaagca agtttgagct ctaacttgaa gagagcctct   1080

gggtgcctgc caggaaacct cacgagtgga cccttaacat tcatgtgtca ccacaaacta   1140

ggggctgccc tttagttttg accagtctca gtgtcactca cttaccctta ccttttcaaa   1200

aaaaagtcct aagaatataa agtaattcaa tggttctaca attttagcat gtaactgagt   1260

cacctggcag ggttgctttg gtgagctcaa gataaaattt tatcagcatt tctacatttt   1320

ctggaatatt ccttaatcca ggcttttaat cccttggtgc ttttctgaac cactgcaatg   1380

agcttctaac tgttctcact gtgtgcaggc tcttttcctt ctaatctaat ttacacactt   1440

ctgaacacaa atctctcaca gcctgtttcc ttcatgttac ctccagctca agacttttttg   1500

cctacaaaat aaaattcaaa cttgttagct aagcaccttc tcatgtctat gctttggctc   1560

atatttcagc catcgtgtgc cccacttatt cttatagcca acctgaaaag ccatctttta   1620

taagaaacta cctctgctct ccatgattgg atataattaa tcctccttcc acatcacctc   1680

gccacaaaat tgtatctgtg ttgatctcat gccacatacc tgtatgtatt ttatattata   1740

aatatttgca gacttgttta atttgccatg ttagactaag ttccatgaag acagctccat   1800

atccattcca tttttatata tccacaacat ttggtcgggt tgatgcttaa taaatgttta   1860

ttgaaggaac aggagtctcc cacttctgac ataatgaact tatttccccc agtgttaacc   1920
```

```
ctacatctgg ttcctgtcca agagtctctt cccaaatcat tctgattcaa ctgttcattc   1980
tgatctcatt aaacatttaa atgatatatc taacttcgct tgctttattc tatgctcatc   2040
ctgcagtctc ctcataactt ggtttcaatg atgcttgctt ctagagaaaa aaatgtatta   2100
aataagctta tgattcagtc ctccagctgt gatggttctc actgaacatt agctcagtgg   2160
ttttcgaagt atggtctcta gcataaccta gaaacttgtt agaaatgcaa attcttgggc   2220
tcaccaagac atactaaatc aaaaattctg acattggggc ctagaaatct gtgttttaac   2280
aagcctgcca gtgcagcctg gtccctttc ttctcggagc cccactcaaa gctttcagtg   2340
ctcatctccc accaatgaca gggtcctcta tggaaaccgg caggacggtt tccaactcta   2400
actacgtttt agagtttgct tcctagggct atccaggcac caagtatcac aggttagttt   2460
cccagggaag cagactctga gacttgcatg cagggagtgt ctctggggtg ctctcaacca   2520
acaccttcag gaagagaagg aagcagcatt gggcagaggc atagtcaaac tacagtgctg   2580
ttggcacaga agactgaagg gagtcagagc caggggggtag aggtgggccc ttagcatcca   2640
tccttcacca ttaggtgtga gttgccccac ctccttgatg gtgtaacctc agtcccaagg   2700
tgggtgggag tgcagcagag cagcccctac aagggccaaa ccagagatac accaggcgcc   2760
agaagtgctg ccagggaata gagaggaaag gatgggctta aggtaggatc cacagaactt   2820
ggcaatggat tagaagacag gatgagaagt gacaggttaa cactaacaca gaaatgtcta   2880
acttcggtag ataatggtgc cattggctag aagaggaaac cgaaatgaaa gcaggttgtt   2940
cagggagaca aaagttcact gtggacatct cagcagagtg attcagtggg gaaaggaatg   3000
gatgcccaga ccacctcaga ggaagatcta agctggagcc agcaataaag atacaagatg   3060
aacaatccct aacgaactgc tcctcagcca tgctccccag acacgctgct tcagatttat   3120
agtccgggtg aggctaggag gtgcgcctcc ctcagtggag gacagcaaag caccagtggc   3180
tccagggagt taaaatcttt tgataatttt tgttctagca tctgtctgca gagctgtctc   3240
tcagccattg cctgccttta cacaggagtg cagtccgaaa ttgggagatg agtgaaattt   3300
attatgccta gagatctgga tccccagttg tttgggagta tattttctga accacttgtt   3360
ggtttaagta atgcagattt attgatgcca cttctcttga atctgtgact ctggacccac   3420
catctaagtg aatgtgcaga gggaacggaa tggctgcaat agatctccat taaaaccagt   3480
gcatcctccc agacacatac agtagtaggg aggtgagtca atgtcaggac agcaccagct   3540
cccgcttcgg tacatttcca aagttctcag tctgtgtaca aaggtttgct ctggggcagc   3600
agaaatagcc ctgggcaggt agtcaaaggc ctggtttgat ttcctccact tccaggcaag   3660
tcactcgaag gctcacaggc tttttcctca cctgccacat gggtccagtg agatctactg   3720
agctgtaaat aatgaaatga gtgtgtgtgc agtcatctat aagttgtaaa gtactagaaa   3780
atggtgaaac tttgggattt gggctattta aggctgaatg ctaaaaatgt caggcattgt   3840
ggagaaagga atttaaatat aagattgatt gactgggatt taaagacaaa tgaaggcaca   3900
cacgcaagtg cacacccaca ctgacactgc acagctcccg ttggaggcat atcctgacca   3960
tgcagacctg gggctctgcc tgtccaagtg cactccttta ctacataaac cctccttctc   4020
ttttggggct gtcaccccac cagagctggc accgagccct tgctgctgcg cttccctggg   4080
gtgtcagctt ttgacagggt gtttcctccc tctgcaggag ccttaacatc ccttggactt   4140
ccttcccccc acccaccccc agcagtttta tctcttccta actcgggacc cttttttttcc   4200
cacacaaagt ttattgtcag ttgctggttt catctgtttg agcggctgca acaaaatacc   4260
```

```
atagactggg tggcatatgc acgacaaaaa tttatttctc acaggagaag tcaaagatta   4320
atgcaccagc agatctggtg tctgaggggc caccttctgg tttgtagatg atgctttcta   4380
gttaaaacac ctatttaaca cactattaaa cactaagtgt gttaaatagt gcagttgatg   4440
tatttgtcat gtcaccttta tcatacacta aatccttctt tgtctttttt tctgtactct   4500
aatctctttc tgtaagtaat ctttgcttgc agcagtagga tatttagagt actgtggctt   4560
gacaatatat ttagtatttc aagatttcca tgaaattctt ctgatgtatg agttccctag   4620
ttaatcttac atatgtatcc ctttgtaaaa acactttgaa catttaaaat gatacatgaa   4680
tagtactcta atacaatgcc ataaaaatta taaatcattt gtatagactg gtaagtaaag   4740
attgtgagat taagaaacgc atcaaaggcc attgagctgg aaagtggtat aatgagaatt   4800
caaaccaggg tctcttgact caaaatctaa ggatcatacc atttctcatg ataatatgag   4860
tattattgtt atctctatcc catagacaaa gtgttaacac tgaatgagca gtgaaatagt   4920
ctcagaattt tttattttat ttagcaattc acttgtcatt tctggtcctc agtttattca   4980
cgagtaaaat aaaatagttg gactagataa tttctatagt acattcttac acaaaaaatc   5040
tatgattttg ttatttttaa tgtgatatac tcatggcact cattcacctc attttcccag   5100
cctgcctcac tggtcattac ttctctgtgt tctttacagg ctccccctcc tctacactgc   5160
cattaaatat tgaaacacct caaagcttta cttatgtcca cctctcctct gacactatca   5220
ttctgtctag atgatcccat acatacatgc ccattacttc aacctgtatt tatacgccaa   5280
tgattcacta tatttccagc ctagacattc ttttgtactc tagttaccag cttgatatcc   5340
ttacatggct gtttcaaaac aactcaaata tattatctct caaaatcaaa ctcatgatgt   5400
ccccacacca tcctagcttt ccaccaacaa tacctatccc tattaatagc aataccattt   5460
attcagttat ccaaatcaaa aacctagaat tcatccttaa aattctacta tcattccaaa   5520
tatcctatcc atcagcagcc actgtattct taatcccctg tatttccttc aaatccattc   5580
acctctctcc atatccattg ctgcatgact atccaagcca tcgcctctac cctagggtac   5640
caaaatagca acaaacctaa tctgttcatt tgcattattt tttctccaaa actgattatc   5700
tatatgtagc aagacagatt gttctcaaat tgcaaatccc actatattat cctcttgctt   5760
caaacacttc catggtttcc cattgtttat gataaaacca aatgcttcaa gttcgaagac   5820
cggcatgatt gggaatttcc tgtcacccta gcctacttgc tctccatggt acagttgcac   5880
tggctttctt tcattcctta agtacaacct gtttcctccc acctcaggac tgtgcatgtg   5940
ccattcattc tgctgaggag ccttttttcct tccacttcaa tcagctaagt ctgattcttc   6000
ctgacaatct cagctcaata agcatttcct ctaagaaatg tctctaatat cattaattgg   6060
ctcaggtccc tctactgtat tgctgcactt ttcacagtta taattttact taattatgaa   6120
tgattatttg attaggtcta tttccatcca ttagacataa gcttcatgat ggccagatta   6180
ctgttttcta tccatcgttg tattccaata cctgacagaa ggagggcggg aggtggtggc   6240
acacaagaga tgctcaaaaa caattgttga ataagtaaat gaatgaggcc atttagaaat   6300
aacgaaagta cctgtttaca aagtacatgt atcaaaacta tgaatgcatt ctacttacat   6360
ggttttctcc aaataaaaca aaagacttca atcaggatta atacctggga taaactgagt   6420
cattaaatct ctcctttgcc atcaggagtg acattgaaac aaatgtctgc aaacaacaaa   6480
tactttttttc ccaaaatata ttgaatggca tttccataaa caaactagaa catgggagga   6540
gaaagaaagc aatattaatt taaaattaat cttatcacat aacttatacc atcaggggatt   6600
tcgggtaaaa ttcctttcag gcacatccat ttaacaagaa ttgattgtta ctgaaagcct   6660
```

```
agaagagaat ttggcacata cttggtgttc aaatatttgt tgactgagtg aataaatgat   6720
gcaagtgtct aagaaacaca aaataaggac atgattacag tcacggtgga gttcacagtc   6780
atctccaaaa tgaggatatg catcccaggg aggaccaaca attcattgga gtgctgaaat   6840
aaaatactca aaggtcattt tacatgtatt ttttctctaa attacttttc ttaagacaca   6900
gaaaacaaaa aaagaaactt agctttgtta ctttctaaca aatagttaaa tcattaaaca   6960
ggattgacac tagcatcctt gtttggtctt atgccttagg ggaacatgaa atgtgtgaag   7020
acattctgag atctgaggga agggtagaca gtaatacagt gggactgacc aggcttcagc   7080
acacctttac ctcctctcag cagatttcag tgatgagcag tttacaacta gattgaaaga   7140
ttatattatc tagttctaaa agaaaactaa gcctcccaaa agcaacaagg gaactgagag   7200
gaatcctgca aaacaaaaac aaattttaaa acttgcactt tgtaataacc ctaatatgta   7260
atcacagtaa tgaacagtaa gataatgaca gaactgacat atttccttat ctattaaagc   7320
catattaaca ggtaaagcaa tgccagtcag tggtacactt cttagaagat atttaataca   7380
tactagacac atacacacac acaacatttt ccttcaaggt gtatgtatca gaaaatcact   7440
ttttaaggcc ggatgcagtg gctcaggcct gtaatcccag cactttggga ggccgacgtg   7500
ggcggatcat ctgaggtcag gagttcaaga ccagcctgcc caacatggcg aaaccccatc   7560
tctacaaaaa tacaaaaatt agccagggat gatggtggat gcttgtagtc ccagctactc   7620
aagaggcaga ggcaggagaa tcacttgaac ctgggaggca gaggttgcag tgagccaaga   7680
tcacccattg cactccagcc tgggcaacag agtgagactc tgtctcaaaa aaaaaaaaat   7740
cactttttag ataaaattca tgctatagag agaagactat gaaaatatgt ttagcaatgt   7800
gtccatcatt aggtgattga gtttcctttt gttttgtttt actgaaaatc atataaagta   7860
tgttatctgt aaaagttctc tgacatgcac acataaaaat ttgggagaaa agattaacta   7920
taatgtttaa tagattttgt acacatttct ttaaaaatat ataaaacaca acacctttca   7980
attggtttgc aagaataacc aattgacatc atggaaaatg gaaattcact tgctgaattt   8040
taacaaaaat ttgcatgatg agtgagactg acaacttagt gtcatgattt aatgaattat   8100
gccaatggta aacttcatgc acatggggcc aggtaattat gtggaaactt tttcaatgct   8160
taaagccaag tattgaaatt aaacttagaa tcagaccttt gaaccatttt atgacaatgt   8220
tcaaaaatta taaattctat ccacttatat tataatatta aaaatatcat tacaaaaaaa   8280
acctgtgttt attttataac tcagcctttt taatttctaa tttcataaat atattataat   8340
ggatattgtt agtaatgtag tattattaca tgtatataat ttataagtaa atatacatgt   8400
tttggctact catgcataaa atgtttcacc cataggagca cataatcaga aatgtctgga   8460
gaccattata gtaatagata gatcatattg ccacatattt tatctcctcc ttgacaactg   8520
agctttccag atcttctggt gaaacgaaag agaaagttgt aacagaagag tgattaaaat   8580
gacaaaagca ttacttctat tacttctatt ctaataatat gagcaaagct ataactatca   8640
agtaataatg cactaaagaa ggtgattaat ctgatatatt cacaggcaac taataagacc   8700
tttctattgc agccatgaaa aatatgtgac aattatagat atcctgtgtg cagtgtttca   8760
acctttatgt gacctgttct actaacagat ttagtgatgt tcactttgtt agaattttct   8820
tacacatgcc ataacttgct tcagtctttt gattatgaat attatggata ttaaggattc   8880
tagactattc tagatttaaa aaataatatt gtcacctcaa tcagaaggga aatattaaat   8940
agttctcatt ttttcaatgt ttactcagtt tttgtccaat gtaatgaaag tgtcagcagt   9000
```

```
acaggttaca aaataaaatg tgtattaaag taaactcatt tgaacaggtt aataattgta   9060
gagggaggga aaaggctaaa agattgaatg taaaacttat gaaaagtaga tacatcgtct   9120
ctatgatttg cagtagtcaa ctgcatacag atgaatcatt ttaatacacg ttaactactt   9180
tccttttaca gatggagaaa ctgagaggaa gaaagtttat atggttcatt aaactttgtg   9240
atgcaagcta aactaacctg tctctgtatt ttccatctac tgcccttatc actatctcat   9300
tagaatactc ttcaagcatc tccttactga ttttcttacc aagcatttgt taagttctaa   9360
tgagagttgg tagtaacatt ttcacccact ctgtgaaata tgaaatctta ttcataggcc   9420
tcttctttta ttcttgtatt tgcatatcaa ccaattaatc aacttgcttt ctttatgttg   9480
cttattatct tagtccttac taaattgcct cttaatgttg tccacataac agaaatgtta   9540
aggtggatac ttaacatttt agtccagtct agccggtgcc agtgcaatgc caaatcatga   9600
attaaaatat aattacaaga accacttatc aaattttaac aattccttca gctttgtgac   9660
agtttttct acttcgatta aagtcaagta aaattaaagt taaatatttt tattaaaata   9720
tctcctttaa cattccatat taataaacat attaaagctc atgcttctaa gtagattact   9780
agaagttact ttatcgaatt acagcaatgg ttaattctag atcatagaat ttagaatgac   9840
tttttgcctt cttctttttt ttccttttttt ttaaacagag tcttgctctg ttgtccaggc   9900
tggagtgtac tggcgcgatc ttgactcact gcgacctctg ccctgcaggt tcaagtgatt   9960
ctcctgcccc agcctcttaa gtagttggga ttacaggtgc ctgccaccac acctggctaa  10020
ttttttttt gtatttttag gagagacagg gtttcaccat gttggccaga ctggtctcga  10080
actcctgacc tcaagtgatc cacttgcctc agcctcccaa agtgctggga ttacaggtgt  10140
gagccactgt gcctggcctg actttttgct ttcttcttaa tacttactag tatttcttga  10200
atttttaaaa aagaaacata aagtactttg ataaaaccaa cagtctcatt gttcttaaaa  10260
ttgttcaaag gttctctgga aaaaaaaaag aaaattatca tttggttaag aatcatgttg  10320
gtctgacatc aatcatccta taggagtgaa tattgaaaaa gtaagatata ttgtggtata  10380
atcgagattg cataaatttt accatttttg agaagaatct gctccaaatc ctggcttaat  10440
gtaatatcca gcatgctact taattttctt gtcttcacct tttcatatcc acatccacct  10500
aggtgccacc tcacagtata agccagcata atccattctt ctcaatgaaa ccacaataca  10560
tctgaccctg catctcagga gaactgtatc agccacagca cttccagttg actatgaatc  10620
tgaatgttat gcctcaggag aaacatcctt gctgggactg agtagtgatt caaggagata  10680
gttatgattc agtcaagaaa ttaataatta gtgttatttt tattattgag acagagtctc  10740
gttctgtagc ccaggctgga gtacagtggc atgatctcgg ctcactgcaa cctctacctc  10800
cccggttcaa gtgattctcc tgcctcagcc tcccaaataa ctgggacagc aggcacttgc  10860
caccacgcct agctaatttt ttgtattttt agtagagacg gagtttcacc gtgttagcca  10920
ggatggtctc gatctcctga cctcaaggtc cacctgcctc agcctcccaa agtgctggga  10980
ttacaggcgt gagccactgc gcccggccat aaattattaa ctgagccagg cacagtggta  11040
cacacttata gtcccagata ctcaggagac tgaggttgga gtatcctttt ttatgttatt  11100
ttatttttaa ttattatggg tacataatag gtgtacatac ccatggagta caagtcatgt  11160
tctgatacag acacataatg tttaataatc acatcagggt aattgggata tccatcacct  11220
caagcattta tctttctttg tgttaggaac attccacctc cactcttgga ataggcaccc  11280
tgttgtgcta ttaaatacga ggtcttattc atttcatcta actatatttt tctacccatt  11340
aaccatcacc tcttttcccc tcttccccac tacctttcct gtgaggctgc aggattctta  11400
```

```
agcacaacag ttagaggcca gcctggacaa catagtgaga ctcaatttct aaaaaataaa  11460
aaagaaatta ccaactaatg ctaaaaaaat agtctctgat gcttaggtat gaattagaaa  11520
tgaccaaaaa aaaaaaaaaa aaaaagactg ccctttgctt ccttctcccc ttctcttcaa  11580
gttttccatt gctactcatt ttagtctggt ttaatcaggt ttcatccatt aaaagcaatt  11640
gttgggatca cacattttga gttgtgtcag tggacttccc tcatgctggc atgattcctg  11700
ccccaagccc ttagtaaaag ccaccaagcc atataacata atctctcatt gagtaaaaca  11760
tctgatgtgt ttagaatgac ttctagcaaa aaaccagcct gtccagcatc atctctgtat  11820
aacagataaa ggaataggta ctgcatcaaa aggttataga acctgcccaa atcaatccca  11880
tgtgttttgc aatggaatta ggttgaacta aagtgaaaat tcagttttct actcctcatt  11940
aacatgtctc atgttgcaag gttgagagga aggagaagaa gaactgtatt tacagagaga  12000
ttccccctct ctttctttct acagattact aaaacattca aagaatcaaa tttaagaaat  12060
cagttcatca gagctcatgt tgccaaactg aggtgagtgg aactgtagaa aaaatattta  12120
agtatagata caatgtggca tacttgactt tttgtcacag aatgaatagt aaatgacatg  12180
ttcagataag ttgttgtaat attatgaaaa tagtatttta gtcagcttaa aaaccaatgc  12240
caaaaaagcc aaacatatga tctatttagc tactaatgta aataaccata ttatatctat  12300
tcttattggg aagaggaaga aggggtggag agagagttgg ggtgaaggta cagtaacaag  12360
gccatcctat tgtaaaactc cagtggatat cattcacagt gcagcctatg taaacagtcc  12420
ctcctggagt tgtacaatgc tgtggtttgg gtgtatccat ccaagatcaa gacactatga  12480
ccaacatcaa aagtggcttt ttggttttat ctgcctgatg tgctataata aaagggtatt  12540
atggccaaat ccaaggcatg tctatcatga attaataata ggaggagtag cagcatgcat  12600
gctagttatt tgccattcct gccttagtta aatatgatgt gataaaacca gcctttccaa  12660
ctgaaatagt cacctttact gactctcccg caaatgtctc aaatgaccac attgctctag  12720
tctttaaata atatgcaata gttctttggt agaagaggaa ttatactaat tctttctcaa  12780
atactagcat cacaagaaaa ttaattcttg ttctctggag agtcacctag taagtatctg  12840
gagcacagat gtctggtcag gtaagttttg atgaggagtt aaagggataa gaagagtcca  12900
tgagaagggt attttccaaa acacctttcg gtcaattcag tgcacattca cttagtactt  12960
tcttgtcagt atctgtatca gccactaatg ttcaaaagtg agtaagccct gaaaacctgt  13020
aggactacat gagccttctg ccttttctct ccttttgttc acttcccact tatcactcaa  13080
tcctctgcaa cctggcttca ataccaccat aaaatatcaa ctgctcttgc cgattcaaca  13140
atgacatcca gataacaaaa tccaaagaaa ccacatcagt cctattcttg gacctttcaa  13200
cagtatttgg tcctgttggc ctgtcactcc ttgaaatagg actatccctt ggtttgcatg  13260
gccttgtata ccctgatttt ccccttacct ccctagctat tccttcttag tttcctttac  13320
taggtcttac ttctttgtat attccttaaa tgttgctgaa catcaggctg tgctctaggc  13380
ctctcatctt ctcaggtcac actctctcct ttccttggcc ttcactgcca cccatatgct  13440
gagtgctctc aaagttgtat ctctaggcca gtcctctttt gcctccaaac atgaatatat  13500
gcagccatct acttggtacc atcacatgga taattctcat gatctcttcc agtatgactg  13560
cttctttatt tttttctggg ctctttttta gcattgcttt acatggaact ttatcatgtc  13620
tctcaacctc tattttatct tttatctatg tatgtagagt ctgtgtaatt tcttcatctc  13680
ttttagataa ctaatatctc ttcagctttg acttgtattc tgtgtaaccc atttattgcg  13740
```

```
ttttcaattt caatgagtat gttttcctat ctgcaagttc tatttgtttc ttttgagaat  13800
cttcctggtc ttttaaacac atttcttatt ttaattttg ggggtaccta gtagttgtat  13860
gtatttttgg agtacatgag atgttttgat acaagcaaac aatgcataat aatcacattg  13920
tgtaaaatgg ggtatccatc ccctcaagca tttatccttt gtgttacaaa caatccaatt  13980
atattctttt agttattttt aaatgtacaa ttaaattatt attgaccata gtgactctgt  14040
tgtgctatca gatactaggt gatcttttaa aaataatgtt ttctacttaa tctcattttt  14100
atgattccct cttttacgtc atttgtcatt tcaaatacag tcacttgtct gttgattcta  14160
ttatgtgaag tttttgagga taatcttttt gttactttga ttccaccttg gtatggtttg  14220
gctgtgcccc cactaaaatc tcatcttgaa ctctggttcc cataataccc acatgttgtg  14280
ggagggacct tgtgggaggt gattagatta tagggacgtt tcccccctt gctctgttct  14340
ttttcctgcc accatgtaag aaagatgtgt ttgcttcccc ttctgccatg attgtaaatt  14400
tcctgaggcc tccgcagcca tgcaggacct cttttctttg taaattaccc agtctccggc  14460
ggttctttat agctccgtga gaaaaaacta atacacacct catgatgtat tgtttaccac  14520
tgaaattgta tgcttaaatt taatctcact tgggaccctg tacaacctag acttaacata  14580
tctacctcca gagcagttac atctgtcaga cattctagag gaatcagcag cacatggact  14640
ttgttgttgt taatttgttg tcgggggagg ggggagggat agcattagga gatacaccta  14700
atgctaaatg acgagttaat gggtgcagca caccaacatg gcacatgtat acatatgtaa  14760
caaacctgca cgttgtgcac atatacccta aaacttaaag tataataata ataaaattaa  14820
aaaaaaaaag gttctgggag tattcaggta gtattaatga agattcagac atcgtgcagc  14880
caggcccatg cttatgaatt ttcaggtgat acttcttttt cttttttctt aatttaaagc  14940
tggatctcgg aaacagataa atttattttt ttatgacatg acgagcattt ttttcattct  15000
agttcatgct gttattgggt gtttagttct ttgagactcc tggccttttt ctaaaacctc  15060
aagttcaact tcctattttg cactggccca aggtcccatc tccagtctct atgtaaatgc  15120
taaacataag cctgtggaat attctagtct caccacatac tattcacatt cttctttgtt  15180
tttggtcttc caggattttc cttacttttc tatgaaccca gtcttgcatt tgaaatggaa  15240
tttattatat attatctatc ctttctattt gttttatgca gaaagtgttt tctaaaatta  15300
tttaggcttc catattgcta gacatggaag ttgtaattat ttgttcagtg cctgtttcta  15360
catctaaact gcaagaccca tatggcaact gtgaatctta gtcccagcta atttctgaag  15420
cttagaatag tgcctagcac aagaagttgt ttatctaaca tttttaaaaa taaatattaa  15480
attcatatct ggaatgaata ttaagttaga gctggtcatt gaggtgagag gaggaagcca  15540
agagagaata tgagagcctc aaagccaaat atctttaatg tactttttca gaaaagaaga  15600
cagccaatgt caggtggagg aactggttta tgaggtaact ttcctggaag aaaatagaaa  15660
ttactgaggt tttagataat ccaaatattt aatcaagtca ccaaggttta ttgtggggaa  15720
tctttattat taattaaaat gagtgatgaa atcttaatat acgacaaaag ttaaaatttg  15780
cttttgcagg cagatgaatg gtctaggtat caaaaaatta agttgagtct ctaactcaca  15840
caaatttaca accctatcac tttatgaatt tgtttaggag attattttta ataacactgg  15900
tgaagtctaa gaatagctaa aatttatagt acacttattg tgtgctattg actcttcttt  15960
gaagttttgc atatagtgat tcatctaatc ttcataaccc attttacatg tgaagaaact  16020
tagatataga aagattaaga aacttacata acttatccaa agttacacag taaaactctg  16080
gcattataac ttcaaaatca gctatcctac agtgagtaca gtgttctgtg cattgaaatc  16140
```

```
aaataagtga gatagcatcg tgatatagta ttacgtatgc aaacactgtt acagagatct  16200
gtctaaagtt aaattccaca aatgaattct ttaaaagggt ttaatcaaga agaatatata  16260
aacaggatgg tgaaaaattg tcatattatt tgttttttaa aatatcttta tgatttacag  16320
gcaagatggt agtggtgtga gagcggatgt tgtcatgaaa tttcaattca ctagaaataa  16380
caatggagca tcaatgaaaa gcagaattga gtctgtttta cgacaaatgc tgaataactc  16440
tggaaacctg gaaataaacc cttcaactga gataacatgt aagtataatt tttcataaac  16500
aattttattt caatatatcc ctcaagttta ccaattcaaa ttcatatttt aattgagagg  16560
ctgacttttc tttctttgaa actaaactgt gaaaacaatc cattaaaaag ctaaatatac  16620
catatagctc cctaacgtaa atcattctaa gacttaaaga atcatttggc atttatatag  16680
taaattttat ttgctaaaaa ttctcattaa ttatccctgc aacattcctt atgagtgatg  16740
ttactgtcag atgtcattag tggataggcc ataggagggg tacatagatg ctcaaggtca  16800
gagaactatt taattaatga tccacctcag aggcttcttc atttttcttt gtaacattta  16860
tcacaattga aattacaaag ttatctgtgt aaattttgta ttgtttggct tcatcctaca  16920
ctgtaatcat cctaaaagaa agaaccagtc aaccttcttc atcctactac cctcctacca  16980
cccagtctcc atcatataac acatattcaa taaataattc ttgcatgact gaaagaaaag  17040
aaataatata tgcatagaat ttaaggacat tcctccaagt tggttacatt ctgctagttt  17100
aataagccat tatttcttct cgatgagctc aagattaaaa ggattttgat gattcccata  17160
ctagactggt aggtaccagt tacagatgta ctaactgtta aatattgaaa tgctttccta  17220
tttgttggta aacaattact gcatcaggcc cacaaagttg tcttccgaga tgtttcaaat  17280
ccactgcccc tgctgctaaa gagttatgct tagcaaagca aagcactcta agacactgct  17340
ccaactccat ggcctgattg catcttttat gactggccaa tgctcacgca ctgcagtttg  17400
ttaggtagtt gaatattacc tctgcttcca cacattaagg aatgctcccg aacgcacttc  17460
ccaagtgttt atttatttat cattatacta gacaatatgg tgatacgatg gtcacagaat  17520
agcggtttcc acctccagag cccataatct agttgaaggg aaagatattc caacacaaga  17580
gtgttgacaa tcaagataga atatgatcaa gggcccagtg tgaggcccag gcaatgatca  17640
ctgcaggaat ctggggaaga aagagaccag cgtgcttggg atatctagca aaagtttcat  17700
gaaggagaat ggactttgac tttgaaatat gggtaggatt tacatatttt gagatgagaa  17760
aaagaaagtt cccagagaag gaaagcatga aaaggcaaac agtctgtact gaacgcgatg  17820
ctttgacaga ataatgaaga aagggacctg ctggaatgat tgatcagtgt tcatcattca  17880
caccatcatc atcaaaacac ttatttaatg agaacttact gtttttttagg catggcttta  17940
atgccctata tgaatttttt tcttgattaa tccttacaac aaacatatcc catagatagt  18000
tttattgtcc cccttagaaa agataaattg cctaggctga cacagtcagt atatgaggca  18060
gtcaggattc aaactaagtc tgtttgttca aaaaattaag aatggccagc tttttaaaat  18120
tttctgtctc cagaagtatg atttggctcc actgaagttt gcaaaacaaa tgtgataccc  18180
aaaccttgtg aaacttttag tgggaaataa ctttgcataa gtcggtttga gagagcgtgg  18240
aaacctgtct tgaaaagttt taatttaact tgcaggaaat aaaaaatgatg ggtttctcaa  18300
ttaaaaattt caatcaagga aggatatgag ctaacataac atttttttaa aaagatcagt  18360
ctggtaaggt agaggtgcat aaactgaaaa ggagcaaaag tggtggaatt cagttagaaa  18420
attattgtaa ctgtactgat gtcaaatgat gaaaccatga actaaagtag taccaaaagg  18480
```

```
agtgaggagg atggaataat tcaaaagata gaggacagat gtgcagaacc tggagattat  18540
aagatgtgaa aggaggagtt tgagaaaatt tcagattttg gaagtggtgt cattttacta  18600
aaaggatata ataagtagca aattttggat aaagttgggt cccactgagt ttgagatggc  18660
tgttggacat gcagagaaaa ctgtcttgta tgctgttctt aaattgaaat agacagacct  18720
ttaccctctg atactgacat attttccttt ccaggctcac cctccatttc cctaaacaca  18780
acacatgcac tagctctcct tactttattg ctccacaaac atcttacacc tccaagcatt  18840
tgtgcccact gtaccttcta tctggaatct cttttgtcct cttgtgtgcc tgaaaaattc  18900
ctttcagatc ttcaaaatac agtgcagatg ctatttcttc tagctcaaat attatctcct  18960
ccatataatt taattactct cttttttctt ttctctactt tgcacttaca tttatttgaa  19020
tgattgcttg attaatttct acctgtaaat tatgtgaggg caggtcctct atattttgct  19080
cgcagttaaa tctgcagcac ttattataga gtggtatcat tagagtaata tacatatatt  19140
tgaggacatg ataaattaac ttcccctata gtatttatca cattgcatct caatgacttg  19200
cttatgtttc tgttttccca tataaattga gtaacttgaa aaaagagata tctattaagt  19260
atttaatgag aaattaaagt acaaacttta gtatgcataa caacaaattg ggaaaaggtt  19320
gtaaacaaag agatttgtag ggcccatgag ttagagatcg tttcagcagg tctgaaagga  19380
agcctaggaa tctgcatttt agaggaccac ctcccaaccc caacaagtaa ttctgcttct  19440
tgttgtctgg gtactgtact ttaagaaatt atggtgaaat gatatcagcc tttattgtat  19500
ttatcttatt ctcatttttt aatactagca cttactgacc aggctgcagc aaattggctt  19560
attaatggta agttttaata ttattttgta actgtaattt gccaaatcat aaagagtaaa  19620
agtgcaagtc ttttgtgtac ttttggccaa ggcagtatct atcaagttga tgtctttgtt  19680
cttagttcgc tcaggtggtg ttgaaacaag acagtgctga tcccaagtgt cccatggagt  19740
ggactttagg tttccccttt ccttttagaa aaaggaagaa gttgtagtgg aggactaccc  19800
actctgcact caaaattgcc ctcatgaaaa tttctttggc agctttgaga accttttact  19860
gccctggttc taaggtggca tttctgtaga cttacaaatt atgtttgatg acaccgttta  19920
tgtagcttct cctaaccacc agagtagctt gctttgttgt gaattcaggt taatcacaaa  19980
gtataataaa aaagaattgt cagaagtctt cccagctttg ggtctataac ctgaaggaaa  20040
agtcactact cttcaacatc atcctatgta ctctcaggct aggatagcag aaatgcaatc  20100
cctagaaaac agcaacttac ttctctgacc aaaaaaatgc agttaaaaat tagttcaatg  20160
tacctggtag ctggcctatc ttaggtactt cagtgatttt acaaagtgat ggtagtccta  20220
tgggtgtttt tcagcttcac tacgtattta attcatgctt attgttaatg aaactgtgat  20280
aagcaattta ctagggtatt tgtttgggag atgccacaaa ggaacacatg tatctcttaa  20340
tggaagcctg gtcctccttt atccaggaaa tttgctagga aaaaaaagcc tttaggtggt  20400
tgtgctatta aaccagggca ctacttaaaa gccagcccag caatagttgt gtgatttacc  20460
attaatttct tagtaataga ccacacaaaa gaagaaaatt atgggaatgc gagttgagag  20520
gaattgggtg atcagcctac cccagcccgt ttcagctctg gccagtagac tattcacgag  20580
ctctttgaaa acatttaaat aaaccttatt tagatactag aaaccctctg tcaccctcaa  20640
gaatattctg tggtatagcg actcctttat gagggcatgt ttggtaatac agcatcagtc  20700
ttggaggtgg actggattct acaaggtgaa ctgcagtcac taaggagtct tttggatgag  20760
accagttttc ctccaacttc aatgtgtgca tgaacctcac atcaaaatgt agctttagat  20820
ttgtcccatg atgtggttcc aagaatcagc acttctaata agtttccagg ggatgcccat  20880
```

```
gctgcaggcc cacaaaccac actgagcata gcaagactat tgagaaaaag gaaatttccc  20940
aggagtctgt ggcctgagct ggcacatcca ataatgacct atcttaacct caactcatga  21000
ggaattccag ggaactctga agctgctcaa aatttgaagc ctatatgcca actaaattca  21060
gaaatgttct ccaaaatgct atctataagc aacagtagtc acaaatgcat tgtagaaata  21120
tatcgatcat gctttttgga aaatccagca tgtcctgagg aagaatgtat aagacataaa  21180
agtcataaat tatggaaaga ctcttcagct tcttccaaat gtaaaggaat catgatcttc  21240
ccagcacatt aatgcccttt ctcattagaa tgtggggccg gtccagacct aataacattg  21300
tctgagcaga gaatccttgg aggcactgag gctgaggagg gaagctggcc gtggcaagtc  21360
agtctgcggc tcaataatgc ccaccactgt ggaggcagcc tgatcaataa catgtggatc  21420
ctgacagcag ctcactgctt cagaaggtga ggccaccact acctacccat ctgggaacaa  21480
ttagaataga caggtcatga agactgcacc ctctacccta ggattgaatt gagccagaaa  21540
taattcaatg caaaaaaatc agtaagaatt ttcttcctat tcatgaaagg aaaaggattt  21600
ttccccttta gcatgctaat ttagtgctat ttctctgttt caggtaataa tatattagca  21660
cagtaaagaa caaagattta tatgtcagaa tgttttttaa atcctagcta taaaagctta  21720
agaaatttac taaatctcca taagctttat tttttttcca aattaaggga caacactgtt  21780
atctgtgact tagtgttact ggtagcattg agtacactaa tgtaaacata cgttaaatgt  21840
tagcgaaacg aattgctgtg gaagatttgc acattatatc atgggagctg atggctaacc  21900
tagagactgc cccatgccat taatttattc attcataaag attattgagt atctagtatg  21960
agcacagtgt tatatattgt agaagctact agtataaaca aagtattgcc tctgccttca  22020
aagagcttac actcgaatgt tggaatcaga atgcacaaaa ataatgatca attacaatga  22080
gtagcataaa taaaattaat gtaggcaact tacaagaatt cttaattgag gtgactaaac  22140
tattgccaac actagggtga tatgctacca gtggcgagta ggttgcataa acttacctta  22200
ttggtaaaaa gaaaagttca cattgctcat aaaagaagga ttttagattt cagcataact  22260
aaaatctgtt tcaaacctgc cttgttactg gggcatcgca gaccacaaca gttgttggga  22320
acttaactca aaaagttcac ccagaaaaat aatggagatt tgaactcgtg tgcccctgac  22380
catatcaatt ttcttctcag actcttactc taaactggac ctccttatca cacacacaaa  22440
gccttccata ggcagatcaa tccagtctta tttctcaaag catgtacctt gagcttcaga  22500
taaacagcat tgttctcttc ccctggactc ttcctacatt tccctaccta tgagtatctg  22560
atcaatctgc ttatccttga aatgttaata tatttaccac atctctattt gaattttatg  22620
aaatttttga taatttctaa gtagtttttt cagatttata ggcactactt catggtacag  22680
tgactgttac aaacgtattt gttaaattta gaaggaataa agatttaaaa gactagggta  22740
gttactgaac taaagtttta ggaaatccca aattatttca aatttttctt atggtaattt  22800
tatgacttaa tatttttata tgcagtgaac aaatttgaaa ctttaaaaga tactcccaga  22860
attatcagtt ttctgatgta gattggcaaa tttattacta tatcccaaat aacccaagag  22920
acaaaattca caaaaacatt tcaattttca ttgccacttg aaaggccaaa aagcagaaat  22980
ggcacgcatt gatttcaatc gtactcttga gtgtgggaac caggaattaa aatacctgga  23040
cttatcaggc acttagcata accaagaacg gaatagaaac ctccctggat tctaagccct  23100
attcagtccc aatcaccaaa aaccaagtaa acgatatcac tataatgaaa gccacagtta  23160
taaatatcga caacgattac caaaggaatc catggaactt tgaattttgc caccccacat  23220
```

```
ccttctattc attaccatga ttgatccact aaagctaaca gactctgtga accttgtatt  23280
ggacccctcc ctaaagacct gattgtcact gagaaccatc agtgaggatt tgtttggggc  23340
atgaccagcc ttacatcaaa gtacatagaa gtgatgaggt cttatcaaag aggattattg  23400
aattatcacc tcttctatgt agctttccct gatactctct ttcctctcca ttgagttcca  23460
cagaaatttt tttatctgcc tttaacagtt gtcctcatga tttgtgatat ttgacttacc  23520
tcttgtcagt ttccttcact agtgtagagt tcctcaaaga aagagaccat aattacttat  23580
atttttattc ctggagactc atactattcc ttatacaaag tagacactta acaatggctt  23640
gttgaactat aattaatgaa aataatagct accttcatga aagttcactt tgtgccaaac  23700
actatagttg acataataca tttgtctcat taatacttaa caattgtgtg agaaggtatc  23760
accaatcaca ttttatatgt aaataaaccc cagagctatt aattaacttg tcataaataa  23820
cacttttcat atgtggcata gccaagattt aaatataaat gttactggtt ccaaaatgat  23880
gctctaattc acttgctgga aagaaggaaa ggaagaaaat aaacgagtgg aaggaagaga  23940
gggagggaag agagaaaagg aaggaaagaa aaaagagtct cttcagaacc ttcactgtaa  24000
agactccgag caaaagaagt tgaatataaa aacaacatag gtttgtttgt tttctaatat  24060
tttttcttca aaatttttaa ctcaggttca ctcttacaca aactactgtg tcttataaaa  24120
gtatttccgg tcatagaatt tttattttct gtattaactc cactatctaa tctccataaa  24180
actcctaaat tggtattatc ggtaacattt tgtttttact caacccttag gaacaatgtt  24240
aagttaatca gccctccaca tcacagatcc ttattttcat cagtctgtac aaggcatttc  24300
tctcatttta attttttttc ctcctgtcat ccctggattt cactttcact gccctccttc  24360
cacccatatg cctcatacta atatattcga aatatacatg tcttaaaggt acatgcacgc  24420
acctacaaaa cctatagtgt ttttttgtat gtatatgtct ttaatttaaa taagtagcat  24480
tgtgtaaaag tctaatattg tttcttactg ttttcactca attcttggaa ttttcatctg  24540
atgcactgct gcatagcacc ccatggtatg cagccaccat atttccttca tccaattagg  24600
ttgcatgacc taccttccca ttgccacaaa gagtacacac aaaatatttg tacttatctt  24660
tctgtaaacc ttcaggaatt tcagaagcac acatgcaggc tgctaaatat accagaatac  24720
tttccagcca cttaaatctt taccagtatt gcaaaagagg ccccatttcc ctccacatca  24780
acatttagta ttattctttt gtttaagttt tatcaatctt ttaaatgtac acaagatgct  24840
catttttata attttaattt ctcagattac tagtttgagt atcttttcat atatctaaga  24900
gctgttttga tctcccctac catgaactgc cactaatatt ctttgcctat tttacaatgg  24960
tttttctgct tatttattac tggtttacag acttttaaaa tatattctac aaaaatttta  25020
gacattaaac attaccaata ttttcccatg gttcctcatc catctggtaa acttgtctat  25080
ggtatatcta attttgattt aatagaattc attctatttt taccttttag tttgtgtttt  25140
tgttgtttag ccaaaaagtc cccattccta ggtcataaag gtaatgtcct tttttttttt  25200
ttaacgctac tgttctctct ctgtctcccc ctatgtatat aggtgcacat atacttgtac  25260
acacatacat atacctatat atgaggggag ttcgataagt ttatggaaaa taaaattaaa  25320
agataaaata aaaaattata aactttattt ctcaacataa gctccttcaa gttcaagaca  25380
cttttgtaag caataatacc agccatatcg tccatcccta aagaactgag ggtcctgaga  25440
atttaactat gtcaatgcag tcttttttac attacttttt tacagtactt attgatgaaa  25500
aatgggtgcc ttttaaagat tgttttaaga ttagggaaca aaaataagtc agaggaagtc  25560
aaatcaggac tgaaaggtgg atgcctagtg atttattgct gaaactttca taaaactaac  25620
```

```
cttatttgat gagaggaatg agcatgagca tggttgtgat ggagaagaac tctggtggag  25680
ctttcctgga cactttttct actaaagctt tggctaactt tcttactctc ataagaagaa  25740
gatgttattt ttcactgacc ctttagaagg tcaacaagca aaatgccttc agcatcccaa  25800
atgtctgttg tcatgacttt tgttcttgac tagtctggtt ttgctttgac tggaccactt  25860
ctacctcttt atagccattg ctttgatggt gctttgtctt caagattgta ttagtaaagc  25920
catatttcat cttctgttac aattcttcaa agaaatactt cagaatcttg atctgacatg  25980
tttaaaattt ctattggaag ctctgacctt gggtgcagct gatctgggcg aaacagtttt  26040
ggcatccatc aagtagaaag tttgctcaac tttagttttt cagtcagaat tgtataagct  26100
gaaccagttg agatgtctat ggtgttgtct attgtttctc acagttaatt gttggtcctc  26160
tttgagacat gaacaagatg aaatttttcc tagcaaactg atgtggatga tctgttgctg  26220
cgggcttcac cctcaacaac atctctttct ttcttgaaac aaattatcca ttagtaaact  26280
gatgattggg ggagatgctg tccccataaa ctttttgtaa ggcataaata atttcaccat  26340
tcttccagtt tcaccataaa tttgacgttt ttttgcttca attttagcag cattcatgtt  26400
gctttgataa gagctctttt caaattcatg tcttattcct cttagtgcct caaactagat  26460
cttgttcagt atgacaagtt agtatgagtt tatctgcatg caaaaatctt tgaaatccat  26520
gcatagtttg tttataatat acattttcaa tgaacttttg aagaccccat acatacatat  26580
gtatatatat gcacacacac acacacacac acaccaaaat cttcaaccat tatcagactt  26640
agtgcagaaa aattattcat ccattaacaa gataagaatg ccccttatca tcactactat  26700
ttaaatggag ctcctggcta aaggaaaaga cagggattga aaaaaattag ttaaatctaa  26760
aatgtttatt atttcaggtt tcttagttgc ttaaatggga agggaggtat ggacaaaaga  26820
gaaatcaaag atatttgtgt tatgctactt atcattaaag tatcagaata acttcattgg  26880
aatagaaaaa caccaagatc accccacgat atgttttcta aaatcttctc catttcttta  26940
gacaagtgac catgtattcg gccagtgaag aattaaactc acttgccagc ttataatgca  27000
ggaaaatata gcaaagagat gtggatccaa tagtttctag atagtggtac aggatggcta  27060
agatgaattt atatatctga aatgttcaca aattccctac tcatatagca tgttttcata  27120
atgttttagc aactctaatc ctcgtgactg gattgccacg tctggtattt ccacaacatt  27180
tcctaaacta agaatgagag taagaaatat tttaattcat aacaattata aatctgcaac  27240
tcatgaaaat gacattgcac ttgtgagact tgagaacagt gtcaccttta ccaaagatat  27300
ccatagtgtg tgtctcccag ctgctaccca gaatattcca cctggctcta ctgcttatgt  27360
aacaggatgg ggcgctcaag aatatgctgg taagtgtctc ggaaaaaaaa attaacaata  27420
gaaatgtctt atatttgcta ttaggtaatt ttttaaatta ggaaacatct ggaataggtg  27480
tttctattct tctacagaca gaaccattct atattctgct cagcccaagc tctggctacc  27540
cctgagtctc cttagcaaag caaagcaatg ctccagaaac tatgggaatt ctcaaatata  27600
gtaataggaa aatgtaaaag aaagttatga agacacgagt tctttaataa tccagagatt  27660
ctataagatt caaatagctt ccctataaac aataaaaaag attttgtttg tttgtttgtt  27720
tgcttgtttt ttagagacaa agactttctc agactggagt gcagtggtgc aatcatggct  27780
tactgcagcc tcaaactctg gtcttaagaa atcctcttgc ttcagcctcc caagtagcta  27840
gaattataaa taagtgtgta ccaccatacc cagctttttt tttttttttc tacagacagg  27900
ttcttgctct gttgcccagg ctggtctgga attcctgccc tcaagccatc ctcctgcctt  27960
```

-continued

```
gttggcctcc caaagcaatg ggaggattta gattagacat tgtatgaggg cttaataatc  28020
cttaaggtat taactgccct ttaaagtatt ctgggatatg gcaaaaactc gatgtgtata  28080
taaacattgg tcatatttgt ttattgaatg aataaaatgg aaactaaaat gaggacaatg  28140
cacaagagct actagaacca gtaagagtat cagcgaagga gtggaagggt agcattgaca  28200
atttccctgg gcttttaccc atgttgtaga ttgtctctcc aaggaataat acaaagcctt  28260
aatagtccta gaacacattc tattgtgttc ttatggccca aagtaaattg gtgtagtaga  28320
taacatttgc accagtcatg aaaaactatt ggtgtcattc tgagagtaca tcaatataaa  28380
atagactagt tctttagcct tgaaactaga ctggtttctc ttttgctgct aggttaaagg  28440
ttattcaata tgtaatcttc caatccaaaa tctgtcagtg gataatttaa aagcttttag  28500
tcaattttaa gatatttgtt ttcttaaaat tttaaggggc actgtgtcac aaagctaaag  28560
aaaaaaaaga aaaaaaaact gatctgtgaa aggggttatc ctcatctact tggggaattt  28620
tggctgcgaa gaaactccaa agtaaatctt tagaagcctt cattgttaaa tatgaaataa  28680
tgtttggagt acatttattt cttctcaaat ttattatagg gtcaataatg tacacatctt  28740
gaagtccatt tttttcctgc ttttataaca aacaggccac acagttccag agctaaggca  28800
aggacaggtc agaataataa gtaatgatgt atgtaatgca ccacatagtt ataatggagc  28860
catcttgtct ggaatgctgt gtgctggagt acctcaaggt ggagtggacg catgtcaggt  28920
aagctcaaga caatctcatc catgtcatca tccaagaagt gtataagcac ttcctagtat  28980
gtgataatgt gatagacata agtgtaacag ttacaataca cagccctgtt cctctaaaat  29040
ttataatcta gattttagaa ataaattttt ttatgaatga agtttatcta tcatgaaagc  29100
attaactctg agaggccaaa ttacagagta gttaaccatc caaagctcaa gaatcagaaa  29160
gacctcgatt tgaattcctt aacctctatt accaagtctc taactaaaag ctggggataa  29220
tcataatagc acctaacttt ttgggtacta agaaaagtta aatgaagact aaatatatca  29280
ggcacatggt aaacaacaaa gaaatctcat ctatttcact attattaatg tagaccatgg  29340
tcactcgtgt taataacttt aacctcaacc ttttaactgc tgtgaaggat taaataaaaa  29400
attaatcact atattataaa aattaattga tatataataa atgaatttta agagatacgt  29460
aataattcat ggactccttg aagatagaaa atttatacaa aatcctagta atttgagtca  29520
caaaagctcc tacaataatg aaacagtatg aatgaaaaag aaaagaaata actattatat  29580
ttggatctag cccataattt ttaaccaaat gcacaaaaac aaacaacaaa tatgaaattc  29640
tcactgtaaa gtgattaaaa tcaaatttga attctaaaat tttaaattaa attatctaaa  29700
cataattgat gcagttatat gttttaatag gttttgttca catatctgaa atccaactcc  29760
acacagtagc aggaacagct ggtgtcagaa attaaatatt cttttagtct ggagttttaa  29820
aaaatcaatc tgtttacttg agtaatttgt tgctgttttc atgggtgaat tgtatacaga  29880
aggataagaa ttattcttcg catcaaaagg tcactgactt tcatatttag tgctcatggt  29940
ctttaaaaag tggataaaaa gtagttctca catttcatgg aaagccccca atccatgagc  30000
acatttccca aaatgaaaca tttttatcaa ctgcaagttg tgtgtaggtg gagatttgtt  30060
tttcaattgt caagatactg ttaattaccc agtcctttat ctccttttgg tggagatgtc  30120
tctgtgctag gaaacccttc ttgctctcct tcctgtttct cttttactac tggccctgaa  30180
acaacaaatt ctcaagtttc atgacagctt tccaaagaat ccatcaatca aataagcaac  30240
acaactcgac actgacaatt ccagacctac taagagcatt aattaagact taaaaataaa  30300
catgagtttt aaaagggtgt tattcattat tttcccattt ataacgtccc ttaccttctg  30360
```

tccttcagtg catacaaatt attatcttcc ttgaagccca gttcaagccg tacctcacca 30420
tgataccttc catgtatatt ccactctagg cctcactgat ttttaactga aatactataa 30480
tgcatagttc acacttaaaa aaaaaaaaaa aacacagcac tttacataag agcttacagg 30540
atcctatttg ttttatccat tcttttgttc atttttacaa tcattaattc aaaggaatta 30600
tattaattac tttctatgca cccgacgttg tgttaacaca acaatactat ccctgcattc 30660
agcaagtcta tggtctacaa gagaggacac aaattcaaat gtctgtagtc aagcagtgaa 30720
gctggctaga tatggaaaaa ttacaagtcc ctcttgcttt aacatttgct tgcccacatt 30780
tggtcagaca tcatgcaaaa taatttctca ctatagaaaa aaaaacacta caaaaacaat 30840
aatataaaga actgagaact ggttaactga agcatgcata tgtcatctaa aagaagcagg 30900
tgacgaccag cttcatgaag tacttgccat gcatattggc acttcacaca ctgacccttc 30960
tccccaccta gaccagtaat taaacaggta tggatgagct agctactaag agcagccaac 31020
tgaatagctg actaacttag aagcacactt ggtaataata gctgactttt attagtactg 31080
actatactat atgctaagct gtactcaaag tgctttgagt tttaaactga tacaaacatt 31140
atatgaggaa acagaggtac agagagctat tcaccagctt accaaaggtc acatagctgg 31200
taagtggagg acttaaaccc agactatcta gtttcagaac ccacagactt aatccatcgt 31260
gcagaacata agacatactc catctgtctc cccaactagg ttattatgtg cacaaatatt 31320
tattggttgg ttggttcatt attatgactg ggtggtaagt atgtcattag gagtgttttg 31380
cttatgacta tataaatttc ttcaccaaaa gaagactttc tgatgatata ctatgcatca 31440
gacaccacgc agggtgctaa ggttaggaag ataagtgaga cttctagaaa ctcattcatt 31500
caacaaatat ctcctaaggg ctagaagctt aggtttcagc agtgaacaga ataggtatgt 31560
tctctttcgt gttggacctt atagtatatc tgggaaaaca gacattgaat aaatatcaca 31620
aatgcaagtg agtgtttcag agacatgcag ctgctacatc aaaacaaaac agaacaaaac 31680
aaacaaacaa aaactgacca gtgggattaa gtgtaaatag gcacacaaat gcacaaatat 31740
gcttttataa aatagtgaag cagtgacaga gacacacaca agatataaag acacaatgaa 31800
gaacaattga gcccaaagct ggaaagggtg agagtgtgaa ggaaaaaggt tgatcagaga 31860
agttttcccg aaggagagaa agcctggatg attaggaggc aaccactcgg tgactgaggg 31920
aaatctgaaa aatgtatttg tcatcttctc agacttgctg aaggaatgac ttgggtactt 31980
tgaggatttc agtaattttt ccatgacttg gtataatatt tcaaaaggaa ataggctgac 32040
tttatttgta taatgaatgt gactccttcc tcgactgcca tagaaataaa ctccttaata 32100
ttttgggttt gtctttgcac ttaagtaatc agtcattctg ttttttttaca gggtgactct 32160 ggtggcccac tagtacaaga agactcacgg cggctttggt ttattgtggg gatagtaagc 32220
tggggagatc agtgtggcct gccggataag ccaggagtgt atactcgagt gacagcctac 32280
cttgactgga ttaggcaaca aactgggatc tagtgcaaca agtgcatccc tgttgcaaag 32340
tctgtatgca ggtgtgcctg tcttaaattc caaagcttta catttcaact gaaaaagaaa 32400
ctagaaatgt cctaatttaa catcttgtta cataaatatg gtttaacaaa cactgtttaa 32460
cctttcttta ttattaaagg ttttctattt tctccagaga actatatgaa tgttgcatag 32520
tactgtggct gtgtaacaga agaaacacac taaactaatt acaaagttaa caatttcatt 32580
acagttgtgc taaatgcccg tagtgagaag aacaggaacc ttgagcatgt atagtagagg 32640
aacctgcaca ggtctgatgg gtcagagggg tcttctctgg gtttcactga ggatgagaag 32700

```
taagcaaact gtggaaacat gcaaaggaaa aagtgataga ataatattca agacaaaaag  32760

aacagtatga ggcaagagaa ataatatgta tttaaaattt ttggttactc aatatcttat  32820

acttagtatg agtcctaaaa ttaaaaatgt gaaactgttg tactatacgt ataacctaac  32880

cttaattatt ctgtaagaac atgcttccat aggaaatagt ggataatttt cagctattta  32940

aggcaaaagc taaaatagtt cactcctcaa ctgagaccca aagaattata gatatttttc  33000

atgatgaccc atgaaaaata tcactcatct acataaagga gagactatat ctattttata  33060

gagaagctaa gaaatatacc tacacaaact tgtcaggtgc tttacaacta catagtactt  33120

tttaacaaca aaataataat tttaagaatg aaaaatttaa tcatcgggaa gaacgtccca  33180

ctacagactt cctatcactg gcagttatat ttttgagcgt aaaagggtcg tcaaacgcta  33240

aatctaagta acgaattgaa agtttaaaga gggggaagag ttggtttgca aaggaaaagt  33300

ttaaatagct taatatcaat agaatgatcc tgaagacaga aaaaactttg tcactcttcc  33360

tctctcattt tctttctctc tctctcccct tctcatacac atgcctcccc caccaaagaa  33420

tataatgtaa attaaatcca ctaaaatgta atggcatgaa aatctctgta gtctgaatca  33480

ctaatattcc tgagttttta tgagctccta gtacagctaa agtttgccta tgcatgatca  33540

tctatgcgtc agagcttcct ccttctacaa gctaactccc tgcatctggg catcaggact  33600

gctccataca tttgctgaaa acttcttgta tttcctgatg taaaattgtg caaacaccta  33660

caataaagcc atctactttt agggaaaggg agttgaaaat gcaaccaact cttggcgaac  33720

tgtacaaaca aatctttgct atactttatt tcaaataaat tctttttaaa ataatttccc  33780

tgcctaatta tttatggaag ttatgacttt tgaaggacaa ttcaaaacca tttatttaat  33840

tggttctgca atgaaagaac tgccccatat actctactaa aggcttggca ctttctgctg  33900

ccttttaatc cagcgctata attgaggcaa gcgtccagct tgacacctcg agataacttc  33960

gtataatgta tgctatacga agttatgcta gtaactataa cggtcctaag gtagcgagct  34020

agctgcaacc gaggaaaaaa cgtgccatga ggtctctgta tccaagtgtg act         34073
```

```
<210> SEQ ID NO 21
<211> LENGTH: 418
<212> TYPE: PRT
<213> ORGANISM: Artificial Sequence
<220> FEATURE:
<223> OTHER INFORMATION: Recombinant protein

<400> SEQUENCE: 21

Met Tyr Arg Pro Arg Pro Met Leu Ser Pro Ser Arg Phe Phe Thr Pro
1               5                   10                  15

Phe Ala Val Ala Phe Val Val Ile Ile Thr Val Gly Leu Leu Ala Met
            20                  25                  30

Met Ala Gly Leu Leu Ile His Phe Leu Ala Phe Asp Gln Lys Ser Tyr
        35                  40                  45

Phe Tyr Arg Ser Ser Phe Gln Leu Leu Asn Val Glu Tyr Asn Ser Gln
    50                  55                  60

Leu Asn Ser Pro Ala Thr Gln Glu Tyr Arg Thr Leu Ser Gly Arg Ile
65                  70                  75                  80

Glu Ser Leu Ile Thr Lys Thr Phe Lys Glu Ser Asn Leu Arg Asn Gln
                85                  90                  95

Phe Ile Arg Ala His Val Ala Lys Leu Arg Gln Asp Gly Ser Gly Val
            100                 105                 110

Arg Ala Asp Val Val Met Lys Phe Gln Phe Thr Arg Asn Asn Asn Gly
        115                 120                 125
```

```
Ala Ser Met Lys Ser Arg Ile Glu Ser Val Leu Arg Gln Met Leu Asn
    130                 135                 140

Asn Ser Gly Asn Leu Glu Ile Asn Pro Ser Thr Glu Ile Thr Ser Leu
145                 150                 155                 160

Thr Asp Gln Ala Ala Ala Asn Trp Leu Ile Asn Glu Cys Gly Ala Gly
                165                 170                 175

Pro Asp Leu Ile Thr Leu Ser Glu Gln Arg Ile Leu Gly Gly Thr Glu
            180                 185                 190

Ala Glu Glu Gly Ser Trp Pro Trp Gln Val Ser Leu Arg Leu Asn Asn
        195                 200                 205

Ala His His Cys Gly Gly Ser Leu Ile Asn Asn Met Trp Ile Leu Thr
    210                 215                 220

Ala Ala His Cys Phe Arg Ser Asn Ser Asn Pro Arg Asp Trp Ile Ala
225                 230                 235                 240

Thr Ser Gly Ile Ser Thr Thr Phe Pro Lys Leu Arg Met Arg Val Arg
                245                 250                 255

Asn Ile Leu Ile His Asn Asn Tyr Lys Ser Ala Thr His Glu Asn Asp
            260                 265                 270

Ile Ala Leu Val Arg Leu Glu Asn Ser Val Thr Phe Thr Lys Asp Ile
        275                 280                 285

His Ser Val Cys Leu Pro Ala Ala Thr Gln Asn Ile Pro Pro Gly Ser
    290                 295                 300

Thr Ala Tyr Val Thr Gly Trp Gly Ala Gln Glu Tyr Ala Gly His Thr
305                 310                 315                 320

Val Pro Glu Leu Arg Gln Gly Gln Val Arg Ile Ile Ser Asn Asp Val
                325                 330                 335

Cys Asn Ala Pro His Ser Tyr Asn Gly Ala Ile Leu Ser Gly Met Leu
            340                 345                 350

Cys Ala Gly Val Pro Gln Gly Gly Val Asp Ala Cys Gln Gly Asp Ser
        355                 360                 365

Gly Gly Pro Leu Val Gln Glu Asp Ser Arg Arg Leu Trp Phe Ile Val
    370                 375                 380

Gly Ile Val Ser Trp Gly Asp Gln Cys Gly Leu Pro Asp Lys Pro Gly
385                 390                 395                 400

Val Tyr Thr Arg Val Thr Ala Tyr Leu Asp Trp Ile Arg Gln Gln Thr
                405                 410                 415

Gly Ile


<210> SEQ ID NO 22
<211> LENGTH: 257
<212> TYPE: DNA
<213> ORGANISM: Artificial Sequence
<220> FEATURE:
<223> OTHER INFORMATION: synthetic oligonucleotide

<400> SEQUENCE: 22

agcacccctc tcttccgcag agtctaagaa atcgctgtgt ttagccctcg ccctgggcac     60

tgtcctcacg ggagctgctg tggctgctgt cttgctttgg aagttcagta agtgcaggga    120

gcctcgatcc caccatgtgc tcctgcagtc cccagtgctc tgagccagac cctgctctct    180

gggctattga gacctctgga ggccctccgt gaggttcctc tcttacataa cgaggctgtc    240

tctcttccct tctcttg                                                   257


<210> SEQ ID NO 23
```

<211> LENGTH: 190
<212> TYPE: DNA
<213> ORGANISM: Artificial Sequence
<220> FEATURE:
<223> OTHER INFORMATION: synthetic oligonucleotide

<400> SEQUENCE: 23
ggtcagagga ccaaaggtga ggcaaggcca gacttggtgc tcctgtggtt ctcgagataa 60
cttcgtataa tgtatgctat acgaagttat atgcatggcc tccgcgccgg gttttggcgc 120
ctcccgcggg cgcccccctc ctcacggcga gcgctgccac gtcagacgaa gggcgcagcg 180
agcgtcctga 190

<210> SEQ ID NO 24
<211> LENGTH: 171
<212> TYPE: DNA
<213> ORGANISM: Artificial Sequence
<220> FEATURE:
<223> OTHER INFORMATION: synthetic oligonucleotide

<400> SEQUENCE: 24
attgttttgc caagttctaa ttccatcaga cctcgacctg cagcccctag ataacttcgt 60
ataatgtatg ctatacgaag ttatgctagt aactataacg gtcctaaggt agcgagctag 120
ctccacgtgg ctttgtccca gacttccttt gtcttcaaca accttctgca a 171

<210> SEQ ID NO 25
<211> LENGTH: 177
<212> TYPE: DNA
<213> ORGANISM: Artificial Sequence
<220> FEATURE:
<223> OTHER INFORMATION: synthetic oligonucleotide

<400> SEQUENCE: 25
ggtcagagga ccaaaggtga ggcaaggcca gacttggtgc tcctgtggtt ctcgagataa 60
cttcgtataa tgtatgctat acgaagttat gctagtaact ataacggtcc taaggtagcg 120
agctagctcc acgtggcttt gtcccagact tcctttgtct tcaacaacct tctgcaa 177

<210> SEQ ID NO 26
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 26
gccgtgactg tgaccttctc 20

<210> SEQ ID NO 27
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 27
tggaggagcc acctgatgcc tc 22

<210> SEQ ID NO 28
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 28
gccttgccct caatggaaac 20

<210> SEQ ID NO 29
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 29
ggttgcacag caaggaagaa g 21

<210> SEQ ID NO 30
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 30
ccaggagttc ctgtgagcct accc 24

<210> SEQ ID NO 31
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 31
tggaatggaa ggagctggag 20

<210> SEQ ID NO 32
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 32
gtcccacctc ctgcaactg 19

<210> SEQ ID NO 33
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 33
tgagccttcc catcagcctg gg 22

<210> SEQ ID NO 34
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 34
ccacaatggc acatgggtct g 21

<210> SEQ ID NO 35

<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 35
ggtgcttgct ccccaaga 18

<210> SEQ ID NO 36
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 36
cctaaaaggt gttgtaatgg 20

<210> SEQ ID NO 37
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 37
ggcaataaag aaggaagacg tttt 24

<210> SEQ ID NO 38
<211> LENGTH: 120
<212> TYPE: DNA
<213> ORGANISM: Artificial Sequence
<220> FEATURE:
<223> OTHER INFORMATION: synthetic oligonucleotide

<400> SEQUENCE: 38
ccagtcaggg acacacatgc tcacacgccc gcccacccgc acacactaca gtcgagataa 60
cttcgtataa tgtatgctat acgaagttat atgcatggcc tccgcgccgg gttttggcgc 120

<210> SEQ ID NO 39
<211> LENGTH: 198
<212> TYPE: DNA
<213> ORGANISM: Artificial Sequence
<220> FEATURE:
<223> OTHER INFORMATION: synthetic oligonucleotide

<400> SEQUENCE: 39
attctagttg tggtttgtcc aaactcatca atgtatctta tcatgtctgg aataacttcg 60
tataatgtat gctatacgaa gttatgctag taactataac ggtcctaagg tagcgagcta 120
gccaagtctg tgtgctacca agtagcaaaa ctgagcctgg aactcacaca tgcgtgtctg 180
agagcccagc actatcgc 198

<210> SEQ ID NO 40
<211> LENGTH: 100
<212> TYPE: DNA
<213> ORGANISM: Artificial Sequence
<220> FEATURE:
<223> OTHER INFORMATION: synthetic oligonucleotide

<400> SEQUENCE: 40
taatctgact ttctcttcat cggtctctct tattctaggc tgagctgtaa cgctgccgtc 60
ccccacatcc agaagctgct tcccttcaga cctacctacg 100

<210> SEQ ID NO 41
<211> LENGTH: 177
<212> TYPE: DNA
<213> ORGANISM: Artificial Sequence
<220> FEATURE:
<223> OTHER INFORMATION: synthetic oligonucleotide

<400> SEQUENCE: 41
ccagtcaggg acacacatgc tcacacgccc gcccacccgc acacactaca gtcgagataa 60
cttcgtataa tgtatgctat acgaagttat gctagtaact ataacggtcc taaggtagcg 120
agctagccaa gtctgtgtgc taccaagtag caaaactgag cctggaactc acacatg 177

<210> SEQ ID NO 42
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 42
gagcagggcc atgacacat 19

<210> SEQ ID NO 43
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 43
accattagat cccagcactg gaca 24

<210> SEQ ID NO 44
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 44
aaacccttcc cgagagagaa 20

<210> SEQ ID NO 45
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 45
gaggaacact gtgtcaagga ctt 23

<210> SEQ ID NO 46
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 46
cctgaaaagc ccggagtggc ag 22

<210> SEQ ID NO 47

<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 47
gggcagagac cacatctga 19

<210> SEQ ID NO 48
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 48
ggaagccctc tctcgatact tg 22

<210> SEQ ID NO 49
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 49
ttctaccctg agggcatgca gc 22

<210> SEQ ID NO 50
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 50
tgggatgtag aaggttgtca ga 22

<210> SEQ ID NO 51
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 51
ctgagcctgg aactcacaca tg 22

<210> SEQ ID NO 52
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 52
tctgagagcc cagcactatc gcc 23

<210> SEQ ID NO 53
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 53
gctgagggtc aggcttgag 19

<210> SEQ ID NO 54
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 54
tctgcagggt agggagagaa g 21

<210> SEQ ID NO 55
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 55
tgtttcagaa aaggaagact cacgttaca 29

<210> SEQ ID NO 56
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 56
gagaccgatg aagagaaagt caga 24

<210> SEQ ID NO 57
<211> LENGTH: 100
<212> TYPE: DNA
<213> ORGANISM: Artificial Sequence
<220> FEATURE:
<223> OTHER INFORMATION: synthetic oligonucleotide

<400> SEQUENCE: 57
gaccatttta aggttttgct tggttgtttt ggagggaggg tggtgctttg ctaatggtga 60
attactaact cctcaataaa gaatattatt tgaaataatt 100

<210> SEQ ID NO 58
<211> LENGTH: 190
<212> TYPE: DNA
<213> ORGANISM: Artificial Sequence
<220> FEATURE:
<223> OTHER INFORMATION: synthetic oligonucleotide

<400> SEQUENCE: 58
gctgcctttt aatccagcgc tataattgag gcaagcgtcc agcttgacac ctcgagataa 60
cttcgtataa tgtatgctat acgaagttat atgcatggcc tccgcgccgg gttttggcgc 120
ctcccgcggg cgcccccctc ctcacggcga gcgctgccac gtcagacgaa gggcgcagcg 180
agcgtcctga 190

<210> SEQ ID NO 59
<211> LENGTH: 171
<212> TYPE: DNA
<213> ORGANISM: Artificial Sequence
<220> FEATURE:
<223> OTHER INFORMATION: synthetic oligonucleotide

<400> SEQUENCE: 59
attgttttgc caagttctaa ttccatcaga cctcgacctg cagcccctag ataacttcgt 60
ataatgtatg ctatacgaag ttatgctagt aactataacg gtcctaaggt agcgagctag 120
ctgcaaccga ggaaaaaacg tgccatgagg tctctgtatc caagtgtgac t 171

<210> SEQ ID NO 60
<211> LENGTH: 177
<212> TYPE: DNA
<213> ORGANISM: Artificial Sequence
<220> FEATURE:
<223> OTHER INFORMATION: synthetic oligonucleotide

<400> SEQUENCE: 60
ccagtcaggg acacacatgc tcacacgccc gcccacccgc acacactaca ctcgagataa 60
cttcgtataa tgtatgctat acgaagttat gctagtaact ataacggtcc taaggtagcg 120
agctagctgc aaccgaggaa aaaacgtgcc atgaggtctc tgtatccaag tgtgact 177

<210> SEQ ID NO 61
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 61
tcctctccag acaagaaagc t 21

<210> SEQ ID NO 62
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 62
tcatagcagc tttcaaatcc taaacgttga 30

<210> SEQ ID NO 63
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 63
tcgtgtgtag ctggtgagtt 20

<210> SEQ ID NO 64
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 64
catgcgatca caggaggaga tc 22

<210> SEQ ID NO 65
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 65
aattgggccc gaagccagat gc 22

<210> SEQ ID NO 66
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 66
cggaaggctt ctgtgacttc 20

<210> SEQ ID NO 67
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 67
gtctcccact tctgacataa tgaac 25

<210> SEQ ID NO 68
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 68
cccagtgtta accctacatc tggttcc 27

<210> SEQ ID NO 69
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 69
tgggaagaga ctcttggaca 20

<210> SEQ ID NO 70
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 70
atgagctcct agtacagcta aagtt 25

<210> SEQ ID NO 71
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 71
atgcatgatc atctatgcgt cagagc 26

<210> SEQ ID NO 72

```
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 72

tgcccagatg cagggagtta g                                              21
```